(12) United States Patent
Srivastava et al.

(10) Patent No.: US 7,449,557 B2
(45) Date of Patent: Nov. 11, 2008

(54) COMPLEXES OF ALPHA (2) MACROGLOBULIN AND ANTIGENIC MOLECULES FOR IMMUNOTHERAPY

(75) Inventors: Pramod K. Srivastava, Avon, CT (US); Robert J. Binder, Farmington, CT (US)

(73) Assignee: University of Connecticut Health Center, Farmington, CT (US)

( * ) Notice: Subject to any disclaimer, the term of this patent is extended or adjusted under 35 U.S.C. 154(b) by 0 days.

(21) Appl. No.: 09/873,403

(22) Filed: Jun. 4, 2001

(65) Prior Publication Data
US 2002/0028207 A1     Mar. 7, 2002

Related U.S. Application Data

(63) Continuation-in-part of application No. 09/625,139, filed on Jul. 25, 2000, now abandoned.

(60) Provisional application No. 60/209,266, filed on Jun. 2, 2000.

(51) Int. Cl.
*C07K 17/00*     (2006.01)
(52) U.S. Cl. ..................................... 530/402
(58) Field of Classification Search .................. 530/300, 530/350; 424/184.1, 277.1, 198.1; 514/2
See application file for complete search history.

(56) References Cited

U.S. PATENT DOCUMENTS

| | | | |
|---|---|---|---|
| 4,690,915 A | 9/1987 | Rosenberg | |
| 5,112,298 A | 5/1992 | Prince et al. | |
| 5,188,964 A | 2/1993 | McGuire et al. | |
| 5,232,833 A | 8/1993 | Sanders et al. | |
| 5,273,965 A | 12/1993 | Kensil et al. | |
| 5,348,945 A | 9/1994 | Berberian et al. | |
| 5,554,293 A | 9/1996 | Uhoch | |
| 5,580,859 A | 12/1996 | Felgner et al. | |
| 5,637,082 A | 6/1997 | Pages et al. | |
| 5,652,115 A | 7/1997 | Marks et al. | |
| 5,736,146 A | 4/1998 | Cohen | |
| 5,747,332 A | 5/1998 | Wallen et al. | |
| 5,750,119 A | 5/1998 | Srivastava | |
| 5,830,464 A | 11/1998 | Srivastava et al. | |
| 5,837,251 A | 11/1998 | Srivastava | |
| 5,846,928 A | 12/1998 | Kishida | |
| 5,869,058 A | 2/1999 | Cohen | |
| 5,891,653 A | 4/1999 | Attfield | |
| 5,910,306 A | 6/1999 | Alving et al. | |
| 5,935,576 A | 8/1999 | Srivastava | |
| 5,948,646 A | 9/1999 | Srivastava | |
| 5,961,979 A | 10/1999 | Srivastava | |
| 5,968,526 A | 10/1999 | Garman et al. | |
| 5,985,270 A | 11/1999 | Srivastava | |
| 5,997,873 A | 12/1999 | Srivastava et al. | |
| 6,007,821 A | 12/1999 | Srivastava et al. | |
| 6,017,540 A | 1/2000 | Srivastava | |
| 6,027,731 A | 2/2000 | Pauza | |
| 6,030,618 A | 2/2000 | Srivastava | |
| 6,033,561 A | 3/2000 | Schoendorfer | |
| 6,048,530 A | 4/2000 | Srivastava | |
| 6,136,315 A | 10/2000 | Srivastava | |
| 6,156,311 A | 12/2000 | Strickland et al. | |
| 6,162,436 A | 12/2000 | Srivastava | |
| 6,168,793 B1 | 1/2001 | Srivastava et al. | |
| 6,312,711 B1 | 11/2001 | Duchateau et al. | |
| 6,333,311 B1 | 12/2001 | Nuijens et al. | |
| 6,338,945 B1 | 1/2002 | Nicolette | |
| 6,403,092 B1 | 6/2002 | Pizzo et al. | |
| 6,433,141 B1 | 8/2002 | Wallen et al. | |
| 6,689,363 B1 | 2/2004 | Sette et al. | |
| 6,709,672 B2 | 3/2004 | Henot et al. | |
| 6,713,608 B2 | 3/2004 | Wallen et al. | |
| 6,730,302 B1 | 5/2004 | Fujihara et al. | |
| 6,797,480 B1 | 9/2004 | Srivastava | |
| 6,984,389 B2 | 1/2006 | Li | |
| 7,132,109 B1 | 11/2006 | Srivastava | |
| 7,179,462 B2 | 2/2007 | Srivastava et al. | |
| 7,176,515 B2 | 3/2007 | Srivastava et al. | |
| 2001/0034042 A1 | 10/2001 | Srivastava | |
| 2002/0001841 A1 | 1/2002 | Kaltoft et al. | |
| 2002/0028207 A1 | 3/2002 | Srivastava | |
| 2002/0037290 A1 | 3/2002 | Armen | |
| 2002/0172682 A1 | 11/2002 | Srivastava | |
| 2002/0192230 A1 | 12/2002 | Srivastava | |
| 2003/0129296 A1 | 7/2003 | Srivastava | |
| 2003/0211971 A1 | 11/2003 | Srivastava | |

(Continued)

FOREIGN PATENT DOCUMENTS

DE     196 02 985 A1     1/1996

(Continued)

OTHER PUBLICATIONS

Otto A et al (J. Urol Jan. 1998;159(1):297-303).*

(Continued)

*Primary Examiner*—Christopher Yaen
(74) *Attorney, Agent, or Firm*—Jones Day

(57) ABSTRACT

The present invention relates to complexes of alpha (2) macroglobulin associated with antigenic molecules for use in immunotherapy. The invention relates to methods for using such compositions in the diagnosis and treatment of immune disorders, proliferative disorders, and infectious diseases.

10 Claims, 65 Drawing Sheets

U.S. PATENT DOCUMENTS

Figure 1A:
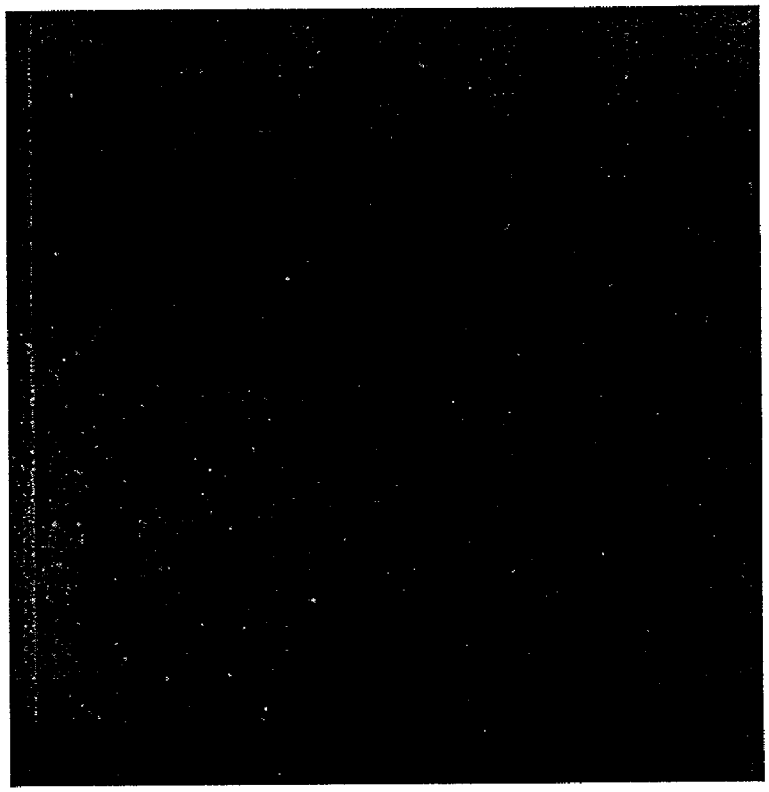
Figure 1A:
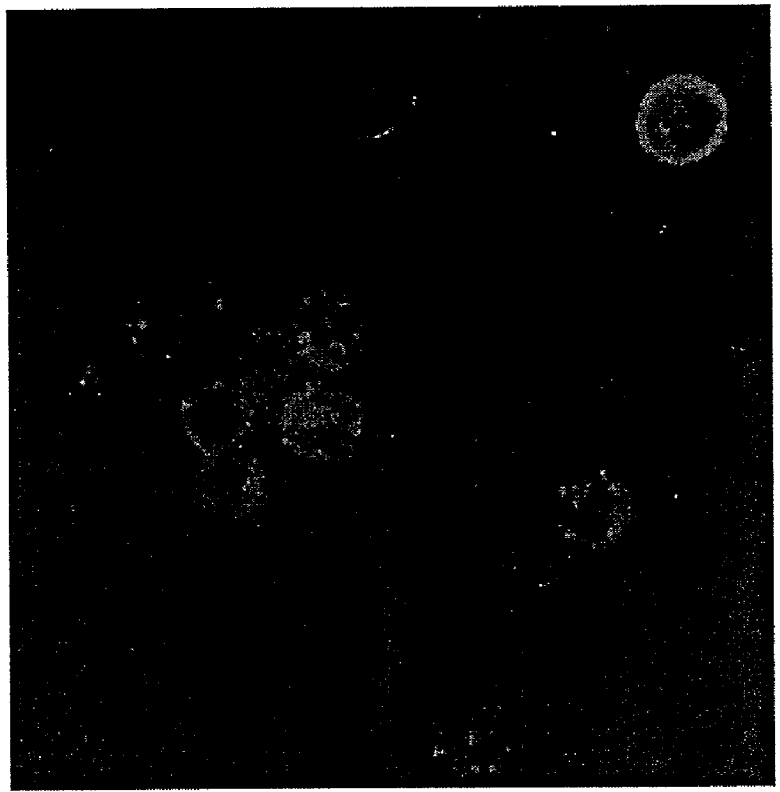

| | | | |
|---|---|---|---|
| 2004/0022796 A1 | 2/2004 | Srivastava | |
| 2004/0253228 A1 | 12/2004 | Srivastava | |
| 2006/0165710 A1 | 7/2006 | Srivastava | |

FOREIGN PATENT DOCUMENTS

| | | |
|---|---|---|
| GB | 2 251 186 A | 7/1992 |
| WO | WO 89/12455 | 12/1989 |
| WO | WO 90/02564 | 3/1990 |
| WO | WO 91/15572 | 10/1991 |
| WO | WO 92/01717 | 2/1992 |
| WO | WO 92/08484 | 5/1992 |
| WO | WO 92/08488 | 5/1992 |
| WO | WO 93/14118 | 7/1993 |
| WO | WO 93/17712 | 9/1993 |
| WO | WO 93/18146 | 9/1993 |
| WO | WO 93/18147 | 9/1993 |
| WO | WO 93/18150 | 9/1993 |
| WO | WO 93/21529 | 10/1993 |
| WO | WO 93/24136 | 12/1993 |
| WO | WO 94/03208 | 2/1994 |
| WO | WO 94/04676 | 3/1994 |
| WO | WO 94/11513 | 5/1994 |
| WO | WO 94/14471 | 7/1994 |
| WO | WO 94/14976 | 7/1994 |
| WO | WO 94/29459 | 12/1994 |
| WO | WO 95/24923 | 9/1995 |
| WO | WO 96/10411 | 4/1996 |
| WO | WO 97/04794 | 2/1997 |
| WO | WO 97/06685 | 2/1997 |
| WO | WO 97/06821 | 2/1997 |
| WO | WO 97/06828 | 2/1997 |
| WO | WO 97/10000 | 3/1997 |
| WO | WO 97/10001 | 3/1997 |
| WO | WO 97/10002 | 3/1997 |
| WO | WO 97/26910 | 7/1997 |
| WO | WO 98/46739 | 7/1997 |
| WO | WO 98/42752 | 10/1998 |
| WO | WO 98/46743 | 10/1998 |
| WO | WO 99/29834 | 6/1999 |
| WO | WO 99/50303 | 10/1999 |
| WO | WO 00/03003 | 1/2000 |
| WO | WO 00/10597 | 3/2000 |
| WO | WO 00/34494 | 6/2000 |
| WO | WO 00/38760 | 7/2000 |
| WO | WO 00/46246 | 8/2000 |
| WO | WO 00/54801 | 9/2000 |
| WO | WO 01/91787 | 6/2001 |
| WO | WO 01/92474 | 12/2001 |
| WO | WO 02/07755 | 1/2002 |
| WO | WO 02/11669 | 2/2002 |
| WO | WO 02/15930 | 2/2002 |
| WO | WO 02/30434 | 4/2002 |
| WO | WO 02/32923 | 4/2002 |
| WO | WO 02/34205 | 5/2002 |
| WO | WO 03/015712 | 2/2003 |
| WO | WO 03/090686 | 11/2003 |
| WO | WO 03/092624 | 11/2003 |
| WO | WO 04/035602 | 4/2004 |
| WO | WO 04/74454 | 9/2004 |
| WO | WO 04/075636 | 9/2004 |
| WO | WO 05/120558 | 12/2005 |

OTHER PUBLICATIONS

Beyrer C (The Hopkins HIV Report Jan. 2003; 15(1):6-7).*
Gura (Science, v278, 1997, pp. 1041-1042).*
Byers, T. (CA Journal, vol. 49, No. 6, Nov./Dec. 1999).*
Bizik et al (Int. J. Cancer 1986; 37:81-88).*
Fields et al (J. Virol. Methods 1988; 22:283-294).*
U.S. Appl. No. 09/411,075, filed Oct. 4, 1999, P. Srivastava.
Arnold-Schild et al., 1999, "Cutting edge: receptor-mediated endocytosis of heat shock proteins by professional antigen-presenting cells", J. Immunol. 162: 3757-3760.
Arnold et al., 1995, "Cross-priming of minor histocompatibility antigen-specific cytotoxic T cells upon immunization with the heat shock protein gp96", J Exp Med. Sep. 1;182(3):885-9.
Asea et al., 2000, "HSP70 stimulates cytokine production through a CD14 dependant pathway, demonstrating its dual role as a chaperone and cytokine", Nature Med. 6: 435-42.
Bardwell et al., 1984, "Major heat shock gene of *Drosophila* and the *Escherichia coli* heat-inducible dnaK gene are homologous", Proc Natl Acad Sci U S A. 81(3):848-52.
Bhattacharjee et al., 1999, "Incorporation of non-proteolytic proteins by murine α-2 macroglobulin", Biochimica et Biophysica Acta 1432:49-56.
Bevan, 1995, "Antigen presentation to cytotoxic T lymphocytes in vivo", J.Exp. Med. 192: 639-41.
Binder et al., 1998, Cell Stress & Chaperones 3 (Supp. 1): 2.
Blachere et al., 1997, "Heat shock protein-peptide complexes, reconstituted in vitro, elicit peptide-specific cytotoxic T lymphocyte response and tumor immunity", J Exp Med. 186(8):1315-22.
Castellino et al., 2000, "Receptor-mediated Uptake of Antigen/Heat Shock Protein Complexes Results in Major Histocmpatibility Complex Class I Antigen Presentation via Two Distinct Processing Pathways", J. Exp. Med. 191: 1957-64.
Chen et al., 1999, "Human 60-kDa Heat-Shock Protein: A Danger Signal to the Innate Immune System", J. Immunology 162: 3212-3219.
Chu et al., 1994, "Adjuvant-free in vivo targeting. Antigen delivery by α$_2$-macroglobulin enhances antibody formation", J. Immun. 152(4):1538-45.
Chu et al., 1994, "Alpha 2-macroglobulin: a sensor for proteolysis", Ann N Y Acad Sci. 737:291-307.
Chu and Pizzo, 1994, "Alpha 2-Macroglobulin, complement, and biologic defense: antigens, growth factors, microbial proteases, and receptor ligation", Lab Invest. Dec. 1994;71(6):792-812.
Chu and Pizzo, 1993, "Receptor mediated antigen delivery into macrophages. Complexing antigen to α$_2$-macroglobulin enhances presentation into T cells", J. Immun. 150(1):48-58.
Ciupitu et al., 1998, "Immunization with a lymphocytic choriomeningitis virus peptide mixed with heat shock protein 70 results in protective antiviral immunity and specific cytotoxic T lymphocytes", J Exp Med. 187(5):685-91.
Coutinho et al., 1998, "Alpha-2-macroglobulin receptor is differently expressed in peritoneal macrophages from C3H and C57/B16 mice and up-regulated during *Trypanosoma cruzi* infection", Tissue and Cell 30: 407-15.
Craig et al., 1993, "Chaperones: helpers along the pathways to protein folding", Science. 260(5116):1902-3.
Day et al., 1997, "Direct delivery of exogenous MHC class I molecule-binding oligopeptides to the endoplasmic reticulum of viable cells", Proc Natl Acad Sci. USA 94: 8064-8069.
Dennis et al., 1989, "Alpha 2-macroglobulin is a binding protein for basic fibroblast growth factor", J Biol Chem. 264 (13) :7210-6.
Fadok et al., 2000, "A receptor for phosphatidylserine-specific clearance of apoptotic cells", Nature 405(6782):85-90.
Forrester et al., 1983, "Effect of modified alpha 2macroglobulin on leucocyte locomotion and chemotaxis", Immunology. 50(2):251-9.
Gething et al., 1992, "Protein folding in the cell", Nature. 355(6355):33-45.
Greenstone et al., 1998, "Chimeric papillomavirus virus-like particle elicit antitumor immunity against the E7 oncoprotein in an HPV16 tumor model", Proc. Natl. Acad. Sci. USA 95:1800-1805.
Gron and Pizzo, 1998, "Non proteolytic Incorporation of Protein Ligands into Human α2 macroglobulin: Implications for the binding mechanism of α$_2$- macroglobulin", Biochem. 37:6009-6014.
Haas et al., 1988, "cDNA cloning of the immunoglobulin heavy chain binding protein", Proc Natl Acad Sci U S A. 85(7):2250-4.
Hall et al., 1981, "Proteolytic cleavage sites on alpha 2-macroglobulin resulting in proteinase binding are different for trypsin and *Staphylococcus aureus* V-8 proteinase", Biochem Biophys Res Commun. May 15, 1981;100(1):8-16.

Herz et al., 1988, "Surface location and high affinity for calcium of a 500-kd liver membrane protein closely related to the LDL-receptor suggest a physiological role as lipoprotein receptor", EMBO J. 7(13):4119-27.

Hickey et al., 1989, "Sequence and regulation of a gene encoding a human 89-kilodalton heat shock protein", Mol Cell Biol. 9(6):2615-26.

Hickey et al., 1986, "Sequence and organization of genes encoding the human 27 kDa heat shock protein", Nucleic Acids Res. 14(10):4127-45.

Hilliker et al., 1992, "Assignment of the gene coding for the alpha 2-macroglobulin receptor to mouse chromosome 15 and to human chromosome 12q13-q14 by isotopic and nonisotopic in situ hybridization", Genomics. 13(2):472-4.

Holtet et al., 1994, "Receptor-binding domain of human alpha 2-macroglobulin. Expression, folding and biochemical characterization of a high-affinity recombinant derivative", FEBS Lett. 344(2-3):242-6.

Holtet et al., 1994, "Recombinant $\alpha_{-2}$M Receptor binding domain binds to the $\alpha_{-2}$M receptor with high affinity", Ann N Y Acad Sci. 737:480-2.

Huang et al., 1996, "The immunodominant major histocompatibility complex class I-restricted antigen of a murine colon tumor derives from an endogenous retroviral gene product", Proc Natl Acad Sci U S A. 93(18):9730-5.

Huang et al., 1999, "NMR solution structure of complement-like repeat CR8 from the low density lipoprotein receptor -related protein", J. of Biolog. Chem. 274: 14130-14136.

Huang et al., 1984, Specific covalent binding of platelet-derived growth factor to human plasma alpha 2-macroglobulin. Proc Natl Acad Sci U S A. 81(2):342-6.

Hunt et al., 1990, "Characterization and sequence of a mouse hsp70 gene and its expression in mouse cell lines", Gene. 87(2):199-204.

Ishii et al., 1999, "Isolation of MHC class I-restricted tumor antigen peptide and its precursors associated with heat shock proteins hsp70, hsp90, and gp96", J Immunol. 162(3):1303-9.

Jensen et al., 1989, "Comparison of $\alpha$-macroglobulin receptors from human, baboon, rat and mouse liver", Biochem. Arch. 5:171-6.

Jindal et al., 1989, Primary structure of a human mitochondrial protein homologous to the bacterial and plant chaperonins and to the 65-kilodalton mycobacterial antigen. Mol Cell Biol. 9(5):2279-83.

Kan et al., 1985, "Nucleotide sequence of cDNA encoding human alpha 2-macroglobulin and assignment of the chromosomal locus", Proc Natl Acad Sci U S A. 82(8):2282-6.

Kol et al., 2000, "Cutting edge: heat shock protein (HSP)60 activates the innate immune response: CD14 is an essential receptor for HSP60 activation of monomuclear cells", J Immunol. 164(1):13-17.

Krieger and Herz, 1994, "Structures and functions of multiligand lipoprotein receptors: macrophage scavengenr receptors and LDL receptor-related protein (LRP)", Annu Rev Biochem. 63:601-37.

Kristensen et al., 1990, "Evidence that the newly cloned low-density-lipoprotein receptor related protein (LRP) is the alpha 2-macroglobulin receptor", FEBS Lett. 276(1-2):151-5.

Lindquist et al., 1988, "The heat-shock proteins", Annu Rev Genet. 22:631-77.

Maki et al., 1990, "Human homologue of murine tumor rejection antigen gp96: 5'-regulatory and coding regions and relationship to stress-induced proteins", Proc Natl Acad Sci U S A. 87(15):5658-62.

Maki et al., 1993, "Mapping of the genes for human endoplasmic reticular heat shock protein gp96/grp9", Somat Cell Mol Genet. 19(1):73-81.

McKee and Collins, 1974, "Intravascular Leukocyte thrombi and aggregates as a cause of morbidity and mortality in leukemia", Medicine 53: 463-478.

Menoret et al., 1999, "Association of peptides with heat shock protein gp96 occurs in vivo and not after cell lysis", Biochem Biophys Res Commun. Sep. 7, 1999;262(3):813-8.

Misra et al., 1993, "Receptor-recognized alpha 2-macroglobulin-methylamine elevates intracellular calcium, inositol phosphates and cyclic AMP in murine peritoneal macrophages", Biochem J. 290 (Pt 3):885-91.

Mitsuda et al., 1993, "A receptor-mediated antigen delivery and incorporation system", Biochem. and Biophys. Res. Comm. 191: 1326-31.

Mitsuda et al., 1993, "A receptor mediated delivery of an HIV 1 derived peptide vaccine", Biochem Biophys Res Commun 194(3): 1155-60.

Moestrup et al., 1993, "$\alpha_{-2}$ macroglobulin-proteinase complexes, plasminogen activator inhibitor type-1-plasminogen activator complexes, and receptor-associated protein bind to a region of the $\alpha_{-2}$-macroglobulin receptor containing a cluster of eight complement type repeats", J. of Biolog. Chem. 268: 13691-13696.

Moestrup et al., 1992, "Distribution of the alpha 2-macroglobulin receptor/low density lipoprotein receptor-related protein in human tissues", Cell Tissue Res. 269(3):375-82.

Nicchitta et al., 1998, "Biochemical, cell biological and immunological issues surrounding the endoplasmic reticulum chaperone GRP94/gp96", Curr Opin Immunol. 10(1):103-9.

Nielsen et al., 1996, "Identification of residues in alpha-macroglobulins important for binding to the alpha2-macroglobulin receptor/Low density lipoprotein receptor-related protein", J Biol Chem. 271(22):12909-12.

Norbury et al., 1997, "Constitutive macropinocytosis allows TAP-dependent major histocompatibility complex class I presentation of exogenous soluble antigen by bone marrow-derived dendritic cells", Eur J Immunol. Jan. 1997;27(1):280-8.

Nykjaer et al., 1992, "Purified alpha 2-macroglobulin receptor/LDL receptor-related protein binds urokinase.plasminogen activator inhibitor type-1 complex. Evidence that the alpha 2-macroglobulin receptor mediates cellular degradation of urokinase receptor-bound complexes", J Biol Chem. 267(21):14543-6.

O'Connor-McCourt et al., 1987, "Latent transforming growth factor-beta in serum. A specific complex with alpha 2-macroglobulin", J Biol Chem. 262(29):14090-9.

Orth et al., 1992, "Complexes of tissue-type plasminogen activator and its serpin inhibitor plasminogen-activator inhibitor type 1 are internalized by means of the low density lipoprotein receptor-related protein/alpha 2-macroglobulin receptor", Proc Natl Acad Sci U S A. 89(16):7422-6.

Osada et al., 1987, "Murine T cell proleferation can be specifically augmented by macrophages fed with specific antigen: $\alpha$-2-macroglobulin conjugate", Biochem. and Biophys. Res. Comm. 146: 26-31.

Osada et al., 1988, "Antibodies against viral proteins can be produced effectively in response to the increased uptake of alpha 2 macroglobulin: viral protein conjugate by macrophages", Biochem and Biophys. Res. Comm. 150: 883-889.

Qiu et al., 1999, "$\alpha 2$ macroglobulin enhances the clearance of endogenous soluble $\beta$-amyloid peptide via low density lipoprotein receptor-related protein in cortical neurons", J. Neurochem. 73(4):1393-1398.

Sargent et al., 1989, "Human major histocompatibility complex contains genes for the major heat shock protein HSP70", Proc Natl Acad Sci U S A. 86(6):1968-72.

Savill et al., 1992, "Thrombospondin cooperates with CD36 and the vitronectin receptor in macrophage recognition of neutrophils undergoing apoptosis", J Clin Invest. 90(4):1513-22.

Schuler and Steinman, 1997, "Dendritic cells as adjuvants for immune-mediated resistance to tumors", J Exp Med. 186(8):1183-7.

Singh-Jasjua et al., 2000, "Cross Presentation of Glycoprotein 96-associated antigens on major histocompatibility complex class I molecules requires receptor-mediated endocytosis", J. Exp. Med. 191:1965-74.

Soeiro et al., 2000, "*Trypanosoma cruzi*: Acute Infection Affects Expression of $\alpha$-2-macroglobulin and A2MR/LRP Receptor Differently in C3H and C57BL/6 Mice", Exper. Parasitology 96: 97-107.

Srivastava et al., 1991, "Stress-induced proteins in immune response to cancer", Curr Top Microbiol Immunol. 167:109-23.

Srivastava et al., 1987, "5'-structural analysis of genes encoding polymorphic antigens of chemically induced tumors." Proc. Natl. Acad. Sci USA 85:3807-3811.

Srivastava PK, 1993, "Peptide-binding heat shock proteins in the endoplasmic reticulum: role in immune response to cancer and in antigen presentation", Adv Cancer Res. 1993;62:153-77.

Srivastava PK, 1994, "Heat shock proteins in immune response to cancer: the Fourth Paradigm", Experientia. (11-12):1054-60.
Srivastava PK, 1988, "Individually distinct transplantation antigens of chemically induced mouse tumors", Immunol Today. 9(3):78-83.
Srivastava et al., 1988, "Chromosomal assignment of the gene encoding the mouse tumor rejection antigen gp96", Immunogenetics. 28(3):205-7.
Srivastava et al., 1994, "Heat shock proteins transfer peptides during antigen processing and CTL priming", Immunogenetics. 39(2):93-8. Review.
Srivastava PK, 1986, "Tumor rejection antigens of chemically induced sarcomas of inbred mice", Proc Natl Acad Sci U S A. 83(10):3407-11.
Srivastava et al., 1998, "Heat shock proteins come of age: primitive functions acquire new roles in an adaptive world", Immunity. 8(6):657-65.
Strickland et al., 1990, "Sequence identity between the alpha 2-macroglobulin receptor and low density lipoprotein receptor-related protein suggests that this molecule is a multifunctional receptor", J Biol Chem. 15;265(29):17401-4.
Suto and Srivastava, 1995, "A mechanism for the specific immunogenicity of heat shock protein-chaperoned peptides", Science 269(5230):1585-8.
Tamura et al., 1997, "Immunotherapy of tumors with autologous tumor-derived heat shock protein preparations", Science. 278(5335):117-20.
Ting et al., 1988, "Human gene encoding the 78,000-dalton glucose-regulated protein and its pseudogene: structure, conservation, and regulation", DNA. 7(4):275-86.
Udono H, Srivastava PK, 1994, "Comparison of tumor-specific immunogenicities of stress-induced proteins gp96, hsp90, and hsp70", J. Immunol. 152(11):5398-403.
Udono et al., 1994, "Cellular requirements for tumor-specific immunity elicited by heat shock proteins: tumor rejection antigen gp96 primes CD8+ T cells in vivo", Proc Natl Acad Sci U S A. 91(8):3077-81.
Udono H, Srivastava PK, 1993, "Heat shock protein 70-associated peptides elicit specific cancer immunity", J Exp Med.178(4):1391-6.
Ullrich et al., 1986, "A mouse tumor-specific transplantation antigen is a heat shock-related protein", Proc Natl Acad Sci U S A. 83(10):3121-5.
Van Leuven et al., 1993, "Molecular cloning and sequencing of the murine alpha-2-macroglobulin receptor cDNA", Biochim Biophys Acta. 1173(1):71-4.
Wassenberg et al., 1999, Receptor mediated and fluid phase pathways for internalization of the ER Hsp90 chaperone GRP94 in murine macrophages. J. Cell Science 112: 2167-2175.
Welch et al., 1993, "How cells respond to stress", Sci Am. 268(5):56-64.
Willnow et al., 1994, "Molecular dissection of ligand binding sites on the low density lipoprotein receptor-related protein", J. of Biolog. Chem. 269: 15827-15832.
Wu et al., 1998, "Oxidized $\alpha_2$-Macroglobulin ($\alpha_2$M) Differentially Regulates Receptor Binding by Cytokines/Growth Factors: Implications for Tissue Injury and Repair Mechanisms in Inflammation", J.Immun. 4356-4365.
Yamazaki et al., 1989, "Nucleotide sequence of a full-length cDNA for 90 kDa heat-shock protein from human peripheral blood lymphocytes", Nucleic Acids Res. 17(17):7108.
Young et al., 1990, "Stress proteins and immunology", Annu Rev Immunol. 8:401-20.
Heiser et al., 2000, "Human Dendritic Cells Transfected with RNA Encoding Prostate-Specific Antigen Stimulate Prostate-Specific CTL Responses In Vitro" Journal of Immunology, 164(10):5508-5514.
Kucera et al., 1997, "Prostate Specific Antigen (PSA) in Breast and Ovarian Cancer," Anticancer Research 17:4735-4738.
Levesque et al., 1995, "Prostate-Specific Antigen Expression by Various Tumors," J. Clin. Lab. Anal. 9:123-128.
Mannello et al., 2001, "Prostate-specific antigen (PSA/hK3): a Further Player in the Field of Brest Cancer Diagnostics?" Breast Cancer Res. 3:238-243 Review.
Oesterling, 1991, "Prostate Specific Antigen: A Critical Assessment of the Most Useful Tumor Marker for Adenocarcinoma of the Prostate," Journal of Urology, 145(5):907-23.
Yu, 1995, "expression of the Prostate-Specific Antigen Gene by a Primary Ovarian Carcinoma," Cancer Research 55:1603-1606.
Binder et al., 2002, "Naturally Formed or Artificially Reconstituted Non-Covalent Alpha2-Macroglobulin-Peptide Complexes Elicit CD91-Dependent Cellular Immunity," Cancer Immunity 2:16.
Binder et al., 2001,"Adjuvanticity of $\alpha_2$-Macroglobulin, an Independent Ligand for the Heat Shock Protein Receptor CD91," J. Immunol. 166:4968-4972.
Huang et al., 1996, "The Immunodominant Major Histocompatibility Complex Class I-Restricted Antigen of a Murine Colon Tumor Derives from an Endogenous Retroviral Gene Product," PNAS USA 93:9730-9735.
Noguchi et al., 1994, "A Mouse p53 Product Recognized by CD4$^+$ CD8$^+$ T Cells," PNAS 91:3171-3175.
Ibe et al., 1998, "Identification and characterization of a cytotoxic T cell epitope of hepatitis C virus presented by HLA-B3501 in acute hepatitis", J. Gen. Virol. 79:1735-1744.
Obata et al., 2000, "SEREX analysis of gastric cancer antigens", Cancer Chemother. Pharmacol. 46(Suppl.):S37-S42.
Pfreundschuh, 2000, "Exploitation of the B cell repertoire for the identification of human tumor antigens", Cancer Chemother. Pharmacol. 46(Suppl.):S3-S7.
Roberts et al., 1996, "Prediction of HIV peptide epitopes by a novel algorithm", AIDS Research and Human Retroviruses 12:593-610.
Sette et al., 1989, "Prediction of major histocompatibility complex binding regions of protein antigens by sequence pattern analysis", Proc. Natl. Acad. Sci. USA 86:3296-3300.
ePitope Informatics—prediction and analysis of protein epitopes—references [online] [retrieved Mar. 15, 2004] <URRL: http://www.epitope-informatics.com/References>.
Binder et al. "Naturally formed or artificially reconstituted non-covalent alpha2-macroglobulin-peptide complexes elicit CD91-dependent cellular immunity," *Cancer Immun*. Dec. 18, 2002;2:16.
Bhattacharjee et al. "The conformation-dependent interaction of alpha 2-macroglobulin with vascular endothelial growth factor. A novel mechanism of alpha 2-macroglobulin/growth factor binding." *J Biol Chem*. Sep. 1, 2000;275(35):26806-11.
Birkenmeier et al. "Human leptin forms complexes with alpha 2-macroglobulin which are recognized by the alpha 2-macroglobulin receptor/low density lipoprotein receptor-related protein." *Eur J Endocrinol*. Aug. 1998;139(2):224-30.
Krimbou et al. "Interaction of lecithin:cholesterol acyltransferase (LCAT).alpha 2-macroglobulin complex with low density lipoprotein receptor-related protein (LRP). Evidence for an alpha 2-macroglobulin/LRP receptor-mediated system participating in LCAT clearance." *J Biol Chem*. Aug. 31, 2001;276(35):33241-8. Epub Jul. 2, 2001.
Kessler. "Rapid isolation of antigens from cells with a staphylococcal protein A-antibody adsorbent: parameters of the interaction of antibody-antigen complexes with protein A." *J Immunol*. Dec. 1975;115(6):1617-24.
Bizik et al. "Release of an Mr 140,000 glycoprotein in the culture media of certain human sarcoma and melanoma cell lines." *Eur J Cancer Clin Oncol*. Mar. 1985;21(3):317-24.
Borth. "Alpha 2-macroglobulin, a multifunctional binding protein with targeting characteristics." *FASEB J*. Dec. 1992;6(15):3345-53.
Binder et al., 2000, "CD91:A receptor for heat shock protein gp96," Nature Immunol. 1(2):151-155.
Rammensee et al. 1995 "MHC ligands and peptide motifs: first listing" *Immunogenetics* 41:178-228.
Rammensee et al. 1999 SYFPEITHI: the database for MHC ligands and peptide motifs *Immunogenetics* 50:213-219.
Lovett et al. 1993 "Rubella virus specific cytotoxic T-lymphocyte responses: identification of the capsid as a target of MHC class I-restricted lysis and definition of two epitopes" J. Virology 76:5849-5858.
Thomson et al. 1996 "Recombinant polytopic vaccines for the delivery of multiple CD8 cytotoxic T cell epitopes" J. Immunol. 157:822-826.

Abbas et al., 1991, Cellular and Molecular Immunology, W.B. Saunders Co., Philadelphia (Chapters 15-18).
Agostoni et al., 1994, "Activation of complement and kinin systems after thrombolytic therapy in patients with acute myocardial infarction. A comparison between streptokinase and recombinant tissue-type plasminogen activator." Circulation. 90(6):2666-70.
Aldovini et al., 1992, "The New Vaccines", *Technology Review* pp. 24-31.
Amato et al., 1999, "Active Specific Immunotherapy in Patients with Renal Cell Carcinoma (RCC) Using Autologous Tumor Derived Heat Shock Protein-Peptide Complex-96 (HSPP-96) Vaccine" *American Society Clinical Onocology Meeting*, abstract 1278.
Andersen, P. 1994, "Effective vaccination of mice against Mycobacterium tuberculosis infection with a soluble mixture of secreted mycobacterial proteins," Infect. Immun. 62(6):2536-44.
Andus et al., Synthesis of alpha 2-macroglobulin in rat hepatocytes and in a cell-free system. FEBS Lett. Jan. 10, 1983;151(1):10-14.
Anthony et al.,1999, "Priming of CD8+ CTL effector cells in mice by immunizationwith a stress protein-influenza virus nucleoprotein fusion molecule," Vaccine 17(4):373-83.
Banchereau et al., 1998, "Dendritic cells and the control of immunity," Nature 392:245-252.
Barrios et al., 1992, "Mycobacterial heat-shock proteins as carrier molecules. II: The use of the 70-kDa mycobacterial heat-shock protein as carrier for conjugated vaccines can circumvent the need for adjuvants and BacillusCalmette Guerin priming," Eur. J. Immunol. 22(6):1365-72.
Barrios et al., 1994, "Heat shock proteins as carrier molecules: in vivo helper effect mediated by *Escherichia coli* GroEL and Dna K proteins requires cross-linking with antigen," Clin. Exp. Immunol. 98(2):229-233.
Barrios et al., 1994, "Specificity of antibodies induced after immunization of mice with the mycobacterial heat shock protein of 65 kD." Clin Exp Immunol. 98(2):224-8.
Bartlett, 1972 "Effect Of Host Immunity On The Antigenic Strength Of Primary Tumors." *J. Natl. Cancer Inst.* 49:493-504.
Basombrío (1970) "Search for common antigenicities among twenty-five sarcomas induced by methylcholanthrene", *The Institute for Cancer Research* 30:2458-2462.
Basu and Srivastava, 1999, "Calreticulin, a peptide-binding chaperone of the endoplasmic reticulum, elicits tumor- and peptide-specific immunity" *J. Exp. Med.* 189:797-802.
Basu et al., 2000, "Necrotic but not apoptotic cell death releases heat shock proteins , which deliver a partial maturation signal to dendritic cells and activate the NF-kappa B pathway," Int. Immunol. 12(11):1539-46.
Basu et al., 2001, "CD91 is a common receptor for heat shock proteins gp96, hsp90, hsp70, and calreticulin," Immunity 14:303-313.
Bednar et al., 1997, "Activation of complement by tissue plasminogen activator, but not acute cerebral ischemia, in a rabbit model of thromboembolic stroke." J. Neurosurg. 86(1):139-42.
Bellone et al., 1999, "Cancer Immunotherapy: synthetic and natural peptides in balance," Immunology Today 20(10): 457-462.
Beverly, 1988, "Tumour Immunology." *Immunology*, 3rd Edition, Roitt, Ed., Mosby, London, pp. 17.1-17.12.
Binder and Srivastava, 2004, "Essential role of CD91 in re-presentation of gp96-chaperoned peptides," Proc. Natl. Acad. Sci. U.S.A. 101:6128-6133.
Binder et al., 2000, "CD91: a receptor for heat shock protein gp96," Nature Immunol. 1(2):151-155.
Binder et al., 2001, "Heat shock protein-chaperoned peptides but not free peptides introduced into the cytosol are presented efficiently by major histocompatability complex I molecules," J. Biol. Chem. 276(20): 17163-17171.
Birkenmeier G., 2001, "Targetting the Proteinase Inhibitor and Immune Modulatory Function of Human α2-Macroglobulin." Mod. Asp. Immunobiol. 2(1):32-36.
Blachere and Srivastava (1993) "Immunization with GP96 heat shock proteins isolated from tumors or influenza virus infected cells elicits MHC-restricted, antigen-specific cytotoxic T lymphocytes against the corresponding cells", *J. Cellular Biochem. Keystone Symposia*, 17D: pp. 124, Abstract NZ 502.

Blachere et al., 1993, "Heat Shock Protein Vaccines Against Cancer," *Journal of Immunotherapy* 14:352-356.
Blander et al., 1993, "Major cytoplasmic membrane protein of *Legionella pnumophila*, a genus common antigen and member of the hsp 60 family of heat shock proteins, induces protective immunity in a guinea pig model of Legionnaires' disease," J. Clin. Invest. 91(2):717-23.
Bodey et al., 2000, Anticancer Res 20:2665-2676 Abs.
Bosch et al., 1999, "State of the art of therapeutic apheresis in Europe", Ther. Apher. 3(3):197-8.
Breloer et al., 1999, "in vivo and in vitro activation of T cells after administration of Ag-negative heat shock proteins," J. Immunol. 162:3141-3147.
Bumol et al., 1988 "Characterization Of The Human Tumor And Normal Tissue Reactivity Of The KS 1/4 Monoclonal Antibody." *Hybridoma* 7:407-415.
Carswell et al., 1970, "Immunogenic Properties Of Reticulum Cell Sarcomas Of SJL/J Mice." *Natl. Cancer Inst.* 44:1281-1288.
Cassel et al., 1977, "Viral oncolysate in the management of malignant melanoma. I. Preparation of the oncolysate and measurement of immunologic responses," Cancer 40:672-679.
Cassel et al., 1983 "A Phase II Study On The Postsurgical Management Of Stage II Malignant Melanoma With A Newcastle Disease Virus Oncolysate." *Cancer*, 52:856-860.
Castelli et al., 2001, "Human Heat Shock Protein 70 Peptide Complexes Specifically Active Antimelanoma T cells." Cancer Res 61:222-227.
Chandawarkar et al., 2004, "Immune modulation with high-dose heat shock protein gp96: therapy of murine autoimmune diabetes and encephalomyelitis," Int'l. Immunol. 16:315-324.
Chu et al., 1994, $\alpha_2$-Macroglobulin: A Sensor for Proteolysis, Ann. N.Y. Acad. Sci. 737:291-307.
Clarke et al. 1988, "Purification of Complexes of Nuclear Oncogene p.53 with Rat and *Escherichia coli* Heat Shock Proteins: In Vitro Dissociation of hsc70 and dnaK from Murine p 53 by ATP" Mol. and Cell. Biol. vol. 8 (3) 1206-1215.
Collen et al., 1989, "Tissue-type plasminogen activator. A review of its pharmacology and therapeutic use as a thrombolytic agent." Drugs. 38(3):346-88.
Costanzo, 1996, "New monoclonal antibodies," Curr. Opin. Cardiol. 11(2):204-7.
Craig, 1993, "Chaperones: Helpers Along the Pathways to Protein Folding," Science 260:1902-4.
D'Andrea, 2005, "Add Alzheimer's disease to the list of autoimmune diseases," Med. Hypotheses 64(3):458-463.
Dash, et al., 2002 "Slow-Tight Binding Inhibition of Xylanase by an Aspartic Protease Inhibitor." *J. Biol. Chem.* 277:17978-17986.
Davidoff et al., 1992, Immune response to p53 is dependent upon p53/HSP70 complexes in breast cancers.
Del Giudice et al., 1994, "Hsp70: a carrier molecule with built-in adjuvanticity", Experientia 30;50(11-12):1061-6.
Dermer, 1994, "Another Anniversary for the War on Cancer," Biotechnology 12:320.
Deutscher et al., 1992 "Guide to protein purification." *Meth. Enzymol.*, 182:610-611.
Dubois et al., 1980, "Immunogenic properties of soluble cytosol fractions on Meth A sarcoma cells," Cancer Res. 40:4204-4208.
Dubois, et al., 1982 "Purification and Biochemical Properties of Tumor-Associated Transplantation Antigens From Methylcholanthrene-Induced Murine Sarcomas." *Proc. Natl. Acad. Sci USA*, 79:7669-7673.
Ellgaard et al., 1997,"Dissection of the domain architecture of the alpha2macrglobulin-receptor associated protein." Eur. J. Biochem 244:544-51.
Epplen et al., 1997, "Genetic predisposition to multiple sclerosis as revealed by immunoprinting," Ann. Neurol. 41(3):341-52.
Espana et al., 1996, Clin. Chem 42(3):545-550.
Estin et al., 1989, "Transfected mouse melanoma lines that express various levels of human melanoma-associated antigen p97," J. Natl. Cancer Inst. 81:445-448.
Evans et al., 1999, Q.J. Med 92:299-307.

Falk et al., 1990, "Cellular Peptide Composition Governed by Major Histocompatibility Complex Class I Molecules", Nature 348:248-251.

Falk et al., 1991, "Identification of Naturally Processed Viral Nonapeptides Allows Their Quantification in Infected Cells and Suggests an Allele-specific T Cell Epitope Forecast". J Exp. Med 174:425-434.

Falk et al., 1991, "Allele-specific Motifs Revealed by Sequencing of Self-peptides Eluted from MHC Molecules", Nature 351:290-296.

Falk et al., 1992, "Specificity of antigen processing for MHC class I restricted presentation is conserved between mouse and man", Eur. J. Immunol. 22:1323-1326.

Fay et al., 1979, "Leukopheresis Therapy of Leukemic Reticuloendotheliosis (Hairy Cell Leukemia)", Blood 54: 747-749.

Fedweg and Srivastava "Evidence for biochemical heterogeneity of gp96 heat shock protein/tumor rejecion antigen", Mount Sinai School of Medicine NZ 206, p. 108.

Feng et al., 2002, "Exogenous heat shock proteins provide adjuvant effects on enhancing the immunogenicity of apoptotic tumor cells and inducing antitumor immunity," AACR 93rd Annual Meeting, vol. 43, Apr. 6-10, Abstract #2214.

Ferrero et al., 1995, The GroES homolog of Helicobacter pylori confers protective immunity against mucosal infection in mice. Proc Natl Acad Sci USA 92(14):6499-503.

Flynn et al., 1989, "Peptide binding and release by proteins implicated as catalysts of protein assembly", Science 245:385-390.

Flynn et al., 1991, "Peptide-binding Specificity of the Molecular Chaperone BiP", Nature 353:726-730.

Forrester et al., 1983, "Effect of modified alpha 2macroglobulin on leucocyte locomotion and chemotaxis", Immunology 50(2):251-9.

Freshney, 1983, "Culture of Animal Cells, A Manual of Basic Technique," Alan R. Liss Inc., New York p. 4.

Gaiger et al., 2000, "Immunity to WT1 in the animal model and in patients with acute myeloid leukemia," Blood 96(4):1480-1489.

Gallucci et al., 1999, "Natural adjuvants: endogenous activators of dendritic cells," Nat. Med. 5:1249-55.

Gelber et al., 1992, "Vaccination of mice with a soluble protein fraction of Mycobacterium leprae provides consistent and long-term protection against M. leprae infection," Infect Immun. 60(5):1840-4.

Gelber et al., 1994, "Vaccination with pure Mycobacterium leprae proteins inhibits M. leprae multiplication in mouse footpads," Infect Immun. 62(10):4250-5.

Gomez et al., 1991, "Protective efficacy of a 62-kilodalton antigen, HIS-62, from the cell wall and cell membrane of Histoplasma capsulatum yeast cells." Infect Immun. 59(12):4459-64.

Gomez et al., 1992, "An 80-kilodalton antigen from Histoplasma capsulatum that has homology to heat shock protein 70 induces cell-mediated immune responses and protection in mice," Infect Immun. 60(7):2565-71.

Gomez et al., 1995, "Vaccination with recombinant heat shock protein 60 from Histoplasma capsulatum protects mice against pulmonary histoplasmosis." Infect Immun. 63(7):2587-95.

Goto and Tanzi, 2002, "The role of the low-density lipoprotein receptor-related protein (LRPI) in Alzheimer's Abeta generation," J. Mol. Neurosci. 19:37-41.

Graham, et al. 1955,. "Antibodies Elicited by Cancer in Patients.", Cancer 8:409-416.

Graner et al. 2000, "Immunoprotective activities of multiple chaperone proteins isolated from murine B-cell leukemia/lymphoma" Clin. Can. Res.6:909.

Graner et al., 2000, "Tumor-derived multiple chaperone enrichment by free-solution isoelectric focusing yields potent antitumor vaccines" Cancer Immunol. Immunother. 49:476.

Graner et al., 2003, "Tumor-derived chaperone-rich cell lysates are effective therapeutic vaccines against a variety of cancers," Cancer Immunol. Immunother. 52(4):226-234.

Griffen, Jr., et al. 1972, "Colon Carcinoma and Immunologic Phenomena." Surgical Clinics of North America, vol. 52:839-846.

Grobmann et al., 1997, "Active-Specific Immunotherapy Of Pancreatic Carcinoma: Usefulness Of Human Pancreatic Carcinomas In Preparing Autologous Tumor Vaccines." Anticancer Res. 17: 3117-3120.

Halevy et al. 1990, "Different Tumor-Derived p53 Mutants Exhibit Distinct Biological Activities", Science vol. 250 113-116.

Hanover et al., 1986, "Monoclonal antibodies against a glycoprotein localized in coated pits and endocytic vesicles inhibit alpha2-macroglobulin binding and uptake", J. of Biol. Chem. 261(35): 16732-16737.

Harlow et al., 1988, "Antibodies: A Laboratory Manual" ch 6:139-243.

Heeb et al., 1995, "Prostate specific antigen-alpha 2-macroglobulin complexes in prostate cancer patient sera," Biochem. Mol. Biol. Int. 37(5):917-23.

Heiskala et al., 1988 "Characteristics Of Soluble Tumour-Derived Proteins That Inhibit Natural Killer Activity." Scand. J. Immunol. 28:19-27.

Henttu and Vihko, 1989 "cDNA Coding For The Entire Human Prostate Specific Antigen Shows High Homologies To The Human Tissue Kallikrein Genes." Biochem. Biophys. Res. Comm. 160:903-910.

Herz and Strickland, 2001, "LRP: a multifunctional scavenger and signaling receptor," J. Clin. Invest. 108:779-784.

Herz et al., 1990, "Low density lipoprotein receptor-related protein mediates endocytosis of monoclonal antibodies in cultured cells and rabbit liver", J. of Biol. Chem. 265(34): 21355-21362.

Herz et al., 1991, "39-kDa protein modulates binding of ligands to low density lipoprotein receptor-related protein/alpha-2-macroglobulin receptor." J.Biol.Chem. 266(31):21232-21238.

Hey et al., 1988, "Cloning of a novel member of the low-density lipoprotein receptor family", Gene 216: 103-111.

Hinds et al., 1987, "Immunological Evidence for the Association of p53 with a Heat Shock Protein, hsc70, in p53-plus-ras-Transformed Cell Lines" Mol. and Cell. Biol. vol. 7(8) 2863-2869.

Hinds et al., 1990, "Mutant p53 DNA Clones from Human Colon Carcinomas Cooperate with ras in Transforming Primary Rat Cells: A Comparison of the "Hot Spot" Mutant Phenotypes" Cell Growth and Differentiation vol. 1 571-580.

Hollinshead, 1988, "Immunotherapy," in:Cancer: The Outlaw Cell, LaFond, ed., American Chemical Society, Washington, DC pp. 237-250 (Chapter 14).

Horn et al., 1995, "Analysis of the binding of Pro-urokinase and urokinase-plasminogen activator inhibitor-1 complex to the low density lipoprotein receptor-related protein using a Fab fragment selected from a phage-displayed Fab library", J. of Biol. Chem. 270 (20): 11770-11775.

Horwitz et al., 1995, Protective immunity against tuberculosis induced by vaccination with major extracellular proteins of Mycobacterium tuberculosis. Proc Natl Acad Sci U S A. 92(5):1530-4.

Houghten et al., 1991, "Generation and use of synthetic peptide combinatorial libraries for basic research and drug discovery," Science 354:84-86.

Hubbard et al., 1992, "Immunization of mice with mycobacterial culture filtrate proteins," Clin. Exp. Immunol. 87(1):94-8.

Hughes et al., 1970, "A Sudy In Clinical Cancer Immunotherapy", Cancer, 26:269-278.

Hughes et al., 1981, "Characterization of plasma membrane proteins identified by monoclonal antibodies", J. of Biol./ Chem. 256(2): 664-671.

Humphrey et al., 1984, "Adjuvant immunotherapy for melanoma," J. Surg. Concol. 25:303-305.

Hunter, N. et al., 1991, "Suppression of experimental allergic encephalomyelitis by alpha(2)-macroglobulin," Immunology 73:58-63.

Isaacs et al., 1988, "Use of anti-idiotypic antibodies to establish that monoclonal antibody 7H1 1D6 binds to the alpha2-macroglobulin receptor recognition site", J. Biol. Chem. 263(14): 6709-6714.

Ishii et al., 1999, "Isolation of MHC class I-restricted tumor antigen peptide and its precursors associated with heat shock proteins hsp70, hsp90, and gp96", J Immunol. 162(3):1303-9.

Israeli et al., 1993, "Molecular Cloning Of A Complementary DNA Encoding A Prostate-Specific Membrane Antigen." Cancer Res. 53:227-230.

Jain et al., 1994, "Barriers to drug delivery in solid tumors." Sc Am 171(1):58-65.

Jakob et al., 1993, "Small Heat Shock Proteins Are Molecular Chaperones", *J. Biol. Chem.* 268:1517-1520.

James, K., 1980, "Alpha (2) macroglobulin and its possible importance in immune systems," Trends in Biol. Sci. pp. 43-47.

Janetzki et al., 2000, "Immunization of cancer patients with autologous cancer-derived heat shock protein gp96 preparations: a pilot study" *Int. J. of Cancer* 88:232-238.

Janeway, Travers, Walport, and Shlomchick, 2001, Immunobiology, 5th ed., Garland Publishing, New York (Part V, Sections 13-1 to 13-15).

Jardetzky et al., 1991, "Identification of Self Peptides Bound to Purified HLA-B27", *Nature* 353:326-329.

Jindal et al., 1989, Primary structure of a human mitochondrial protein homologous to the bacterial and plant chaperonins and to the 65-kilodalton mycobacterial antigen. Mol Cell Biol. 9(5):2279-83.

Jocham et al.,2004, "Adjuvant Autologous Renal Tumour Cell Vaccine and Risk of Tumour Progression in Patients with Renal-Cell Carcinoma After Radical Nephrectomy: Phase III, Randomised Controlled Trial." *The Lancet*, vol. 363:594-599.

Katsanis et al., 2000, "Augmentation of Tumor Lysate Immunogencity by enrichment of Chaperone Proteins Using Free Solution Isoelectric Focusing (FS-IEF)" *Keystone Symposia on Cellular Immunity and Immunotherapy of Cancer*, abstract 431.

Katsutani et al., 1992, "Immunogenic properties of structurally modified human tissue plasminogen activators in chimpanzees and mice." Fundam Appl Toxicol.19(4):555-62.

Kim et al., 1998, "A new low density lipoprotein receptor related protein, LRP5, is expressed in hepatocytes and adrenal cortex, and recognized apolipoprotein E", J. Biochem. 124: 1072-1076.

Kimber et al., 2002, "Lactoferrin: influences on langerhans cells, epidermal cytokines, and cutaneous inflammation." Biochem Cell Biol. 2002:80(1):103-7.

Kojima et al., 2002, "Combination therapy of tumor-derived gp96 and GM-CSF or IL-12-gene transduced tumor cells in the control of LLC tumor," AACR 93$^{rd}$ Annual Meeting, vol. 43, Abstract #5516.

Kol et al., 2000, "Cutting edge: heat shock protein (HSP)60 activates the innate immune response: CD14 is an essential receptor for HSP60 activation of monomuclear cells", J Immunol. 164(1):13-17.

Koo, 1982, "Characterization of growth-inhibitory activities associated with an alpha-macroglobulin of mice," Cancer Res. 42(5):1788-97.

Kornfeld et al., 1980, "Plasmapheresis in Myasthenia Gravis," Plasma Therapy, 2(3): 127-133.

Kripke, 1974 "Antigenicity Of Murine Skin Tumors Induced By Ultraviolet Light." *J. Natl. Cancer Inst.* 53:1333-1336.

Kristensen et al., 1990, "Evidence that the newly cloned low-density-lipoprotein receptor related protein (LRP) is the alpha 2-macroglobulin receptor", FEBS Lett. 276(1-2):151-5.

Kuhlmann et al., 1997, "Drug Research: from the idea to the product," International Journal of Pharmacology and Therapeutics 35:541-552.

Lakey et al., 1987, "Identification of a peptide binding protein that plays a role in antigen presentation", *Proc. Natl. Acad. Sci. USA* 84:1659-1663.

Lanzavecchia, 1993, "Identifying Strategies for Immune Intervention", *Science* 260:937-944.

Levy, 1991, "ATP is Required for In Vitro Assembly of MHC Class I Antigens but Not for Transfer of Peptides across the ER Membrane", *Cell* 67:265-274.

Li and Srivastava, 1993, "Tumor rejection antigen gp96/grp94 is an ATPase: Implications for protein folding and antigen presentation", *EMBO J.* 12(8):3143-3151.

Livingston et al. 1985,. "Serological Response of Melanoma Patients to Vaccines Prepared from VSV Lysates of Autologous and Allogeneic Cultured Melanoma Cells." *Cancer*, 55:713-720.

Lodish et al., *Molecular Cell Biology*, ch. 17.3 "Overview of the Secretory Pathway". pp. 691-696, W.H. Freeman and Company 2000.

Luescher et al., 1991, "Specific Binding of Antigenic Peptides to Cell-associated MHC Class I Molecules", *Nature* 351:72-77.

Lukacs et al., 1993, "Tumor cells transfected with a bacterial heat-shock gene lose tumorigenicity and induce protection against tumors", *J. Exp. Med.* 178:343-348.

Lussow et al., 1991, "Mycobacterial heat-shock proteins as carrier molecules", Eur J Immunol. 21(10):2297-302.

Madden et al., 1991, "The Structure of HLA-B27 Reveals Nonamer Self-peptides Bound in an Extended Conformation", *Nature* 353:321-325.

Maki (1991) "The Human Homologue of the Mouse Tumor Rejection Antigen GP96", Ph.D. thesis, Cornell University.

Martin et al., 1986, "Role of Murine Tumor Models in Cancer Treatment Research", Cancer Research 46:2189-2192.

Matsutake et al., 2001, "The immunoprotective MHC II epitope of a chemically induced tumor harbors a unique mutation in a ribosomal protein," PNAS 98(7):3992-3997.

Melcher et al., 1998, "Tumor immunogenicity is determined by the mechanism of cell death via induction of heat shock protein expression", Nat. Med. 5:581-7.

Melief et al., 1992, "Lessons from T Cell Responses to Virus Induced Tumours for Cancer Eradication in General", *Career Surveys* 13:81-99.

Melnick, 1985, "Virus Vaccines: An Overview", Proceedings of the First Annual Southwest Foundation for Biomedical Research International Symposium, Houston, Texas, Nov. 8-10, 1984, *American Society for Microbiology* pp. 1-13.

Ménoret and Chandawarkar, 1998, "Heat-shock protein-based anti-cancer immunotherapy: an idea whose time has come" *Semin. in Oncology* 25:654.

Menoret et al., 1995, "Co-segregation of tumor immunogenicity with expression of inducible but not constitutive hsp70 in rat colon carcinomas," J. Immunol. 155:740-7.

Millward and Hoeltge, 1982, "The Historical Development of Automated Hemapheresis", J. of Clin. Apheresis 1: 25-32.

Mizzen et al., 1998, "Immune responses to stress proteins: applications to infectious disease and cancer," Biotherapy 10:173-185.

Moestrup et al., 1990, "Immunocytochemical identification of the human aplpha 2-macroglobulin receptor in monocytes and fibroblasts: monoclonal antibodies define the receptor as a monocyte differentiation antigen", Exper. Cell Res. 190: 195-203.

Moestrup et al., 1991, Analysis of Ligand Recognition by the purified alpha-2M-macroglobulin receptor (low density lipoprotein receptor-related protein). J. Biol. Chem. 266(21):14011-14017.

Moroi et al., 2000, "Induction of Cellular Immunity by Immunization with Novel Hybrid Peptides Complexed to Heat Shock PRotein 70." Proc. Natl. Acad. Sci. 97(7):3485-3490.

MSNBC News Services, 2000, "Mixed Results on new cancer drug."

Mulé et al., 1984, "Adoptive Immunotherapy of Established Pulmonary Metastases with LAK Cells and Recombinant Interleukin-2", Science 225:1487-1489.

Munro et al., 1986, "An Hsp70-like protein in the ER: identity with the 78 kd glucose-regulated protein and immunoglobulin heavy chain binding protein", Cell 46(2):291-300.

Murray et al., 1977 "Viral Oncolysate in the Management of Malignant Melanoma II, Clinical Studies." *Cancer* 40:680-686.

Nair et al., 1977 "Antigen-Presenting Cells Pulsed With Unfractionated Tumor-Derived Peptides Are Potent Tumor Vaccines." *Eur. J. Immunol.* 27:589-597.

Nair et al., 1999, "Calreticulin displays in vivo peptide-binding activity and can elicit CTL responses against bound peptides" *J. Immunol.* 162:6426.

Natali et al., 1987 "Immunohistochemical Detection Of Antigen In Human Primary And Metastatic Melanomas By The Monoclonal Antibody 140.240 And Its Possible Prognostic Significance." *Cancer*, 59:55-63.

Nieland et al., 1996, "Isolation of an immunodominant viral peptide that is endogenously bound to the stress protein GP96/GRP94", Proc. Natl. Acad. Sci. USA 93:6135-6139.

Norby, 1985, "Summary," in: *Vaccines* 85, Lerner et al., eds., Cold Spring Harbor Laboratory, Cold Spring Harbor, NY pp. 387-394.

Oettgen and Old, 1991 "The History Of Cancer Immunotherapy." In: *Introduction To The Biologic Therapy Of Cancer*, Devitta et al., Eds., Lippincott, Philadelphia, PA, pp. 87-119 (Chapter 6).

Office Action mailed on Feb. 26, 2002 for U.S. Appl. No. 09/625,137 filed Jul. 25, 2000.

Office Action mailed on May 18, 2005, for U.S. Appl. No. 09/625,137 filed Jul. 25, 2000.

Office Action mailed on Oct. 5, 2004 for U.S. Appl. No. 09/625,137 filed Jul. 25, 2000.
Office Action mailed on Nov. 2, 2005 for U.S. Appl. No. 09/625,137 filed Jul. 25, 2000.
Office Action mailed on Dec. 31, 2002 for U.S. Appl. No. 09/625,137 filed Jul. 25, 2000.
Office Action mailed on Feb. 8, 2006 for U.S. Appl. No. 09/668,724 filed Sep. 22, 2000.
Office Action mailed on Feb. 25, 2003 for U.S. Appl. No. 09/668,724 filed Sep. 22, 2000.
Office Action mailed on May 7, 2002 for U.S. Appl. No. 09/668,724 filed Sep. 22, 2000.
Office Action mailed on Jun. 20, 2007 for U.S. Appl. No. 09/668,724 filed Sep. 22, 2000.
Office Action mailed on Jul. 7, 2004 for U.S. Appl. No. 09/668,724 filed Sep. 22, 2000.
Office Action mailed on sep. 21, 2006 for U.S. Appl. No. 09/668,724 filed Sep. 22, 2000.
Office Action mailed on Mar. 13, 2006 for U.S. Appl. No. 09/668,724 filed Sep. 22, 2000.
Office Action mailed on Jun. 5, 2002 for U.S. Appl. No. 09/750,972 filed Dec. 28, 2000.
Office Action mailed on Aug. 28, 2003 for U.S. Appl. No. 09/750,972 filed Dec. 28, 2000.
Office Action mailed on Jan. 11, 2006 for U.S. Appl. No. 10/225,367 filed Aug. 20, 2002.
Office Action mailed on Mar. 30, 2005 for U.S. Appl. No. 10/225,367 filed Aug. 20, 2002.
Office Action mailed on Apr. 18, 2007 for U.S. Appl. No. 10/225,367 filed Aug. 20, 2002.
Office Action mailed on Sep. 25, 2006 for U.S. Appl. No. 10/225,367 filed Aug. 20, 2002.
Office Action mailed on Oct. 19, 2007 for U.S. Appl. No. 10/225,367 filed Aug. 20, 2002.
Office Action mailed on Jan. 3, 2006 for U.S. Appl. No. 10/427,857 filed May 1, 2003.
Office Action mailed on Oct. 15, 2007 for U.S. Appl. No. 10/546,106 filed Oct. 11, 2005.
Office Action mailed on Feb. 22, 2007 for U.S. Appl. No. 10/784,012 filed Feb. 20, 2004.
Office Action mailed on Aug. 7, 2006 for U.S. Appl. No. 10/784,012 filed Feb. 20, 2004.
Office Action mailed on Nov. 2, 2007 for U.S. Appl. No. 10/784,012 filed Feb. 20, 2004.
Ohashi et al., 2000, Cutting edge: heat shock protein 60 is a putative endogenous ligand of the toll-like receptor-4 complex. J. Immunol. 164:558-561.
Old et al., 1962 "Part II. Antigens Of Tumor Cells. Antigenic Properties Of Chemically-Induced Tumors." *Ann. N.Y. Acad. Sci.* 101:80-106.
Opekun et al., 1999, "Novel therapies for Helicobacter pylori infection." Aliment Pharmacol Ther. 13(1):35-42.
Pal P.G., et al., 1992, "Immunization with extracellular proteins of Mycobacterium tuberculosis induces cell-mediated immune responses and substantial protective immunity in a guinea pig model of pulmonary tuberculosis." Infect Immun. 60(11):4781-92.
Palladino et al., 1987, "Expression of shared tumor-specific antigen by two chemically induced BALB/c sarcomas", *Cancer Research* 47:5074-5079.
Pardoll, 2000, "Therapeutic vaccination for cancer", Clin. Immunol. 95(1 Pt 2): S44-62.
Pattillo, 1974 "Combination Chemotherapy-Immunotherapy Indirect Chemotherapy Sensitivity Testing and Specific and Non-Specific Immunostimulation." In: *Neoplasm Immunity: Theory and Application: Proceeding of a Chicago Symposium*, Crispen, Ed. ITR, Chicago, IL, pp. 189-204.
Paul, Ed., 1993 *Fundamental Immunology*, 3rd Edition, Raven Press, NY, p. 1158 and References 189-220 Cited On pp. 1173-1174.
Paul. Fundamental Immunology. 1993 Third Edition, Raven PRess, NY.
PCT International Preliminary Examination Report mailed on Jan. 16, 2006 for Intl. Application No. PCT/US03/14390.
PCT International Preliminary Examination Report mailed on Jun. 17, 2003 for Intl. Application No. PCT/US01/23098.
PCT International Preliminary Examination Report mailed on Sep. 23, 2004 for Intl. Application No. PCT/US01/18041.
PCT International Preliminary Examination Report mailed on Oct. 6, 2005 for Intl. Application No. PCT/US02/26573.
PCT International Preliminary Examination Report mailed on Oct. 11, 2006 for Intl. Application No. PCT/US2004/005110.
PCT Written Opinion mailed on Oct. 11, 2006 for Intl. Application No. PCT/US2004/005110.
Peng et al., 1997, "Purification of immunogenic heat shock protein 70-peptide complexes by ADP-affinity chromatography" *J. Immunol. Meth.* 204:13.
Perez and Walker, 1989, "Isolation And Characterization Of A CcDNA Encoding The KS1/4 Epithelial Carcinoma Marker", *J. Immunol.* 142:3662-3667.
Pineda et al., 1994, "Applications of therapeutic apheresis," Mayo Clin. Proc. 69(9):893-4.
Pinhasi-Kimhi et al. 1986, "Specific interaction between the p53 cellular tumour antigen and major heat shock protiens", Nature vol. 320 (13) 182-184.
Pinilla-Ibarz et al., 2000, "Vaccination of patients with chronic myelogenous leukemia with bcr-abl oncogene breakpoint fusion peptides generates specific immune responses," Blood 95(5):1781-1787.
Prehn and Main, 1957 "Immunity To Methylcholanthrene-Induced Sarcomas." *J. Natl. Cancer Inst.* 18:769-778.
Proud, G. et al., 1979, "Blood transfusion and renal transplantation," Br. J. Sur. 66:678-82.
Rapley, 1995, "The biotechnology and applications of antibody engineering," Mol. Biotechnol. 3(2):139-54.
Reed et al., 1990, "Low incidence of antibodies to recombinant human tissue-type plasminogen activator in treated patients." Thromb Haemost. 64(2):276-80.
Repmann et al. 1997 "Adjuvant Therapy Of Renal Cell Carcinoma With Active-Specific-Immunotherapy (ASI) Using Autologous Tumor Vaccine." *Anticancer Res.* 17:2879-2882.
Report of the AMA Panel on Therapeutic Plasmapheresis, Current Status of Therapeutic Plasmapheresis and Related Techniques, Dec. 1984.
Rogers et al., 1981, "Some immunogenic acid biochemical properties of tumor-associated transplantation antigens (TATA) obtained in soluble form or solubilized from two methylcholanthrene-induced sarcomas, Meth A and CI-4," Int. J. Cancer 27:789-796.
Rothman, 1989, "Polypeptide Chain Binding Proteins: Catalysts of Protein Folding and Related Processes in Cells", *Cell* 59:591-601.
Rötzschke et al., 1990, "Isolation and Anlysis of Naturally Processed Viral Peptides as Recognized by Cytotoxic T cells", *Nature* 348:248-251.
Rotzschke, 1990, "Characterization of Naturally Occurring Minor Histocompatibility Peptides including H-4 and H-Y" Science 249: 283-287.
Salk et al., 1993, "A Strategy for Prophylactic Vaccination Against HIV", *Science* 260:1270-1272.
Sallusto et al., 1994, "Efficient presentation of soluble antigen by cultured human dendritic cells is maintained by granulocyte/macrophage colony-stimulating factor plus interleukin 4 and downregulated by tumor necrosis factor alpha," J. Exp. Med. 179(4): 1109-1118.
Sano et al., 1987, "The augmentation of tumor-specific immunity using haptenic muramyl dipeptide (MDP) derivatives. II. Establishment of tumor-specific immunotherapy models utilizing MDP hapten-reactive helper T cell activity," Cancer Immunol. Immunother. 25(3):180-184.
Sauter et al., 2000, "Consequences of cell death: exposure to necrotic tumor cells, but not primary tissue cells or apoptotic cells, induces the maturation of immunostimulatory dendritic cells", J. Exp. Med. 191:423-434.
Schreiber, 1989 "Tumor Immunology." In: *Fundamental Immunology*, 2nd Edition, Paul, ed., pp: 923-955.
Schumacher et al., 1991, "Peptide Selection by MHC Class I Molecules", *Nature* 350:703-706.

Sengupta et al., 2004, "Heat shock protein-mediated cross-presentation of exogenous HIV antigen on HLA Class I and Class II," J. Immunol. 173:1987-1993.

Silva et al., 1994, "A single mycobacterial protein (hsp 65) expressed by a transgenic antigen-presenting cell vaccinates mice against tuberculosis", Immunology 82(2):244-8.

Singh, 1997, "Neuroautoimmunity: pathogenic implications for Alzheimer's disease," Gerontology 43:79-94.

Smorodin et al., 1991, "The complex of α-2 Macroglobulin with CD2 in the Plasma of Gastric Carcinoma Patients." Scand J. Immunol 33:699-706.

Sorger and Pelham, 1987, "The glucose-regulated protein grp94 is related to heat shock protein hsp90", J. Mol. Biol. 194(2):341-4.

Sotgiu et al., 1998, "Genetic susceptibility to multiple sclerosis in Sardinians: an immunological study," Acta. Neurol. Scand. 98(5):314-7.

Sparks et al., 1976, "Immunology and adjuvant chemoimmunotherapy of breast cancer," Arch. Surg. 111:1057-1062.

Spero et al., 1980, "Plasma Exchange in Preparation of Mild Factor IX Deficient Hemophiliacs for Surgical Procedures," 19-22.

Srivastava and Heike, 1986, "Tumor-specific immunogenicity of stress-induced proteins: Convergence of two evolutionary pathways of antigen presentation?", Seminars in Immunology 3:57-64.

Srivastava and Old (1989) "Gp96 Molecules: Recognition Elements in Tumor Immunity", Human Tumor Antigens and Specific Tumor Therapy. pp. 63-71.

Srivastava and Udono, 1994, "Heat shock protein-peptide complexes in cancer immunotherapy" Curr. Opin. Immunol. 6:728.

Srivastava et al. (1990) Immunization with Soluble Gp96 Antigens Elicits Tumor-Specific Cellular Immunity:, Cellular Immunity and the Immunotherapy of Cancer, pp. 307-314.

Srivastava et al., 1984, "The Serologically Unique Cell Surface Antigen of Zajdela Ascitic Hepatoma is also its Tumor-Associated Transplantation Antigen", Int. J. Cancer 33:417-422.

Srivastava et al., 1987, "5'-structural analysis of genes encoding polymorphic antigens of chemically induced tumors." Proc. Natl. Acad. Sci USA 84(11):3807-3811.

Srivastava et al., 1988, "Individually distinct transplantation antigens of chemically induced mouse tumors," Immunol. Today 9:78-83.

Srivastava et al., 1989, "Identification of a Human Homologue of the Murine Tumor Rejection Antigen GP96,"Cancer Res. 49:1341-1343.

Srivastava et al., 1991, "Protein Tumor Antigens", Curr. Opin. Immunol. 3:654-658.

Srivastava et al., 1993, "Evidence for peptide-chaperoning by the endoplasmic reticular heat shock protein GP96: Implications for vaccination against cancer and infectious diseases", J Cell Biochem Suppl 17D:94 (Abstract NZ014).

Srivastava et al., 1998, "Heat shock proteins come of age: primitive functions acquire new roles in an adaptive world", Immunity 8(6):657-65.

Srivastava PK, 1994, "Heat shock proteins in immune response to cancer: the Fourth Paradigm", Experientia. (11-12):1054-60.

Srivastava, 1993, "Peptide-Binding Heat Shock Proteins in the Endoplasmic Reticulum: Role in Immune Response to Cancer and in Antigen Presentation," Adv. Cancer Res. 62:153-177.

Srivastava, 2002, "Roles of heat-shock proteins in innate and adaptive immunity," Nature Rev. Immunol. 2(3): 185-194.

Stack et al., 1982, "Autologous x-irradiated tumour cells and percutaneous BCG in operable lung cancer," Thorax 37(8):588-593.

Steinman, L., 2001, "Myelin-specific CD8+ T cells in the pathogenesis of experimental allergic encephalitis and multiple sclerosis," J. Exp. Med. 194:F27-F30.

Stenman et al., 1991, "A complex between prostate-specific antigen and alpha 1-antichymotrypsin is the major form of prostate-specific antigen in serum of patients with prostatic cancer: assay of the complex improves clinical sensitivity for cancer," Cancer Res. 51(1):222-6.

Stevenson, 1999, "DNA vaccines against cancer: from genes to therapy," Ann. Oncol. 10:1413-8 Review.

Subbarao et al., 1992, "A General Overview of Viral Vaccine Development," Genetically Engineered Vaccines 327:51-57.

Suzue et al., 1997, "Heat shock fusion proteins as vehicles for antigen delivery into the major histocompatibility complex class I presentation pathway," Proc. Natl. Acad. Sci. USA 94(24):13146-51.

Suzue K., Young R.A., 1996, "Heat shock proteins as immunological carriers and vaccines. in: Stress-Inducible Cellular Responses" (U. Feige, R. I. Morimoto, I. Yahara, B.S. Polla, eds.), Birkhauser/Springer, 77: 451-465.

Suzue K., Young R.A., 1996, "Adjuvant-free hsp70 fusion protein system elicits humoral and cellular immune responses to HIV-1" p24. J Immunol. 156(2):873-9.

Tailor et al., 1990, "Nucleotide Sequence Of Human Prostatic Acid Phosphatase Determined From A Full-Length cDNA Clone." Nucl. Acids Res. 18:4928 (1990).

Tait, BD, 1990, "Genetic susceptibility to type I diabetes: a review," J. Autoimmun. 3 Suppl. 1:3-11.

The Merck Manual of Diagnosis and Therapy, 1999, Beers and Berkow eds., Merck Research Laboratories, Whitehouse Station N.J., pp. 1871 and 1872.

Thomas et al., 1982, "Molecular and Cellular Effects of Heat Shock and Related Treatments of Mammalian Tissue-Culture Cells", Cold Springs Harbor Symp Quant Biol 46:985-996.

Todryk et al., 1999, "Heat shock protein 70 induced during tumor cell killing induces Th 1 cytokines and targets immature dendritic cell precursors to enhance antigen uptake," J. Immunol. 163:1398-1408.

Twining et al., 1977, "Large scale separation of protease inhibitors from malignant human breast tissue," Mol. Cell. Biochem. 18(2-3):101-7.

Udono et al., 1994, "Comparison of Tumor-Specific Immunogenicities of Stress-Induced Proteins gp96, hsp90, and hsp70," J. Immunol., 152(11):5398-5403.

Udono, 1993, "Heat shock proteins HSP70, HSP90 and GP96 elicit tumor specific immunity to the tumors from which they are isolated", J. Cell Biochem. Suppl. 17D:113 (Abstract NZ225).

Ullrich et al., 1986, "A mouse tumor-specific transplantation antigen is a heat shock-related protein," Proc. Natl. Acad. Sci. USA 83(10):3121-3125.

Urbaniak and Robinson, 1990, "ABC of transfusion. Therapeutic apheresis," BMJ 300(6725):662-5 Review.

Vaage, 1968 "Nonvirus-Associated Antigens In Virus-Induced Mouse Mammary Tumors." Cancer Res. 28:2477-2483.

Vanbuskirk et al., 1989, "Peptide binding protein having a role in antigen presentation is a member of the hsp70 heat shock family", J. Exp. Med. 170:1799-1809.

Vijayasaradhi et al., 1990 "The Melanoma Antigen gp75 Is The Human Homologue Of The Mouse b (Brown) Locus Gene Product." J. Exp. Med. 171:1375-1380.

Wallny et al., 1992, "Gene transfer experiments imply instructive role of major histocompatibility complex class I molecules in cellular peptide processing". Eur. J. Immunol 22:655-659.

Wang et al., 2001, "Characterization of heat shock protein 110 and glucose-regulated protein 170 as cancer vaccines and the effect of fever-range hyperthermia on vaccine activity," J. Immunol. 166(1):490-497.

Warshawaky et al., 1993, "Identification of domains in the 39-kDa protein that inhibit the binding of ligands to the low density lipoprotein receptor-related protein," J. Biol. Chem. 268(29):22046-22054.

Weiner et al., 1980, "Plasmapheresis in multiple sclerosis: preliminary study," Neurology 30: 1029-33.

Weiner et al., 2002, "Inflammation and therapeutic vaccination in CNS diseases," Nature 420:879-884.

Welch et al., 1982, "Purification of the Major Mammalian Heat Shock Proteins", J. Biol. Chem. 257:14949-14959.

Welch et al., 1985, "Rapid Purification of Mammalian 70,000-Dalton Stress Proteins: Affinity of the Proteins for Nucleotides", Mol. Cell. Biol. 5:1229-1237.

Welch et al., 1995, "Morphological study of the mammalian stress response: characterization of changes in cytoplasmic organelles, cytoskeleton, and nucleoli, and appearance of intranuclear actin filaments in rat fibroblasts after heat-shock treatment," J. Cell. Biol. 101:1198-1211.

Welch, 1993, "How Cells Respond to Stress," Scientific American 268(5):56-64.

Wllnow et al., 1996. "The low-density-lipoprotein receptor-related protein (LRP) is processed by furin in vivo and in vitro." The Biochemical Journal. England 313:71-76.

Wong et al., 1991, "Susceptibility to type I diabetes in women is associated with the CD3 epsilon locus on chromosome 11," Clin. Exp. Immunol. 83(1):69-73.

Xiao et al., 1995, "Characterization of hormonogenic sites in an N-terminal, cyanogen bromide fragment of human thyroglobulin." *Arch Biochem Biophys.* 20:320(1):96-105.

Yamauchi et al., 2000, "Oral administration of bovine lactoferrin for treatment of tinea pedis. A placebo-controlled, double-blind study." Mycoses.43(5):197-202.

Yang et al., 1999, "Murine dendritic cells transfected with human GP100 elicit both antigen-specific CD8+ and CD4+ T-cell responses and are more effective than DNA vaccines at generating anti-tumor immunity," Int. J. Cancer 83:532-540.

Yedavelli et al., 1999, "Preventive and therapeutic effect of tumor derived heat shock protein, gp96, in an experimental prostate cancer model" *Int. J. Mol. Med.* 3:243.

Yu et al., 1991, "Sequence Analysis of Peptides Bound to MHC Class II Molecules", *Nature* 353:622-627.

Zimecki et al., 1998, "Immunoregulatory effects of a nutritional preparation containing bovine lactoferrin taken orally by healthy individuals." Arch Immunol Ther Exp (Warsz). 46(4):231-40.

Zimecki et al., 1999, "Lactoferrin increases the output of neutrophil precursors and attenuates the spontaneous production of TNF-alpha and IL-6 by peripheral blood cells." Arch Immunol Ther Exp (Warsz). 47(2):113-8.

U.S. Appl. No. 09/393,652, filed Sep. 10, 1999, Srivastava.

\* cited by examiner

| Seq | # | b | y | +1 |
|---|---|---|---|---|
| G | 1 | 58.1 | – | 10 |
| G | 2 | 115.1 | 1095.2 | 9 |
| A | 3 | 186.2 | 1038.2 | 8 |
| L | 4 | 299.3 | 967.1 | 7 |
| H | 5 | 436.5 | 853.9 | 6 |
| I | 6 | 549.6 | 716.8 | 5 |
| Y | 7 | 712.8 | 603.6 | 4 |
| H | 8 | 850.0 | 440.5 | 3 |
| Q | 9 | 978.1 | 303.3 | 2 |
| R | 10 | – | 175.2 | 1 |

FIG.3A

| POSITION | MH+ | SEQUENCE | |
|---|---|---|---|
| 509-518 | 955.0122 | SGFSLGSDGK | (SEQ ID NO: 9) |
| 328-337 | 973.1753 | GIALDPAMGK | (SEQ ID NO: 10) |
| 460-469 | 1152.3010 | GGALHIYHQR | (SEQ ID NO: 11) |
| 338-348 | 1315.5116 | VFFTDYGQIPK | (SEQ ID NO: 12) |

FIG.3C

```
CGCTGCTCCC CGCCAGTGCA CTGAGGAGGC GGAAACGGGG GAGCCCCTAG TGCTCCATCA     60
GGCCCCTACC AAGGCACCCC CATCGGGTCC ACGCCCCCA CCCCCCACCC CGCCTCCTCC    120
CAATTGTGCA TTTTTGCAGC CGGAGTCGGC TCCGAGATGG GGCTGTGAGC TTCGCCCTGG   180
GAGGGGGAGA GGAGCGAGGA GTAAAGCAGG GGTGAAGGGT TCGAATTTGG GGGCAGGGGG   240
CGCACCCGCG TCAGCAGGCC CTTCCCAGGG GGCTCGGAAC TGTACCATTT CACCTATGCC   300
CCTGGTTCGC TTTGCTTAAG GAAGGATAAG ATAGAAGAGT CGGGGAGAGG AAGATAAAGG   360
GGGACCCCCC AATTGGGGGG GGCGAGGACA AGAAGTAACA GGACCAGAGG GTGGGGGCTG   420
CTGTTTGCAT CGGCCCACAC C ATG CTG ACC CCG CCG TTG CTG CTG CTC GTG     471
                        Met Leu Thr Pro Pro Leu Leu Leu Leu Val
                         1               5                   10
```

```
CCG CTG CTT TCA GCT CTG GTC TCC GGG GCC ACT ATG GAT GCC CCT AAA     519
Pro Leu Leu Ser Ala Leu Val Ser Gly Ala Thr Met Asp Ala Pro Lys
            15                  20                  25
```

```
ACT TGC AGC CCT AAG CAG TTT GCC TGC AGA GAC CAA ATC ACC TGT ATC     567
Thr Cys Ser Pro Lys Gln Phe Ala Cys Arg Asp Gln Ile Thr Cys Ile
            30                  35                  40
```

```
TCA AAG GGC TGG CGG TGT GAC GGT GAA AGA GAT TGC CCC GAC GGC TCT     615
Ser Lys Gly Trp Arg Cys Asp Gly Glu Arg Asp Cys Pro Asp Gly Ser
            45                  50                  55
```

```
GAT GAA GCC CCT GAG ATC TGT CCA CAG AGT AAA GCC CAG AGA TGC CCG     663
Asp Glu Ala Pro Glu Ile Cys Pro Gln Ser Lys Ala Gln Arg Cys Pro
60                  65                  70
```

```
CCA AAT GAG CAC AGT TGT CTG GGG ACT GAG CTA TGT GTC CCC ATG TCT    711
Pro Asn Glu His Ser Cys Leu Gly Thr Glu Leu Cys Val Pro Met Ser
75                  80                  85                  90
```

```
CGT CTC TGC AAC GGG ATC CAG GAC TGC ATG GAT GGC TCA GAC GAG GGT    759
Arg Leu Cys Asn Gly Ile Gln Asp Cys Met Asp Gly Ser Asp Glu Gly
                95                  100                 105
```

```
GCT CAC TGC CGA GAG CTC CGA GCC AAC TGT TCT CGA ATG GGT TGT CAA    807
Ala His Cys Arg Glu Leu Arg Ala Asn Cys Ser Arg Met Gly Cys Gln
            110                 115                 120
```

```
CAC CAT TGT GTA CCT ACA CCC AGT GGG CCC ACG TGC TAC TGT AAC AGC    855
His His Cys Val Pro Thr Pro Ser Gly Pro Thr Cys Tyr Cys Asn Ser
            125                 130                 135
```

FIG.6A-1

```
AGC TTC CAG CTC GAG GCA GAT GGC AAG ACG TGC AAA GAT TTT GAC GAG      903
Ser Phe Gln Leu Glu Ala Asp Gly Lys Thr Cys Lys Asp Phe Asp Glu
    140                 145                 150

TGT TCC GTG TAT GGC ACC TGC AGC CAG CTT TGC ACC AAC ACA GAT GGC      951
Cys Ser Val Tyr Gly Thr Cys Ser Gln Leu Cys Thr Asn Thr Asp Gly
155                 160                 165                 170

TCC TTC ACA TGT GGC TGT GTT GAA GGC TAC CTG CTG CAA CCG GAC AAC      999
Ser Phe Thr Cys Gly Cys Val Glu Gly Tyr Leu Leu Gln Pro Asp Asn
                175                 180                 185

CGC TCC TGC AAG GCC AAG AAT GAG CCA GTA GAT CGG CCG CCA GTG CTA     1047
Arg Ser Cys Lys Ala Lys Asn Glu Pro Val Asp Arg Pro Pro Val Leu
            190                 195                 200

CTG ATT GCC AAC TCT CAG AAC ATC CTA GCT ACG TAC CTG AGT GGG GCC     1095
Leu Ile Ala Asn Ser Gln Asn Ile Leu Ala Thr Tyr Leu Ser Gly Ala
        205                 210                 215

CAA GTG TCT ACC ATC ACA CCC ACC AGC ACC CGA CAA ACC ACG GCC ATG     1143
Gln Val Ser Thr Ile Thr Pro Thr Ser Thr Arg Gln Thr Thr Ala Met
220                 225                 230

GAC TTC AGT TAT GCC AAT GAG ACC GTA TGC TGG GTG CAC GTT GGG GAC     1191
Asp Phe Ser Tyr Ala Asn Glu Thr Val Cys Trp Val His Val Gly Asp
235                 240                 245                 250

AGT GCT GCC CAG ACA CAG CTC AAG TGT GCC CGG ATG CCT GGC CTG AAG     1239
Ser Ala Ala Gln Thr Gln Leu Lys Cys Ala Arg Met Pro Gly Leu Lys
                255                 260                 265

GGC TTT GTG GAT GAG CAT ACC ATC AAC ATC TCC CTC AGC CTG CAC CAC     1287
Gly Phe Val Asp Glu His Thr Ile Asn Ile Ser Leu Ser Leu His His
            270                 275                 280

GTG GAG CAG ATG GCA ATC GAC TGG CTG ACG GGA AAC TTC TAC TTT GTC     1335
Val Glu Gln Met Ala Ile Asp Trp Leu Thr Gly Asn Phe Tyr Phe Val
        285                 290                 295

GAC GAC ATT GAC GAC AGG ATC TTT GTC TGT AAC CGA AAC GGG GAC ACC     1383
Asp Asp Ile Asp Asp Arg Ile Phe Val Cys Asn Arg Asn Gly Asp Thr
300                 305                 310
```

FIG.6A-2

```
TGT GTC ACT CTG CTG GAC CTG GAA CTC TAC AAC CCC AAA GGC ATC GCC   1431
Cys Val Thr Leu Leu Asp Leu Glu Leu Tyr Asn Pro Lys Gly Ile Ala
315             320             325             330

TTG GAC CCC GCC ATG GGG AAG GTG TTC TTC ACT GAC TAC GGG CAG ATC   1479
Leu Asp Pro Ala Met Gly Lys Val Phe Phe Thr Asp Tyr Gly Gln Ile
                335             340             345

CCA AAG GTG GAG CGC TGT GAC ATG GAT GGA CAG AAC CGC ACC AAG CTG   1527
Pro Lys Val Glu Arg Cys Asp Met Asp Gly Gln Asn Arg Thr Lys Leu
        350             355             360

GTG GAT AGC AAG ATC GTG TTT CCA CAC GGC ATC ACC CTG GAC CTG GTC   1575
Val Asp Ser Lys Ile Val Phe Pro His Gly Ile Thr Leu Asp Leu Val
            365             370             375

AGC CGC CTC GTC TAC TGG GCG GAC GCC TAC CTA GAC TAC ATC GAG GTG   1623
Ser Arg Leu Val Tyr Trp Ala Asp Ala Tyr Leu Asp Tyr Ile Glu Val
        380             385             390

GTA GAC TAC GAA GGG AAG GGT CGG CAG ACC ATC ATC CAA GGC ATC CTG   1671
Val Asp Tyr Glu Gly Lys Gly Arg Gln Thr Ile Ile Gln Gly Ile Leu
395             400             405             410

ATC GAG CAC CTG TAC GGC CTG ACC GTG TTT GAG AAC TAT CTC TAC GCC   1719
Ile Glu His Leu Tyr Gly Leu Thr Val Phe Glu Asn Tyr Leu Tyr Ala
            415             420             425

ACC AAC TCG GAC AAT GCC AAC ACG CAG CAG AAG ACG AGC GTG ATC CGA   1767
Thr Asn Ser Asp Asn Ala Asn Thr Gln Gln Lys Thr Ser Val Ile Arg
                430             435             440

GTG AAC CGG TTC AAC AGT ACT GAG TAC CAG GTC GTC ACC CGT GTG GAC   1815
Val Asn Arg Phe Asn Ser Thr Glu Tyr Gln Val Val Thr Arg Val Asp
        445             450             455

AAG GGT GGT GCC CTG CAT ATC TAC CAC CAG CGA CGC CAG CCC CGA GTG   1863
Lys Gly Gly Ala Leu His Ile Tyr His Gln Arg Arg Gln Pro Arg Val
            460             465             470

CGG AGT CAC GCC TGT GAG AAT GAC CAG TAC GGG AAG CCA GGT GGC TGC   1911
Arg Ser His Ala Cys Glu Asn Asp Gln Tyr Gly Lys Pro Gly Gly Cys
475             480             485             490
```

FIG.6A-3

```
TCC GAC ATC TGC CTC CTG GCC AAC AGT CAC AAG GCA AGG ACC TGC AGG    1959
Ser Asp Ile Cys Leu Leu Ala Asn Ser His Lys Ala Arg Thr Cys Arg
            495                 500                 505

TGC AGG TCT GGC TTC AGC CTG GGA AGT GAT GGG AAG TCT TGT AAG AAA    2007
Cys Arg Ser Gly Phe Ser Leu Gly Ser Asp Gly Lys Ser Cys Lys Lys
            510                 515                 520

CCT GAA CAT GAG CTG TTC CTC GTG TAT GGC AAG GGC CGA CCA GGC ATC    2055
Pro Glu His Glu Leu Phe Leu Val Tyr Gly Lys Gly Arg Pro Gly Ile
        525                 530                 535

ATT AGA GGC ATG GAC ATG GGG GCC AAG GTC CCA GAT GAG CAC ATG ATC    2103
Ile Arg Gly Met Asp Met Gly Ala Lys Val Pro Asp Glu His Met Ile
        540                 545                 550

CCC ATC GAG AAC CTT ATG AAT CCA CGC GCT CTG GAC TTC CAC GCC GAG    2151
Pro Ile Glu Asn Leu Met Asn Pro Arg Ala Leu Asp Phe His Ala Glu
555                 560                 565                 570

ACC GGC TTC ATC TAC TTT GCT GAC ACC ACC AGC TAC CTC ATT GGC CGC    2199
Thr Gly Phe Ile Tyr Phe Ala Asp Thr Thr Ser Tyr Leu Ile Gly Arg
            575                 580                 585

CAG AAA ATT GAT GGC ACG GAG AGA GAG ACT ATC CTG AAG GAT GGC ATC    2247
Gln Lys Ile Asp Gly Thr Glu Arg Glu Thr Ile Leu Lys Asp Gly Ile
            590                 595                 600

CAC AAT GTG GAG GGC GTA GCC GTG GAC TGG ATG GGA GAC AAT CTT TAC    2295
His Asn Val Glu Gly Val Ala Val Asp Trp Met Gly Asp Asn Leu Tyr
            605                 610                 615

TGG ACT GAT GAT GGC CCC AAG AAG ACC ATT AGT GTG GCC AGG CTG GAG    2343
Trp Thr Asp Asp Gly Pro Lys Lys Thr Ile Ser Val Ala Arg Leu Glu
        620                 625                 630

AAA GCC GCT CAG ACC CGG AAG ACT CTA ATT GAG GGC AAG ATG ACA CAC    2391
Lys Ala Ala Gln Thr Arg Lys Thr Leu Ile Glu Gly Lys Met Thr His
        635                 640                 645                 650

CCC AGG GCC ATT GTA GTG GAT CCA CTC AAT GGG TGG ATG TAC TGG ACA    2439
Pro Arg Ala Ile Val Val Asp Pro Leu Asn Gly Trp Met Tyr Trp Thr
            655                 660                 665
```

FIG.6A-4

| | |
|---|---|
| GAC TGG GAG GAG GAC CCC AAG GAC AGT CGG CGA GGG CGG CTC GAG AGG<br>Asp Trp Glu Glu Asp Pro Lys Asp Ser Arg Arg Gly Arg Leu Glu Arg<br>670                675                680 | 2487 |
| GCT TGG ATG GAC GGC TCA CAC CGA GAT ATC TTT GTC ACC TCC AAG ACA<br>Ala Trp Met Asp Gly Ser His Arg Asp Ile Phe Val Thr Ser Lys Thr<br>685                690                695 | 2535 |
| GTG CTT TGG CCC AAT GGG CTA AGC CTG GAT ATC CCA GCC GGA CGC CTC<br>Val Leu Trp Pro Asn Gly Leu Ser Leu Asp Ile Pro Ala Gly Arg Leu<br>700                705                710 | 2583 |
| TAC TGG GTG GAT GCC TTC TAT GAC CGA ATT GAG ACC ATA CTG CTC AAT<br>Tyr Trp Val Asp Ala Phe Tyr Asp Arg Ile Glu Thr Ile Leu Leu Asn<br>715                720                725                730 | 2631 |
| GGC ACA GAC CGG AAG ATT GTA TAT GAG GGT CCT GAA CTG AAT CAT GCC<br>Gly Thr Asp Arg Lys Ile Val Tyr Glu Gly Pro Glu Leu Asn His Ala<br>735                740                745 | 2679 |
| TTC GGC CTG TGT CAC CAT GGC AAC TAC CTC TTT TGG ACC GAG TAC CGG<br>Phe Gly Leu Cys His His Gly Asn Tyr Leu Phe Trp Thr Glu Tyr Arg<br>750                755                760 | 2727 |
| AGC GGC AGC GTC TAC CGC TTG GAA CGG GGC GTG GCA GGC GCA CCG CCC<br>Ser Gly Ser Val Tyr Arg Leu Glu Arg Gly Val Ala Gly Ala Pro Pro<br>765                770                775 | 2775 |
| ACT GTG ACC CTT CTG CGC AGC GAG AGA CCG CCT ATC TTT GAG ATC CGA<br>Thr Val Thr Leu Leu Arg Ser Glu Arg Pro Pro Ile Phe Glu Ile Arg<br>780                785                790 | 2823 |
| ATG TAC GAC GCG CAC GAG CAG CAA GTG GGT ACC AAC AAA TGC CGG GTA<br>Met Tyr Asp Ala His Glu Gln Gln Val Gly Thr Asn Lys Cys Arg Val<br>795                800                805                810 | 2871 |
| AAT AAC GGA GGC TGC AGC AGC CTG TGC CTC GCC ACC CCC GGG AGC CGC<br>Asn Asn Gly Gly Cys Ser Ser Leu Cys Leu Ala Thr Pro Gly Ser Arg<br>815                820                825 | 2919 |
| CAG TGT GCC TGT GCC GAG GAC CAG GTG TTG GAC ACA GAT GGT GTC ACC<br>Gln Cys Ala Cys Ala Glu Asp Gln Val Leu Asp Thr Asp Gly Val Thr<br>830                835                840 | 2967 |

FIG.6A-5

```
TGC TTG GCG AAC CCA TCC TAC GTG CCC CCA CCC CAG TGC CAG CCG GGC    3015
Cys Leu Ala Asn Pro Ser Tyr Val Pro Pro Pro Gln Cys Gln Pro Gly
        845             850             855

CAG TTT GCC TGT GCC AAC AAC CGC TGC ATC CAG GAG CGC TGG AAG TGT    3063
Gln Phe Ala Cys Ala Asn Asn Arg Cys Ile Gln Glu Arg Trp Lys Cys
    860             865             870

GAC GGA GAC AAC GAC TGT CTG GAC AAC AGC GAT GAG GCC CCA GCA CTG    3111
Asp Gly Asp Asn Asp Cys Leu Asp Asn Ser Asp Glu Ala Pro Ala Leu
875             880             885             890

TGC CAT CAA CAC ACC TGT CCC TCG GAC CGA TTC AAG TGT GAG AAC AAC    3159
Cys His Gln His Thr Cys Pro Ser Asp Arg Phe Lys Cys Glu Asn Asn
                895             900             905

CGG TGT ATC CCC AAC CGC TGG CTC TGT GAT GGG GAT AAT GAT TGT GGC    3207
Arg Cys Ile Pro Asn Arg Trp Leu Cys Asp Gly Asp Asn Asp Cys Gly
            910             915             920

AAC AGC GAG GAC GAA TCC AAT GCC ACG TGC TCA GCC CGC ACC TGT CCA    3255
Asn Ser Glu Asp Glu Ser Asn Ala Thr Cys Ser Ala Arg Thr Cys Pro
        925             930             935

CCC AAC CAG TTC TCC TGT GCC AGT GGC CGA TGC ATT CCT ATC TCA TGG    3303
Pro Asn Gln Phe Ser Cys Ala Ser Gly Arg Cys Ile Pro Ile Ser Trp
    940             945             950

ACC TGT GAT CTG GAT GAT GAC TGT GGG GAC CGG TCC GAT GAG TCA GCC    3351
Thr Cys Asp Leu Asp Asp Asp Cys Gly Asp Arg Ser Asp Glu Ser Ala
955             960             965             970

TCA TGC GCC TAC CCC ACC TGC TTC CCC CTG ACT CAA TTT ACC TGC AAC    3399
Ser Cys Ala Tyr Pro Thr Cys Phe Pro Leu Thr Gln Phe Thr Cys Asn
                975             980             985

AAT GGC AGA TGT ATT AAC ATC AAC TGG CGG TGT GAC AAC GAC AAT GAC    3447
Asn Gly Arg Cys Ile Asn Ile Asn Trp Arg Cys Asp Asn Asp Asn Asp
            990             995             1000

TGT GGG GAC AAC AGC GAC GAA GCC GGC TGC AGT CAC TCC TGC TCC AGT    3495
Cys Gly Asp Asn Ser Asp Glu Ala Gly Cys Ser His Ser Cys Ser Ser
        1005            1010            1015
```

FIG.6A-6

```
ACC CAG TTC AAG TGC AAC AGT GGC AGA TGC ATC CCC GAG CAC TGG ACG         3543
Thr Gln Phe Lys Cys Asn Ser Gly Arg Cys Ile Pro Glu His Trp Thr
    1020            1025                1030

TGT GAT GGG GAC AAT GAT TGT GGG GAC TAC AGC GAC GAG ACA CAC GCC         3591
Cys Asp Gly Asp Asn Asp Cys Gly Asp Tyr Ser Asp Glu Thr His Ala
1035            1040                1045                1050

AAC TGT ACC AAC CAG GCT ACA AGA CCT CCT GGT GGC TGC CAC TCG GAT         3639
Asn Cys Thr Asn Gln Ala Thr Arg Pro Pro Gly Gly Cys His Ser Asp
            1055                1060                1065

GAG TTC CAG TGC CCG CTA GAT GGC CTG TGC ATC CCC CTG AGG TGG CGC         3687
Glu Phe Gln Cys Pro Leu Asp Gly Leu Cys Ile Pro Leu Arg Trp Arg
                1070                1075                1080

TGC GAC GGG GAC ACC GAC TGC ATG GAT TCC AGC GAT GAG AAG AGC TGT         3735
Cys Asp Gly Asp Thr Asp Cys Met Asp Ser Ser Asp Glu Lys Ser Cys
            1085                1090                1095

GAG GGC GTG ACC CAT GTT TGT GAC CCG AAT GTC AAG TTT GGC TGC AAG         3783
Glu Gly Val Thr His Val Cys Asp Pro Asn Val Lys Phe Gly Cys Lys
        1100                1105                1110

GAC TCC GCC CGG TGC ATC AGC AAG GCG TGG GTG TGT GAT GGC GAC AGC         3831
Asp Ser Ala Arg Cys Ile Ser Lys Ala Trp Val Cys Asp Gly Asp Ser
1115                1120                1125                1130

GAC TGT GAA GAT AAC TCC GAC GAG GAG AAC TGT GAG GCC CTG GCC TGC         3879
Asp Cys Glu Asp Asn Ser Asp Glu Glu Asn Cys Glu Ala Leu Ala Cys
            1135                1140                1145

AGG CCA CCC TCC CAT CCC TGC GCC AAC AAC ACC TCT GTC TGC CTG CCT         3927
Arg Pro Pro Ser His Pro Cys Ala Asn Asn Thr Ser Val Cys Leu Pro
                1150                1155                1160

CCT GAC AAG CTG TGC GAC GGC AAG GAT GAC TGT GGA GAC GGC TCG GAT         3975
Pro Asp Lys Leu Cys Asp Gly Lys Asp Asp Cys Gly Asp Gly Ser Asp
            1165                1170                1175

GAG GGC GAG CTC TGT GAC CAG TGT TCT CTG AAT AAT GGT GGC TGT AGT         4023
Glu Gly Glu Leu Cys Asp Gln Cys Ser Leu Asn Asn Gly Gly Cys Ser
        1180                1185                1190
```

FIG.6A-7

```
CAC AAC TGC TCA GTG GCC CCT GGT GAA GGC ATC GTG TGC TCT TGC CCT    4071
His Asn Cys Ser Val Ala Pro Gly Glu Gly Ile Val Cys Ser Cys Pro
1195                1200                1205                1210

CTG GGC ATG GAG CTG GGC TCT GAC AAC CAC ACC TGC CAG ATC CAG AGC    4119
Leu Gly Met Glu Leu Gly Ser Asp Asn His Thr Cys Gln Ile Gln Ser
            1215                1220                1225

TAC TGT GCC AAG CAC CTC AAA TGC AGC CAG AAG TGT GAC CAG AAC AAG    4167
Tyr Cys Ala Lys His Leu Lys Cys Ser Gln Lys Cys Asp Gln Asn Lys
        1230                1235                1240

TTC AGT GTG AAG TGC TCC TGC TAC GAG GGC TGG GTC TTG GAG CCT GAC    4215
Phe Ser Val Lys Cys Ser Cys Tyr Glu Gly Trp Val Leu Glu Pro Asp
    1245                1250                1255

GGG GAA ACG TGC CGC AGT CTG GAT CCC TTC AAA CTG TTC ATC ATC TTC    4263
Gly Glu Thr Cys Arg Ser Leu Asp Pro Phe Lys Leu Phe Ile Ile Phe
1260                1265                1270

TCC AAC CGC CAC GAG ATC AGG CGC ATT GAC CTT CAC AAG GGG GAC TAC    4311
Ser Asn Arg His Glu Ile Arg Arg Ile Asp Leu His Lys Gly Asp Tyr
1275                1280                1285                1290

AGC GTC CTA GTG CCT GGC CTG CGC AAC ACT ATT GCC CTG GAC TTC CAC    4359
Ser Val Leu Val Pro Gly Leu Arg Asn Thr Ile Ala Leu Asp Phe His
            1295                1300                1305

CTC AGC CAG AGT GCC CTC TAC TGG ACC GAC GCG GTA GAG GAC AAG ATC    4407
Leu Ser Gln Ser Ala Leu Tyr Trp Thr Asp Ala Val Glu Asp Lys Ile
        1310                1315                1320

TAC CGT GGG AAA CTC CTG GAC AAC GGA GCC CTG ACC AGC TTT GAG GTG    4455
Tyr Arg Gly Lys Leu Leu Asp Asn Gly Ala Leu Thr Ser Phe Glu Val
    1325                1330                1335

GTG ATT CAG TAT GGC TTG GCC ACA CCA GAG GGC CTG GCT GTA GAT TGG    4503
Val Ile Gln Tyr Gly Leu Ala Thr Pro Glu Gly Leu Ala Val Asp Trp
1340                1345                1350

ATT GCA GGC AAC ATC TAC TGG GTG GAG AGC AAC CTG GAC CAG ATC GAA    4551
Ile Ala Gly Asn Ile Tyr Trp Val Glu Ser Asn Leu Asp Gln Ile Glu
1355                1360                1365                1370
```

FIG.6A-8

```
GTG GCC AAG CTG GAC GGA ACC CTC CGA ACC ACT CTG CTG GCG GGT GAC    4599
Val Ala Lys Leu Asp Gly Thr Leu Arg Thr Thr Leu Leu Ala Gly Asp
        1375            1380            1385

ATT GAG CAC CCG AGG GCC ATC GCT CTG GAC CCT CGG GAT GGG ATT CTG    4647
Ile Glu His Pro Arg Ala Ile Ala Leu Asp Pro Arg Asp Gly Ile Leu
        1390            1395            1400

TTT TGG ACA GAC TGG GAT GCC AGC CTG CCA CGA ATC GAG GCT GCA TCC    4695
Phe Trp Thr Asp Trp Asp Ala Ser Leu Pro Arg Ile Glu Ala Ala Ser
        1405            1410            1415

ATG AGT GGA GCT GGC CGC CGA ACC ATC CAC CGG GAG ACA GGC TCT GGG    4743
Met Ser Gly Ala Gly Arg Arg Thr Ile His Arg Glu Thr Gly Ser Gly
        1420            1425            1430

GGC TGC GCC AAT GGG CTC ACC GTG GAT TAC CTG GAG AAG CGC ATC CTC    4791
Gly Cys Ala Asn Gly Leu Thr Val Asp Tyr Leu Glu Lys Arg Ile Leu
1435            1440            1445            1450

TGG ATT GAT GCT AGG TCA GAT GCC ATC TAT TCA GCC CGG TAT GAC GGC    4839
Trp Ile Asp Ala Arg Ser Asp Ala Ile Tyr Ser Ala Arg Tyr Asp Gly
        1455            1460            1465

TCC GGC CAC ATG GAG GTG CTT CGG GGA CAC GAG TTC CTG TCA CAC CCA    4887
Ser Gly His Met Glu Val Leu Arg Gly His Glu Phe Leu Ser His Pro
        1470            1475            1480

TTT GCC GTG ACA CTG TAC GGT GGG GAG GTG TAC TGG ACC GAC TGG CGA    4935
Phe Ala Val Thr Leu Tyr Gly Gly Glu Val Tyr Trp Thr Asp Trp Arg
        1485            1490            1495

ACA AAT ACA CTG GCT AAG GCC AAC AAG TGG ACT GGC CAC AAC GTC ACC    4983
Thr Asn Thr Leu Ala Lys Ala Asn Lys Trp Thr Gly His Asn Val Thr
        1500            1505            1510

GTG GTA CAG AGG ACC AAC ACC CAG CCC TTC GAC CTG CAG GTG TAT CAC    5031
Val Val Gln Arg Thr Asn Thr Gln Pro Phe Asp Leu Gln Val Tyr His
1515            1520            1525            1530

CCT TCC CGG CAG CCC ATG GCT CCA AAC CCA TGT GAG GCC AAT GGC GGC    5079
Pro Ser Arg Gln Pro Met Ala Pro Asn Pro Cys Glu Ala Asn Gly Gly
        1535            1540            1545
```

FIG.6A-9

```
CGG GGC CCC TGT TCC CAT CTG TGC CTC ATC AAC TAC AAC CGG ACC GTC          5127
Arg Gly Pro Cys Ser His Leu Cys Leu Ile Asn Tyr Asn Arg Thr Val
    1550            1555            1560

TCC TGG GCC TGT CCC CAC CTC ATG AAG CTG CAC AAG GAC AAC ACC ACC          5175
Ser Trp Ala Cys Pro His Leu Met Lys Leu His Lys Asp Asn Thr Thr
    1565            1570            1575

TGC TAT GAG TTT AAG AAG TTC CTG CTG TAC GCA CGT CAG ATG GAG ATC          5223
Cys Tyr Glu Phe Lys Lys Phe Leu Leu Tyr Ala Arg Gln Met Glu Ile
    1580            1585            1590

CGG GGC GTG GAC CTG GAT GCC CCG TAC TAC AAT TAT ATC ATC TCC TTC          5271
Arg Gly Val Asp Leu Asp Ala Pro Tyr Tyr Asn Tyr Ile Ile Ser Phe
1595            1600            1605            1610

ACG GTG CCT GAT ATC GAC AAT GTC ACG GTG CTG GAC TAT GAT GCC CGA          5319
Thr Val Pro Asp Ile Asp Asn Val Thr Val Leu Asp Tyr Asp Ala Arg
            1615            1620            1625

GAG CAG CGA GTT TAC TGG TCT GAT GTG CGG ACT CAA GCC ATC AAA AGG          5367
Glu Gln Arg Val Tyr Trp Ser Asp Val Arg Thr Gln Ala Ile Lys Arg
            1630            1635            1640

GCA TTT ATC AAC GGC ACT GGC GTG GAG ACC GTT GTC TCT GCA GAC TTG          5415
Ala Phe Ile Asn Gly Thr Gly Val Glu Thr Val Val Ser Ala Asp Leu
            1645            1650            1655

CCC AAC GCC CAC GGG CTG GCT GTG GAC TGG GTC TCC CGA AAT CTG TTT          5463
Pro Asn Ala His Gly Leu Ala Val Asp Trp Val Ser Arg Asn Leu Phe
            1660            1665            1670

TGG ACA AGT TAC GAC ACC AAC AAG AAG CAG ATT AAC GTG GCC CGG CTG          5511
Trp Thr Ser Tyr Asp Thr Asn Lys Lys Gln Ile Asn Val Ala Arg Leu
1675            1680            1685            1690

GAC GGC TCC TTC AAG AAT GCG GTG GTG CAG GGC CTG GAG CAG CCC CAC          5559
Asp Gly Ser Phe Lys Asn Ala Val Val Gln Gly Leu Glu Gln Pro His
                1695            1700            1705

GGC CTG GTC GTC CAC CCG CTT CGT GGC AAG CTC TAC TGG ACT GAT GGG          5607
Gly Leu Val Val His Pro Leu Arg Gly Lys Leu Tyr Trp Thr Asp Gly
                1710            1715            1720
```

FIG.6A-10

```
GAC AAC ATC AGC ATG GCC AAC ATG GAT GGG AGC AAC CAC ACT CTG CTC        5655
Asp Asn Ile Ser Met Ala Asn Met Asp Gly Ser Asn His Thr Leu Leu
    1725            1730            1735

TTC AGT GGC CAG AAG GGC CCT GTG GGG TTG GCC ATT GAC TTC CCT GAG        5703
Phe Ser Gly Gln Lys Gly Pro Val Gly Leu Ala Ile Asp Phe Pro Glu
    1740            1745            1750

AGC AAA CTC TAC TGG ATC AGC TCT GGG AAC CAC ACA ATC AAC CGT TGC        5751
Ser Lys Leu Tyr Trp Ile Ser Ser Gly Asn His Thr Ile Asn Arg Cys
1755            1760            1765            1770

AAT CTG GAT GGG AGC GAG CTG GAG GTC ATC GAC ACC ATG CGG AGC CAG        5799
Asn Leu Asp Gly Ser Glu Leu Glu Val Ile Asp Thr Met Arg Ser Gln
            1775            1780            1785

CTG GGC AAG GCC ACT GCC CTG GCC ATC ATG GGG GAC AAG CTG TGG TGG        5847
Leu Gly Lys Ala Thr Ala Leu Ala Ile Met Gly Asp Lys Leu Trp Trp
            1790            1795            1800

GCA GAT CAG GTG TCA GAG AAG ATG GGC ACG TGC AAC AAA GCC GAT GGC        5895
Ala Asp Gln Val Ser Glu Lys Met Gly Thr Cys Asn Lys Ala Asp Gly
    1805            1810            1815

TCT GGG TCC GTG GTG CTG CGG AAC AGT ACC ACG TTG GTT ATG CAC ATG        5943
Ser Gly Ser Val Val Leu Arg Asn Ser Thr Thr Leu Val Met His Met
    1820            1825            1830

AAG GTG TAT GAC GAG AGC ATC CAG CTA GAG CAT GAG GGC ACC AAC CCC        5991
Lys Val Tyr Asp Glu Ser Ile Gln Leu Glu His Glu Gly Thr Asn Pro
1835            1840            1845            1850

TGC AGT GTC AAC AAC GGA GAC TGT TCC CAG CTC TGC CTG CCA ACA TCA        6039
Cys Ser Val Asn Asn Gly Asp Cys Ser Gln Leu Cys Leu Pro Thr Ser
            1855            1860            1865

GAG ACG ACT CGC TCC TGT ATG TGT ACA GCC GGT TAC AGC CTC CGG AGC        6087
Glu Thr Thr Arg Ser Cys Met Cys Thr Ala Gly Tyr Ser Leu Arg Ser
            1870            1875            1880

GGA CAG CAG GCC TGT GAG GGT GTG GGC TCT TTT CTC CTG TAC TCT GTA        6135
Gly Gln Gln Ala Cys Glu Gly Val Gly Ser Phe Leu Leu Tyr Ser Val
            1885            1890            1895
```

FIG.6A-11

```
CAT GAG GGA ATT CGG GGG ATT CCA CTA GAT CCC AAT GAC AAG TCG GAT      6183
His Glu Gly Ile Arg Gly Ile Pro Leu Asp Pro Asn Asp Lys Ser Asp
    1900            1905                1910

GCC CTG GTC CCA GTG TCC GGA ACT TCA CTG GCT GTC GGA ATC GAC TTC      6231
Ala Leu Val Pro Val Ser Gly Thr Ser Leu Ala Val Gly Ile Asp Phe
1915            1920                1925                1930

CAT GCC GAA AAT GAC ACT ATT TAT TGG GTG GAT ATG GGC CTA AGC ACC      6279
His Ala Glu Asn Asp Thr Ile Tyr Trp Val Asp Met Gly Leu Ser Thr
        1935                1940                1945

ATC AGC AGG GCC AAG CGT GAC CAG ACA TGG CGA GAG GAT GTG GTG ACC      6327
Ile Ser Arg Ala Lys Arg Asp Gln Thr Trp Arg Glu Asp Val Val Thr
            1950                1955                1960

AAC GGT ATT GGC CGT GTG GAG GGC ATC GCC GTG GAC TGG ATC GCA GGC      6375
Asn Gly Ile Gly Arg Val Glu Gly Ile Ala Val Asp Trp Ile Ala Gly
                1965                1970                1975

AAC ATA TAC TGG ACG GAC CAG GGC TTC GAT GTC ATC GAG GTT GCC CGG      6423
Asn Ile Tyr Trp Thr Asp Gln Gly Phe Asp Val Ile Glu Val Ala Arg
        1980                1985                1990

CTC AAT GGC TCT TTT CGT TAT GTG GTC ATT TCC CAG GGT CTG GAC AAG      6471
Leu Asn Gly Ser Phe Arg Tyr Val Val Ile Ser Gln Gly Leu Asp Lys
1995                2000                2005                2010

CCT CGG GCC ATC ACT GTC CAC CCA GAG AAG GGG TAC TTG TTC TGG ACC      6519
Pro Arg Ala Ile Thr Val His Pro Glu Lys Gly Tyr Leu Phe Trp Thr
            2015                2020                2025

GAG TGG GGT CAT TAC CCA CGT ATT GAG CGG TCT CGC CTT GAT GGC ACA      6567
Glu Trp Gly His Tyr Pro Arg Ile Glu Arg Ser Arg Leu Asp Gly Thr
                2030                2035                2040

GAG AGA GTG GTG TTG GTT AAT GTC AGC ATC AGC TGG CCC AAT GGC ATC      6615
Glu Arg Val Val Leu Val Asn Val Ser Ile Ser Trp Pro Asn Gly Ile
        2045                2050                2055

TCA GTA GAC TAT CAG GGC GGC AAG CTC TAC TGG TGT GAT GCT CGG ATG      6663
Ser Val Asp Tyr Gln Gly Gly Lys Leu Tyr Trp Cys Asp Ala Arg Met
            2060                2065                2070
```

FIG.6A-12

```
GAC AAG ATC GAG CGC ATC GAC CTG GAA ACG GGC GAG AAC CGG GAG GTG     6711
Asp Lys Ile Glu Arg Ile Asp Leu Glu Thr Gly Glu Asn Arg Glu Val
2075            2080            2085            2090

GTC CTG TCC AGC AAT AAC ATG GAT ATG TTC TCC GTG TCC GTG TTT GAG     6759
Val Leu Ser Ser Asn Asn Met Asp Met Phe Ser Val Ser Val Phe Glu
        2095            2100            2105

GAC TTC ATC TAC TGG AGT GAC AGA ACT CAC GCC AAT GGC TCC ATC AAG     6807
Asp Phe Ile Tyr Trp Ser Asp Arg Thr His Ala Asn Gly Ser Ile Lys
            2110            2115            2120

CGC GGC TGC AAA GAC AAT GCT ACA GAC TCC GTG CCT CTG AGG ACA GGC     6855
Arg Gly Cys Lys Asp Asn Ala Thr Asp Ser Val Pro Leu Arg Thr Gly
            2125            2130            2135

ATT GGT GTT CAG CTT AAA GAC ATC AAG GTC TTC AAC AGG GAC AGG CAG     6903
Ile Gly Val Gln Leu Lys Asp Ile Lys Val Phe Asn Arg Asp Arg Gln
        2140            2145            2150

AAG GGT ACC AAT GTG TGC GCG GTA GCC AAC GGC GGG TGC CAG CAG CTC     6951
Lys Gly Thr Asn Val Cys Ala Val Ala Asn Gly Gly Cys Gln Gln Leu
2155            2160            2165            2170

TGC TTG TAT CGG GGT GGC GGA CAG CGA GCC TGT GCC TGT GCC CAC GGG     6999
Cys Leu Tyr Arg Gly Gly Gly Gln Arg Ala Cys Ala Cys Ala His Gly
            2175            2180            2185

ATG CTG GCA GAA GAC GGG GCC TCA TGC CGA GAG TAC GCT GGC TAC CTG     7047
Met Leu Ala Glu Asp Gly Ala Ser Cys Arg Glu Tyr Ala Gly Tyr Leu
            2190            2195            2200

CTC TAC TCA GAG CGG ACC ATC CTC AAG AGC ATC CAC CTG TCG GAT GAG     7095
Leu Tyr Ser Glu Arg Thr Ile Leu Lys Ser Ile His Leu Ser Asp Glu
        2205            2210            2215

CGT AAC CTC AAC GCA CCG GTG CAG CCC TTT GAA GAC CCC GAG CAC ATG     7143
Arg Asn Leu Asn Ala Pro Val Gln Pro Phe Glu Asp Pro Glu His Met
        2220            2225            2230

AAA AAT GTC ATC GCC CTG GCC TTT GAC TAC CGA GCA GGC ACC TCC CCG     7191
Lys Asn Val Ile Ala Leu Ala Phe Asp Tyr Arg Ala Gly Thr Ser Pro
2235            2240            2245            2250
```

FIG.6A-13

```
GGG ACC CCT AAC CGC ATC TTC TTC AGT GAC ATC CAC TTT GGG AAC ATC        7239
Gly Thr Pro Asn Arg Ile Phe Phe Ser Asp Ile His Phe Gly Asn Ile
            2255                2260                2265

CAG CAG ATC AAT GAC GAT GGC TCG GGC AGG ACC ACC ATC GTG GAA AAT        7287
Gln Gln Ile Asn Asp Asp Gly Ser Gly Arg Thr Thr Ile Val Glu Asn
            2270                2275                2280

GTG GGC TCT GTG GAA GGC CTG GCC TAT CAC CGT GGC TGG GAC ACA CTG        7335
Val Gly Ser Val Glu Gly Leu Ala Tyr His Arg Gly Trp Asp Thr Leu
            2285                2290                2295

TAC TGG ACA AGC TAC ACC ACA TCC ACC ATC ACC CGC CAC ACC GTG GAC        7383
Tyr Trp Thr Ser Tyr Thr Thr Ser Thr Ile Thr Arg His Thr Val Asp
            2300                2305                2310

CAG ACT CGC CCA GGG GCC TTC GAG AGG GAG ACA GTC ATC ACC ATG TCC        7431
Gln Thr Arg Pro Gly Ala Phe Glu Arg Glu Thr Val Ile Thr Met Ser
2315            2320                2325                2330

GGA GAC GAC CAC CCG AGA GCC TTT GTG CTG GAT GAG TGC CAG AAC CTG        7479
Gly Asp Asp His Pro Arg Ala Phe Val Leu Asp Glu Cys Gln Asn Leu
            2335                2340                2345

ATG TTC TGG ACC AAT TGG AAC GAG CTC CAT CCA AGC ATC ATG CGG GCA        7527
Met Phe Trp Thr Asn Trp Asn Glu Leu His Pro Ser Ile Met Arg Ala
            2350                2355                2360

GCC CTA TCC GGA GCC AAC GTC CTG ACC CTC ATT GAG AAG GAC ATC CGC        7575
Ala Leu Ser Gly Ala Asn Val Leu Thr Leu Ile Glu Lys Asp Ile Arg
            2365                2370                2375

ACG CCC AAT GGG TTG GCC ATC GAC CAC CGG GCG GAG AAG CTG TAC TTC        7623
Thr Pro Asn Gly Leu Ala Ile Asp His Arg Ala Glu Lys Leu Tyr Phe
            2380                2385                2390

TCG GAT GCC ACC TTG GAC AAG ATC GAG CGC TGC GAG TAC GAC GGC TCC        7671
Ser Asp Ala Thr Leu Asp Lys Ile Glu Arg Cys Glu Tyr Asp Gly Ser
2395            2400                2405                2410

CAC CGC TAT GTG ATC CTA AAG TCG GAG CCC GTC CAC CCC TTT GGG TTG        7719
His Arg Tyr Val Ile Leu Lys Ser Glu Pro Val His Pro Phe Gly Leu
            2415                2420                2425
```

FIG.6A-14

```
GCG GTG TAC GGA GAG CAC ATT TTC TGG ACT GAC TGG GTG CGG CGG GCT     7767
Ala Val Tyr Gly Glu His Ile Phe Trp Thr Asp Trp Val Arg Arg Ala
            2430                2435                2440

GTG CAG CGA GCC AAC AAG TAT GTG GGC AGC GAC ATG AAG CTG CTT CGG     7815
Val Gln Arg Ala Asn Lys Tyr Val Gly Ser Asp Met Lys Leu Leu Arg
            2445                2450                2455

GTG GAC ATT CCC CAG CAA CCC ATG GGC ATC ATC GCC GTG GCC AAT GAC     7863
Val Asp Ile Pro Gln Gln Pro Met Gly Ile Ile Ala Val Ala Asn Asp
            2460                2465                2470

ACC AAC AGC TGT GAA CTC TCC CCC TGC CGT ATC AAC AAT GGA GGC TGC     7911
Thr Asn Ser Cys Glu Leu Ser Pro Cys Arg Ile Asn Asn Gly Gly Cys
2475                2480                2485                2490

CAG GAT CTG TGT CTG CTC ACC CAC CAA GGC CAC GTC AAC TGT TCC TGT     7959
Gln Asp Leu Cys Leu Leu Thr His Gln Gly His Val Asn Cys Ser Cys
            2495                2500                2505

CGA GGG GGC CGG ATC CTC CAG GAG GAC TTC ACC TGC CGG GCT GTG AAC     8007
Arg Gly Gly Arg Ile Leu Gln Glu Asp Phe Thr Cys Arg Ala Val Asn
            2510                2515                2520

TCC TCT TGT CGG GCA CAA GAT GAG TTT GAG TGT GCC AAT GGG GAA TGT     8055
Ser Ser Cys Arg Ala Gln Asp Glu Phe Glu Cys Ala Asn Gly Glu Cys
            2525                2530                2535

ATC AGC TTC AGC CTC ACC TGT GAT GGC GTC TCC CAC TGC AAG GAC AAG     8103
Ile Ser Phe Ser Leu Thr Cys Asp Gly Val Ser His Cys Lys Asp Lys
            2540                2545                2550

TCC GAT GAG AAG CCC TCC TAC TGC AAC TCA CGC CGC TGC AAG AAG ACT     8151
Ser Asp Glu Lys Pro Ser Tyr Cys Asn Ser Arg Arg Cys Lys Lys Thr
2555                2560                2565                2570

TTC CGC CAG TGT AAC AAT GGC CGC TGT GTA TCC AAC ATG CTG TGG TGC     8199
Phe Arg Gln Cys Asn Asn Gly Arg Cys Val Ser Asn Met Leu Trp Cys
            2575                2580                2585

AAT GGG GTG GAT TAC TGT GGG GAT GGC TCT GAT GAG ATA CCT TGC AAC     8247
Asn Gly Val Asp Tyr Cys Gly Asp Gly Ser Asp Glu Ile Pro Cys Asn
            2590                2595                2600
```

FIG.6A-15

```
AAG ACT GCC TGT GGT GTG GGT GAG TTC CGC TGC CGG GAT GGG TCC TGC    8295
Lys Thr Ala Cys Gly Val Gly Glu Phe Arg Cys Arg Asp Gly Ser Cys
        2605            2610            2615

ATC GGG AAC TCC AGT CGC TGC AAC CAG TTT GTG GAT TGT GAG GAT GCC    8343
Ile Gly Asn Ser Ser Arg Cys Asn Gln Phe Val Asp Cys Glu Asp Ala
        2620            2625            2630

TCG GAT GAG ATG AAT TGC AGT GCC ACA GAC TGC AGC AGC TAT TTC CGC    8391
Ser Asp Glu Met Asn Cys Ser Ala Thr Asp Cys Ser Ser Tyr Phe Arg
2635            2640            2645            2650

CTG GGC GTG AAA GGT GTC CTC TTC CAG CCG TGC GAG CGG ACA TCC CTG    8439
Leu Gly Val Lys Gly Val Leu Phe Gln Pro Cys Glu Arg Thr Ser Leu
        2655            2660            2665

TGC TAC GCA CCT AGC TGG GTG TGT GAT GGC GCC AAC GAC TGT GGA GAC    8487
Cys Tyr Ala Pro Ser Trp Val Cys Asp Gly Ala Asn Asp Cys Gly Asp
        2670            2675            2680

TAC AGC GAT GAA CGT GAC TGT CCA GGT GTG AAG CGC CCT AGG TGC CCG    8535
Tyr Ser Asp Glu Arg Asp Cys Pro Gly Val Lys Arg Pro Arg Cys Pro
        2685            2690            2695

CTC AAT TAC TTT GCC TGC CCC AGC GGG CGC TGT ATC CCC ATG AGC TGG    8583
Leu Asn Tyr Phe Ala Cys Pro Ser Gly Arg Cys Ile Pro Met Ser Trp
        2700            2705            2710

ACG TGT GAC AAG GAG GAT GAC TGT GAG AAC GGC GAG GAT GAG ACC CAC    8631
Thr Cys Asp Lys Glu Asp Asp Cys Glu Asn Gly Glu Asp Glu Thr His
2715            2720            2725            2730

TGC AAC AAG TTC TGC TCA GAG GCA CAG TTC GAG TGC CAG AAC CAC CGG    8679
Cys Asn Lys Phe Cys Ser Glu Ala Gln Phe Glu Cys Gln Asn His Arg
        2735            2740            2745

TGT ATC TCC AAG CAG TGG CTG TGT GAC GGT AGC GAT GAT TGC GGG GAT    8727
Cys Ile Ser Lys Gln Trp Leu Cys Asp Gly Ser Asp Asp Cys Gly Asp
        2750            2755            2760

GGC TCC GAT GAG GCA GCT CAC TGT GAA GGC AAG ACA TGT GGC CCC TCC    8775
Gly Ser Asp Glu Ala Ala His Cys Glu Gly Lys Thr Cys Gly Pro Ser
        2765            2770            2775
```

FIG.6A-16

```
TCC TTC TCC TGT CCC GGC ACC CAC GTG TGT GTC CCT GAG CGC TGG CTC    8823
Ser Phe Ser Cys Pro Gly Thr His Val Cys Val Pro Glu Arg Trp Leu
    2780                2785                2790

TGT GAT GGC GAC AAG GAC TGT ACC GAT GGC GCG GAT GAG AGT GTC ACT    8871
Cys Asp Gly Asp Lys Asp Cys Thr Asp Gly Ala Asp Glu Ser Val Thr
2795                2800                2805                2810

GCT GGC TGC CTG TAC AAC AGC ACC TGT GAT GAC CGT GAG TTC ATG TGC    8919
Ala Gly Cys Leu Tyr Asn Ser Thr Cys Asp Asp Arg Glu Phe Met Cys
            2815                2820                2825

CAG AAC CGC TTG TGT ATT CCC AAG CAT TTC GTG TGC GAC CAT GAC CGT    8967
Gln Asn Arg Leu Cys Ile Pro Lys His Phe Val Cys Asp His Asp Arg
        2830                2835                2840

GAC TGT GCT GAT GGC TCT GAT GAA TCC CCT GAG TGT GAG TAC CCA ACC    9015
Asp Cys Ala Asp Gly Ser Asp Glu Ser Pro Glu Cys Glu Tyr Pro Thr
    2845                2850                2855

TGC GGG CCC AAT GAA TTC CGC TGT GCC AAT GGG CGT TGT CTG AGC TCC    9063
Cys Gly Pro Asn Glu Phe Arg Cys Ala Asn Gly Arg Cys Leu Ser Ser
    2860                2865                2870

CGT CAG TGG GAA TGT GAT GGG GAG AAT GAC TGT CAC GAC CAC AGC GAT    9111
Arg Gln Trp Glu Cys Asp Gly Glu Asn Asp Cys His Asp His Ser Asp
2875                2880                2885                2890

GAG GCT CCC AAG AAC CCA CAC TGC ACC AGC CCA GAG CAC AAA TGC AAT    9159
Glu Ala Pro Lys Asn Pro His Cys Thr Ser Pro Glu His Lys Cys Asn
            2895                2900                2905

GCC TCA TCA CAG TTC CTG TGC AGC AGC GGG CGC TGC GTG GCT GAG GCG    9207
Ala Ser Ser Gln Phe Leu Cys Ser Ser Gly Arg Cys Val Ala Glu Ala
        2910                2915                2920

TTG CTC TGC AAC GGC CAG GAC GAC TGT GGG GAC GGT TCA GAC GAA CGC    9255
Leu Leu Cys Asn Gly Gln Asp Asp Cys Gly Asp Gly Ser Asp Glu Arg
    2925                2930                2935

GGG TGC CAT GTC AAC GAG TGT CTC AGC CGC AAG CTC AGT GGC TGC AGT    9303
Gly Cys His Val Asn Glu Cys Leu Ser Arg Lys Leu Ser Gly Cys Ser
    2940                2945                2950
```

FIG.6A-17

```
CAG GAC TGC GAG GAC CTC AAG ATA GGC TTT AAG TGC CGC TGT CGC CCG       9351
Gln Asp Cys Glu Asp Leu Lys Ile Gly Phe Lys Cys Arg Cys Arg Pro
2955            2960            2965            2970

GGC TTC CGG CTA AAG GAC GAT GGC AGG ACC TGT GCC GAC CTG GAT GAG       9399
Gly Phe Arg Leu Lys Asp Asp Gly Arg Thr Cys Ala Asp Leu Asp Glu
            2975            2980            2985

TGC AGC ACC ACC TTC CCC TGC AGC CAG CTC TGC ATC AAC ACC CAC GGA       9447
Cys Ser Thr Thr Phe Pro Cys Ser Gln Leu Cys Ile Asn Thr His Gly
        2990            2995            3000

AGT TAC AAG TGT CTG TGT GTG GAG GGC TAT GCA CCC CGT GGC GGT GAC       9495
Ser Tyr Lys Cys Leu Cys Val Glu Gly Tyr Ala Pro Arg Gly Gly Asp
        3005            3010            3015

CCC CAC AGC TGC AAA GCT GTG ACC GAT GAG GAG CCA TTT CTC ATC TTT       9543
Pro His Ser Cys Lys Ala Val Thr Asp Glu Glu Pro Phe Leu Ile Phe
        3020            3025            3030

GCC AAC CGG TAC TAC CTG CGG AAG CTC AAC CTG GAC GGC TCC AAC TAC       9591
Ala Asn Arg Tyr Tyr Leu Arg Lys Leu Asn Leu Asp Gly Ser Asn Tyr
3035            3040            3045            3050

ACA CTG CTT AAG CAG GGC CTG AAC AAT GCG GTC GCC TTG GCA TTT GAC       9639
Thr Leu Leu Lys Gln Gly Leu Asn Asn Ala Val Ala Leu Ala Phe Asp
            3055            3060            3065

TAC CGA GAG CAG ATG ATC TAC TGG ACG GGC GTG ACC ACC CAG GGC AGC       9687
Tyr Arg Glu Gln Met Ile Tyr Trp Thr Gly Val Thr Thr Gln Gly Ser
            3070            3075            3080

ATG ATT CGC AGG ATG CAC CTC AAC GGC AGC AAC GTG CAG GTT CTG CAC       9735
Met Ile Arg Arg Met His Leu Asn Gly Ser Asn Val Gln Val Leu His
            3085            3090            3095

CGG ACG GGC CTT AGT AAC CCA GAT GGG CTC GCT GTG GAC TGG GTG GGT       9783
Arg Thr Gly Leu Ser Asn Pro Asp Gly Leu Ala Val Asp Trp Val Gly
            3100            3105            3110

GGC AAC CTG TAC TGG TGT GAC AAG GGC AGA GAT ACC ATT GAG GTG TCC       9831
Gly Asn Leu Tyr Trp Cys Asp Lys Gly Arg Asp Thr Ile Glu Val Ser
3115            3120            3125            3130
```

FIG.6A-18

```
AAG CTT AAC GGG GCC TAT CGG ACA GTG CTG GTC AGC TCT GGC CTC CGG      9879
Lys Leu Asn Gly Ala Tyr Arg Thr Val Leu Val Ser Ser Gly Leu Arg
            3135                3140                3145

GAG CCC AGA GCT CTG GTA GTG GAT GTA CAG AAT GGG TAC CTG TAC TGG      9927
Glu Pro Arg Ala Leu Val Val Asp Val Gln Asn Gly Tyr Leu Tyr Trp
            3150                3155                3160

ACA GAC TGG GGT GAC CAC TCA CTG ATC GGC CGG ATT GGC ATG GAT GGA      9975
Thr Asp Trp Gly Asp His Ser Leu Ile Gly Arg Ile Gly Met Asp Gly
            3165                3170                3175

TCT GGC CGC AGC ATC ATC GTG GAC ACT AAG ATC ACA TGG CCC AAT GGC     10023
Ser Gly Arg Ser Ile Ile Val Asp Thr Lys Ile Thr Trp Pro Asn Gly
            3180                3185                3190

CTG ACC GTG GAC TAC GTC ACG GAA CGC ATC TAC TGG GCT GAC GCC CGT     10071
Leu Thr Val Asp Tyr Val Thr Glu Arg Ile Tyr Trp Ala Asp Ala Arg
3195                3200                3205                3210

GAG GAC TAC ATC GAG TTC GCC AGC CTG GAT GGC TCC AAC CGT CAC GTT     10119
Glu Asp Tyr Ile Glu Phe Ala Ser Leu Asp Gly Ser Asn Arg His Val
            3215                3220                3225

GTG CTG AGC CAA GAC ATC CCA CAC ATC TTT GCG CTG ACC CTA TTT GAA     10167
Val Leu Ser Gln Asp Ile Pro His Ile Phe Ala Leu Thr Leu Phe Glu
            3230                3235                3240

GAC TAC GTC TAC TGG ACA GAC TGG GAA ACG AAG TCC ATC AAC CGG GCC     10215
Asp Tyr Val Tyr Trp Thr Asp Trp Glu Thr Lys Ser Ile Asn Arg Ala
            3245                3250                3255

CAC AAG ACC ACG GGT GCC AAC AAA ACA CTC CTC ATC AGC ACC CTG CAC     10263
His Lys Thr Thr Gly Ala Asn Lys Thr Leu Leu Ile Ser Thr Leu His
            3260                3265                3270

CGG CCC ATG GAC TTA CAT GTA TTC CAC GCC CTG CGC CAG CCA GAT GTG     10311
Arg Pro Met Asp Leu His Val Phe His Ala Leu Arg Gln Pro Asp Val
3275                3280                3285                3290

CCC AAT CAC CCC TGC AAA GTC AAC AAT GGT GGC TGC AGC AAC CTG TGC     10359
Pro Asn His Pro Cys Lys Val Asn Asn Gly Gly Cys Ser Asn Leu Cys
            3295                3300                3305
```

FIG.6A-19

```
CTG CTG TCC CCT GGG GGT GGT CAC AAG TGC GCC TGC CCC ACC AAC TTC    10407
Leu Leu Ser Pro Gly Gly Gly His Lys Cys Ala Cys Pro Thr Asn Phe
        3310            3315            3320

TAT CTG GGT GGC GAT GGC CGT ACC TGT GTG TCC AAC TGC ACA GCA AGC    10455
Tyr Leu Gly Gly Asp Gly Arg Thr Cys Val Ser Asn Cys Thr Ala Ser
        3325            3330            3335

CAG TTT GTG TGC AAA AAT GAC AAG TGC ATC CCC TTC TGG TGG AAG TGT    10503
Gln Phe Val Cys Lys Asn Asp Lys Cys Ile Pro Phe Trp Trp Lys Cys
        3340            3345            3350

GAC ACG GAG GAC GAC TGT GGG GAT CAC TCA GAC GAG CCT CCA GAC TGT    10551
Asp Thr Glu Asp Asp Cys Gly Asp His Ser Asp Glu Pro Pro Asp Cys
3355            3360            3365            3370

CCC GAG TTC AAG TGC CGC CCA GGC CAG TTC CAG TGC TCC ACC GGC ATC    10599
Pro Glu Phe Lys Cys Arg Pro Gly Gln Phe Gln Cys Ser Thr Gly Ile
        3375            3380            3385

TGC ACC AAC CCT GCC TTC ATC TGT GAT GGG GAC AAT GAC TGC CAA GAC    10647
Cys Thr Asn Pro Ala Phe Ile Cys Asp Gly Asp Asn Asp Cys Gln Asp
        3390            3395            3400

AAT AGT GAC GAG GCC AAT TGC GAC ATT CAC GTC TGC TTG CCC AGC CAA    10695
Asn Ser Asp Glu Ala Asn Cys Asp Ile His Val Cys Leu Pro Ser Gln
        3405            3410            3415

TTC AAG TGC ACC AAC ACC AAC CGC TGC ATT CCT GGC ATC TTC CGT TGC    10743
Phe Lys Cys Thr Asn Thr Asn Arg Cys Ile Pro Gly Ile Phe Arg Cys
        3420            3425            3430

AAT GGG CAG GAC AAC TGC GGG GAC GGC GAG GAT GAG CGG GAT TGC CCT    10791
Asn Gly Gln Asp Asn Cys Gly Asp Gly Glu Asp Glu Arg Asp Cys Pro
3435            3440            3445            3450

GAG GTG ACC TGC GCC CCC AAC CAG TTC CAG TGC TCC ATC ACC AAG CGC    10839
Glu Val Thr Cys Ala Pro Asn Gln Phe Gln Cys Ser Ile Thr Lys Arg
        3455            3460            3465

TGC ATC CCT CGC GTC TGG GTC TGT GAC AGG GAT AAT CAC TGT GTG GAC    10887
Cys Ile Pro Arg Val Trp Val Cys Asp Arg Asp Asn His Cys Val Asp
        3470            3475            3480
```

FIG.6A-20

```
GGC AGT GAT GAG CCT GCC AAC TGT ACC CAA ATG ACC TGT GGA GTG GAT    10935
Gly Ser Asp Glu Pro Ala Asn Cys Thr Gln Met Thr Cys Gly Val Asp
    3485                3490                3495

GAG TTC CGC TGC AAG GAT TCT GGC CGC TGC ATC CCC GCG CGC TGG AAG    10983
Glu Phe Arg Cys Lys Asp Ser Gly Arg Cys Ile Pro Ala Arg Trp Lys
    3500                3505                3510

TGT GAC GGA GAA GAT GAC TGT GGG GAT GGT TCA GAT GAG CCC AAG GAA    11031
Cys Asp Gly Glu Asp Asp Cys Gly Asp Gly Ser Asp Glu Pro Lys Glu
3515                3520                3525                3530

GAG TGT GAT GAG CGC ACC TGT GAG CCA TAC CAG TTC CGC TGC AAA AAC    11079
Glu Cys Asp Glu Arg Thr Cys Glu Pro Tyr Gln Phe Arg Cys Lys Asn
                3535                3540                3545

AAC CGC TGT GTC CCA GGC CGT TGG CAA TGT GAC TAC GAC AAC GAC TGC    11127
Asn Arg Cys Val Pro Gly Arg Trp Gln Cys Asp Tyr Asp Asn Asp Cys
                3550                3555                3560

GGA GAT AAC TCG GAC GAG GAG AGC TGC ACA CCT CGG CCC TGC TCT GAG    11175
Gly Asp Asn Ser Asp Glu Glu Ser Cys Thr Pro Arg Pro Cys Ser Glu
    3565                3570                3575

AGT GAG TTT TTC TGT GCC AAT GGC CGC TGC ATC GCT GGG CGC TGG AAG    11223
Ser Glu Phe Phe Cys Ala Asn Gly Arg Cys Ile Ala Gly Arg Trp Lys
    3580                3585                3590

TGT GAT GGG GAC CAT GAC TGT GCC GAC GGC TCA GAC GAG AAA GAC TGC    11271
Cys Asp Gly Asp His Asp Cys Ala Asp Gly Ser Asp Glu Lys Asp Cys
3595                3600                3605                3610

ACC CCC CGC TGT GAT ATG GAC CAG TTC CAG TGC AAG AGT GGC CAC TGC    11319
Thr Pro Arg Cys Asp Met Asp Gln Phe Gln Cys Lys Ser Gly His Cys
                3615                3620                3625

ATC CCC CTG CGC TGG CCG TGT GAC GCG GAT GCT GAC TGT ATG GAC GGC    11367
Ile Pro Leu Arg Trp Pro Cys Asp Ala Asp Ala Asp Cys Met Asp Gly
                3630                3635                3640

AGT GAC GAG GAA GCC TGT GGC ACT GGG GTG AGG ACC TGC CCA TTG GAT    11415
Ser Asp Glu Glu Ala Cys Gly Thr Gly Val Arg Thr Cys Pro Leu Asp
    3645                3650                3655
```

FIG.6A-21

```
GAG TTT CAA TGT AAC AAC ACC TTG TGC AAG CCG CTG GCC TGG AAG TGT      11463
Glu Phe Gln Cys Asn Asn Thr Leu Cys Lys Pro Leu Ala Trp Lys Cys
    3660            3665            3670

GAT GGA GAG GAC GAC TGT GGG GAC AAC TCA GAT GAG AAC CCC GAG GAA      11511
Asp Gly Glu Asp Asp Cys Gly Asp Asn Ser Asp Glu Asn Pro Glu Glu
3675            3680            3685            3690

TGC GCC CGG TTC ATC TGC CCT CCC AAC CGG CCT TTC CGC TGC AAG AAT      11559
Cys Ala Arg Phe Ile Cys Pro Pro Asn Arg Pro Phe Arg Cys Lys Asn
        3695            3700            3705

GAC CGA GTC TGC CTG TGG ATT GGG CGC CAG TGT GAT GGC GTG GAC AAC      11607
Asp Arg Val Cys Leu Trp Ile Gly Arg Gln Cys Asp Gly Val Asp Asn
            3710            3715            3720

TGT GGA GAT GGG ACT GAC GAG GAG GAC TGT GAG CCC CCC ACG GCC CAG      11655
Cys Gly Asp Gly Thr Asp Glu Glu Asp Cys Glu Pro Pro Thr Ala Gln
    3725            3730            3735

AAC CCC CAC TGC AAA GAC AAG AAG GAG TTC CTG TGC CGA AAC CAG CGC      11703
Asn Pro His Cys Lys Asp Lys Lys Glu Phe Leu Cys Arg Asn Gln Arg
        3740            3745            3750

TGT CTA TCA TCC TCC CTG CGC TGT AAC ATG TTC GAT GAC TGC GGC GAT      11751
Cys Leu Ser Ser Ser Leu Arg Cys Asn Met Phe Asp Asp Cys Gly Asp
3755            3760            3765            3770

GGC TCC GAT GAA GAA GAT TGC AGC ATC GAC CCC AAG CTG ACC AGC TGT      11799
Gly Ser Asp Glu Glu Asp Cys Ser Ile Asp Pro Lys Leu Thr Ser Cys
        3775            3780            3785

GCC ACC AAT GCC AGC ATG TGT GGG GAC GAA GCT CGT TGT GTG CGC ACT      11847
Ala Thr Asn Ala Ser Met Cys Gly Asp Glu Ala Arg Cys Val Arg Thr
            3790            3795            3800

GAG AAA GCT GCC TAC TGT GCC TGC CGC TCG GGC TTC CAT ACT GTG CCG      11895
Glu Lys Ala Ala Tyr Cys Ala Cys Arg Ser Gly Phe His Thr Val Pro
    3805            3810            3815

GGC CAG CCC GGA TGC CAG GAC ATC AAC GAG TGC CTG CGC TTT GGT ACC      11943
Gly Gln Pro Gly Cys Gln Asp Ile Asn Glu Cys Leu Arg Phe Gly Thr
        3820            3825            3830
```

FIG.6A-22

```
TGC TCT CAG CTC TGG AAC AAA CCC AAG GGA GGC CAC CTC TGC AGC TGT    11991
Cys Ser Gln Leu Trp Asn Lys Pro Lys Gly Gly His Leu Cys Ser Cys
3835            3840            3845            3850

GCC CGC AAC TTC ATG AAG ACA CAC AAC ACC TGC AAA GCT GAA GGC TCC    12039
Ala Arg Asn Phe Met Lys Thr His Asn Thr Cys Lys Ala Glu Gly Ser
            3855            3860            3865

GAG TAC CAG GTG CTA TAC ATC GCG GAT GAC AAC GAG ATC CGC AGC TTG    12087
Glu Tyr Gln Val Leu Tyr Ile Ala Asp Asp Asn Glu Ile Arg Ser Leu
        3870            3875            3880

TTC CCG GGC CAC CCC CAC TCA GCC TAC GAG CAG ACA TTC CAG GGC GAT    12135
Phe Pro Gly His Pro His Ser Ala Tyr Glu Gln Thr Phe Gln Gly Asp
        3885            3890            3895

GAG AGT GTC CGC ATA GAT GCC ATG GAT GTC CAT GTC AAG GCC GGC CGT    12183
Glu Ser Val Arg Ile Asp Ala Met Asp Val His Val Lys Ala Gly Arg
    3900            3905            3910

GTC TAC TGG ACT AAC TGG CAC ACG GGC ACA ATC TCC TAC AGG AGC CTG    12231
Val Tyr Trp Thr Asn Trp His Thr Gly Thr Ile Ser Tyr Arg Ser Leu
3915            3920            3925            3930

CCC CCT GCC GCC CCT CCT ACC ACT TCC AAC CGC CAC CGG AGG CAG ATC    12279
Pro Pro Ala Ala Pro Pro Thr Thr Ser Asn Arg His Arg Arg Gln Ile
            3935            3940            3945

GAC CGG GGT GTC ACC CAC CTC AAT ATT TCA GGG CTG AAG ATG CCG AGG    12327
Asp Arg Gly Val Thr His Leu Asn Ile Ser Gly Leu Lys Met Pro Arg
        3950            3955            3960

GGT ATC GCT ATC GAC TGG GTG GCC GGG AAT GTG TAC TGG ACC GAT TCC    12375
Gly Ile Ala Ile Asp Trp Val Ala Gly Asn Val Tyr Trp Thr Asp Ser
        3965            3970            3975

GGC CGA GAC GTG ATT GAG GTG GCG CAA ATG AAG GGC GAG AAC CGC AAG    12423
Gly Arg Asp Val Ile Glu Val Ala Gln Met Lys Gly Glu Asn Arg Lys
        3980            3985            3990

ACG CTC ATC TCG GGC ATG ATT GAT GAG CCC CAT GCC ATC GTG GTG GAC    12471
Thr Leu Ile Ser Gly Met Ile Asp Glu Pro His Ala Ile Val Val Asp
3995            4000            4005            4010
```

FIG.6A-23

```
CCT CTG AGG GGC ACC ATG TAC TGG TCA GAC TGG GGG AAC CAC CCC AAG         12519
Pro Leu Arg Gly Thr Met Tyr Trp Ser Asp Trp Gly Asn His Pro Lys
        4015            4020            4025

ATT GAA ACA GCA GCG ATG GAT GGC ACC CTT CGG GAG ACT CTC GTG CAA         12567
Ile Glu Thr Ala Ala Met Asp Gly Thr Leu Arg Glu Thr Leu Val Gln
        4030            4035            4040

GAC AAC ATT CAG TGG CCT ACA GGG CTG GCT GTG GAC TAT CAC AAT GAA         12615
Asp Asn Ile Gln Trp Pro Thr Gly Leu Ala Val Asp Tyr His Asn Glu
        4045            4050            4055

CGG CTC TAC TGG GCA GAT GCC AAG CTT TCG GTC ATC GGC AGC ATC CGG         12663
Arg Leu Tyr Trp Ala Asp Ala Lys Leu Ser Val Ile Gly Ser Ile Arg
        4060            4065            4070

CTC AAC GGC ACT GAC CCC ATT GTG GCT GCT GAC AGC AAA CGA GGC CTA         12711
Leu Asn Gly Thr Asp Pro Ile Val Ala Ala Asp Ser Lys Arg Gly Leu
4075            4080            4085            4090

AGT CAC CCC TTC AGC ATC GAT GTG TTT GAA GAC TAC ATC TAC GGA GTC         12759
Ser His Pro Phe Ser Ile Asp Val Phe Glu Asp Tyr Ile Tyr Gly Val
        4095            4100            4105

ACT TAC ATC AAT AAT CGT GTC TTC AAG ATC CAC AAG TTT GGA CAC AGC         12807
Thr Tyr Ile Asn Asn Arg Val Phe Lys Ile His Lys Phe Gly His Ser
        4110            4115            4120

CCC TTG TAC AAC CTA ACT GGG GGC CTG AGC CAT GCC TCT GAT GTA GTC         12855
Pro Leu Tyr Asn Leu Thr Gly Gly Leu Ser His Ala Ser Asp Val Val
        4125            4130            4135

CTT TAC CAT CAA CAC AAG CAG CCT GAA GTG ACC AAC CCC TGT GAC CGC         12903
Leu Tyr His Gln His Lys Gln Pro Glu Val Thr Asn Pro Cys Asp Arg
        4140            4145            4150

AAG AAA TGC GAA TGG CTG TGT CTG CTG AGC CCC AGC GGG CCT GTC TGC         12951
Lys Lys Cys Glu Trp Leu Cys Leu Leu Ser Pro Ser Gly Pro Val Cys
4155            4160            4165            4170

ACC TGT CCC AAT GGA AAG AGG CTG GAT AAT GGC ACC TGT GTG CCT GTG         12999
Thr Cys Pro Asn Gly Lys Arg Leu Asp Asn Gly Thr Cys Val Pro Val
        4175            4180            4185
```

FIG.6A-24

```
CCC TCT CCA ACA CCC CCT CCA GAT GCC CCT AGG CCT GGA ACC TGC ACT        13047
Pro Ser Pro Thr Pro Pro Pro Asp Ala Pro Arg Pro Gly Thr Cys Thr
        4190            4195                4200

CTG CAG TGC TTC AAT GGT GGT AGT TGT TTC CTC AAC GCT CGG AGG CAG        13095
Leu Gln Cys Phe Asn Gly Gly Ser Cys Phe Leu Asn Ala Arg Arg Gln
    4205            4210                4215

CCC AAG TGC CGT TGC CAG CCC CGT TAC ACA GGC GAT AAG TGT GAG CTG        13143
Pro Lys Cys Arg Cys Gln Pro Arg Tyr Thr Gly Asp Lys Cys Glu Leu
    4220            4225                4230

GAT CAG TGC TGG GAA TAC TGT CAC AAC GGA GGC ACC TGT GCG GCT TCC        13191
Asp Gln Cys Trp Glu Tyr Cys His Asn Gly Gly Thr Cys Ala Ala Ser
4235            4240                4245                4250

CCA TCT GGC ATG CCC ACG TGC CGC TGT CCC ACT GGC TTC ACG GGC CCC        13239
Pro Ser Gly Met Pro Thr Cys Arg Cys Pro Thr Gly Phe Thr Gly Pro
        4255            4260                4265

AAA TGC ACC GCA CAG GTG TGT GCA GGC TAC TGC TCT AAC AAC AGC ACC        13287
Lys Cys Thr Ala Gln Val Cys Ala Gly Tyr Cys Ser Asn Asn Ser Thr
    4270            4275                4280

TGC ACC GTC AAC CAG GGC AAC CAG CCC CAG TGC CGA TGT CTA CCT GGC        13335
Cys Thr Val Asn Gln Gly Asn Gln Pro Gln Cys Arg Cys Leu Pro Gly
    4285            4290                4295

TTC CTG GGC GAC CGT TGC CAG TAC CGG CAG TGC TCT GGC TTC TGT GAG        13383
Phe Leu Gly Asp Arg Cys Gln Tyr Arg Gln Cys Ser Gly Phe Cys Glu
    4300            4305                4310

AAC TTT GGC ACC TGT CAG ATG GCT GCT GAT GGC TCC CGA CAA TGT CGC        13431
Asn Phe Gly Thr Cys Gln Met Ala Ala Asp Gly Ser Arg Gln Cys Arg
4315            4320                4325                4330

TGC ACC GTC TAC TTT GAG GGA CCA AGG TGT GAG GTG AAC AAG TGT AGT        13479
Cys Thr Val Tyr Phe Glu Gly Pro Arg Cys Glu Val Asn Lys Cys Ser
    4335            4340                4345

CGC TGT CTC CAA GGC GCC TGT GTG GTC AAT AAG CAG ACC GGA GAT GTC        13527
Arg Cys Leu Gln Gly Ala Cys Val Val Asn Lys Gln Thr Gly Asp Val
    4350            4355                4360
```

FIG.6A-25

```
ACA TGC AAC TGC ACT GAT GGC CGG GTA GCC CCC AGT TGT CTC ACC TGC     13575
Thr Cys Asn Cys Thr Asp Gly Arg Val Ala Pro Ser Cys Leu Thr Cys
        4365                4370                4375

ATC GAT CAC TGT AGC AAT GGT GGC TCC TGC ACC ATG AAC AGC AAG ATG     13623
Ile Asp His Cys Ser Asn Gly Gly Ser Cys Thr Met Asn Ser Lys Met
        4380                4385                4390

ATG CCT GAG TGC CAG TGC CCG CCC CAT ATG ACA GGA CCC CGG TGC CAG     13671
Met Pro Glu Cys Gln Cys Pro Pro His Met Thr Gly Pro Arg Cys Gln
4395                4400                4405                4410

GAG CAG GTT GTT AGT CAG CAA CAG CCT GGG CAT ATG GCC TCC ATC CTG     13719
Glu Gln Val Val Ser Gln Gln Gln Pro Gly His Met Ala Ser Ile Leu
            4415                4420                4425

ATC CCT CTG CTG CTG CTT CTC CTG CTG CTT CTG GTG GCT GGC GTG GTG     13767
Ile Pro Leu Leu Leu Leu Leu Leu Leu Leu Val Ala Gly Val Val
            4430                4435                4440

TTC TGG TAT AAG CGG CGA GTC CGA GGG GCT AAG GGC TTC CAG CAC CAG     13815
Phe Trp Tyr Lys Arg Arg Val Arg Gly Ala Lys Gly Phe Gln His Gln
            4445                4450                4455

CGG ATG ACC AAT GGG GCC ATG AAT GTG GAA ATT GGA AAC CCT ACC TAC     13863
Arg Met Thr Asn Gly Ala Met Asn Val Glu Ile Gly Asn Pro Thr Tyr
        4460                4465                4470

AAG ATG TAT GAA GGT GGA GAG CCC GAT GAT GTC GGG GGC CTA CTG GAT     13911
Lys Met Tyr Glu Gly Gly Glu Pro Asp Asp Val Gly Gly Leu Leu Asp
4475                4480                4485                4490

GCT GAT TTT GCC CTT GAC CCT GAC AAG CCT ACC AAC TTC ACC AAC CCA     13959
Ala Asp Phe Ala Leu Asp Pro Asp Lys Pro Thr Asn Phe Thr Asn Pro
            4495                4500                4505

GTG TAT GCC ACG CTC TAC ATG GGG GGC CAC GGC AGC CGC CAT TCC CTG     14007
Val Tyr Ala Thr Leu Tyr Met Gly Gly His Gly Ser Arg His Ser Leu
            4510                4515                4520

GCC AGC ACG GAC GAG AAG CGA GAA CTG CTG GGC CGG GGA CCT GAA GAC     14055
Ala Ser Thr Asp Glu Lys Arg Glu Leu Leu Gly Arg Gly Pro Glu Asp
            4525                4530                4535
```

FIG.6A-26

```
GAG ATA GGA GAT CCC TTG GCA TAGGGCCCTG CCCCGACGGA TGTCCCCAGA AAGC    14110
CCCCTGCCAC ATGAGTCTTT CAATGAACCC CCTCCCCAGC CGGCCCTTCT CCGGCCCTGC    14170
Glu Ile Gly Asp Pro Leu Ala
    4540                4545

CGGGTGTACA AATGTAAAAA TGAAGGAATT ACTTTTTATA TGTGAGCGAG CAAGCGAGCA    14230

AGCACAGTAT TATCTCTTTG CATTTCCTTC CTGCCTGCTC CTCAGTATCC CCCCCATGCT    14290
GCCTTGAGGG GGCGGGGAGG GCTTTGTGGC TCAAAGGTAT GAAGGAGTCC ACATGTTCCC    14350
TACCGAGCAT ACCCCTGGAA GCCTGGCGGC ACGGCCTCCC CACCACGCCT GTGCAAGACA    14410
CTCAACGGGG CTCCGTGTCC CAGCTTTCCT TTCCTTGGCT CTCTGGGGTT AGTTCAGGGG    14470
AGGTGGAGTC CTCTGCTGAC CCTGTCTGGA AGATTTGGCT CTAGCTGAGG AAGGAGTCTT    14530
TTAGTTGAGG GAAGTCACCC CAAACCCCAG CTCCCACTTT CAGGGGCACC TCTCAGATGG    14590
CCATGCTCAG TATCCCTTCC AGACAGGCCC TCCCCTCTCT AGCGCCCCCT CTGTGGCTCC    14650
TAGGGCTGAA CACATTCTTT GGTAACTGTC CCCCAAGCCT CCCATCCCCC TGAGGGCCAG    14710
GAAGAGTCGG GGCACACCAA GGAAGGGCAA GCGGGCAGCC CCATTTTGGG GACGTGAACG    14770
TTTTAATAAT TTTTGCTGAA TTCCTTTACA ACTAAATAAC ACAGATATTG TTATAAATAA    14830
AATTGTAAAA AAAAAAAA
```

FIG.6A-27

```
Met Leu Thr Pro Pro Leu Leu Leu Val Pro Leu Leu Ser Ala Leu
 1           5               10              15
Val Ser Gly Ala Thr Met Asp Ala Pro Lys Thr Cys Ser Pro Lys Gln
            20              25              30
Phe Ala Cys Arg Asp Gln Ile Thr Cys Ile Ser Lys Gly Trp Arg Cys
            35              40              45
Asp Gly Glu Arg Asp Cys Pro Asp Gly Ser Asp Glu Ala Pro Glu Ile
     50              55              60
Cys Pro Gln Ser Lys Ala Gln Arg Cys Pro Pro Asn Glu His Ser Cys
65              70              75              80
Leu Gly Thr Glu Leu Cys Val Pro Met Ser Arg Leu Cys Asn Gly Ile
                85              90              95
Gln Asp Cys Met Asp Gly Ser Asp Glu Gly Ala His Cys Arg Glu Leu
            100             105             110
Arg Ala Asn Cys Ser Arg Met Gly Cys Gln His His Cys Val Pro Thr
        115             120             125
Pro Ser Gly Pro Thr Cys Tyr Cys Asn Ser Ser Phe Gln Leu Glu Ala
    130             135             140
Asp Gly Lys Thr Cys Lys Asp Phe Asp Glu Cys Ser Val Tyr Gly Thr
145             150             155             160
Cys Ser Gln Leu Cys Thr Asn Thr Asp Gly Ser Phe Thr Cys Gly Cys
                165             170             175
Val Glu Gly Tyr Leu Leu Gln Pro Asp Asn Arg Ser Cys Lys Ala Lys
            180             185             190
Asn Glu Pro Val Asp Arg Pro Pro Val Leu Leu Ile Ala Asn Ser Gln
        195             200             205
Asn Ile Leu Ala Thr Tyr Leu Ser Gly Ala Gln Val Ser Thr Ile Thr
    210             215             220
Pro Thr Ser Thr Arg Gln Thr Thr Ala Met Asp Phe Ser Tyr Ala Asn
225             230             235             240
Glu Thr Val Cys Trp Val His Val Gly Asp Ser Ala Ala Gln Thr Gln
                245             250             255
Leu Lys Cys Ala Arg Met Pro Gly Leu Lys Gly Phe Val Asp Glu His
            260             265             270
Thr Ile Asn Ile Ser Leu Ser Leu His His Val Glu Gln Met Ala Ile
        275             280             285
Asp Trp Leu Thr Gly Asn Phe Tyr Phe Val Asp Asp Ile Asp Asp Arg
    290             295             300
Ile Phe Val Cys Asn Arg Asn Gly Asp Thr Cys Val Thr Leu Leu Asp
305             310             315             320
```

FIG.6B-1

```
Leu Glu Leu Tyr Asn Pro Lys Gly Ile Ala Leu Asp Pro Ala Met Gly
              325                 330                 335
Lys Val Phe Phe Thr Asp Tyr Gly Gln Ile Pro Lys Val Glu Arg Cys
            340                 345                 350
Asp Met Asp Gly Gln Asn Arg Thr Lys Leu Val Asp Ser Lys Ile Val
            355                 360                 365
Phe Pro His Gly Ile Thr Leu Asp Leu Val Ser Arg Leu Val Tyr Trp
        370                 375                 380
Ala Asp Ala Tyr Leu Asp Tyr Ile Glu Val Val Asp Tyr Glu Gly Lys
385                 390                 395                 400
Gly Arg Gln Thr Ile Ile Gln Gly Ile Leu Ile Glu His Leu Tyr Gly
                405                 410                 415
Leu Thr Val Phe Glu Asn Tyr Leu Tyr Ala Thr Asn Ser Asp Asn Ala
            420                 425                 430
Asn Thr Gln Gln Lys Thr Ser Val Ile Arg Val Asn Arg Phe Asn Ser
            435                 440                 445
Thr Glu Tyr Gln Val Val Thr Arg Val Asp Lys Gly Gly Ala Leu His
    450                 455                 460
Ile Tyr His Gln Arg Arg Gln Pro Arg Val Arg Ser His Ala Cys Glu
465                 470                 475                 480
Asn Asp Gln Tyr Gly Lys Pro Gly Gly Cys Ser Asp Ile Cys Leu Leu
                485                 490                 495
Ala Asn Ser His Lys Ala Arg Thr Cys Arg Cys Arg Ser Gly Phe Ser
            500                 505                 510
Leu Gly Ser Asp Gly Lys Ser Cys Lys Lys Pro Glu His Glu Leu Phe
            515                 520                 525
Leu Val Tyr Gly Lys Gly Arg Pro Gly Ile Ile Arg Gly Met Asp Met
    530                 535                 540
Gly Ala Lys Val Pro Asp Glu His Met Ile Pro Ile Glu Asn Leu Met
545                 550                 555                 560
Asn Pro Arg Ala Leu Asp Phe His Ala Glu Thr Gly Phe Ile Tyr Phe
                565                 570                 575
Ala Asp Thr Thr Ser Tyr Leu Ile Gly Arg Gln Lys Ile Asp Gly Thr
            580                 585                 590
Glu Arg Glu Thr Ile Leu Lys Asp Gly Ile His Asn Val Glu Gly Val
    595                 600                 605
Ala Val Asp Trp Met Gly Asp Asn Leu Tyr Trp Thr Asp Asp Gly Pro
    610                 615                 620
Lys Lys Thr Ile Ser Val Ala Arg Leu Glu Lys Ala Ala Gln Thr Arg
625                 630                 635                 640
Lys Thr Leu Ile Glu Gly Lys Met Thr His Pro Arg Ala Ile Val Val
                645                 650                 655
```

FIG.6B-2

```
Asp Pro Leu Asn Gly Trp Met Tyr Trp Thr Asp Trp Glu Glu Asp Pro
            660             665             670
Lys Asp Ser Arg Arg Gly Arg Leu Glu Arg Ala Trp Met Asp Gly Ser
            675             680             685
His Arg Asp Ile Phe Val Thr Ser Lys Thr Val Leu Trp Pro Asn Gly
            690             695             700
Leu Ser Leu Asp Ile Pro Ala Gly Arg Leu Tyr Trp Val Asp Ala Phe
705             710             715             720
Tyr Asp Arg Ile Glu Thr Ile Leu Leu Asn Gly Thr Asp Arg Lys Ile
                725             730             735
Val Tyr Glu Gly Pro Glu Leu Asn His Ala Phe Gly Leu Cys His His
                740             745             750
Gly Asn Tyr Leu Phe Trp Thr Glu Tyr Arg Ser Gly Ser Val Tyr Arg
                755             760             765
Leu Glu Arg Gly Val Ala Gly Ala Pro Pro Thr Val Thr Leu Leu Arg
    770             775             780
Ser Glu Arg Pro Pro Ile Phe Glu Ile Arg Met Tyr Asp Ala His Glu
785             790             795             800
Gln Gln Val Gly Thr Asn Lys Cys Arg Val Asn Asn Gly Gly Cys Ser
            805                 810             815
Ser Leu Cys Leu Ala Thr Pro Gly Ser Arg Gln Cys Ala Cys Ala Glu
            820             825             830
Asp Gln Val Leu Asp Thr Asp Gly Val Thr Cys Leu Ala Asn Pro Ser
            835             840             845
Tyr Val Pro Pro Pro Gln Cys Gln Pro Gly Gln Phe Ala Cys Ala Asn
    850             855             860
Asn Arg Cys Ile Gln Glu Arg Trp Lys Cys Asp Gly Asp Asn Asp Cys
865             870             875             880
Leu Asp Asn Ser Asp Glu Ala Pro Ala Leu Cys His Gln His Thr Cys
                885             890             895
Pro Ser Asp Arg Phe Lys Cys Glu Asn Asn Arg Cys Ile Pro Asn Arg
            900             905             910
Trp Leu Cys Asp Gly Asp Asn Asp Cys Gly Asn Ser Glu Asp Glu Ser
            915             920             925
Asn Ala Thr Cys Ser Ala Arg Thr Cys Pro Pro Asn Gln Phe Ser Cys
    930             935             940
Ala Ser Gly Arg Cys Ile Pro Ile Ser Trp Thr Cys Asp Leu Asp Asp
945             950             955             960
Asp Cys Gly Asp Arg Ser Asp Glu Ser Ala Ser Cys Ala Tyr Pro Thr
                965             970             975
Cys Phe Pro Leu Thr Gln Phe Thr Cys Asn Asn Gly Arg Cys Ile Asn
            980             985             990
```

FIG.6B-3

```
Ile Asn Trp Arg Cys Asp Asn Asp Asn Asp Cys Gly Asp Asn Ser Asp
       995                1000               1005
Glu Ala Gly Cys Ser His Ser Cys Ser Ser Thr Gln Phe Lys Cys Asn
    1010              1015               1020
Ser Gly Arg Cys Ile Pro Glu His Trp Thr Cys Asp Gly Asp Asn Asp
025              1030               1035                1040
Cys Gly Asp Tyr Ser Asp Glu Thr His Ala Asn Cys Thr Asn Gln Ala
             1045               1050              1055
Thr Arg Pro Pro Gly Gly Cys His Ser Asp Glu Phe Gln Cys Pro Leu
         1060               1065              1070
Asp Gly Leu Cys Ile Pro Leu Arg Trp Arg Cys Asp Gly Asp Thr Asp
         1075              1080               1085
Cys Met Asp Ser Ser Asp Glu Lys Ser Cys Glu Gly Val Thr His Val
         1090              1095              1100
Cys Asp Pro Asn Val Lys Phe Gly Cys Lys Asp Ser Ala Arg Cys Ile
105              1110              1115                1120
Ser Lys Ala Trp Val Cys Asp Gly Asp Ser Asp Cys Glu Asp Asn Ser
             1125              1130              1135
Asp Glu Glu Asn Cys Glu Ala Leu Ala Cys Arg Pro Pro Ser His Pro
         1140              1145              1150
Cys Ala Asn Asn Thr Ser Val Cys Leu Pro Pro Asp Lys Leu Cys Asp
         1155              1160              1165
Gly Lys Asp Asp Cys Gly Asp Gly Ser Asp Glu Gly Glu Leu Cys Asp
         1170              1175              1180
Gln Cys Ser Leu Asn Asn Gly Gly Cys Ser His Asn Cys Ser Val Ala
185              1190              1195                1200
Pro Gly Glu Gly Ile Val Cys Ser Cys Pro Leu Gly Met Glu Leu Gly
         1205              1210              1215
Ser Asp Asn His Thr Cys Gln Ile Gln Ser Tyr Cys Ala Lys His Leu
         1220              1225              1230
Lys Cys Ser Gln Lys Cys Asp Gln Asn Lys Phe Ser Val Lys Cys Ser
         1235              1240              1245
Cys Tyr Glu Gly Trp Val Leu Glu Pro Asp Gly Glu Thr Cys Arg Ser
         1250              1255              1260
Leu Asp Pro Phe Lys Leu Phe Ile Ile Phe Ser Asn Arg His Glu Ile
265              1270              1275                1280
Arg Arg Ile Asp Leu His Lys Gly Asp Tyr Ser Val Leu Val Pro Gly
             1285              1290              1295
Leu Arg Asn Thr Ile Ala Leu Asp Phe His Leu Ser Gln Ser Ala Leu
         1300              1305              1310
Tyr Trp Thr Asp Ala Val Glu Asp Lys Ile Tyr Arg Gly Lys Leu Leu
         1315              1320              1325
```

FIG.6B-4

```
Asp Asn Gly Ala Leu Thr Ser Phe Glu Val Val Ile Gln Tyr Gly Leu
    1330               1335                1340
Ala Thr Pro Glu Gly Leu Ala Val Asp Trp Ile Ala Gly Asn Ile Tyr
345                1350                1355                1360
Trp Val Glu Ser Asn Leu Asp Gln Ile Glu Val Ala Lys Leu Asp Gly
               1365                1370                1375
Thr Leu Arg Thr Thr Leu Leu Ala Gly Asp Ile Glu His Pro Arg Ala
           1380                1385                1390
Ile Ala Leu Asp Pro Arg Asp Gly Ile Leu Phe Trp Thr Asp Trp Asp
       1395                1400                1405
Ala Ser Leu Pro Arg Ile Glu Ala Ala Ser Met Ser Gly Ala Gly Arg
    1410                1415                1420
Arg Thr Ile His Arg Glu Thr Gly Ser Gly Gly Cys Ala Asn Gly Leu
425                1430                1435                1440
Thr Val Asp Tyr Leu Glu Lys Arg Ile Leu Trp Ile Asp Ala Arg Ser
               1445                1450                1455
Asp Ala Ile Tyr Ser Ala Arg Tyr Asp Gly Ser Gly His Met Glu Val
           1460                1465                1470
Leu Arg Gly His Glu Phe Leu Ser His Pro Phe Ala Val Thr Leu Tyr
       1475                1480                1485
Gly Gly Glu Val Tyr Trp Thr Asp Trp Arg Thr Asn Thr Leu Ala Lys
    1490                1495                1500
Ala Asn Lys Trp Thr Gly His Asn Val Thr Val Val Gln Arg Thr Asn
505                1510                1515                1520
Thr Gln Pro Phe Asp Leu Gln Val Tyr His Pro Ser Arg Gln Pro Met
           1525                1530                1535
Ala Pro Asn Pro Cys Glu Ala Asn Gly Gly Arg Gly Pro Cys Ser His
       1540                1545                1550
Leu Cys Leu Ile Asn Tyr Asn Arg Thr Val Ser Trp Ala Cys Pro His
    1555                1560                1565
Leu Met Lys Leu His Lys Asp Asn Thr Thr Cys Tyr Glu Phe Lys Lys
    1570                1575                1580
Phe Leu Leu Tyr Ala Arg Gln Met Glu Ile Arg Gly Val Asp Leu Asp
585                1590                1595                1600
Ala Pro Tyr Tyr Asn Tyr Ile Ile Ser Phe Thr Val Pro Asp Ile Asp
           1605                1610                1615
Asn Val Thr Val Leu Asp Tyr Asp Ala Arg Glu Gln Arg Val Tyr Trp
       1620                1625                1630
Ser Asp Val Arg Thr Gln Ala Ile Lys Arg Ala Phe Ile Asn Gly Thr
    1635                1640                1645
Gly Val Glu Thr Val Val Ser Ala Asp Leu Pro Asn Ala His Gly Leu
    1650                1655                1660
```

FIG.6B-5

```
Ala Val Asp Trp Val Ser Arg Asn Leu Phe Trp Thr Ser Tyr Asp Thr
665                 1670            1675            1680
Asn Lys Lys Gln Ile Asn Val Ala Arg Leu Asp Gly Ser Phe Lys Asn
            1685            1690            1695
Ala Val Val Gln Gly Leu Glu Gln Pro His Gly Leu Val Val His Pro
        1700            1705            1710
Leu Arg Gly Lys Leu Tyr Trp Thr Asp Gly Asp Asn Ile Ser Met Ala
            1715            1720            1725
Asn Met Asp Gly Ser Asn His Thr Leu Leu Phe Ser Gly Gln Lys Gly
        1730            1735            1740
Pro Val Gly Leu Ala Ile Asp Phe Pro Glu Ser Lys Leu Tyr Trp Ile
745                 1750            1755            1760
Ser Ser Gly Asn His Thr Ile Asn Arg Cys Asn Leu Asp Gly Ser Glu
            1765            1770            1775
Leu Glu Val Ile Asp Thr Met Arg Ser Gln Leu Gly Lys Ala Thr Ala
            1780            1785            1790
Leu Ala Ile Met Gly Asp Lys Leu Trp Trp Ala Asp Gln Val Ser Glu
        1795            1800            1805
Lys Met Gly Thr Cys Asn Lys Ala Asp Gly Ser Gly Ser Val Val Leu
    1810            1815            1820
Arg Asn Ser Thr Thr Leu Val Met His Met Lys Val Tyr Asp Glu Ser
825                 1830            1835            1840
Ile Gln Leu Glu His Glu Gly Thr Asn Pro Cys Ser Val Asn Asn Gly
            1845            1850            1855
Asp Cys Ser Gln Leu Cys Leu Pro Thr Ser Glu Thr Thr Arg Ser Cys
        1860            1865            1870
Met Cys Thr Ala Gly Tyr Ser Leu Arg Ser Gly Gln Gln Ala Cys Glu
    1875            1880            1885
Gly Val Gly Ser Phe Leu Leu Tyr Ser Val His Glu Gly Ile Arg Gly
    1890            1895            1900
Ile Pro Leu Asp Pro Asn Asp Lys Ser Asp Ala Leu Val Pro Val Ser
905                 1910            1915            1920
Gly Thr Ser Leu Ala Val Gly Ile Asp Phe His Ala Glu Asn Asp Thr
        1925            1930            1935
Ile Tyr Trp Val Asp Met Gly Leu Ser Thr Ile Ser Arg Ala Lys Arg
            1940            1945            1950
Asp Gln Thr Trp Arg Glu Asp Val Val Thr Asn Gly Ile Gly Arg Val
        1955            1960            1965
Glu Gly Ile Ala Val Asp Trp Ile Ala Gly Asn Ile Tyr Trp Thr Asp
    1970            1975            1980
Gln Gly Phe Asp Val Ile Glu Val Ala Arg Leu Asn Gly Ser Phe Arg
985                 1990            1995            2000
```

FIG.6B-6

```
Tyr Val Val Ile Ser Gln Gly Leu Asp Lys Pro Arg Ala Ile Thr Val
            2005                2010                2015
His Pro Glu Lys Gly Tyr Leu Phe Trp Thr Glu Trp Gly His Tyr Pro
            2020                2025            2030
Arg Ile Glu Arg Ser Arg Leu Asp Gly Thr Glu Arg Val Val Leu Val
    2035                2040                2045
Asn Val Ser Ile Ser Trp Pro Asn Gly Ile Ser Val Asp Tyr Gln Gly
  2050                2055                2060
Gly Lys Leu Tyr Trp Cys Asp Ala Arg Met Asp Lys Ile Glu Arg Ile
065             2070                2075                2080
Asp Leu Glu Thr Gly Glu Asn Arg Glu Val Val Leu Ser Ser Asn Asn
                2085                2090                2095
Met Asp Met Phe Ser Val Ser Val Phe Glu Asp Phe Ile Tyr Trp Ser
                2100                2105            2110
Asp Arg Thr His Ala Asn Gly Ser Ile Lys Arg Gly Cys Lys Asp Asn
        2115                2120                2125
Ala Thr Asp Ser Val Pro Leu Arg Thr Gly Ile Gly Val Gln Leu Lys
        2130                2135            2140
Asp Ile Lys Val Phe Asn Arg Asp Arg Gln Lys Gly Thr Asn Val Cys
145             2150                2155                2160
Ala Val Ala Asn Gly Gly Cys Gln Gln Leu Cys Leu Tyr Arg Gly Gly
                2165                2170                2175
Gly Gln Arg Ala Cys Ala Cys Ala His Gly Met Leu Ala Glu Asp Gly
            2180                2185            2190
Ala Ser Cys Arg Glu Tyr Ala Gly Tyr Leu Leu Tyr Ser Glu Arg Thr
        2195                2200                2205
Ile Leu Lys Ser Ile His Leu Ser Asp Glu Arg Asn Leu Asn Ala Pro
    2210                2215            2220
Val Gln Pro Phe Glu Asp Pro Glu His Met Lys Asn Val Ile Ala Leu
225             2230                2235                2240
Ala Phe Asp Tyr Arg Ala Gly Thr Ser Pro Gly Thr Pro Asn Arg Ile
            2245                2250            2255
Phe Phe Ser Asp Ile His Phe Gly Asn Ile Gln Gln Ile Asn Asp Asp
            2260                2265            2270
Gly Ser Gly Arg Thr Thr Ile Val Glu Asn Val Gly Ser Val Glu Gly
    2275                2280                2285
Leu Ala Tyr His Arg Gly Trp Asp Thr Leu Tyr Trp Thr Ser Tyr Thr
        2290                2295            2300
Thr Ser Thr Ile Thr Arg His Thr Val Asp Gln Thr Arg Pro Gly Ala
305             2310                2315                2320
Phe Glu Arg Glu Thr Val Ile Thr Met Ser Gly Asp Asp His Pro Arg
            2325                2330                2335
```

FIG.6B-7

```
Ala Phe Val Leu Asp Glu Cys Gln Asn Leu Met Phe Trp Thr Asn Trp
              2340               2345               2350
Asn Glu Leu His Pro Ser Ile Met Arg Ala Ala Leu Ser Gly Ala Asn
              2355               2360               2365
Val Leu Thr Leu Ile Glu Lys Asp Ile Arg Thr Pro Asn Gly Leu Ala
              2370               2375               2380
Ile Asp His Arg Ala Glu Lys Leu Tyr Phe Ser Asp Ala Thr Leu Asp
 385                2390               2395               2400
Lys Ile Glu Arg Cys Glu Tyr Asp Gly Ser His Arg Tyr Val Ile Leu
              2405               2410               2415
Lys Ser Glu Pro Val His Pro Phe Gly Leu Ala Val Tyr Gly Glu His
              2420               2425               2430
Ile Phe Trp Thr Asp Trp Val Arg Arg Ala Val Gln Arg Ala Asn Lys
              2435               2440               2445
Tyr Val Gly Ser Asp Met Lys Leu Leu Arg Val Asp Ile Pro Gln Gln
              2450               2455               2460
Pro Met Gly Ile Ile Ala Val Ala Asn Asp Thr Asn Ser Cys Glu Leu
 465                2470               2475               2480
Ser Pro Cys Arg Ile Asn Asn Gly Gly Cys Gln Asp Leu Cys Leu Leu
              2485               2490               2495
Thr His Gln Gly His Val Asn Cys Ser Cys Arg Gly Gly Arg Ile Leu
              2500               2505               2510
Gln Glu Asp Phe Thr Cys Arg Ala Val Asn Ser Ser Cys Arg Ala Gln
              2515               2520               2525
Asp Glu Phe Glu Cys Ala Asn Gly Glu Cys Ile Ser Phe Ser Leu Thr
              2530               2535               2540
Cys Asp Gly Val Ser His Cys Lys Asp Lys Ser Asp Glu Lys Pro Ser
 545                2550               2555               2560
Tyr Cys Asn Ser Arg Arg Cys Lys Lys Thr Phe Arg Gln Cys Asn Asn
              2565               2570               2575
Gly Arg Cys Val Ser Asn Met Leu Trp Cys Asn Gly Val Asp Tyr Cys
              2580               2585               2590
Gly Asp Gly Ser Asp Glu Ile Pro Cys Asn Lys Thr Ala Cys Gly Val
              2595               2600               2605
Gly Glu Phe Arg Cys Arg Asp Gly Ser Cys Ile Gly Asn Ser Ser Arg
              2610               2615               2620
Cys Asn Gln Phe Val Asp Cys Glu Asp Ala Ser Asp Glu Met Asn Cys
 625                2630               2635               2640
Ser Ala Thr Asp Cys Ser Ser Tyr Phe Arg Leu Gly Val Lys Gly Val
              2645               2650               2655
Leu Phe Gln Pro Cys Glu Arg Thr Ser Leu Cys Tyr Ala Pro Ser Trp
              2660               2665               2670
```

FIG.6B-8

```
Val Cys Asp Gly Ala Asn Asp Cys Gly Asp Tyr Ser Asp Glu Arg Asp
    2675                2680                2685
Cys Pro Gly Val Lys Arg Pro Arg Cys Pro Leu Asn Tyr Phe Ala Cys
    2690                2695            2700
Pro Ser Gly Arg Cys Ile Pro Met Ser Trp Thr Cys Asp Lys Glu Asp
705             2710            2715                    2720
Asp Cys Glu Asn Gly Glu Asp Glu Thr His Cys Asn Lys Phe Cys Ser
            2725                2730                2735
Glu Ala Gln Phe Glu Cys Gln Asn His Arg Cys Ile Ser Lys Gln Trp
        2740                2745                2750
Leu Cys Asp Gly Ser Asp Asp Cys Gly Asp Gly Ser Asp Glu Ala Ala
    2755                2760            2765
His Cys Glu Gly Lys Thr Cys Gly Pro Ser Ser Phe Ser Cys Pro Gly
    2770                2775                2780
Thr His Val Cys Val Pro Glu Arg Trp Leu Cys Asp Gly Asp Lys Asp
785             2790                2795                    2800
Cys Thr Asp Gly Ala Asp Glu Ser Val Thr Ala Gly Cys Leu Tyr Asn
        2805                2810                2815
Ser Thr Cys Asp Asp Arg Glu Phe Met Cys Gln Asn Arg Leu Cys Ile
        2820                2825                2830
Pro Lys His Phe Val Cys Asp His Asp Arg Asp Cys Ala Asp Gly Ser
        2835                2840                2845
Asp Glu Ser Pro Glu Cys Glu Tyr Pro Thr Cys Gly Pro Asn Glu Phe
    2850                2855            2860
Arg Cys Ala Asn Gly Arg Cys Leu Ser Ser Arg Gln Trp Glu Cys Asp
865             2870                2875                    2880
Gly Glu Asn Asp Cys His Asp His Ser Asp Glu Ala Pro Lys Asn Pro
        2885                2890                2895
His Cys Thr Ser Pro Glu His Lys Cys Asn Ala Ser Ser Gln Phe Leu
    2900                2905                2910
Cys Ser Ser Gly Arg Cys Val Ala Glu Ala Leu Leu Cys Asn Gly Gln
    2915                2920            2925
Asp Asp Cys Gly Asp Gly Ser Asp Glu Arg Gly Cys His Val Asn Glu
    2930            2935                2940
Cys Leu Ser Arg Lys Leu Ser Gly Cys Ser Gln Asp Cys Glu Asp Leu
945             2950                2955                    2960
Lys Ile Gly Phe Lys Cys Arg Cys Arg Pro Gly Phe Arg Leu Lys Asp
            2965                2970                2975
Asp Gly Arg Thr Cys Ala Asp Leu Asp Glu Cys Ser Thr Thr Phe Pro
            2980                2985                2990
Cys Ser Gln Leu Cys Ile Asn Thr His Gly Ser Tyr Lys Cys Leu Cys
    2995                3000                3005
```

FIG.6B-9

```
Val Glu Gly Tyr Ala Pro Arg Gly Gly Asp Pro His Ser Cys Lys Ala
    3010                3015                3020
Val Thr Asp Glu Glu Pro Phe Leu Ile Phe Ala Asn Arg Tyr Tyr Leu
025                 3030                3035                3040
Arg Lys Leu Asn Leu Asp Gly Ser Asn Tyr Thr Leu Leu Lys Gln Gly
                3045                3050                3055
Leu Asn Asn Ala Val Ala Leu Ala Phe Asp Tyr Arg Glu Gln Met Ile
            3060                3065                3070
Tyr Trp Thr Gly Val Thr Thr Gln Gly Ser Met Ile Arg Arg Met His
        3075                3080                 3085
Leu Asn Gly Ser Asn Val Gln Val Leu His Arg Thr Gly Leu Ser Asn
    3090                3095                3100
Pro Asp Gly Leu Ala Val Asp Trp Val Gly Gly Asn Leu Tyr Trp Cys
105                 3110                3115                3120
Asp Lys Gly Arg Asp Thr Ile Glu Val Ser Lys Leu Asn Gly Ala Tyr
            3125                3130                3135
Arg Thr Val Leu Val Ser Ser Gly Leu Arg Glu Pro Arg Ala Leu Val
            3140                3145                3150
Val Asp Val Gln Asn Gly Tyr Leu Tyr Trp Thr Asp Trp Gly Asp His
            3155                3160                3165
Ser Leu Ile Gly Arg Ile Gly Met Asp Gly Ser Gly Arg Ser Ile Ile
    3170                3175                3180
Val Asp Thr Lys Ile Thr Trp Pro Asn Gly Leu Thr Val Asp Tyr Val
185                 3190                3195                3200
Thr Glu Arg Ile Tyr Trp Ala Asp Ala Arg Glu Asp Tyr Ile Glu Phe
            3205                3210                3215
Ala Ser Leu Asp Gly Ser Asn Arg His Val Val Leu Ser Gln Asp Ile
            3220                3225                3230
Pro His Ile Phe Ala Leu Thr Leu Phe Glu Asp Tyr Val Tyr Trp Thr
        3235                3240                3245
Asp Trp Glu Thr Lys Ser Ile Asn Arg Ala His Lys Thr Thr Gly Ala
    3250                3255                3260
Asn Lys Thr Leu Leu Ile Ser Thr Leu His Arg Pro Met Asp Leu His
265                 3270                3275                3280
Val Phe His Ala Leu Arg Gln Pro Asp Val Pro Asn His Pro Cys Lys
            3285                3290                3295
Val Asn Asn Gly Gly Cys Ser Asn Leu Cys Leu Leu Ser Pro Gly Gly
            3300                3305                3310
Gly His Lys Cys Ala Cys Pro Thr Asn Phe Tyr Leu Gly Gly Asp Gly
        3315                3320                3325
Arg Thr Cys Val Ser Asn Cys Thr Ala Ser Gln Phe Val Cys Lys Asn
    3330                3335                3340
```

FIG.6B-10

```
Asp Lys Cys Ile Pro Phe Trp Trp Lys Cys Asp Thr Glu Asp Asp Cys
345                 3350              3355              3360
Gly Asp His Ser Asp Glu Pro Pro Asp Cys Pro Glu Phe Lys Cys Arg
                3365              3370              3375
Pro Gly Gln Phe Gln Cys Ser Thr Gly Ile Cys Thr Asn Pro Ala Phe
            3380              3385              3390
Ile Cys Asp Gly Asp Asn Asp Cys Gln Asp Asn Ser Asp Glu Ala Asn
            3395              3400              3405
Cys Asp Ile His Val Cys Leu Pro Ser Gln Phe Lys Cys Thr Asn Thr
        3410              3415              3420
Asn Arg Cys Ile Pro Gly Ile Phe Arg Cys Asn Gly Gln Asp Asn Cys
425             3430              3435              3440
Gly Asp Gly Glu Asp Glu Arg Asp Cys Pro Glu Val Thr Cys Ala Pro
                3445              3450              3455
Asn Gln Phe Gln Cys Ser Ile Thr Lys Arg Cys Ile Pro Arg Val Trp
            3460              3465              3470
Val Cys Asp Arg Asp Asn His Cys Val Asp Gly Ser Asp Glu Pro Ala
        3475              3480              3485
Asn Cys Thr Gln Met Thr Cys Gly Val Asp Glu Phe Arg Cys Lys Asp
    3490              3495              3500
Ser Gly Arg Cys Ile Pro Ala Arg Trp Lys Cys Asp Gly Glu Asp Asp
505             3510              3515              3520
Cys Gly Asp Gly Ser Asp Glu Pro Lys Glu Glu Cys Asp Glu Arg Thr
            3525              3530              3535
Cys Glu Pro Tyr Gln Phe Arg Cys Lys Asn Asn Arg Cys Val Pro Gly
            3540              3545              3550
Arg Trp Gln Cys Asp Tyr Asp Asn Asp Cys Gly Asp Asn Ser Asp Glu
        3555              3560              3565
Glu Ser Cys Thr Pro Arg Pro Cys Ser Glu Ser Glu Phe Phe Cys Ala
    3570              3575              3580
Asn Gly Arg Cys Ile Ala Gly Arg Trp Lys Cys Asp Gly Asp His Asp
585             3590              3595              3600
Cys Ala Asp Gly Ser Asp Glu Lys Asp Cys Thr Pro Arg Cys Asp Met
            3605              3610              3615
Asp Gln Phe Gln Cys Lys Ser Gly His Cys Ile Pro Leu Arg Trp Pro
        3620              3625              3630
Cys Asp Ala Asp Ala Asp Cys Met Asp Gly Ser Asp Glu Glu Ala Cys
    3635              3640              3645
Gly Thr Gly Val Arg Thr Cys Pro Leu Asp Glu Phe Gln Cys Asn Asn
    3650              3655              3660
Thr Leu Cys Lys Pro Leu Ala Trp Lys Cys Asp Gly Glu Asp Asp Cys
665             3670              3675              3680
```

FIG.6B-11

```
Gly Asp Asn Ser Asp Glu Asn Pro Glu Glu Cys Ala Arg Phe Ile Cys
            3685              3690              3695
Pro Pro Asn Arg Pro Phe Arg Cys Lys Asn Asp Arg Val Cys Leu Trp
        3700              3705              3710
Ile Gly Arg Gln Cys Asp Gly Val Asp Asn Cys Gly Asp Gly Thr Asp
    3715              3720              3725
Glu Glu Asp Cys Glu Pro Pro Thr Ala Gln Asn Pro His Cys Lys Asp
  3730              3735              3740
Lys Lys Glu Phe Leu Cys Arg Asn Gln Arg Cys Leu Ser Ser Ser Leu
745              3750              3755              3760
Arg Cys Asn Met Phe Asp Asp Cys Gly Asp Gly Ser Asp Glu Glu Asp
            3765              3770              3775
Cys Ser Ile Asp Pro Lys Leu Thr Ser Cys Ala Thr Asn Ala Ser Met
        3780              3785              3790
Cys Gly Asp Glu Ala Arg Cys Val Arg Thr Glu Lys Ala Ala Tyr Cys
        3795              3800              3805
Ala Cys Arg Ser Gly Phe His Thr Val Pro Gly Gln Pro Gly Cys Gln
    3810              3815              3820
Asp Ile Asn Glu Cys Leu Arg Phe Gly Thr Cys Ser Gln Leu Trp Asn
825              3830              3835              3840
Lys Pro Lys Gly Gly His Leu Cys Ser Cys Ala Arg Asn Phe Met Lys
        3845              3850              3855
Thr His Asn Thr Cys Lys Ala Glu Gly Ser Glu Tyr Gln Val Leu Tyr
            3860              3865              3870
Ile Ala Asp Asp Asn Glu Ile Arg Ser Leu Phe Pro Gly His Pro His
    3875              3880              3885
Ser Ala Tyr Glu Gln Thr Phe Gln Gly Asp Glu Ser Val Arg Ile Asp
3890              3895              3900
Ala Met Asp Val His Val Lys Ala Gly Arg Val Tyr Trp Thr Asn Trp
905              3910              3915              3920
His Thr Gly Thr Ile Ser Tyr Arg Ser Leu Pro Pro Ala Ala Pro Pro
            3925              3930              3935
Thr Thr Ser Asn Arg His Arg Arg Gln Ile Asp Arg Gly Val Thr His
            3940              3945              3950
Leu Asn Ile Ser Gly Leu Lys Met Pro Arg Gly Ile Ala Ile Asp Trp
    3955              3960              3965
Val Ala Gly Asn Val Tyr Trp Thr Asp Ser Gly Arg Asp Val Ile Glu
    3970              3975              3980
Val Ala Gln Met Lys Gly Glu Asn Arg Lys Thr Leu Ile Ser Gly Met
985              3990              3995              4000
Ile Asp Glu Pro His Ala Ile Val Val Asp Pro Leu Arg Gly Thr Met
            4005              4010              4015
```

FIG.6B-12

Tyr Trp Ser Asp Trp Gly Asn His Pro Lys Ile Glu Thr Ala Ala Met
         4020                    4025                4030
Asp Gly Thr Leu Arg Glu Thr Leu Val Gln Asp Asn Ile Gln Trp Pro
         4035                    4040                4045
Thr Gly Leu Ala Val Asp Tyr His Asn Glu Arg Leu Tyr Trp Ala Asp
    4050                    4055                4060
Ala Lys Leu Ser Val Ile Gly Ser Ile Arg Leu Asn Gly Thr Asp Pro
065                     4070                4075                4080
Ile Val Ala Ala Asp Ser Lys Arg Gly Leu Ser His Pro Phe Ser Ile
              4085                  4090                4095
Asp Val Phe Glu Asp Tyr Ile Tyr Gly Val Thr Tyr Ile Asn Asn Arg
         4100                    4105                4110
Val Phe Lys Ile His Lys Phe Gly His Ser Pro Leu Tyr Asn Leu Thr
         4115                    4120                4125
Gly Gly Leu Ser His Ala Ser Asp Val Val Leu Tyr His Gln His Lys
    4130                    4135                4140
Gln Pro Glu Val Thr Asn Pro Cys Asp Arg Lys Lys Cys Glu Trp Leu
145                     4150                4155                4160
Cys Leu Leu Ser Pro Ser Gly Pro Val Cys Thr Cys Pro Asn Gly Lys
              4165                  4170                4175
Arg Leu Asp Asn Gly Thr Cys Val Pro Val Pro Ser Pro Thr Pro Pro
         4180                    4185                4190
Pro Asp Ala Pro Arg Pro Gly Thr Cys Thr Leu Gln Cys Phe Asn Gly
         4195                    4200                4205
Gly Ser Cys Phe Leu Asn Ala Arg Arg Gln Pro Lys Cys Arg Cys Gln
    4210                    4215                4220
Pro Arg Tyr Thr Gly Asp Lys Cys Glu Leu Asp Gln Cys Trp Glu Tyr
225                     4230                4235                4240
Cys His Asn Gly Gly Thr Cys Ala Ala Ser Pro Ser Gly Met Pro Thr
              4245                  4250                4255
Cys Arg Cys Pro Thr Gly Phe Thr Gly Pro Lys Cys Thr Ala Gln Val
         4260                    4265                4270
Cys Ala Gly Tyr Cys Ser Asn Asn Ser Thr Cys Thr Val Asn Gln Gly
    4275                    4280                4285
Asn Gln Pro Gln Cys Arg Cys Leu Pro Gly Phe Leu Gly Asp Arg Cys
         4290                    4295                4300
Gln Tyr Arg Gln Cys Ser Gly Phe Cys Glu Asn Phe Gly Thr Cys Gln
305                     4310                4315                4320
Met Ala Ala Asp Gly Ser Arg Gln Cys Arg Cys Thr Val Tyr Phe Glu
              4325                  4330                4335
Gly Pro Arg Cys Glu Val Asn Lys Cys Ser Arg Cys Leu Gln Gly Ala
         4340                    4345                4350

FIG.6B-13

```
Cys Val Val Asn Lys Gln Thr Gly Asp Val Thr Cys Asn Cys Thr Asp
        4355            4360            4365
Gly Arg Val Ala Pro Ser Cys Leu Thr Cys Ile Asp His Cys Ser Asn
    4370            4375            4380
Gly Gly Ser Cys Thr Met Asn Ser Lys Met Met Pro Glu Cys Gln Cys
385             4390            4395            4400
Pro Pro His Met Thr Gly Pro Arg Cys Gln Glu Gln Val Val Ser Gln
            4405            4410            4415
Gln Gln Pro Gly His Met Ala Ser Ile Leu Ile Pro Leu Leu Leu Leu
        4420            4425            4430
Leu Leu Leu Leu Leu Val Ala Gly Val Val Phe Trp Tyr Lys Arg Arg
        4435            4440            4445
Val Arg Gly Ala Lys Gly Phe Gln His Gln Arg Met Thr Asn Gly Ala
    4450            4455            4460
Met Asn Val Glu Ile Gly Asn Pro Thr Tyr Lys Met Tyr Glu Gly Gly
465             4470            4475            4480
Glu Pro Asp Asp Val Gly Gly Leu Leu Asp Ala Asp Phe Ala Leu Asp
            4485            4490            4495
Pro Asp Lys Pro Thr Asn Phe Thr Asn Pro Val Tyr Ala Thr Leu Tyr
        4500            4505            4510
Met Gly Gly His Gly Ser Arg His Ser Leu Ala Ser Thr Asp Glu Lys
    4515            4520            4525
Arg Glu Leu Leu Gly Arg Gly Pro Glu Asp Glu Ile Gly Asp Pro Leu
    4530            4535            4540
Ala
545
```

FIG.6B-14

| | |
|---|---|
| GCTACAATCC ATCTGGTCTC CTCCAGCTCC TTCTTTCTGC AAC ATG GGG AAG AAC<br>                                      Met Gly Lys Asn<br>                                        1 | 55 |
| AAA CTC CTT CAT CCA AGT CTG GTT CTT CTC CTC TTG GTC CTC CTG CCC<br>Lys Leu Leu His Pro Ser Leu Val Leu Leu Leu Leu Val Leu Leu Pro<br>5         10         15         20 | 103 |
| ACA GAC GCC TCA GTC TCT GGA AAA CCG CAG TAT ATG GTT CTG GTC CCC<br>Thr Asp Ala Ser Val Ser Gly Lys Pro Gln Tyr Met Val Leu Val Pro<br>         25         30         35 | 151 |
| TCC CTG CTC CAC ACT GAG ACC ACT GAG AAG GGC TGT GTC CTT CTG AGC<br>Ser Leu Leu His Thr Glu Thr Thr Glu Lys Gly Cys Val Leu Leu Ser<br>         40         45         50 | 199 |
| TAC CTG AAT GAG ACA GTG ACT GTA AGT GCT TCC TTG GAG TCT GTC AGG<br>Tyr Leu Asn Glu Thr Val Thr Val Ser Ala Ser Leu Glu Ser Val Arg<br>         55         60         65 | 247 |
| GGA AAC AGG AGC CTC TTC ACT GAC CTG GAG GCG GAG AAT GAC GTA CTC<br>Gly Asn Arg Ser Leu Phe Thr Asp Leu Glu Ala Glu Asn Asp Val Leu<br>         70         75         80 | 295 |
| CAC TGT GTC GCC TTC GCT GTC CCA AAG TCT TCA TCC AAT GAG GAG GTA<br>His Cys Val Ala Phe Ala Val Pro Lys Ser Ser Ser Asn Glu Glu Val<br>85         90         95         100 | 343 |
| ATG TTC CTC ACT GTC CAA GTG AAA GGA CCA ACC CAA GAA TTT AAG AAG<br>Met Phe Leu Thr Val Gln Val Lys Gly Pro Thr Gln Glu Phe Lys Lys<br>         105        110        115 | 391 |
| CGG ACC ACA GTG ATG GTT AAG AAC GAG GAC AGT CTG GTC TTT GTC CAG<br>Arg Thr Thr Val Met Val Lys Asn Glu Asp Ser Leu Val Phe Val Gln<br>         120        125        130 | 439 |
| ACA GAC AAA TCA ATC TAC AAA CCA GGG CAG ACA GTG AAA TTT CGT GTT<br>Thr Asp Lys Ser Ile Tyr Lys Pro Gly Gln Thr Val Lys Phe Arg Val<br>         135        140        145 | 487 |
| GTC TCC ATG GAT GAA AAC TTT CAC CCC CTG AAT GAG TTG ATT CCA CTA<br>Val Ser Met Asp Glu Asn Phe His Pro Leu Asn Glu Leu Ile Pro Leu<br>         150        155        160 | 535 |

FIG.7A-1

```
GTA TAC ATT CAG GAT CCC AAA GGA AAT CGC ATC GCA CAA TGG CAG AGT       583
Val Tyr Ile Gln Asp Pro Lys Gly Asn Arg Ile Ala Gln Trp Gln Ser
165             170             175             180

TTC CAG TTA GAG GGT GGC CTC AAG CAA TTT TCT TTT CCC CTC TCA TCA       631
Phe Gln Leu Glu Gly Gly Leu Lys Gln Phe Ser Phe Pro Leu Ser Ser
                185             190             195

GAG CCC TTC CAG GGC TCC TAC AAG GTG GTG GTA CAG AAG AAA TCA GGT       679
Glu Pro Phe Gln Gly Ser Tyr Lys Val Val Val Gln Lys Lys Ser Gly
            200             205             210

GGA AGG ACA GAG CAC CCT TTC ACC GTG GAG GAA TTT GTT CTT CCC AAG       727
Gly Arg Thr Glu His Pro Phe Thr Val Glu Glu Phe Val Leu Pro Lys
        215             220             225

TTT GAA GTA CAA GTA ACA GTG CCA AAG ATA ATC ACC ATC TTG GAA GAA       775
Phe Glu Val Gln Val Thr Val Pro Lys Ile Ile Thr Ile Leu Glu Glu
    230             235             240

GAG ATG AAT GTA TCA GTG TGT GGC CTA TAC ACA TAT GGG AAG CCT GTC       823
Glu Met Asn Val Ser Val Cys Gly Leu Tyr Thr Tyr Gly Lys Pro Val
245             250             255             260

CCT GGA CAT GTG ACT GTG AGC ATT TGC AGA AAG TAT AGT GAC GCT TCC       871
Pro Gly His Val Thr Val Ser Ile Cys Arg Lys Tyr Ser Asp Ala Ser
                265             270             275

GAC TGC CAC GGT GAA GAT TCA CAG GCT TTC TGT GAG AAA TTC AGT GGA       919
Asp Cys His Gly Glu Asp Ser Gln Ala Phe Cys Glu Lys Phe Ser Gly
            280             285             290

CAG CTA AAC AGC CAT GGC TGC TTC TAT CAG CAA GTA AAA ACC AAG GTC       967
Gln Leu Asn Ser His Gly Cys Phe Tyr Gln Gln Val Lys Thr Lys Val
        295             300             305

TTC CAG CTG AAG AGG AAG GAG TAT GAA ATG AAA CTT CAC ACT GAG GCC      1015
Phe Gln Leu Lys Arg Lys Glu Tyr Glu Met Lys Leu His Thr Glu Ala
    310             315             320

CAG ATC CAA GAA GAA GGA ACA GTG GTG GAA TTG ACT GGA AGG CAG TCC      1063
Gln Ile Gln Glu Glu Gly Thr Val Val Glu Leu Thr Gly Arg Gln Ser
325             330             335             340
```

FIG. 7A-2

```
AGT GAA ATC ACA AGA ACC ATA ACC AAA CTC TCA TTT GTG AAA GTG GAC        1111
Ser Glu Ile Thr Arg Thr Ile Thr Lys Leu Ser Phe Val Lys Val Asp
            345             350             355

TCA CAC TTT CGA CAG GGA ATT CCC TTC TTT GGG CAG GTG CGC CTA GTA        1159
Ser His Phe Arg Gln Gly Ile Pro Phe Phe Gly Gln Val Arg Leu Val
            360             365             370

GAT GGG AAA GGC GTC CCT ATA CCA AAT AAA GTC ATA TTC ATC AGA GGA        1207
Asp Gly Lys Gly Val Pro Ile Pro Asn Lys Val Ile Phe Ile Arg Gly
            375             380             385

AAT GAA GCA AAC TAT TAC TCC AAT GCT ACC ACG GAT GAG CAT GGC CTT        1255
Asn Glu Ala Asn Tyr Tyr Ser Asn Ala Thr Thr Asp Glu His Gly Leu
            390             395             400

GTA CAG TTC TCT ATC AAC ACC ACC AAC GTT ATG GGT ACC TCT CTT ACT        1303
Val Gln Phe Ser Ile Asn Thr Thr Asn Val Met Gly Thr Ser Leu Thr
405             410             415             420

GTT AGG GTC AAT TAC AAG GAT CGT AGT CCC TGT TAC GGC TAC CAG TGG        1351
Val Arg Val Asn Tyr Lys Asp Arg Ser Pro Cys Tyr Gly Tyr Gln Trp
            425             430             435

GTG TCA GAA GAA CAC GAA GAG GCA CAT CAC ACT GCT TAT CTT GTG TTC        1399
Val Ser Glu Glu His Glu Glu Ala His His Thr Ala Tyr Leu Val Phe
            440             445             450

TCC CCA AGC AAG AGC TTT GTC CAC CTT GAG CCC ATG TCT CAT GAA CTA        1447
Ser Pro Ser Lys Ser Phe Val His Leu Glu Pro Met Ser His Glu Leu
            455             460             465

CCC TGT GGC CAT ACT CAG ACA GTC CAG GCA CAT TAT ATT CTG AAT GGA        1495
Pro Cys Gly His Thr Gln Thr Val Gln Ala His Tyr Ile Leu Asn Gly
            470             475             480

GGC ACC CTG CTG GGG CTG AAG AAG CTC TCC TTT TAT TAT CTG ATA ATG        1543
Gly Thr Leu Leu Gly Leu Lys Lys Leu Ser Phe Tyr Tyr Leu Ile Met
485             490             495             500

GCA AAG GGA GGC ATT GTC CGA ACT GGG ACT CAT GGA CTG CTT GTG AAG        1591
Ala Lys Gly Gly Ile Val Arg Thr Gly Thr His Gly Leu Leu Val Lys
            505             510             515
```

FIG.7A-3

```
CAG GAA GAC ATG AAG GGC CAT TTT TCC ATC TCA ATC CCT GTG AAG TCA    1639
Gln Glu Asp Met Lys Gly His Phe Ser Ile Ser Ile Pro Val Lys Ser
            520                 525                 530

GAC ATT GCT CCT GTC GCT CGG TTG CTC ATC TAT GCT GTT TTA CCT ACC    1687
Asp Ile Ala Pro Val Ala Arg Leu Leu Ile Tyr Ala Val Leu Pro Thr
            535                 540                 545

GGG GAC GTG ATT GGG GAT TCT GCA AAA TAT GAT GTT GAA AAT TGT CTG    1735
Gly Asp Val Ile Gly Asp Ser Ala Lys Tyr Asp Val Glu Asn Cys Leu
            550                 555                 560

GCC AAC AAG GTG GAT TTG AGC TTC AGC CCA TCA CAA AGT CTC CCA GCC    1783
Ala Asn Lys Val Asp Leu Ser Phe Ser Pro Ser Gln Ser Leu Pro Ala
565                 570                 575                 580

TCA CAC GCC CAC CTG CGA GTC ACA GCG GCT CCT CAG TCC GTC TGC GCC    1831
Ser His Ala His Leu Arg Val Thr Ala Ala Pro Gln Ser Val Cys Ala
                585                 590                 595

CTC CGT GCT GTG GAC CAA AGC GTG CTG CTC ATG AAG CCT GAT GCT GAG    1879
Leu Arg Ala Val Asp Gln Ser Val Leu Leu Met Lys Pro Asp Ala Glu
                600                 605                 610

CTC TCG GCG TCC TCG GTT TAC AAC CTG CTA CCA GAA AAG GAC CTC ACT    1927
Leu Ser Ala Ser Ser Val Tyr Asn Leu Leu Pro Glu Lys Asp Leu Thr
                615                 620                 625

GGC TTC CCT GGG CCT TTG AAT GAC CAG GAC GAT GAA GAC TGC ATC AAT    1975
Gly Phe Pro Gly Pro Leu Asn Asp Gln Asp Asp Glu Asp Cys Ile Asn
            630                 635                 640

CGT CAT AAT GTC TAT ATT AAT GGA ATC ACA TAT ACT CCA GTA TCA AGT    2023
Arg His Asn Val Tyr Ile Asn Gly Ile Thr Tyr Thr Pro Val Ser Ser
645                 650                 655                 660

ACA AAT GAA AAG GAT ATG TAC AGC TTC CTA GAG GAC ATG GGC TTA AAG    2071
Thr Asn Glu Lys Asp Met Tyr Ser Phe Leu Glu Asp Met Gly Leu Lys
                665                 670                 675

GCA TTC ACC AAC TCA AAG ATT CGT AAA CCC AAA ATG TGT CCA CAG CTT    2119
Ala Phe Thr Asn Ser Lys Ile Arg Lys Pro Lys Met Cys Pro Gln Leu
            680                 685                 690
```

FIG.7A-4

```
CAA CAG TAT GAA ATG CAT GGA CCT GAA GGT CTA CGT GTA GGT TTT TAT    2167
Gln Gln Tyr Glu Met His Gly Pro Glu Gly Leu Arg Val Gly Phe Tyr
        695                 700                 705

GAG TCA GAT GTA ATG GGA AGA GGC CAT GCA CGC CTG GTG CAT GTT GAA    2215
Glu Ser Asp Val Met Gly Arg Gly His Ala Arg Leu Val His Val Glu
        710                 715                 720

GAG CCT CAC ACG GAG ACC GTA CGA AAG TAC TTC CCT GAG ACA TGG ATC    2263
Glu Pro His Thr Glu Thr Val Arg Lys Tyr Phe Pro Glu Thr Trp Ile
725                 730                 735                 740

TGG GAT TTG GTG GTG GTA AAC TCA GCA GGG GTG GCT GAG GTA GGA GTA    2311
Trp Asp Leu Val Val Val Asn Ser Ala Gly Val Ala Glu Val Gly Val
                745                 750                 755

ACA GTC CCT GAC ACC ATC ACC GAG TGG AAG GCA GGG GCC TTC TGC CTG    2359
Thr Val Pro Asp Thr Ile Thr Glu Trp Lys Ala Gly Ala Phe Cys Leu
            760                 765                 770

TCT GAA GAT GCT GGA CTT GGT ATC TCT TCC ACT GCC TCT CTC CGA GCC    2407
Ser Glu Asp Ala Gly Leu Gly Ile Ser Ser Thr Ala Ser Leu Arg Ala
        775                 780                 785

TTC CAG CCC TTC TTT GTG GAG CTT ACA ATG CCT TAC TCT GTG ATT CGT    2455
Phe Gln Pro Phe Phe Val Glu Leu Thr Met Pro Tyr Ser Val Ile Arg
        790                 795                 800

GGA GAG GCC TTC ACA CTC AAG GCC ACG GTC CTA AAC TAC CTT CCC AAA    2503
Gly Glu Ala Phe Thr Leu Lys Ala Thr Val Leu Asn Tyr Leu Pro Lys
805                 810                 815                 820

TGC ATC CGG GTC AGT GTG CAG CTG GAA GCC TCT CCC GCC TTC CTT GCT    2551
Cys Ile Arg Val Ser Val Gln Leu Glu Ala Ser Pro Ala Phe Leu Ala
                825                 830                 835

GTC CCA GTG GAG AAG GAA CAA GCG CCT CAC TGC ATC TGT GCA AAC GGG    2599
Val Pro Val Glu Lys Glu Gln Ala Pro His Cys Ile Cys Ala Asn Gly
            840                 845                 850

CGG CAA ACT GTG TCC TGG GCA GTA ACC CCA AAG TCA TTA GGA AAT GTG    2647
Arg Gln Thr Val Ser Trp Ala Val Thr Pro Lys Ser Leu Gly Asn Val
        855                 860                 865
```

FIG. 7A-5

```
AAT TTC ACT GTG AGC GCA GAG GCA CTA GAG TCT CAA GAG CTG TGT GGG    2695
Asn Phe Thr Val Ser Ala Glu Ala Leu Glu Ser Gln Glu Leu Cys Gly
    870             875             880

ACT GAG GTG CCT TCA GTT CCT GAA CAC GGA AGG AAA GAC ACA GTC ATC    2743
Thr Glu Val Pro Ser Val Pro Glu His Gly Arg Lys Asp Thr Val Ile
885             890             895             900

AAG CCT CTG TTG GTT GAA CCT GAA GGA CTA GAG AAG GAA ACA ACA TTC    2791
Lys Pro Leu Leu Val Glu Pro Glu Gly Leu Glu Lys Glu Thr Thr Phe
                905             910             915

AAC TCC CTA CTT TGT CCA TCA GGT GGT GAG GTT TCT GAA GAA TTA TCC    2839
Asn Ser Leu Leu Cys Pro Ser Gly Gly Glu Val Ser Glu Glu Leu Ser
            920             925             930

CTG AAA CTG CCA CCA AAT GTG GTA GAA GAA TCT GCC CGA GCT TCT GTC    2887
Leu Lys Leu Pro Pro Asn Val Val Glu Glu Ser Ala Arg Ala Ser Val
        935             940             945

TCA GTT TTG GGA GAC ATA TTA GGC TCT GCC ATG CAA AAC ACA CAA AAT    2935
Ser Val Leu Gly Asp Ile Leu Gly Ser Ala Met Gln Asn Thr Gln Asn
    950             955             960

CTT CTC CAG ATG CCC TAT GGC TGT GGA GAG CAG AAT ATG GTC CTC TTT    2983
Leu Leu Gln Met Pro Tyr Gly Cys Gly Glu Gln Asn Met Val Leu Phe
965             970             975             980

GCT CCT AAC ATC TAT GTA CTG GAT TAT CTA AAT GAA ACA CAG CAG CTT    3031
Ala Pro Asn Ile Tyr Val Leu Asp Tyr Leu Asn Glu Thr Gln Gln Leu
                985             990             995

ACT CCA GAG GTC AAG TCC AAG GCC ATT GGC TAT CTC AAC ACT GGT TAC    3079
Thr Pro Glu Val Lys Ser Lys Ala Ile Gly Tyr Leu Asn Thr Gly Tyr
            1000            1005            1010

CAG AGA CAG TTG AAC TAC AAA CAC TAT GAT GGC TCC TAC AGC ACC TTT    3127
Gln Arg Gln Leu Asn Tyr Lys His Tyr Asp Gly Ser Tyr Ser Thr Phe
        1015            1020            1025

GGG GAG CGA TAT GGC AGG AAC CAG GGC AAC ACC TGG CTC ACA GCC TTT    3175
Gly Glu Arg Tyr Gly Arg Asn Gln Gly Asn Thr Trp Leu Thr Ala Phe
    1030            1035            1040
```

FIG. 7A-6

```
GTT CTG AAG ACT TTT GCC CAA GCT CGA GCC TAC ATC TTC ATC GAT GAA    3223
Val Leu Lys Thr Phe Ala Gln Ala Arg Ala Tyr Ile Phe Ile Asp Glu
1045            1050            1055            1060

GCA CAC ATT ACC CAA GCC CTC ATA TGG CTC TCC CAG AGG CAG AAG GAC    3271
Ala His Ile Thr Gln Ala Leu Ile Trp Leu Ser Gln Arg Gln Lys Asp
        1065            1070            1075

AAT GGC TGT TTC AGG AGC TCT GGG TCA CTG CTC AAC AAT GCC ATA AAG    3319
Asn Gly Cys Phe Arg Ser Ser Gly Ser Leu Leu Asn Asn Ala Ile Lys
        1080            1085            1090

GGA GGA GTA GAA GAT GAA GTG ACC CTC TCC GCC TAT ATC ACC ATC GCC    3367
Gly Gly Val Glu Asp Glu Val Thr Leu Ser Ala Tyr Ile Thr Ile Ala
        1095            1100            1105

CTT CTG GAG ATT CCT CTC ACA GTC ACT CAC CCT GTT GTC CGC AAT GCC    3415
Leu Leu Glu Ile Pro Leu Thr Val Thr His Pro Val Val Arg Asn Ala
    1110            1115            1120

CTG TTT TGC CTG GAG TCA GCC TGG AAG ACA GCA CAA GAA GGG GAC CAT    3463
Leu Phe Cys Leu Glu Ser Ala Trp Lys Thr Ala Gln Glu Gly Asp His
1125            1130            1135            1140

GGC AGC CAT GTA TAT ACC AAA GCA CTG CTG GCC TAT GCT TTT GCC CTG    3511
Gly Ser His Val Tyr Thr Lys Ala Leu Leu Ala Tyr Ala Phe Ala Leu
        1145            1150            1155

GCA GGT AAC CAG GAC AAG AGG AAG GAA GTA CTC AAG TCA CTT AAT GAG    3559
Ala Gly Asn Gln Asp Lys Arg Lys Glu Val Leu Lys Ser Leu Asn Glu
        1160            1165            1170

GAA GCT GTG AAG AAA GAC AAC TCT GTC CAT TGG GAG CGC CCT CAG AAA    3607
Glu Ala Val Lys Lys Asp Asn Ser Val His Trp Glu Arg Pro Gln Lys
        1175            1180            1185

CCC AAG GCA CCA GTG GGG CAT TTT TAC GAA CCC CAG GCT CCC TCT GCT    3655
Pro Lys Ala Pro Val Gly His Phe Tyr Glu Pro Gln Ala Pro Ser Ala
        1190            1195            1200

GAG GTG GAG ATG ACA TCC TAT GTG CTC CTC GCT TAT CTC ACG GCC CAG    3703
Glu Val Glu Met Thr Ser Tyr Val Leu Leu Ala Tyr Leu Thr Ala Gln
1205            1210            1215            1220
```

FIG. 7A-7

```
CCA GCC CCA ACC TCG GAG GAC CTG ACC TCT GCA ACC AAC ATC GTG AAG    3751
Pro Ala Pro Thr Ser Glu Asp Leu Thr Ser Ala Thr Asn Ile Val Lys
         1225            1230            1235

TGG ATC ACG AAG CAG CAG AAT GCC CAG GGC GGT TTC TCC TCC ACC CAG    3799
Trp Ile Thr Lys Gln Gln Asn Ala Gln Gly Gly Phe Ser Ser Thr Gln
         1240            1245            1250

GAC ACA GTG GTG GCT CTC CAT GCT CTG TCC AAA TAT GGA GCC GCC ACA    3847
Asp Thr Val Val Ala Leu His Ala Leu Ser Lys Tyr Gly Ala Ala Thr
         1255            1260            1265

TTT ACC AGG ACT GGG AAG GCT GCA CAG GTG ACT ATC CAG TCT TCA GGG    3895
Phe Thr Arg Thr Gly Lys Ala Ala Gln Val Thr Ile Gln Ser Ser Gly
     1270            1275            1280

ACA TTT TCC AGC AAA TTC CAA GTG GAC AAC AAC AAT CGC CTG TTA CTG    3943
Thr Phe Ser Ser Lys Phe Gln Val Asp Asn Asn Asn Arg Leu Leu Leu
1285            1290            1295            1300

CAG CAG GTC TCA TTG CCA GAG CTG CCT GGG GAA TAC AGC ATG AAA GTG    3991
Gln Gln Val Ser Leu Pro Glu Leu Pro Gly Glu Tyr Ser Met Lys Val
         1305            1310            1315

ACA GGA GAA GGA TGT GTC TAC CTC CAG ACC TCC TTG AAA TAC AAT ATT    4039
Thr Gly Glu Gly Cys Val Tyr Leu Gln Thr Ser Leu Lys Tyr Asn Ile
         1320            1325            1330

CTC CCA GAA AAG GAA GAG TTC CCC TTT GCT TTA GGA GTG CAG ACT CTG    4087
Leu Pro Glu Lys Glu Glu Phe Pro Phe Ala Leu Gly Val Gln Thr Leu
         1335            1340            1345

CCT CAA ACT TGT GAT GAA CCC AAA GCC CAC ACC AGC TTC CAA ATC TCC    4135
Pro Gln Thr Cys Asp Glu Pro Lys Ala His Thr Ser Phe Gln Ile Ser
         1350            1355            1360

CTA AGT GTC AGT TAC ACA GGG AGC CGC TCT GCC TCC AAC ATG GCG ATC    4183
Leu Ser Val Ser Tyr Thr Gly Ser Arg Ser Ala Ser Asn Met Ala Ile
1365            1370            1375            1380

GTT GAT GTG AAG ATG GTC TCT GGC TTC ATT CCC CTG AAG CCA ACA GTG    4231
Val Asp Val Lys Met Val Ser Gly Phe Ile Pro Leu Lys Pro Thr Val
         1385            1390            1395
```

FIG.7A-8

```
AAA ATG CTT GAA AGA TCT AAC CAT GTG AGC CGG ACA GAA GTC AGC AGC    4279
Lys Met Leu Glu Arg Ser Asn His Val Ser Arg Thr Glu Val Ser Ser
        1400            1405            1410

AAC CAT GTC TTG ATT TAC CTT GAT AAG GTG TCA AAT CAG ACA CTG AGC    4327
Asn His Val Leu Ile Tyr Leu Asp Lys Val Ser Asn Gln Thr Leu Ser
        1415            1420            1425

TTG TTC TTC ACG GTT CTG CAA GAT GTC CCA GTA AGA GAT CTC AAA CCA    4375
Leu Phe Phe Thr Val Leu Gln Asp Val Pro Val Arg Asp Leu Lys Pro
        1430            1435            1440

GCC ATA GTG AAA GTC TAT GAT TAC TAC GAG ACG GAT GAG TTT GCA ATC    4423
Ala Ile Val Lys Val Tyr Asp Tyr Tyr Glu Thr Asp Glu Phe Ala Ile
1445            1450            1455            1460

GCT GAG TAC AAT GCT CCT TGC AGC AAA GAT CTT GGA AAT GCT TGAAGACCA  4474
Ala Glu Tyr Asn Ala Pro Cys Ser Lys Asp Leu Gly Asn Ala
        1465            1470            1

CAAGGCTGAA AAGTGCTTTG CTGGAGTCCT GTTCTCTGAG CTCCACAGAA GACACGTGTT  4534
TTTGTATCTT TAAAGACTTG ATGAATAAAC ACTTTTTCTG GTC                    4577
```

FIG.7A-9

Ser Val Ser Gly Lys Pro Gln Tyr Met Val Leu Val Pro Ser Leu Leu
1               5                       10                      15
His Thr Glu Thr Thr Glu Lys Gly Cys Val Leu Leu Ser Tyr Leu Asn
                20                      25                      30
Glu Thr Val Thr Val Ser Ala Ser Leu Glu Ser Val Arg Gly Asn Arg
            35                      40                      45
Ser Leu Phe Thr Asp Leu Glu Ala Glu Asn Asp Val Leu His Cys Val
        50                      55                      60
Ala Phe Ala Val Pro Lys Ser Ser Asn Glu Glu Val Met Phe Leu
65                      70                      75                  80
Thr Val Gln Val Lys Gly Pro Thr Gln Glu Phe Lys Lys Arg Thr Thr
                85                      90                      95
Val Met Val Lys Asn Glu Asp Ser Leu Val Phe Val Gln Thr Asp Lys
                100                     105                     110
Ser Ile Tyr Lys Pro Gly Gln Thr Val Lys Phe Arg Val Val Ser Met
            115                     120                     125
Asp Glu Asn Phe His Pro Leu Asn Glu Leu Ile Pro Leu Val Tyr Ile
        130                     135                     140
Gln Asp Pro Lys Gly Asn Arg Ile Ala Gln Trp Gln Ser Phe Gln Leu
145                     150                     155                 160
Glu Gly Gly Leu Lys Gln Phe Ser Phe Pro Leu Ser Ser Glu Pro Phe
                165                     170                     175
Gln Gly Ser Tyr Lys Val Val Gln Lys Ser Gly Gly Arg Thr
            180                     185                     190
Glu His Pro Phe Thr Val Glu Glu Phe Val Leu Pro Lys Phe Glu Val
        195                     200                     205
Gln Val Thr Val Pro Lys Ile Ile Thr Ile Leu Glu Glu Met Asn
            210                     215                     220
Val Ser Val Cys Gly Leu Tyr Thr Tyr Gly Lys Pro Val Pro Gly His
225                     230                     235                 240
Val Thr Val Ser Ile Cys Arg Lys Tyr Ser Asp Ala Ser Asp Cys His
                245                     250                     255
Gly Glu Asp Ser Gln Ala Phe Cys Glu Lys Phe Ser Gly Gln Leu Asn
            260                     265                     270
Ser His Gly Cys Phe Tyr Gln Gln Val Lys Thr Lys Val Phe Gln Leu
        275                     280                     285
Lys Arg Lys Glu Tyr Glu Met Lys Leu His Thr Glu Ala Gln Ile Gln
    290                     295                     300
Glu Glu Gly Thr Val Val Glu Leu Thr Gly Arg Gln Ser Ser Glu Ile
305                     310                     315                 320

FIG.7B-1

```
Thr Arg Thr Ile Thr Lys Leu Ser Phe Val Lys Val Asp Ser His Phe
            325             330             335
Arg Gln Gly Ile Pro Phe Phe Gly Gln Val Arg Leu Val Asp Gly Lys
            340             345             350
Gly Val Pro Ile Pro Asn Lys Val Ile Phe Ile Arg Gly Asn Glu Ala
            355             360             365
Asn Tyr Tyr Ser Asn Ala Thr Thr Asp Glu His Gly Leu Val Gln Phe
        370             375             380
Ser Ile Asn Thr Thr Asn Val Met Gly Thr Ser Leu Thr Val Arg Val
385             390             395                         400
Asn Tyr Lys Asp Arg Ser Pro Cys Tyr Gly Tyr Gln Trp Val Ser Glu
                405             410             415
Glu His Glu Glu Ala His His Thr Ala Tyr Leu Val Phe Ser Pro Ser
                420             425             430
Lys Ser Phe Val His Leu Glu Pro Met Ser His Glu Leu Pro Cys Gly
            435             440             445
His Thr Gln Thr Val Gln Ala His Tyr Ile Leu Asn Gly Gly Thr Leu
        450             455             460
Leu Gly Leu Lys Lys Leu Ser Phe Tyr Tyr Leu Ile Met Ala Lys Gly
465             470             475                         480
Gly Ile Val Arg Thr Gly Thr His Gly Leu Leu Val Lys Gln Glu Asp
                485             490             495
Met Lys Gly His Phe Ser Ile Ser Ile Pro Val Lys Ser Asp Ile Ala
            500             505             510
Pro Val Ala Arg Leu Leu Ile Tyr Ala Val Leu Pro Thr Gly Asp Val
            515             520             525
Ile Gly Asp Ser Ala Lys Tyr Asp Val Glu Asn Cys Leu Ala Asn Lys
        530             535             540
Val Asp Leu Ser Phe Ser Pro Ser Gln Ser Leu Pro Ala Ser His Ala
545             550             555                         560
His Leu Arg Val Thr Ala Ala Pro Gln Ser Val Cys Ala Leu Arg Ala
                565             570             575
Val Asp Gln Ser Val Leu Leu Met Lys Pro Asp Ala Glu Leu Ser Ala
            580             585             590
Ser Ser Val Tyr Asn Leu Leu Pro Glu Lys Asp Leu Thr Gly Phe Pro
        595             600             605
Gly Pro Leu Asn Asp Gln Asp Asp Glu Asp Cys Ile Asn Arg His Asn
        610             615             620
Val Tyr Ile Asn Gly Ile Thr Tyr Thr Pro Val Ser Ser Thr Asn Glu
625             630             635                         640
Lys Asp Met Tyr Ser Phe Leu Glu Asp Met Gly Leu Lys Ala Phe Thr
                645             650             655
```

FIG.7B-2

```
Asn Ser Lys Ile Arg Lys Pro Lys Met Cys Pro Gln Leu Gln Gln Tyr
            660                 665                 670
Glu Met His Gly Pro Glu Gly Leu Arg Val Gly Phe Tyr Glu Ser Asp
            675                 680                 685
Val Met Gly Arg Gly His Ala Arg Leu Val His Val Glu Glu Pro His
690             695                 700
Thr Glu Thr Val Arg Lys Tyr Phe Pro Glu Thr Trp Ile Trp Asp Leu
705                 710                 715                 720
Val Val Val Asn Ser Ala Gly Val Ala Glu Val Gly Val Thr Val Pro
            725                 730                 735
Asp Thr Ile Thr Glu Trp Lys Ala Gly Ala Phe Cys Leu Ser Glu Asp
            740                 745                 750
Ala Gly Leu Gly Ile Ser Ser Thr Ala Ser Leu Arg Ala Phe Gln Pro
            755                 760                 765
Phe Phe Val Glu Leu Thr Met Pro Tyr Ser Val Ile Arg Gly Glu Ala
            770                 775                 780
Phe Thr Leu Lys Ala Thr Val Leu Asn Tyr Leu Pro Lys Cys Ile Arg
785                 790                 795                 800
Val Ser Val Gln Leu Glu Ala Ser Pro Ala Phe Leu Ala Val Pro Val
            805                 810                 815
Glu Lys Glu Gln Ala Pro His Cys Ile Cys Ala Asn Gly Arg Gln Thr
            820                 825                 830
Val Ser Trp Ala Val Thr Pro Lys Ser Leu Gly Asn Val Asn Phe Thr
            835                 840                 845
Val Ser Ala Glu Ala Leu Glu Ser Gln Glu Leu Cys Gly Thr Glu Val
            850                 855                 860
Pro Ser Val Pro Glu His Gly Arg Lys Asp Thr Val Ile Lys Pro Leu
865                 870                 875                 880
Leu Val Glu Pro Glu Gly Leu Glu Lys Glu Thr Thr Phe Asn Ser Leu
                    885                 890                 895
Leu Cys Pro Ser Gly Gly Glu Val Ser Glu Glu Leu Ser Leu Lys Leu
                    900                 905                 910
Pro Pro Asn Val Val Glu Glu Ser Ala Arg Ala Ser Val Ser Val Leu
            915                 920                 925
Gly Asp Ile Leu Gly Ser Ala Met Gln Asn Thr Gln Asn Leu Leu Gln
            930                 935                 940
Met Pro Tyr Gly Cys Gly Glu Gln Asn Met Val Leu Phe Ala Pro Asn
945                 950                 955                 960
Ile Tyr Val Leu Asp Tyr Leu Asn Glu Thr Gln Gln Leu Thr Pro Glu
                    965                 970                 975
Val Lys Ser Lys Ala Ile Gly Tyr Leu Asn Thr Gly Tyr Gln Arg Gln
            980                 985                 990
```

FIG.7B-3

```
Leu Asn Tyr Lys His Tyr Asp Gly Ser Tyr Ser Thr Phe Gly Glu Arg
        995                 1000                1005
Tyr Gly Arg Asn Gln Gly Asn Thr Trp Leu Thr Ala Phe Val Leu Lys
    1010                1015                1020
Thr Phe Ala Gln Ala Arg Ala Tyr Ile Phe Ile Asp Glu Ala His Ile
025                 1030                1035                1040
Thr Gln Ala Leu Ile Trp Leu Ser Gln Arg Gln Lys Asp Asn Gly Cys
            1045                1050                1055
Phe Arg Ser Ser Gly Ser Leu Leu Asn Asn Ala Ile Lys Gly Gly Val
            1060                1065                1070
Glu Asp Glu Val Thr Leu Ser Ala Tyr Ile Thr Ile Ala Leu Leu Glu
        1075                1080                1085
Ile Pro Leu Thr Val Thr His Pro Val Val Arg Asn Ala Leu Phe Cys
        1090                1095                1100
Leu Glu Ser Ala Trp Lys Thr Ala Gln Glu Gly Asp His Gly Ser His
105                 1110                1115                1120
Val Tyr Thr Lys Ala Leu Leu Ala Tyr Ala Phe Ala Leu Ala Gly Asn
            1125                1130                1135
Gln Asp Lys Arg Lys Glu Val Leu Lys Ser Leu Asn Glu Glu Ala Val
            1140                1145                1150
Lys Lys Asp Asn Ser Val His Trp Glu Arg Pro Gln Lys Pro Lys Ala
            1155                1160                1165
Pro Val Gly His Phe Tyr Glu Pro Gln Ala Pro Ser Ala Glu Val Glu
        1170                1175                1180
Met Thr Ser Tyr Val Leu Leu Ala Tyr Leu Thr Ala Gln Pro Ala Pro
185                 1190.               1195                1200
Thr Ser Glu Asp Leu Thr Ser Ala Thr Asn Ile Val Lys Trp Ile Thr
            1205                1210                1215
Lys Gln Gln Asn Ala Gln Gly Gly Phe Ser Ser Thr Gln Asp Thr Val
            1220                1225                1230
Val Ala Leu His Ala Leu Ser Lys Tyr Gly Ala Ala Thr Phe Thr Arg
            1235                1240                1245
Thr Gly Lys Ala Ala Gln Val Thr Ile Gln Ser Ser Gly Thr Phe Ser
        1250                1255                1260
Ser Lys Phe Gln Val Asp Asn Asn Asn Arg Leu Leu Leu Gln Gln Val
265                 1270                1275                1280
Ser Leu Pro Glu Leu Pro Gly Glu Tyr Ser Met Lys Val Thr Gly Glu
            1285                1290                1295
Gly Cys Val Tyr Leu Gln Thr Ser Leu Lys Tyr Asn Ile Leu Pro Glu
        1300                1305                1310
Lys Glu Glu Phe Pro Phe Ala Leu Gly Val Gln Thr Leu Pro Gln Thr
            1315                1320                1325
```

FIG.7B-4

```
Cys Asp Glu Pro Lys Ala His Thr Ser Phe Gln Ile Ser Leu Ser Val
     1330              1335                 1340
Ser Tyr Thr Gly Ser Arg Ser Ala Ser Asn Met Ala Ile Val Asp Val
 345              1350                 1355                 1360
Lys Met Val Ser Gly Phe Ile Pro Leu Lys Pro Thr Val Lys Met Leu

Glu Arg Ser Asn His Val Ser Arg Thr Glu Val Ser Ser Asn His Val

Leu Ile Tyr Leu Asp Lys Val Ser Asn Gln Thr Leu Ser Leu Phe Phe

Thr Val Leu Gln Asp Val Pro Val Arg Asp Leu Lys Pro Ala Ile Val
     1410              1415                 1420
Lys Val Tyr Asp Tyr Tyr Glu Thr Asp Glu Phe Ala Ile Ala Glu Tyr
 425              1430                 1435                 1440
Asn Ala Pro Cys Ser Lys Asp Leu Gly Asn Ala
         1445                 1450
```

FIG.7B-5

COMPLEXES OF ALPHA (2) MACROGLOBULIN AND ANTIGENIC MOLECULES FOR IMMUNOTHERAPY

The present application is a continuation-in-part of U.S. patent application Ser. No. 09/625,139, filed Jul. 25, 2000, now abandoned, which claims benefit under 35 U.S.C. §119 (e) of U.S. Provisional Patent Application Ser. No. 60/209, 266, filed Jun. 2, 2000, both of which are incorporated by reference herein in their entireties.

This invention was made with government support under grant number CA64394 awarded by the National Institutes of Health. The government has certain rights in the invention.

1. INTRODUCTION

The present invention relates to complexes of alpha (2) macroglobulin associated with antigenic molecules for use in immunotherapy. The invention relates to methods for using such compositions in the diagnosis and treatment of immune disorders, proliferative disorders, and infectious diseases.

2. BACKGROUND OF THE INVENTION

2.1. Heat Shock Proteins

Heat shock proteins (HSPs), also referred to as stress proteins, were first identified as proteins synthesized by cells in response to heat shock. Hsps have classified into five families, based on molecular weight, Hsp100, Hsp90, Hsp70, Hsp60, and smHsp. Many members of these families were found subsequently to be induced in response to other stressful stimuli including nutrient deprivation, metabolic disruption, oxygen radicals, and infection with intracellular pathogens (see Welch, May 1993, Scientific American 56-64; Young, 1990, Annu. Rev. Immunol. 8:401-420; Craig, 1993, Science 260:1902-1903; Gething et al., 1992, Nature 355:33-45; and Lindquist et al., 1988, Annu. Rev. Genetics 22:631-677).

Heat shock proteins are among the most highly conserved proteins in existence. For example, DnaK, the Hsp70 from *E. coli* has about 50% amino acid sequence identity with Hsp70 proteins from excoriates (Bardwell et al., 1984, Proc. Natl. Acad. Sci. 81:848-852). The Hsp60 and Hsp90 families also show similarly high levels of intra-family conservation (Hickey et al., 1989, Mol. Cell. Biol. 9:2615-2626; Jindal, 1989, Mol. Cell. Biol. 9:2279-2283). In addition, it has been discovered that the Hsp60, Hsp70 and Hsp90 families are composed of proteins that are related to the stress proteins in sequence, for example, having greater than 35% amino acid identity, but whose expression levels are not altered by stress.

Studies on the cellular response to heat shock and other physiological stresses revealed that the HSPs are involved not only in cellular protection against these adverse conditions, but also in essential biochemical and immunological processes in unstressed cells. Hsps accomplish different kinds of chaperoning functions. For example, members of the Hsp70 family, located in the cell cytoplasm, nucleus, mitochondria, or endoplasmic reticulum (Lindquist et al., 1988, Ann. Rev. Genetics 22:631-677), are involved in the presentation of antigens to the cells of the immune system, and are also involved in the transfer, folding and assembly of proteins in normal cells. Hsps are capable of binding proteins or peptides, and releasing the bound proteins or peptides in the presence of adenosine triphosphate (ATP) or low pH.

2.2. Immunogenicity of Hsp-peptide Complexes

Srivastava et al. demonstrated immune response to methylcholanthrene-induced sarcomas of inbred mice (1988, Immunol. Today 9:78-83). In these studies, it was found that the molecules responsible for the individually distinct immunogenicity of these tumors were glycoproteins of 96 kDa (gp96) and intracellular proteins of 84 to 86 kDa (Srivastava et al., 1986, Proc. Natl. Acad. Sci. USA 83:3407-3411; Ullrich et al., 1986, Proc. Natl. Acad. Sci. USA 83:3121-3125). Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counterparts of the same heat shock proteins (Srivastava et al., 1988, Immunogenetics 28:205-207; Srivastava et al., 1991, Curr. Top. Microbiol. Immunol. 167:109-123). Further, Hsp70 was shown to elicit immunity to the tumor from which it was isolated but not to antigenically distinct tumors. However, Hsp70 depleted of peptides was found to lose its immunogenic activity (Udono and Srivastava, 1993, J. Exp. Med. 178:1391-1396). These observations suggested that the heat shock proteins are not immunogenic per se, but form noncovalent complexes with antigenic peptides, and the complexes can elicit specific immunity to the antigenic peptides (Srivastava, 1993, Adv. Cancer Res. 62:153-177; Udono et al., 1994, J. Immunol., 152:5398-5403; Suto et al., 1995, Science 269:1585-1588).

Noncovalent complexes of HSPs and peptide, purified from cancer cells, can be used for the treatment and prevention of cancer and have been described in PCT publications WO 96/10411, dated Apr. 11, 1996, and WO 97/10001, dated Mar. 20, 1997 (U.S. Pat. No. 5,750,119 issued Apr. 12, 1998, and U.S. Pat. No. 5,837,251 issued Nov. 17, 1998, respectively, each of which is incorporated by reference herein in its entirety). The isolation and purification of stress protein-antigen complexes has been described, for example, from pathogen-infected cells, and used for the treatment and prevention of infection caused by the pathogen, such as viruses, and other intracellular pathogens, including bacteria, protozoa, fungi and parasites (see, for example, PCT Publication WO 95/24923, dated Sep. 21, 1995). Immunogenic stress protein-antigen complexes can also be prepared by in vitro complexing of stress protein and antigenic peptides, and the uses of such complexes for the treatment and prevention of cancer and infectious diseases has been described in PCT publication WO 97/10000, dated Mar. 20, 1997 (U.S. Pat. No. 6,030,618 issued Feb. 29, 2000. The use of stress protein-antigen complexes for sensitizing antigen presenting cells in vitro for use in adoptive immunotherapy is described in PCT publication WO 97/10002, dated Mar. 20, 1997 (see also U.S. Pat. No. 5,985,270 issued Nov. 16, 1999).

2.3. Alpha (2) Macroglobulin Receptor

The α-macroglobulins are members of a protein superfamily of structurally related proteins which also comprises complement components C3, C4 and C5. The human plasma protein alpha (2) macroglobulin (α2M) is a 720 kDa homotetrameric protein primarily known as proteinase inhibitor and plasma and inflammatory fluid proteinase scavenger molecule (for review see Chu and Pizzo, 1994, Lab. Invest. 71:792). Alpha (2) macroglobulin is synthesized as a 1474 amino acid precursor, the first 23 of which function as a signal sequence that is cleaved to yield a 1451 amino acid mature protein (Kan et al., 1985, Proc. Natl. Acad. Sci. U.S.A. 82:2282-2286).

Alpha (2) macroglobulin promiscuously binds to proteins and peptides with nucleophilic amino acid side chains in a covalent manner (Chu et al., 1994, Ann. N.Y. Acad. Sci.

737:291-307) and targets them to cells which express the α2M receptor (α2MR) (Chu and Pizzo, 1993, J. Immunol. 150:48). Binding of α2M to the α2M receptor is mediated by the C-terminal portion of α2M (Holtet et al., 1994, FEBS Lett. 344:242-246) and key residues have been identified (Nielsen et al., 1996, J. Biol. Chem. 271:12909-12912).

Generally known for inhibiting protease activity, α2M binds to a variety of proteases thorough multiple binding sites (see, e.g., Hall et al., 1981, Biochem. Biophys. Res. Commun. 100(1):8-16). Protease interaction with α2M results in a complex structural rearrangement called transformation, which is the result of a cleavage within the "bait" region of α2M after the proteinase becomes "trapped" by thioesters. The conformational change exposes residues required for receptor binding, allowing the α2M-proteinase complex to bind to the α2MR. Methylamine can induce similar conformational changes and cleavage as that induced by proteinases. The uncleaved form of α2M, which is not recognized by the receptor, is often referred to as the "slow" form (s-α2M). The cleaved form is referred to as the "fast" form (f-α2M) (reviewed by Chu et al., 1994, Ann. N.Y. Acad. Sci. 737:291-307).

Studies have shown that in addition to its proteinase-inhibitory functions, α2M, when complexed to antigens, can enhance the antigens' ability to be taken up by antigen presenting cells such as macrophages and presented to T cell hybridomas in vitro by up to two orders of magnitude (Chu and Pizzo, 1994, Lab. Invest. 71:792), and induce T cell proliferation (Osada et al., 1987, Biochem. Biophys. Res. Commun.146:26-31). Further evidence suggests that complexing antigen with α2M enhances antibody production by crude spleen cells in vitro (Osada et al., 1988, Biochem. Biophys. Res. Commun. 150:883) elicits an in vivo antibody responses in experimental rabbits (Chu et al., 1994, J. Immunol. 152:1538-1545) and mice (Mitsuda et al., 1993, Biochem. Biophys. Res. Commun. 101:1326-1331). However, none of these studies have shown whether alpha 2M-antigen complexes are capable of eliciting cytotoxic T cell responses in vivo.

2.4. Immunogenicity of Heat Shock/Stress Proteins

Srivastava et al. demonstrated immune response to methylcholanthrene-induced sarcomas of inbred mice (1988, Immunol. Today 9:78-83). In these studies, it was found that the molecules responsible for the individually distinct immunogenicity of these tumors were identified as cell-surface glycoproteins of 96 kDa (gp96) and intracellular proteins of 84 to 86 kDa (Srivastava et al., 1986, Proc. Natl. Acad. Sci. USA 83:3407-3411; Ullrich, S. J. et al., 1986, Proc. Natl. Acad. Sci. USA 83:3121-3125). Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counterparts of the same heat shock proteins (Srivastava et al., 1988, Immunogenetics 28:205-207; Srivastava et al., 1991, Curr. Top. Microbiol. Immunol. 167:109-123). Further, Hsp70 was shown to elicit immunity to the tumor from which it was isolated but not to antigenically distinct tumors. However, Hsp70 depleted of peptides was found to lose its immunogenic activity (Udono and Srivastava, 1993, J. Exp. Med. 178:1391-1396). These observations suggested that the heat shock proteins are not immunogenic per se, but form noncovalent complexes with antigenic peptides, and the complexes can elicit specific immunity to the antigenic peptides (Srivastava, 1993, Adv. Cancer Res. 62:153-177; Udono et al., 1994, J. Immunol., 152:5398-5403; Suto et al., 1995, Science, 269:1585-1588).

The use of noncovalent complexes of stress proteins and peptides, purified from cancer cells, for the treatment and prevention of cancer, as well as the use of such complexes in combination with adoptive immunotherapy, has been described (see U.S. Pat. No. 5,750,199; U.S. Pat. No. 5,830,464; Patent Cooperation Treaty ("PCT") publications WO 96/10411, dated Apr. 11, 1996; and WO 97/10001, dated Mar. 20, 1997; each of which is incorporated by reference herein in its entirety. The purification of stress protein-peptide complexes from cell lysates has been described previously; stress protein-peptide complexes can be isolated from pathogen-infected cells and used for the treatment and prevention of infection caused by pathogens, such as viruses and other intracellular pathogens, including bacteria, protozoa, fungi and parasites (see PCT publication WO 95/24923, dated Sep. 21, 1995).

Immunogenic stress protein-peptide complexes can also be prepared by in vitro complexing of stress protein and antigenic peptides, and the uses of such complexes for the treatment and prevention of infectious diseases and cancer has been described in PCT publication WO 97/10000, dated Mar. 20, 1997. The use of heat shock proteins in combination with a defined antigen for the treatment of infectious diseases and cancer have also been described in PCT publication WO 97/06821, dated Feb. 27, 1997. The administration of expressible polynucleotides encoding eukaryotic heat shock proteins to mammalian cells for stimulating an immune response, and for treatment of infectious diseases and cancer has been described in PCT publications, WO 97/06685 and WO 97/06828, both dated Feb. 27, 1997. The use of stress protein-peptide complexes for sensitizing antigen presenting cells in vitro for use in adoptive immunotherapy is described in PCT publication WO 97/10002, dated Mar. 20, 1997.

2.5. Antigen Presentation

Major histocompatibility complex (MHC) molecules present antigens on the cell surface of antigen-presenting cells. Cytotoxic T lymphocytes (CTLs) then recognize MHC molecules and their associated peptides and kill the target cell. Antigens are processed by two distinct antigen processing routes depending upon whether their origin is intracellular or extracellular. Intracellular or endogenous protein antigens, i.e., antigens synthesized within the antigen-presenting cell, are presented by MHC class I (MHC I) molecules to CD8+cytotoxic T lymphocytes. On the other hand, extracellular or exogenously synthesized antigenic determinants are presented on the cell surface of "specialized" or "professional" APCs (macrophages, for example) by MHC class II molecules to CD4+ T cells (see, generally, Fundamental Immunology, W. E. Paul (ed.), New York: Raven Press, 1984). This compartmental segregation of antigen processing routes is important to prevent tissue destruction that could otherwise occur during an immune response as a result of shedding of neighboring cell MHC I antigens.

The heat shock protein gp96 chaperones a wide array of peptides, depending upon the source from which gp96 is isolated (for review, see Srivastava et al., 1998, Immunity 8: 657-665). Tumor-derived gp96 carries tumor-antigenic peptides (Ishii et al., 1999, J. Immunology 162:1303-1309); gp96 preparations from virus-infected cells carry viral epitopes (Suto and Srivastava, 1995, Science 269:1585-1588; Nieland et al., 1998, Proc. Natl. Acad. Sci. USA 95:1800-1805), and gp96 preparations from cells transfected with model antigens such as ovalbumin or β-galactosidase are associated with the corresponding epitopes (Arnold et al., 1995, J. Exp. Med.182: 885-889; Breloer et al., 1998, Eur. J. Immunol. 28:1016-1021). The association of gp96 with peptides occurs in vivo (Menoret and Srivastava, 1999, Biochem. Biophys. Research Commun. 262:813-818). Gp96-peptide complexes, whether isolated from cells (Tamura et al., 1997, Science 278:117-120), or reconstituted in vitro (Blachere et al., 1997, J. Exp. Med. 186:1183-1406) are excellent immunogens and have been used extensively to elicit CD8+ T cell responses specific for the gp96-chaperoned antigenic peptides.

The capacity of gp96-peptide complexes to elicit an immune response is dependent upon the transfer of the peptide to MHC class I molecules of antigen-presenting cells (Suto and Srivastava, 1995, supra). Endogenously synthesized antigens chaperoned by gp96 in the endoplasmic reticulum [ER] can prime antigen-specific CD8+ T cells (or MHC I-restricted CTLs) in vivo; this priming of CD8+ T cells requires macrophages. However, the process whereby exogenously introduced gp96-peptide complexes elicit the antigen-specific CD8+ T cell response is not completely understood since there is no established pathway for the translocation of extracellular antigens into the class I presentation machinery. Yet antigenic peptides of extracellular origin associated with HSPs are somehow salvaged by macrophages, channeled into the endogenous pathway, and presented by MHC I molecules to be recognized by CD8+lymphocytes (Suto and Srivastava, 1995, supra; Blachere et al., 1997, J. Exp. Med. 186:1315-22).

Several models have been proposed to explain the delivery of extracellular peptides for antigen presentation. One proposal, known as the "direct transfer" model, suggests that HSP-chaperoned peptides are transferred to MHC I molecules on the cell surface of macrophages for presentation to CD8+ T lymphocytes. Another suggestion is that soluble extracellular proteins can be trafficked to the cytosol via constitutive macropinocytosis in bone marrow-derived macrophages and dendritic cells (Norbury et al., 1997, Eur. J. Immunol. 27:280-288). Yet another proposed mechanism is that HSPs are taken up by the MHC class I molecules of the macrophage, which stimulate the appropriate T cells (Srivastava et al., 1994, Immunogenetics 39:93-98. Others have suggested that a novel intracellular trafficking pathway may be involved for the transport of peptides from the extracellular medium into the lumen of ER (Day et al., 1997, Proc. Natl. Acad. Sci. 94:8064-8069; Nicchitta, 1998, Curr. Opin. in Immunol. 10:103-109). Further suggestions include the involvement of phagocytes which (a) possess an ill-defined pathway to shunt protein from the phagosome into the cytosol where it would enter the normal class I pathway; (b) digest ingested material in lysosomes and regurgitate peptides for loading on the surface to class I molecules (Bevan, 1995, J. Exp. Med. 182:639-41).

Still others have proposed a receptor-mediated pathway for the delivery of extracellular peptides to the cell surface of APS for antigen presentation. In view of the extremely small quantity of gp96-chaperoned antigenic peptides required for immunization (Blachere et al., 1997, supra), and the strict dependence of immunogenicity of gp96-peptide complexes on functional antigen presenting cells (APCs) (Udono et al., 1994, Proc. Natl. Acad. Sci. U.S.A. 91:3077-3081), APCs had been proposed to possess receptors for gp96 (Srivastava et al., 1994, Immunogenetics 39:93-98). Preliminary microscopic evidence consistent with such receptors has been recently obtained (Binder et al., 1998, Cell Stress & Chaperones 3 (Supp.1):2.; Arnold-Schild et al., 1999, J. Immunol. 162: 3757-3760; and Wassenberg et al., 1999, J. Cell Sci. 1:12). One hypothesis is that the mannose receptor is used in the uptake of gp96, but no mechanism has been proposed for the non-glycosylated HSPs, such as Hsp70 (Ciupitu et al., 1998, J. Exp. Med., 187:685-691).

The identification and characterization of specific molecules involved in HSP-mediated antigen presentation of peptides, could provide useful reagents and techniques for eliciting specific immunity by HSP and HSP-peptide complexes, and for developing novel diagnostic and therapeutic methods.

Citation or discussion of a reference herein shall not be construed as an admission that such is prior art to the present invention.

3. SUMMARY OF THE INVENTION

The present invention provides complexes comprising alpha (2) macroglobulin ("α2M") and methods for their use in immunotherapy. The invention is based, in part, on the Applicant's discovery that α2M directly competes for the binding of heat shock protein gp96 to the α2M receptor, indicating that α2M and HSPs may bind to a common recognition site on the alpha (2) macroglobulin receptor. Thus, because HSPs and α2M have a number of common functional attributes, such as the ability to bind peptides and the recognition and uptake by the alpha (2) macroglobulin receptor, the Applicants have discovered that α2M can be used in the methods described herein for immunotherapy against cancer and infectious disease. Alpha-2-macroglobulin can form complexes with antigens, which are taken up by antigen presenting cells ("APCs") via the alpha (2) macroglobulin receptor, also known as LDL (low-density lipoprotein) Receptor-Related Protein ("LRP") or CD91. Thus, the invention provides methods and compositions for using specific α2M-antigenic molecule complexes for targeting an immune response against immune disorders, proliferative disorders, and infectious diseases.

The invention encompasses complexes of alpha (2) macroglobulin noncovalently associated antigenic molecules, recombinant cells that express the complexes of α2M associated with antigenic molecules, and antibodies and other molecules that specifically recognize α2M-antigenic molecule complexes. The invention also provides methods for using these compositions in the diagnosis and treatment of immune disorders, proliferative disorders, and infectious diseases.

As used herein, an alpha (2) macroglobulin is associated with an antigenic molecule is bound to the antigenic molecule by a covalent or noncovalent bond. A covalent bond can be a peptide bond or a thioester linkage, for example. Thus, fusion proteins between alpha (2) macroglobulin and an antigenic molecule are within the scope of the invention.

The invention provides a pharmaceutical composition comprising an amount of a molecular complex effective for treatment or prevention of an infectious disease or cancer, and a pharmaceutically acceptable carrier, said molecular complex comprising an alpha (2) macroglobulin polypeptide noncovalently associated with an antigenic molecule which displays the antigenicity of an antigen of an infectious agent or an antigen overexpressed in a cancer cell relative to its expression in a noncancerous cell of said cell type. As used herein a cell type of a cancer cell, refers to the cell type of the tissue of origin, e.g., breast, lung, ovarian. In one embodiment, the antigenic molecule displays the antigenicity of an antigen of an infectious agent. In another embodiment, the antigenic molecule displays the antigenicity of an antigen overexpressed in a cancer cell relative to its expression in a noncancerous cell of said cell type. In another embodiment, the antigenic molecule is a tumor specific antigen or a tumor-associated antigen. In another embodiment, the antigenic molecule displays the antigenicity of an antigen overexpressed in a cancer cell relative to its expression in a noncancerous cell of said cell type.

In another embodiment, the molecular complex effective for treatment or prevention of an infectious disease or cancer, comprising the alpha (2) macroglobulin polypeptide noncovalently associated with the antigenic molecule is purified. In particular, the term "purified" molecular complexes refer to complexes which are at least 65% 75%, 80%, 85%, 90%, 95%, 98% or 100% noncovalent complexes of the alpha (2) macroglobulin polypeptide and the antigenic molecule. In another embodiment, the purified molecular complex comprising an alpha (2) macroglobulin polypeptide associated with an antigenic molecule of an infectious agent or an antigen overexpressed in a cancer cell relative to its expression in a noncancerous cell of said cell type.

The invention further provides a purified population of molecular complexes in which at least 65%, 70%, 75%, 80%, 85%, 90%, 95%, 98%, or 100% of the complexes comprise an alpha (2) macroglobulin noncovalently associated with an antigenic molecule. Also provided by the invention is a purified population of molecular complexes purified from a recombinant cell in which at least 65%, 70%, 75%, 80%, 85%, 90%, 95%, 98%, or 100% of the complexes comprise an alpha (2) macroglobulin noncovalently associated with an antigenic molecule.

The invention also provides a recombinant cell infected with a pathogen and transformed with a nucleic acid comprising a nucleotide sequence that (i) is operably linked to a promoter, and (ii) encodes an alpha (2) macroglobulin polypeptide, which alpha (2) macroglobulin polypeptide associates with an antigenic molecule, when said antigenic molecule is present, to form a complex that in sufficient amount is capable of eliciting an immune response to the antigenic molecule. The invention provides a recombinant cancer cell transformed with a nucleic acid comprising a nucleotide sequence that (i) is operably linked to a promoter, and (ii) encodes an alpha (2) macroglobulin polypeptide, which alpha (2) macroglobulin polypeptide associates with an antigenic molecule, when said antigen is present, to form a complex that in sufficient amount is capable of eliciting an immune response to the antigenic molecule. In another embodiment, the invention provides a recombinant cell transformed with (i) a first nucleic acid comprising a first nucleotide sequence that is operably linked to a first promoter and encodes an alpha (2) macroglobulin polypeptide, and (ii) a second nucleic acid comprising a second nucleotide sequence that is operably linked to a second promoter and encodes an antigenic molecule, such that the alpha (2) macroglobulin polypeptide and the antigenic molecule are expressed within the cell and associate with each other to form a complex that in sufficient amount is capable of eliciting an immune response to the antigenic molecule. In various embodiments, the recombinant cells are human cells. In various embodiments, the pharmaceutical composition comprises a recombinant cell and a pharmaceutically acceptable carrier.

In one embodiment, a method is provided for preparing a complex of an alpha (2) macroglobulin polypeptide noncovalently associated with an antigenic molecule, said alpha (2) macroglobulin polypeptide comprising: (a) culturing a cell transformed with a nucleic acid comprising a nucleotide sequence encoding the alpha (2) macroglobulin polypeptide, under conditions such that said alpha (2) macroglobulin polypeptide is expressed by the cells and associates with an antigenic molecule of the cell; and (b) recovering a population of complexes of the alpha (2) macroglobulin polypeptide noncovalently associated with antigenic molecules from the cells.

The invention further provides a method for preparing an alpha (2) macroglobulin polypeptide noncovalently associated with antigenic molecules derived from one or more antigens of an infectious agent, comprising: culturing infected cells, transformed with a nucleic acid comprising a nucleotide sequence encoding the alpha (2) macroglobulin polypeptide, or fragment, analog, or variant thereof, and operably linked to a promoter, under conditions such that the alpha (2) macroglobulin polypeptideis expressed by the cells and associates with peptides of the cells; and (b) recovering from the cells a population of complexes of the alpha (2) macroglobulin polypeptide noncovalently associated with peptides derived from the infectious agent. In one embodiment, the method further comprises purifying the complexes. In another embodiment, the method further comprising purifying the complexes by affinity chromatography.

The invention further provides a method of treating or preventing an infectious disease in an individual having an infectious disease comprising administering to the individual one or more immunogenic complexes of an alpha (2) macroglobulin polypeptide noncovalently associated with a first antigenic molecule, wherein the first antigenic molecule displays the antigenicity of an antigen of an infectious agent of the infectious disease. In another embodiment, the method further comprises, before, concurrently or after administration of the immunogenic complex, administering to the individual a composition comprising antigen presenting cells sensitized in vitro with a sensitizing amount of a second complex of alpha (2) macroglobulin polypeptide noncovalently associated with a second antigenic molecule, said second antigenic molecule displaying the antigenicity of a second antigenic molecule of said infectious agent.

The invention further provides a method of treating or preventing an infectious disease in a subject having an infectious disease comprising: a) culturing an infected cell transformed with a nucleic acid comprising a nucleotide sequence encoding an alpha (2) macroglobulin polypeptide, said infected cell displaying the antigenicity of an antigen of an infectious agent of the infectious disease, said nucleotide sequence being operably linked to a promoter, under conditions such that the alpha (2) macroglobulin polypeptide is expressed by the infected cells and associates with antigenic molecules of the cell; b) recovering complexes of the alpha (2) macroglobulin polypeptide noncovalently associated with antigenic molecules from the infected cell; and c) administering to the subject an amount of the recovered complexes effective to treat or prevent the infectious disease. In one embodiment, the method further comprises, prior to step (a), the step of obtaining infected cells from the subject and transforming the infected cells with the nucleic acid. In another embodiment, the method further comprises, prior to step (a), the step of obtaining the infected cell from one or more individuals and transforming the infected cells with the nucleic acid, said one or more individuals being different from the subject and having the same type of infectious disease as the subject.

The invention further provides a method of treating or preventing an infectious disease in a subject having an infectious disease comprising: a) culturing a recombinant cell transformed with (i) a first nucleic acid encoding an alpha (2) macroglobulin polypeptide and (ii) a second nucleic acid encoding an antigenic molecule displaying the antigenicity of an antigen of an infectious agent of the infectious disease; b) recovering complexes of the alpha (2) macroglobulin polypeptide noncovalently associated with the antigen; and c) administering to the subject an amount of the recovered complexes effective to treat or prevent the infectious disease. In various embodiments, the infectious disease is caused by an infectious agent selected from the group consisting of a virus, a bacterium, a fingus, and a parasite.

Also provide by the invention is a method of treating or preventing cancer in an individual having a type of cancer or in whom prevention of a type of cancer is desired comprising administering to the individual an immunogenic complex of an alpha (2) macroglobulin polypeptide noncovalently associated with a first antigenic molecule, wherein either (a) the first antigenic molecule displays antigenicity of said type of cancer or a metastasis thereof; or (b) the complex is obtained by recovering complexes from said type of cancer cells or a metastasis thereof that recombinantly express the alpha (2) macroglobulin polypeptide. In one embodiment, this method further comprises, before, concurrently or after administration of the immunogenic complex, administering to the individual a composition comprising antigen presenting cells sensitized in vitro with a sensitizing amount of a second complex of an alpha (2) macroglobulin noncovalently associated with a second antigenic molecule, said second antigenic molecule displaying the antigenicity of an antigen overexpressed in a cancer cell relative to its expression in a noncancerous cell of said cell type. an infectious agent of the infectious disease. In another embodiment, the first antigenic molecule is an antigen overexpressed in a cancer cell relative to its expression in a noncancerous cell of said cell type.

In one embodiment, a method is provided for treating or preventing cancer in a subject having a type of cancer or in whom prevention of a type of cancer is desired comprising: a) culturing a cancer cell of said type transformed with a nucleic acid comprising a nucleotide sequence encoding an alpha (2) macroglobulin polypeptide said nucleotide sequence being operably linked to a promoter, under conditions such that the alpha (2) macroglobulin polypeptide is expressed by the cancer cell and associates with at least one antigenic molecule of the cell; b) recovering complexes of the alpha (2) macroglobulin polypeptide noncovalently associated with at least one antigenic molecule from the cancer cell; and c) administering to the subject an amount of the recovered complexes effective to treat or prevent cancer. In one embodiment, the method further comprises, prior to step (a), the step of obtaining cancer cells from the subject and transforming the cancer cells with the nucleic acid. In another embodiment, the method further comprises, prior to step (a), the step of obtaining cancer cells from one or more individuals and transforming the cancer cells with the nucleic acid, said one or more individuals being different from the subject and having the same type of cancer as the subject.

The invention further provides a method of treating or preventing cancer in a subject having a type of cancer or in whom prevention of a type of cancer is desired comprising: a) culturing a recombinant cell transformed with (i) a first nucleic acid encoding an alpha (2) macroglobulin polypeptide, and (ii) a second nucleic acid encoding an antigenic molecule displaying the antigenicity of an antigen of a cancer cell; b) recovering complexes of the alpha (2) macroglobulin polypeptide noncovalently associated with the antigen; and c) administering to the subject an amount of the recovered complexes effective to treat or prevent cancer.

As used herein a "type of cancer" refers to e.g., melanoma, breast cancer, renal carcinoma, or a metastasis thereof, where a metastasis refers to the same type of cancer as the cell of origin. In various embodiments, the cancer is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenström's macroglobulinemia, and heavy chain disease.

The invention also encompasses a method for treating an autoimmune disorder comprising administering to a mammal in need of such treatment an antibody specific for alpha (2) macroglobulin. In one embodiment, the antibody is purified.

4. BRIEF DESCRIPTION OF THE FIGURES

Figure 1B:
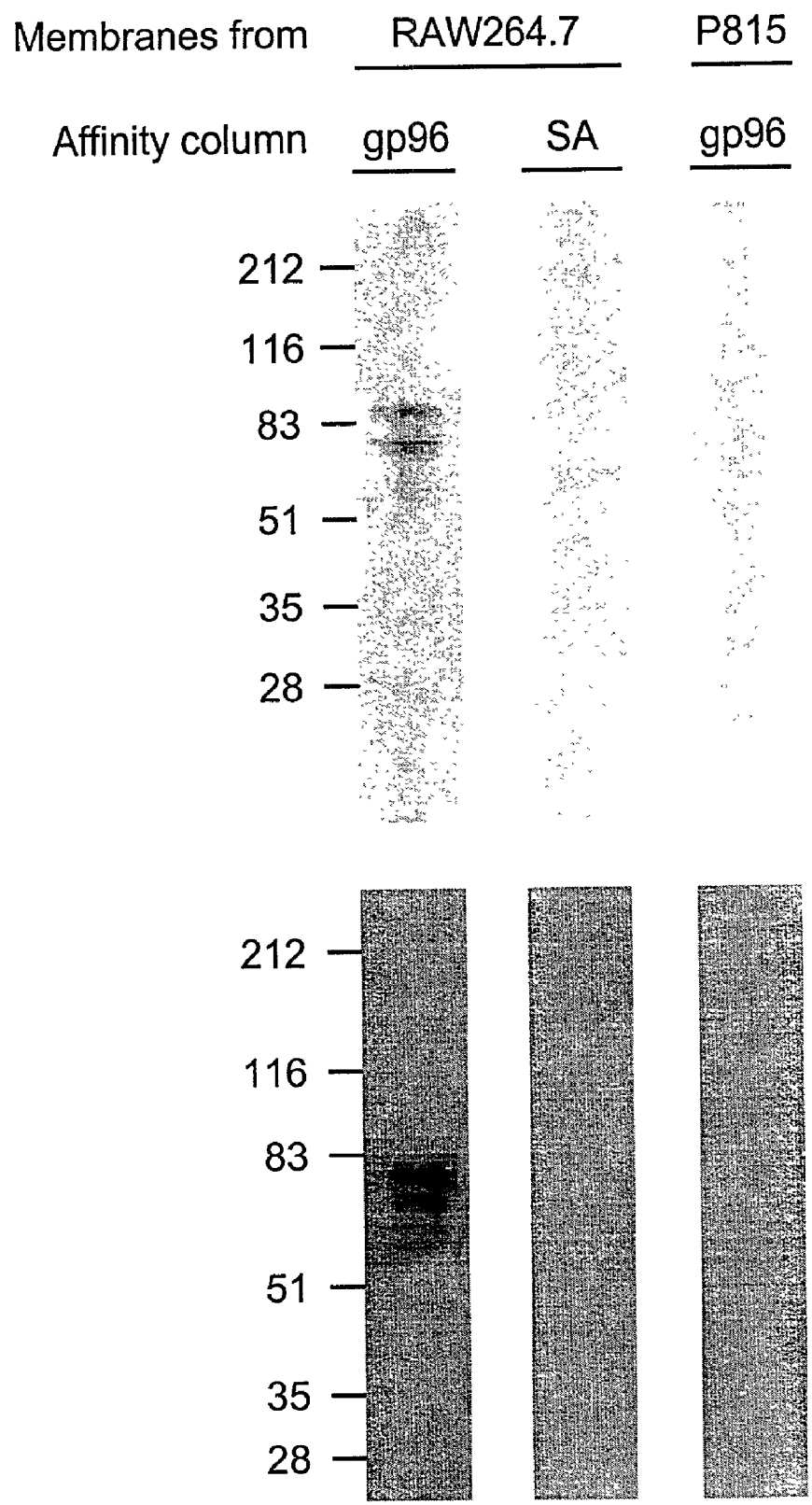
Figure 1C:
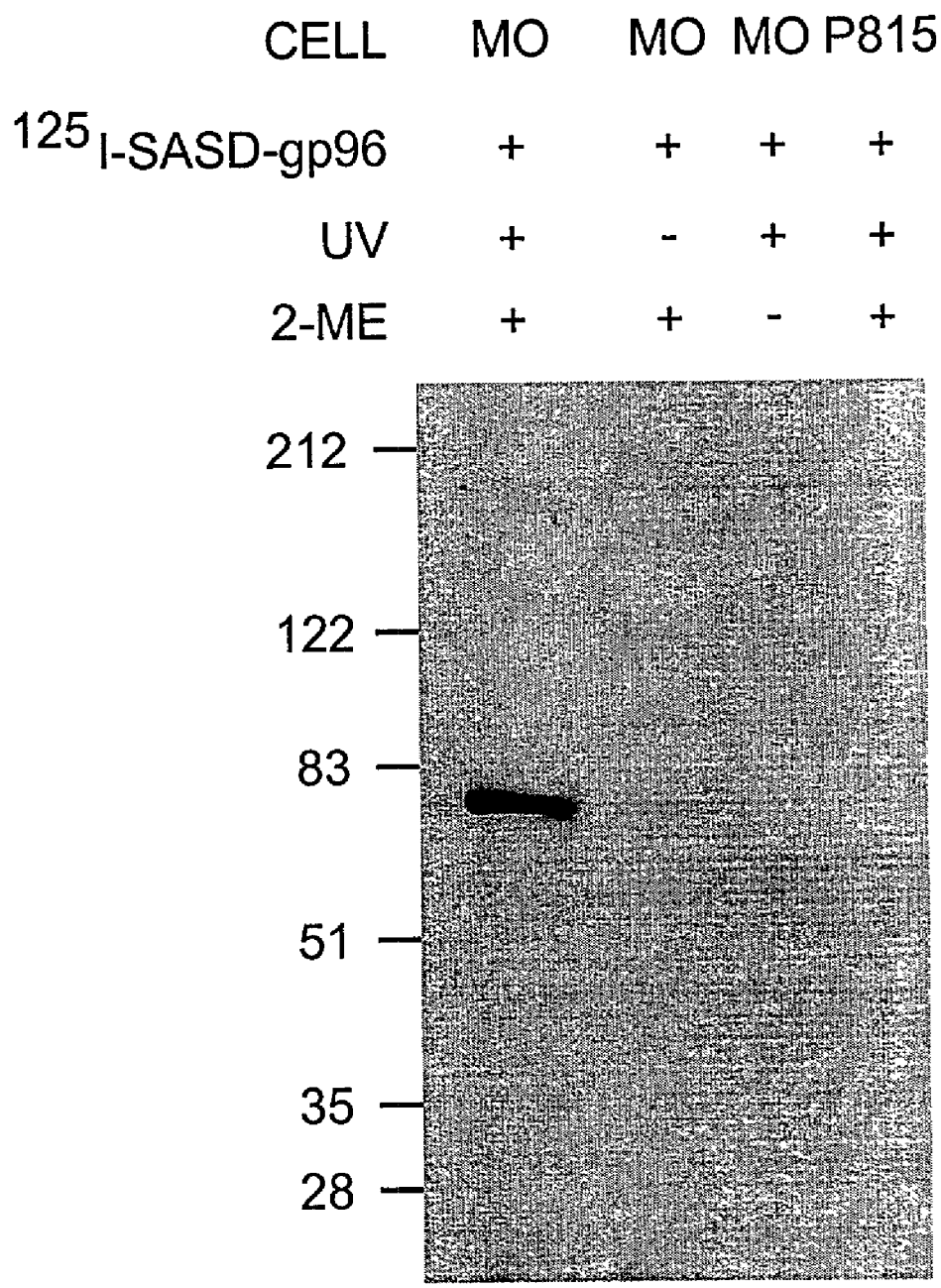

FIG. 1A-C. Identification of an 80 kDa polypeptide as a putative gp96 receptor. A. Confocal microscopy of re-presentation-competent RAW264.7 cells stained with gp96-FITC (left panel) and with albumin-FITC (fight panel). B. SDS-PAGE analysis of detergent extracts of plasma membranes from surface biotinylated RAW264.7 (re-presentation-competent) or P815 cells (representation-incompetent) eluted from gp96 or albumin-Sepharose (SA) columns and stained with silver stain (top) or avidin-peroxidase (bottom). C. gp96-SASD-$I^{125}$ was cross-linked to live peritoneal macrophages (MO) or P815 cells, and the cell lysates examined by SDS-PAGE and autoradiography. Various components were omitted as controls, as indicated.

Figure 2A:
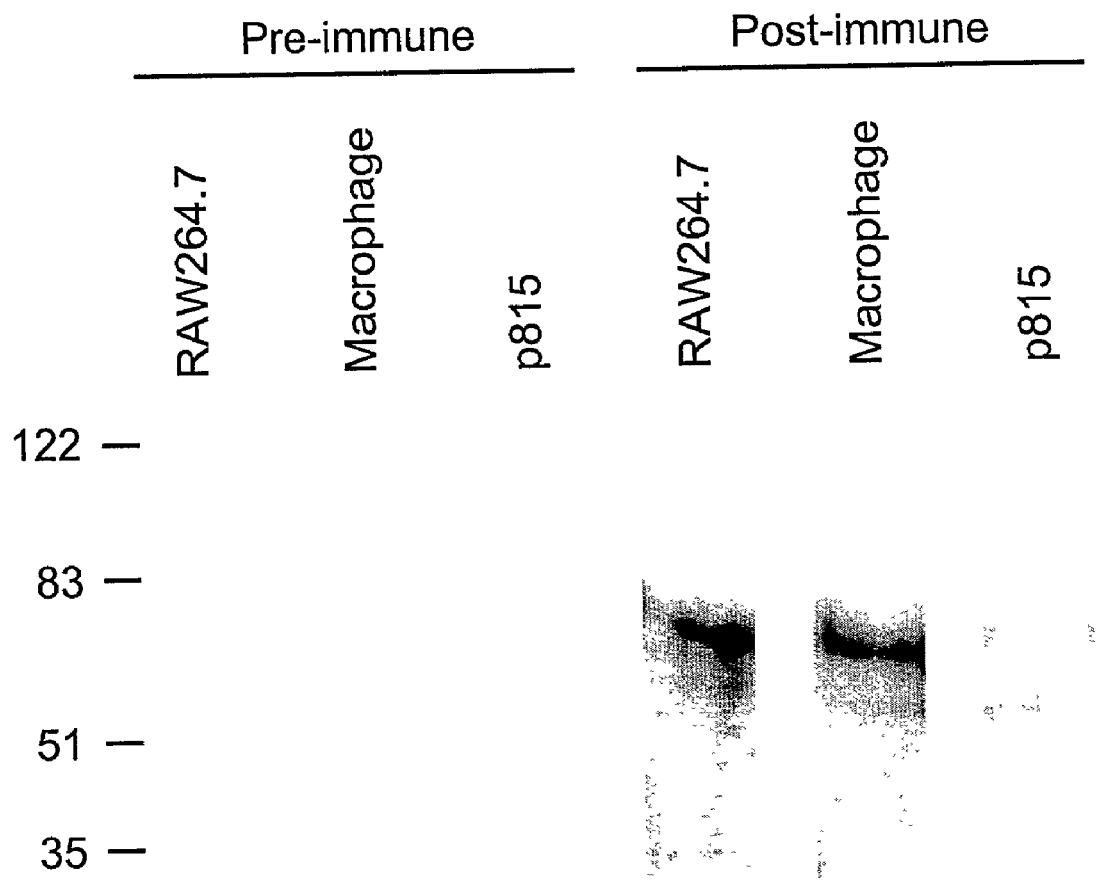
Figure 2B:
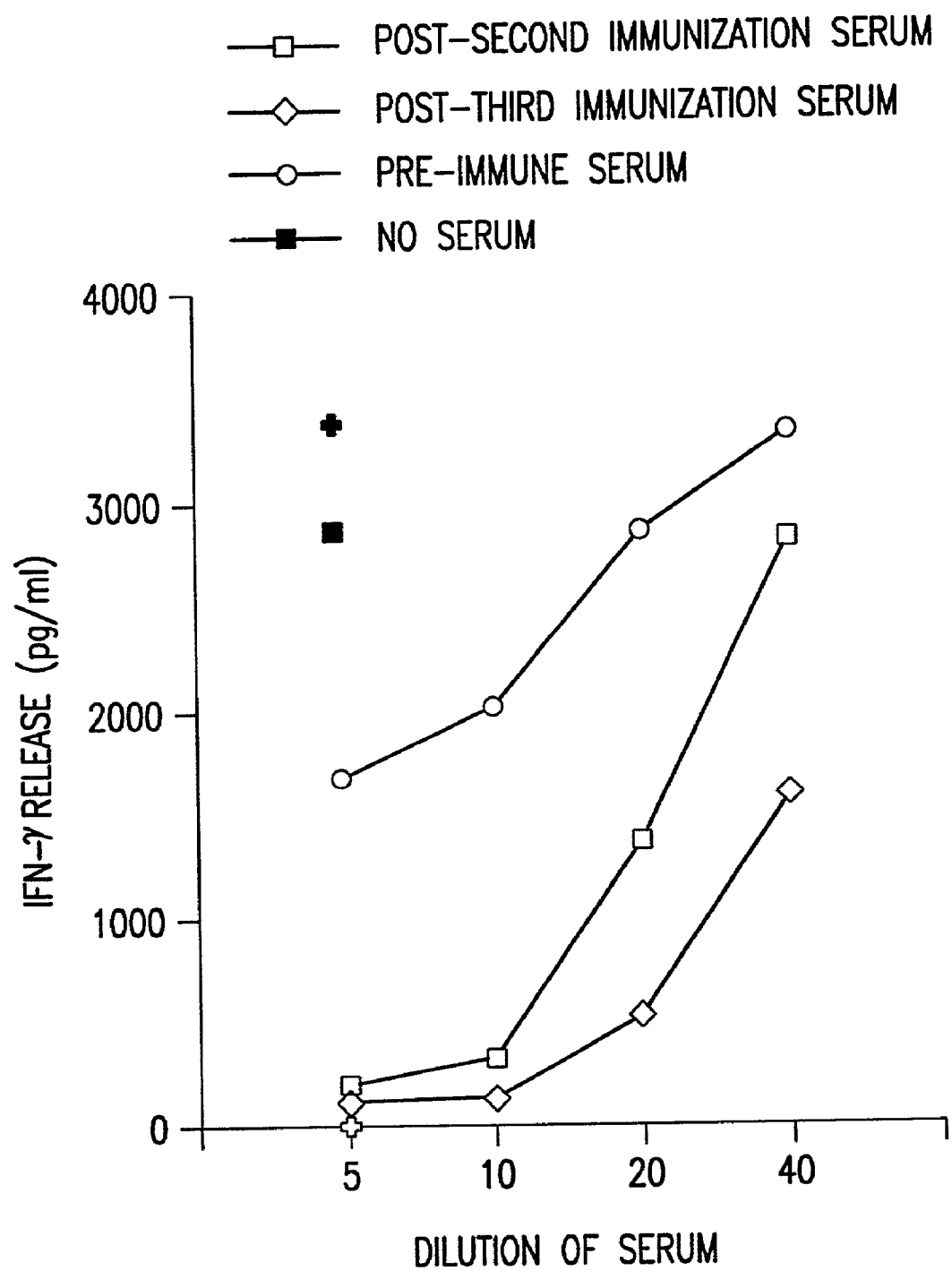

FIGS. 2A-B. Anti-p80 antiserum detects an 80 kDa molecule and inhibits re-presentation of gp96-chaperoned AH1 peptide by macrophage. A. Pre-immune and immune sera were used to probe blots of plasma membrane extracts of RAW264.7, peritoneal macrophages (both cell types re-presentation-competent), or P815 cells. B. Re-presentation of gp96-chaperoned peptide AHI. Sera were added at the final dilution indicated. The solid cross indicates the level of T cell stimulation when the APCs were pulsed directly with the AHi peptide. The open cross indicates the corresponding value with unpulsed APCs.

Figure 3B:
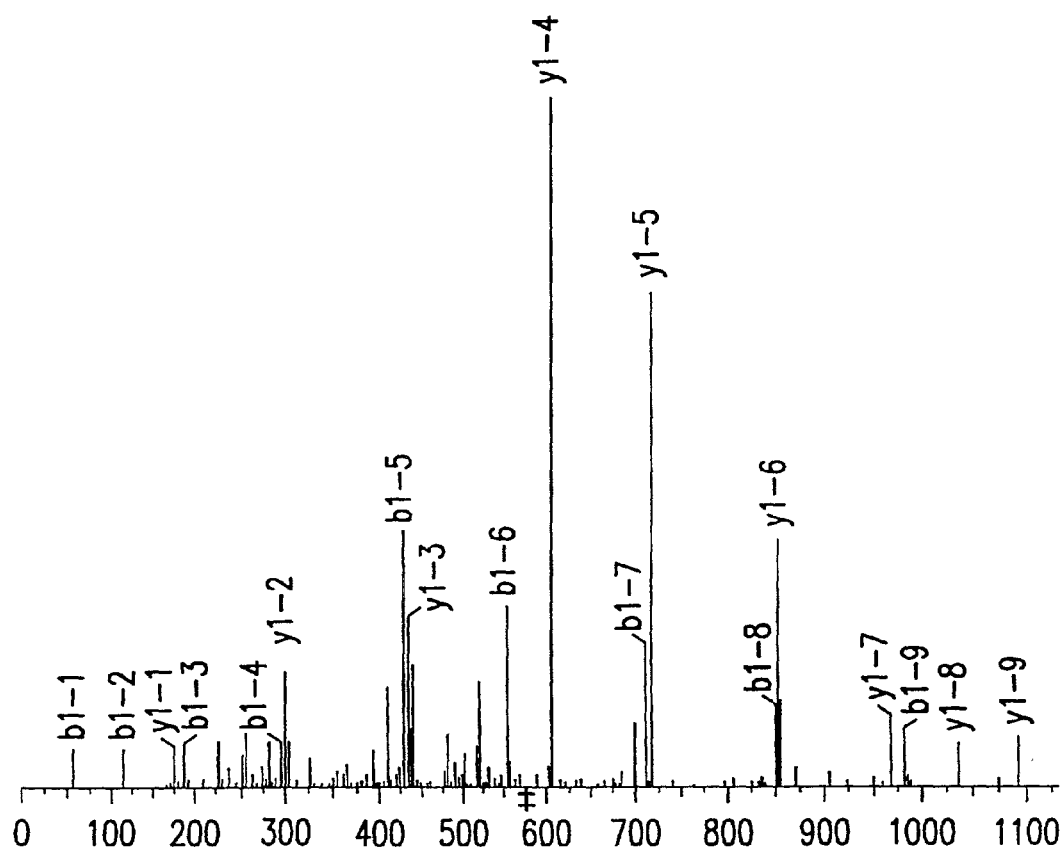

FIG. 3A-C. Protein microsequencing of the 80 kDa protein. A. Analysis of a single tryptic (GGALHIYHQR) (SEQ ID NO: 6) peptide by tandem-mass spectrometry. All possible b- and y-ion series together with identified b-ion series (red) and y-ion series (blue) are shown. B. Collision-induced dissociation (CID) spectrum of this peptide is shown. C. Four identified peptides from the α2M receptor (i.e., SGFSLGS-DGK (SEQ ID NO: 9), GIALDPAMGK (SEQ ID NO: 10), GGALHIYHQR (SEQ ID NO: 11), and VFFTDYGQIPK (SEQ ID NO: 12)), peptide mass, and sequence are shown.

Figure 4:
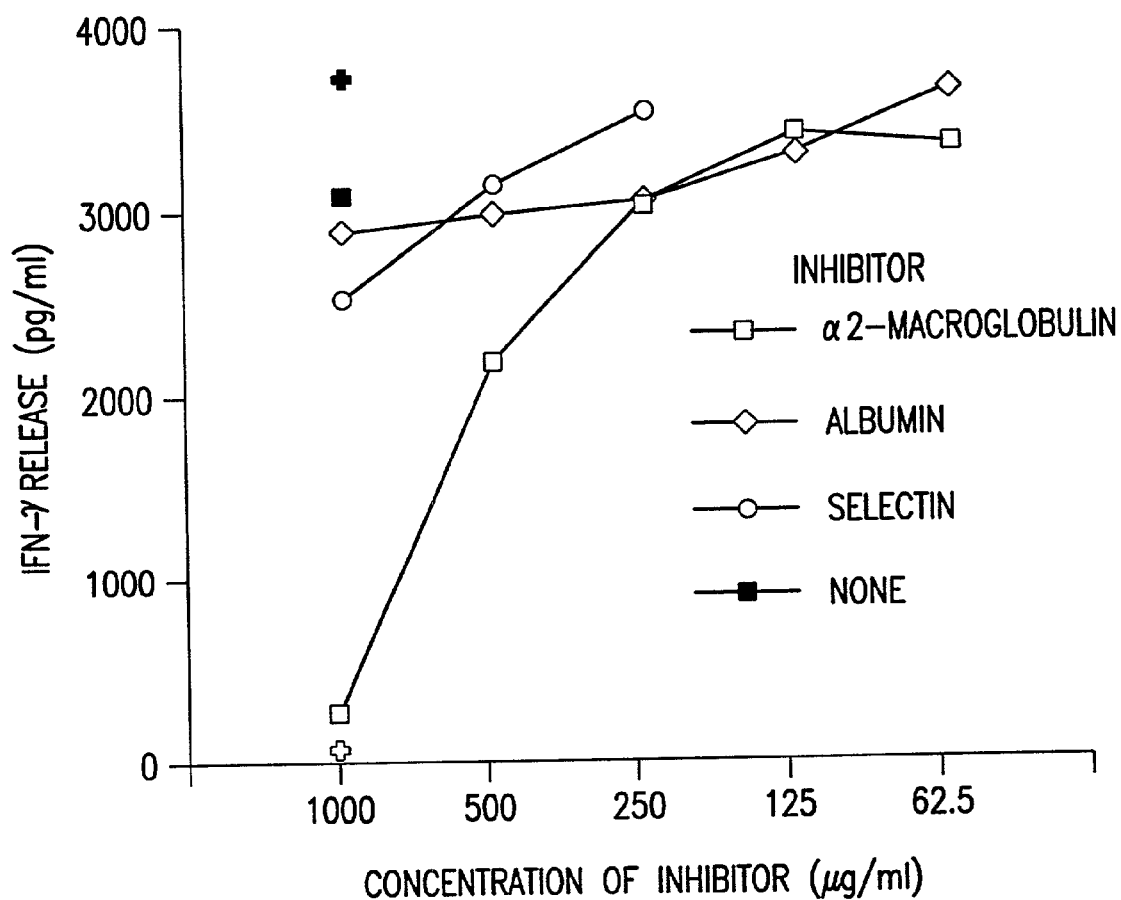

FIG. 4. α2-Macroglobulin inhibits re-presentation of gp96-chaperoned AHI peptide by macrophage. The solid cross indicates the level of T cell stimulation when the APCs were pulsed directly with the AH1 peptide. The open cross indicates the corresponding value with unpulsed APCs.

Figure 5:
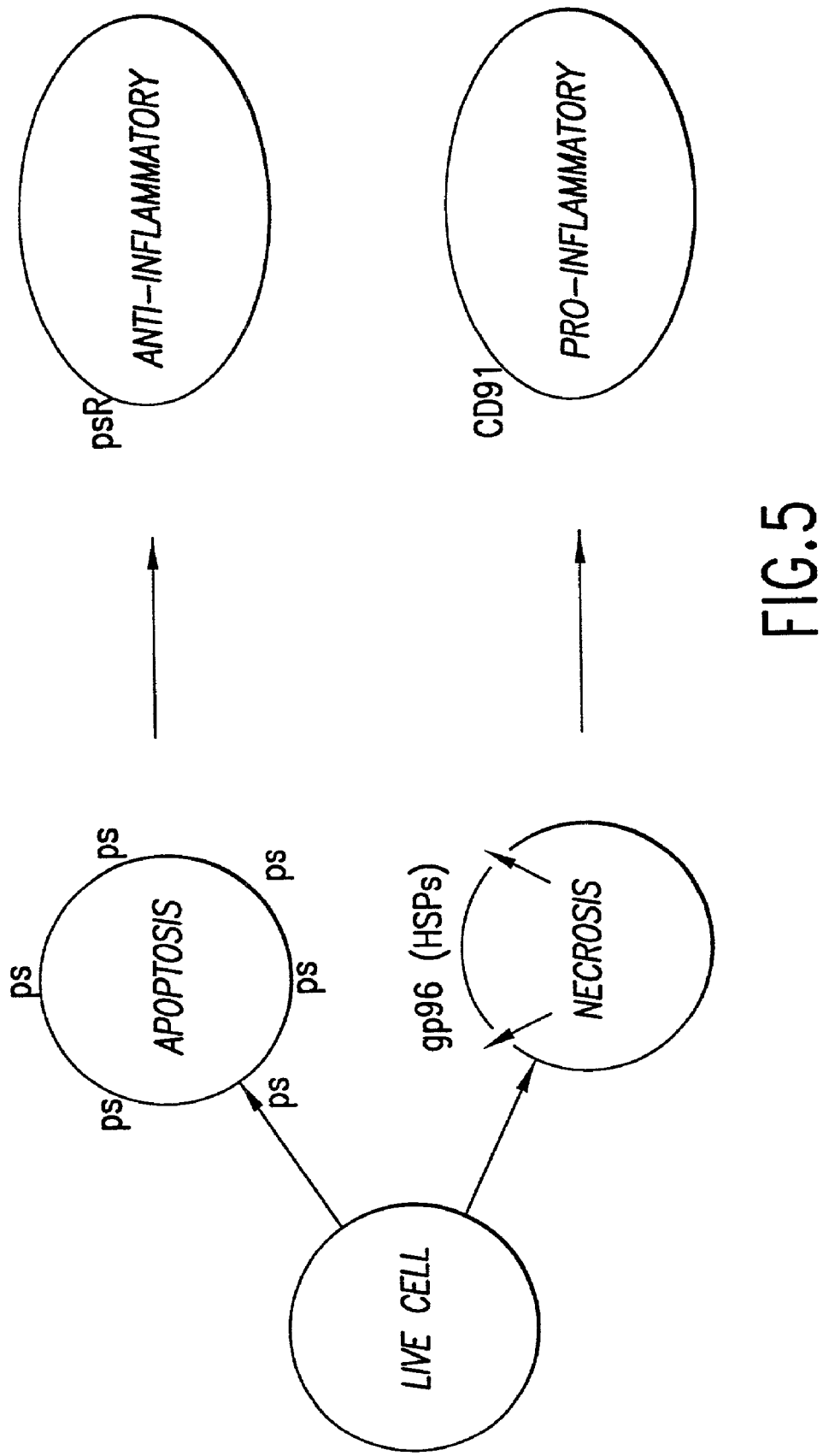

FIG. 5. α2M receptor is a sensor of necrotic cell death due to its ability to detect extracellular gp96. Conversely, receptors (psR) for phosphatidyl serine (ps) detect apoptotic cell death.

FIG. 6A-B. A. The mouse α2MR cDNA (SEQ ID NO: 1) and predicted open reading frame of murine α2MR protein (Genbank accession no. CAA47817). B. The murine α2MR protein (SEQ ID NO: 2), with residues identified by microsequencing an 80 kDa, gp96-interacting fragment of the receptor highlighted in bold.

FIG. 7A-B. A. Translated amino acid sequence of α2M (SEQ ID NO: 3) and nucleotide sequence of α2M (SEQ ID NO: 4). B. Amino acid seciuence of mature α2M (SEQ ID NO.: 8). The 138 amino acid sequence (SEQ ID NO.: 5) of the receptor binding domain from α2M is highlighted.

5. DETAILED DESCRIPTION OF THE INVENTION

The present invention provides compositions and methods for alpha (2) macroglobulin ("α2M") vaccines for use in immunotherapy. The invention is based, in part, on the Applicant's discovery that α2M blocks uptake of heat shock proteins by antigen presenting cells. In particular, the invention provides complexes of α2M associated with antigenic molecules, which are recognized by the alpha (2) macroglobulin receptor on antigen presenting cells ("APCs"), and are presented by such cells to the immune system. Thus, the invention provides methods and compositions for using specific α2M-antigenic molecule complexes for targeting an immune response against immune disorders, proliferative disorders, and infectious diseases.

The human plasma protein alpha (2) macroglobulin is a 720 kDa homotetrameric proteinase inhibitor primarily known as proteinase inhibitor and plasma and inflammatory fluid proteinase scavenger molecule (for review see Chu and Pizzo, 1994, Lab. Invest. 71:792). During proteolytic activation of α2M, non-proteolytic ligands can become incorporated, covalently and noncovalently, to the activated thioesters (see Osada et al, 1987, Biochem. Biophys. Res. Comm. 146:26-31; Osada et al., 1988, Biochem. Biophys. Res. Comm. 150:883-889; Chu and Pizzo, 1993, J. Immunology 150: 48-58; Chu et al., 1994, 152:1538-1545; Mitsuda et al., 1993, Biochem. Biophys. Res. Comm. 191:1326-1331). As described herein, when complexes formed between α2M and an antigenic molecule having the antigenicity of a cancer cell antigen or of a pathogen, such α2M-antigenic molecule complexes can be used to stimulate a cytotoxic T cell response directed against the α2M incorporated antigen. Such complexes can be used as immunotherapeutic agents to treat cancer and infectious diseases.

Described in detailed hereinbelow are methods and compositions for use in preparation and delivery of such therapeutic α2M-antigenic molecule complexes. The invention encompasses complexes of alpha (2) macroglobulin associated antigenic molecules, antigenic cells that express the α2M, and antibodies and other molecules that specifically recognize α2M-antigenic molecule complexes. The invention also relates to methods for using these compositions in the diagnosis and treatment of immune disorders, proliferative disorders, and infectious diseases.

5.1 Compositions of the Invention

The present invention provides compositions that can be used in immunotherapy against proliferative disorders, infectious diseases, and immune disorders. Such compositions include antibodies that specifically recognize α2M complexes, isolated antigenic cells that express α2M complexes, and recombinant cells that contain recombinant α2M and sequences encoding antigenic molecules.

It is contemplated that the definition of α2M, as used herein, embraces other polypeptide fragments, analogs, and variants of α2M having at least 35% to 55%, preferably 55% to 75%, and most preferably 75% to 85% amino acid identity with α2M, and is capable of forming a complex with an antigenic molecule, which complex is capable of being taken up by an antigen presenting cell and eliciting an immune response against the antigenic molecule. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul, et al., 1990, J. Mol. Biol. 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, Nucleic Acids Res.25:3389-3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, 1988, CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The immunogenic α2M-antigenic molecule complexes of the invention may include any complex containing an α2M and an antigenic peptide that is capable of inducing an immune response in a mammal.

α2M and/or antigenic molecules can be purified from natural sources, chemically synthesized, or recombinantly produced.

5.1.1. α2M Polypeptides

The alpha (2) macroglobulin complex of the invention is comprised of an alpha (2) macroglobulin polypeptide associated with an antigenic peptide. Alpha (2) macroglobulin polypeptides may be produced by recombinant DNA techniques, synthetic methods, or by enzymatic or chemical cleavage of native α2M polypeptides. Described herein are methods for producing such α2M polypeptides.

5.1.1.1 Isolation of α2M Gene Sequences

In various aspects, the invention relates to compositions comprising amino acid sequences of α2M, and fragments, derivatives, analogs, and variants thereof. Nucleic acids encoding α2M are provided, as well as nucleic acids complementary to and capable of hybridizing to such nucleic acids.

Any eukaryotic cell may serve as the nucleic acid source for obtaining the coding region of an α2M gene. Nucleic acid sequences encoding α2M can be isolated from vertebrate, mammalian, as well as primate sources, including humans.

Amino acid sequences and nucleotide sequences of naturally occurring α2M polypeptides are generally available in sequence databases, such as GenBank. Non-limiting examples of α2M sequences that can be used for preparation of the α2M polypeptides of the invention are as follows: Genbank Accession Nos. M11313, P01023, AAA51551; Kan et al., 1985, Proc. Nat. Acad. Sci. 82: 2282-2286. Due to the degeneracy of the genetic code, the term "α2M gene", as used herein, refers not only to the naturally occurring nucleotide sequence but also encompasses all the other degenerate DNA sequences that encode an α2M polypeptide. Computer programs, such as Entrez, can be used to browse the database, and retrieve any amino acid sequence and genetic sequence data of interest by accession number. These databases can also be searched to identify sequences with various degrees of similarities to a query sequence using programs, such as FASTA and BLAST, which rank the similar sequences by alignment scores and statistics. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, Nucleic Acids Res.25:3389-3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used.

The DNA may be obtained by standard procedures known in the art by DNA amplification or molecular cloning directly from a tissue, cell culture, or cloned DNA (e.g., a DNA "library"). Clones derived from genomic DNA may contain regulatory and intron DNA regions in addition to coding regions; clones derived from cDNA will contain only exon sequences. Whatever the source, the α2M gene should be cloned into a suitable vector for propagation of the gene.

In a preferred embodiment, DNA can be amplified from genomic or cDNA by polymerase chain reaction (PCR) amplification using primers designed from the known sequence of a related or homologous α2M. PCR is used to amplify the desired sequence in DNA clone or a genomic or cDNA library, prior to selection. PCR can be carried out, e.g., by use of a thermal cycler and Taq polymerase (sold under the trademark GENE AMP). The DNA being amplified can include cDNA or genomic DNA from any species. Oligonucleotide primers representing known nucleic acid sequences of related HSPs can be used as primers in PCR. In a preferred aspect, the oligonucleotide primers represent at least part of the α2M gene that is highly conserved between α2M genes of different species. One can choose to synthesize several different degenerate primers, for use in the PCR reactions. It is also possible to vary the stringency of hybridization conditions used in priming the PCR reactions, to allow for greater or lesser degrees of nucleotide sequence similarity between the known α2M nucleotide sequence and the nucleic acid homolog being isolated. For cross species hybridization, low stringency conditions are preferred. For same species hybridization, moderately stringent conditions are preferred. After successful amplification, the sequence encoding an α2M may be cloned and sequenced. If the size of the coding region of the α2M gene being amplified is too large to be amplified in a single PCR, several PCR covering the entire gene, preferably with overlapping regions, may be carried out, and the products of the PCR ligated together to form the entire coding sequence. Alternatively, if a segment of an α2M gene is amplified, that segment may be cloned, and utilized as a probe to isolate a complete cDNA or genomic clone.

In another embodiment, for the molecular cloning of an α2M gene from genomic DNA, DNA fragments are generated to form a genomic library. Since some of the sequences encoding related α2Ms are available and can be purified and labeled, the cloned DNA fragments in the genomic DNA library may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available.

Alternatives to isolating the α2M genomic DNA include, but are not limited to, chemically synthesizing the gene sequence itself from a known sequence or making cDNA to the mRNA which encodes α2M. For example, RNA for cDNA cloning of the α2M gene can be isolated from cells which express α2M. A cDNA library may be generated by methods known in the art and screened by methods, such as those disclosed for screening a genomic DNA library. If an antibody to α2M is available, α2M may be identified by binding of labeled antibody to the putatively α2M synthesizing clones.

Other specific embodiments for the cloning of a nucleotide sequence encoding an α2M, are presented as examples but not by way of limitation, as follows:

In a specific embodiment, nucleotide sequences encoding α2M proteins within a family can be identified and obtained by hybridization with a probe comprising nucleotide sequence encoding α2M under conditions of low to medium stringency.

By way of example and not limitation, procedures using such conditions of low stringency are as follows (see also Shilo and Weinberg, 1981, Proc. Natl. Acad. Sci. USA 78:6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and reexposed to film. Other conditions of low stringency which may be used are well known in the art (e.g., as employed for cross-species hybridizations).

An α2M gene fragment can be inserted into an appropriate cloning vector and introduced into host cells so that many copies of the gene sequence are generated. A large number of vector-host systems known in the art may be used such as, but not limited to, bacteriophages such as lambda derivatives, or plasmids such as pBR322 or pUC plasmid derivatives or the Bluescript vector (Stratagene).

Any technique for mutagenesis known in the art can be used to modify individual nucleotides in a DNA sequence, for purpose of making amino acid substitution(s) in the expressed peptide sequence, or for creating/deleting restriction sites to facilitate further manipulations. Such techniques include but are not limited to, chemical mutagenesis, in vitro site-directed mutagenesis (Hutchinson et al., 1978, J. Biol. Chem 253:6551), oligonucleotide-directed mutagenesis (Smith, 1985, Ann. Rev. Genet. 19:423-463; Hill et al., 1987, Methods Enzymol. 155:558-568), PCR-based overlap extension (Ho et al., 1989, Gene 77:51-59), PCR-based megaprimer mutagenesis (Sarkar et al., 1990, Biotechniques, 8:404-407), etc. Modifications can be confirmed by double stranded dideoxy DNA sequencing.

The polymerase chain reaction (PCR) is commonly used for obtaining genes or gene fragments of interest. For example, a nucleotide sequence encoding α2M polypeptide of any desired length can be generated using PCR primers that flank the nucleotide sequence encoding α2M, or the peptide-binding domain thereof. Alternatively, an α2M gene sequence can be cleaved at appropriate sites with restriction endonuclease(s) if such sites are available, releasing a fragment of DNA encoding α2M, or the peptide-binding domain thereof. If convenient restriction sites are not available, they may be created in the appropriate positions by site-directed mutagenesis and/or DNA amplification methods known in the art (see, for example, Shankarappa et al., 1992, PCR Method Appl. 1:277-278). The DNA fragment that encodes α2M, or the peptide-binding domain thereof, is then isolated, and ligated into an appropriate expression vector, care being taken to ensure that the proper translation reading frame is maintained.

Alpha (2) macroglobulin polypeptides of the invention may be expressed as fusion proteins to facilitate recovery and purification from the cells in which they are expressed. For example, an α2M polypeptide may contain a signal sequence leader peptide to direct its translocation across the ER membrane for secretion into culture medium. Further, an α2M polypeptide may contain an affinity label, such as a affinity label, fused to any portion of the α2M polypeptide not involved in binding antigenic peptide, such as for example, the carboxyl terminal. The affinity label can be used to facilitate purification of the protein, by binding to an affinity partner molecule.

Various methods for production of such fusion proteins are well known in the art. The manipulations which result in their production can occur at the gene or protein level, preferably at the gene level. For example, the cloned coding region of an α2M polypeptide may be modified by any of numerous recombinant DNA methods known in the art (Sambrook et al., 1990, Molecular Cloning, A Laboratory Manual, 2d ed., Cold Spring Harbor Laboratory, Cold Spring Harbor, N.Y.; Ausubel et al., in Chapter 8 of Current Protocols in Molecular Biology, Greene Publishing Associates and Wiley Interscience, New York). It will be apparent from the following discussion that substitutions, deletions, insertions, or any combination thereof are introduced or combined to arrive at a final nucleotide sequence encoding an α2M polypeptide.

In various embodiments, fusion proteins comprising the α2M polypeptide may be made using recombinant DNA techniques. For example, a recombinant gene encoding an α2M polypeptide may be constructed by introducing an α2M gene fragment in the proper reading frame into a vector containing the sequence of an affinity label, such that the α2M polypeptide is expressed as a peptide-tagged fusion protein. Affinity labels, which may be recognized by specific binding partners, may be used for affinity purification of the α2M polypeptide.

In a preferred embodiment, the affinity label is fused at its amino terminal to the carboxyl terminal of α2M. The precise site at which the fusion is made in the carboxyl terminal is not critical. The optimal site can be determined by routine experimentation.

A variety of affinity labels known in the art may be used, such as, but not limited to, the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell Bio. 4:220-229), the E. coli maltose binding protein (Guan et al., 1987, Gene 67:21-30), and various cellulose binding domains (U.S. Pat. Nos. 5,496,934; 5,202,247; 5,137,819; Tomme et al., 1994, Protein Eng. 7:117-123), etc. Other affinity labels may impart fluorescent properties to an α2M polypeptide, e.g., portions of green fluorescent protein and the like. Other possible affinity labels are short amino acid sequences to which monoclonal antibodies are available, such as but not limited to the following well known examples, the FLAG epitope, the myc epitope at amino acids 408-439, the influenza virus hemagglutinin (HA) epitope. Other affinity labels are recognized by specific binding partners and thus facilitate isolation by affinity binding to the binding partner which can be immobilized onto a solid support. Some affinity labels may afford the α2M polypeptide novel structural properties, such as the ability to form multimers. Dimerization of an α2M polypeptide with a bound peptide may increase avidity of interaction between the α2M polypeptide and its partner in the course of antigen presentation. These affinity labels are usually derived from proteins that normally exist as homopolymers. Affinity labels such as the extracellular domains of CD8 (Shiue et al., 1988, J. Exp. Med. 168:1993-2005), or CD28 (Lee et al., 1990, J. Immunol. 145:344-352), or portions of the immunoglobulin molecule containing sites for interchain disulfide bonds, could lead to the formation of multimers. As will be appreciated by those skilled in the art, many methods can be used to obtain the coding region of the above-mentioned affinity labels, including but not limited to, DNA cloning, DNA amplification, and synthetic methods. Some of the affinity labels and reagents for their detection and isolation are available commercially.

A preferred affinity label is a non-variable portion of the immunoglobulin molecule. Typically, such portions comprise at least a functionally operative CH2 and CH3 domain of the constant region of an immunoglobulin heavy chain. Fusions are also made using the carboxyl terminus of the Fc portion of a constant domain, or a region immediately amino-terminal to the CH1 of the heavy or light chain. Suitable immunoglobulin-based affinity label may be obtained from IgG-1, -2,-3, or -4 subtypes, IgA, IgE, IgD, or IgM, but preferably IgG1. Preferably, a human immunoglobulin is used when the α2M polypeptide is intended for in vivo use for humans. Many DNA encoding immunoglobulin light or heavy chain constant regions is known or readily available from cDNA libraries. See, for example, Adams et al., Biochemistry, 1980, 19:2711-2719; Gough et al., 1980, Biochemistry, 19:2702-2710; Dolby et al., 1980, Proc. Natl. Acad. Sci. U.S.A., 77:6027-6031; Rice et al., 1982, Proc. Natl. Acad. Sci. U.S.A., 79:7862-7865; Falkner et al., 1982, Nature, 298:286-288; and Morrison et al., 1984, Ann. Rev. Immunol, 2:239-256. Because many immunological reagents and labeling systems are available for the detection of immunoglobulins, the α2M polypeptide-Ig fusion protein can readily be detected and quantified by a variety of immunological techniques known in the art, such as the use of enzyme-linked immunosorbent assay (ELISA), immunoprecipitation, fluorescence activated cell sorting (FACS), etc.

Similarly, if the affinity label is an epitope with readily available antibodies, such reagents can be used with the techniques mentioned above to detect, quantitate, and isolate the α2M polypeptide containing the affinity label. In many instances, there is no need to develop specific antibodies to the α2M polypeptide.

A particularly preferred embodiment is a fusion of an α2M polypeptide to the hinge, the CH2 and CH3 domains of human immunoglobulin G-1 (IgG-1; see Bowen et al. ,1996, J. Immunol. 156:442-49). This hinge region contains three cysteine residues which are normally involved in disulfide bonding with other cysteines in the Ig molecule. Since none of the cysteines are required for the peptide to function as a tag, one or more of these cysteine residues may optionally be substituted by another amino acid residue, such as for example, serine.

Various leader sequences known in the art can be used for the efficient secretion of α2M polypeptide from bacterial and mammalian cells (von Heijne, 1985, J. Mol. Biol. 184:99-105). Leader peptides are selected based on the intended host cell, and may include bacterial, yeast, viral, animal, and mammalian sequences. For example, the herpes virus glycoprotein D leader peptide is suitable for use in a variety of mammalian cells. A preferred leader peptide for use in mammalian cells can be obtained from the V-J2-C region of the mouse immunoglobulin kappa chain (Bernard et al., 1981, Proc. Natl. Acad. Sci. 78:5812-5816). Preferred leader sequences for targeting α2M polypeptide expression in bacterial cells include, but are not limited to, the leader sequences of the *E. coli* proteins OmpA (Hobom et al., 1995, Dev. Biol. Stand. 84:255-262), Pho A (Oka et al., 1985, Proc. Natl. Acad. Sci 82:7212-16), OmpT (Johnson et al, 1996, Protein Expression 7:104-113), LamB and OmpF (Hoffman & Wright, 1985, Proc. Natl. Acad. Sci. USA 82:5107-5111), β-lactamase (Kadonaga et al., 1984, J. Biol. Chem. 259:2149-54), enterotoxins (Morioka-Fujimoto et al., 1991, J. Biol. Chem. 266:1728-32), and the *Staphylococcus aureus* protein A (Abrahmsen et al., 1986, Nucleic Acids Res. 14:7487-7500), and the *B. subtilis* endoglucanase (Lo et al., Appl. Environ. Microbiol. 54:2287-2292), as well as artificial and synthetic signal sequences (MacIntyre et al., 1990, Mol. Gen. Genet. 221: 466-74; Kaiser et al., 1987, Science, 235:312-317).

DNA sequences encoding a desired affinity label or leader peptide, which may be readily obtained from libraries, produced synthetically, or may be available from commercial suppliers, are suitable for the practice of this invention. Such methods are well known in the art.

5.1.1.2 Recombinant Expression

In various embodiments of the invention, sequences encoding an α2M polypeptide are inserted into an expression vector for propagation and expression in recombinant cells.

An expression construct, as used herein, refers to a nucleotide sequence encoding an α2M polypeptide operably associated with one or more regulatory regions which allows expression of the α2M polypeptide in an appropriate host cell. "Operably-associated" refers to an association in which the regulatory regions and the α2M polypeptide sequence to be expressed are joined and positioned in such a way as to permit transcription, and ultimately, translation.

Vectors based on *E. coli* are the most popular and versatile systems for high level expression of foreign proteins (Makrides, 1996, Microbiol Rev, 60:512-538). Non-limiting examples of regulatory regions that can be used for expression in *E. coli* may include but not limited to lac, trp, lpp, phoa, recA, tac, λP$_L$ and phage T3 and T7 promoters (Makrides, 1996, Microbiol Rev, 60:512-538). Non-limiting examples of prokaryotic expression vectors may include the λgt vector series such as λgt11 (Huynh et al., 1984 in "DNA Cloning Techniques", Vol. I: A Practical Approach (D. Glover, ed.), pp. 49-78, IRL Press, Oxford), and the pET vector series (Studier et al., 1990, Methods Enzymol., 185: 60-89). However, a potential drawback of a prokaryotic host-vector system is the inability to perform many of the post-translational processing events of mammalian cells. Thus, an eukaryotic host-vector system is preferred, a mammalian host-vector system is more preferred, and a human host-vector system is the most preferred.

The regulatory regions necessary for transcription of the α2M polypeptide can be provided by the expression vector. A translation initiation codon (ATG) may also be provided to express a nucleotide sequence encoding an α2M polypeptide that lacks an initiation codon. In a compatible host-construct system, cellular proteins required for transcription, such as RNA polymerase and transcription factors, will bind to the regulatory regions on the expression construct to effect transcription of the α2M polypeptide sequence in the host organism. The precise nature of the regulatory regions needed for gene expression may vary from host cell to host cell. Generally, a promoter is required which is capable of binding RNA polymerase to initiate the transcription of an operably-associated nucleic acid sequence. Such regulatory regions may include those 5'-non-coding sequences involved with initiation of transcription and translation, such as the TATA box, the cap site, a CAAT box, and the like. The non-coding region 3' to the coding sequence may contain transcriptional termination regulatory sequences, such as terminators and polyadenylation sites.

Both constitutive and inducible regulatory regions may be used for expression of the α2M polypeptide. It may be desirable to use inducible promoters when the conditions optimal for growth of the recombinant cells and the conditions for high level expression of the α2M polypeptide are different. Examples of useful regulatory regions are provided in the next section below.

For expression of α2M polypeptides in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include but are not limited to those associated with the metallothionein II gene, mouse mammary tumor virus glucocorticoid responsive long terminal repeats (MMTV-LTR), the β-interferon gene, and the α2M70 gene (Williams et al., 1989, Cancer Res. 49:2735-42; Taylor et al., 1990, Mol. Cell Biol., 10:165-75).

The following animal regulatory regions, which exhibit tissue specificity and have been utilized in transgenic animals, can also be used in tumor cells of a particular tissue type: elastase I gene control region which is active in pancreatic acinar cells (Swift et al., 1984, Cell 38:639-646; Omitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318: 533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

The efficiency of expression of the α2M polypeptide in a host cell may be enhanced by the inclusion of appropriate transcription enhancer elements in the expression vector, such as those found in SV40 virus, Hepatitis B virus, cytomegalovirus, immunoglobulin genes, metallothionein, β-actin (see Bittner et al., 1987, Methods in Enzymol. 153:516-544; Gorman, 1990, Curr. Op. in Biotechnol. 1:36-47).

The expression vector may also contain sequences that permit maintenance and replication of the vector in more than one type of host cell, or integration of the vector into the host chromosome. Such sequences may include but are not limited to replication origins, autonomously replicating sequences (ARS), centromere DNA, and telomere DNA. It may also be advantageous to use shuttle vectors that can be replicated and maintained in at least two types of host cells.

In addition, the expression vector may contain selectable or screenable marker genes for initially isolating or identifying host cells that contain DNA encoding an α2M polypeptide. For long term, high yield production of α2M polypeptide-antigenic molecule complexes, stable expression in mammalian cells is preferred. A number of selection systems may be used for mammalian cells, including, but not limited to, the Herpes simplex virus thymidine kinase (Wigler et al, 1977, Cell 11:223), hypoxanthine-guanine phosphoribosyltransferase (Szybalski and Szybalski, 1962, Proc. Natl. Acad. Sci. USA 48:2026), and adenine phosphoribosyltransferase (Lowy et al., 1980, Cell 22:817) genes can be employed in tk⁻, hgprt⁻ or aprt⁻ cells, respectively. Also, antimetabolite resistance can be used as the basis of selection for dihydrofolate reductase (dhfr), which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neomycin phosphotransferase (neo), which confers resistance to the aminoglycoside G-418 (Colberre-Garapin et al., 1981, J. Mol. Biol. 150:1); and hygromycin phosphotransferase (hyg), which confers resistance to hygromycin (Santerre et al., 1984, Gene 30:147). Other selectable markers, such as but not limited to histidinol and Zeocin™ can also be used.

In order to insert the α2M polypeptide DNA sequence into the cloning site of a vector, DNA sequences with regulatory functions, such as promoters, must be attached to DNA sequences encoding the α2M peptide-binding region. To do this, linkers or adapters providing the appropriate compatible restriction sites may be ligated to the ends of cDNA or synthetic DNA encoding an α2M polypeptide, by techniques well known in the art (Wu et al., 1987, Methods in Enzymol 152:343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising an α2M polypeptide sequence operably associated with regulatory regions can be directly introduced into appropriate host cells for expression and production of α2M polypeptide-antigenic molecule complexes without further cloning (see, for example, U.S. Pat. No. 5,580,859). The expression constructs may also contain DNA sequences that facilitate integration of the α2M polypeptide sequence into the genome of the host cell, e.g., via homologous recombination. In this instance, it is not necessary to employ an expression vector comprising a replication origin suitable for appropriate host cells in order to propagate and express the α2M polypeptide in the host cells.

Expression constructs containing cloned nucleotide sequence encoding α2M polypeptides can be introduced into the host cell by a variety of techniques known in the art, including but not limited to, for prokaryotic cells, bacterial transformation (Hanahan, 1985, in DNA Cloning, A Practical Approach, 1:109-136), and for eukaryotic cells, calcium phosphate mediated transfection (Wigler et al., 1977, Cell 11:223-232), liposome-mediated transfection (Schaefer-Ridder et al., 1982, Science 215:166-168), electroporation (Wolff et al., 1987, Proc Natl Acad Sci 84:3344), and microinjection (Cappechi, 1980, Cell 22:479-488). Co-expression of an α2M polypeptide and an antigenic molecule in the same host cell can be achieved by essentially the same methods.

For long term, high yield production of properly processed α2M polypeptides or α2M polypeptide-antigenic molecule complexes, stable expression in mammalian cells is preferred. Cell lines that stably express α2M polypeptides or α2M polypeptide-antigenic molecule complexes may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while α2M polypeptide is expressed continuously.

The recombinant cells may be cultured under standard conditions of temperature, incubation time, optical density, and media composition. Alternatively, a recombinant antigenic cells may be cultured under conditions emulating the nutritional and physiological requirements of the cancer cell or infected cell. However, conditions for growth of recombinant cells may be different from those for expression of α2M polypeptides and antigenic proteins. Modified culture conditions and media may also be used to enhance production of α2M-antigenic molecule complexes. Any techniques known in the art may be applied to establish the optimal conditions for producing α2M polypeptide or α2M polypeptide-antigenic molecule complexes.

5.1.1.3 Purification Methods for Recombinant α2M Polypeptides

Generally, the α2M polypeptides of the invention can be recovered and purified from recombinant cell cultures by known methods, including ammonium sulfate precipitation, acid extraction, anion or cation exchange chromatography, phosphocellulose chromatography, immunoaffinity chromatography, hydroxyapatite chromatography, and lectin chromatography.

The invention provides methods for purification of recombinant α2M polypeptides by affinity purification, based on the properties of the affinity label present on the α2M polypeptide. One approach is based on specific molecular interactions between a tag and its binding partner. The other approach relies on the immunospecific binding of an antibody to an epitope present on the tag. The principle of affinity chromatography well known in the art is generally applicable to both of these approaches.

Described below are several methods based on specific molecular interactions of a tag and its binding partner.

A method that is generally applicable to purifying recombinant α2Ms that are fused to the constant regions of immunoglobulin is protein A affinity chromatography, a technique that is well known in the art. Staphylococcus protein A is a 42 kD polypeptide that binds specifically to a region located between the second and third constant regions of heavy chain immunoglobulins. Because of the Fc domains of different classes, subclasses and species of immunoglobulins, affinity of protein A for human Fc regions is strong, but may vary with other species. Subclasses that are less preferred include human IgG-3, and most rat subclasses. For certain subclasses, protein G (of Streptococci) may be used in place of protein A in the purification. Protein-A sepharose (Pharmacia or Biorad) is a commonly used solid phase for affinity purification of antibodies, and can be used essentially in the same manner for the purification of α2M polypeptide fused to an immunoglobulin Fc fragment. Secreted α2M polypeptide present in cell supernatant binds specifically to protein A on the solid phase, while the contaminants are washed away. Bound α2M polypeptide can be eluted by various buffer systems known in the art, including a succession of citrate, acetate and glycine-HCl buffers which gradually lowers the pH. This method is less preferred if the recombinant cells also produce antibodies which will be copurified with the α2M polypeptide. See, for example, Langone, 1982, J. Immunol. meth. 51:3; Wilchek et al., 1982, Biochem. Intl. 4:629; Sjobring et al., 1991, J. Biol. Chem. 26:399; page 617-618, in Antibodies A Laboratory Manual, edited by Harlow and Lane, Cold Spring Harbor laboratory, 1988.

Alternatively, a polyhistidine tag may be used, in which case, the α2M polypeptide can be purified by metal chelate chromatography. The polyhistidine tag, usually a sequence of six histidines, has a high affinity for divalent metal ions, such as nickel ions ($Ni^{2+}$), which can be immobilized on a solid phase, such as nitrilotriacetic acid matrices. Polyhistidine has a well characterized affinity for $Ni^{2+}$-NTA-agarose, and can be eluted with either of two mild treatments: imidazole (0.1-0.2 M) will effectively compete with the resin for binding sites; or lowering the pH just below 6.0 will protonate the histidine side-chains and disrupt the binding. The purification method comprises loading the cell culture supernatant onto the $Ni^{2+}$-NTA-agarose column, washing the contaminants through, and eluting the α2M polypeptide with imidazole or weak acid. $Ni^{2+}$-NTA-agarose can be obtained from commercial suppliers such as Sigma (St. Louis) and Qiagen. Antibodies that recognize the polyhistidine tag are also available which can be used to detect and quantify the α2M polypeptide.

Another exemplary affinity label that can be used is the glutathione-S-transferase (GST) sequence, originally cloned from the helminth, *Schistosoma japonicum*. In general, an α2M-GST fusion expressed in a prokaryotic host cell, such as *E. coli*, can be purified from the cell culture supernatant by absorption with glutathione agarose beads, followed by elution in the presence of free reduced glutathione at neutral pH. Denaturing conditions are not required at any stage during purification, and therefore, it may be desirable for use in the loading of immobilized α2M polypeptides with antigenic peptides. Moreover, since GST is known to form dimers under certain conditions, dimeric α2M polypeptides may be obtained. See, Smith, 1993, Methods Mol. Cell Bio. 4:220-229.

Another useful affinity label that can be used is the maltose binding protein (MBP) of *E. coli*, which is encoded by the malE gene. The secreted α2M polypeptide-MBP present in the cell supernatant binds to amylose resin while contaminants are washed away. The bound α2M polypeptide-MBP is eluted from the amylose resin by maltose. See, for example, Guan et al., 1987, Gene 67:21-30.

The second approach for purifying α2M polypeptide is applicable to affinity labels that contain an epitope for which polyclonal or monoclonal antibodies are available. Various methods known in the art for purification of protein by immunospecific binding, such as immunoaffinity chromatography, and immunoprecipitation, can be used. See, for example, Chapter 13 in "Antibodies A Laboratory Manual", 1988, Harlow and Lane, (eds.), Cold Spring Harbor Laboratory, N.Y. and Chapter 8, Sections I and II, in "Current Protocols in Immunology", 1991, Coligan et al. (eds.), John Wiley, the disclosure of which are both incorporated by reference herein.

The embodiments described above may be used to recover and purify α2M polypeptide-antigenic molecule complexes from the cell culture medium of mammalian cells, such as human cells expressing an α2M polypeptide of the invention. The methods can be adapted to perform medium and large scale purification of an α2M polypeptide and/or α2M-antigenic molecule complexes. Methods that do not require lowering pH or denaturing conditions are most preferred for purification of α2M polypeptide-antigenic molecule complexes. The methods may be used to isolate α2M polypeptides from eukaryotic cells, for example, cancer cells, tissues, isolated cells, or immortalized eukaryote cell lines infected with an intracellular pathogen, or cells obtained from a subject infected with a pathogen.

5.1.1.4 Host-vector Systems

Described herein are systems of vectors and host cells that can be used for the expression of α2M polypeptides. A variety of expression vectors may be used in the present invention which include, but are not limited to, plasmids, cosmids, phage, phagemids, or modified viruses. Typically, such expression vectors comprise a functional origin of replication for propagation of the vector in an appropriate host cell, one or more restriction endonuclease sites for insertion of the α2M polypeptide gene sequence, and one or more selection markers. The expression vector must be used with a compatible host cell which may be derived from a prokaryotic or an eukaryotic organism including but not limited to bacteria, yeasts, insects, mammals, and humans.

Expression constructs and vectors are introduced into host cells for the purpose of producing an α2M polypeptide. Any cell type that can produce α2Ms and is compatible with the expression vector may be used, including those that have been cultured in vitro or genetically engineered. Host cells may be obtained from normal or affected subjects, including healthy humans, cancer patients, and patients with an infectious disease, private laboratory deposits, public culture collections such as the American Type Culture Collection, or from commercial suppliers.

Different host cells have characteristic and specific mechanisms for the post-translational processing and modification of proteins. A host cell may be chosen which modifies and processes the expressed gene products in a specific fashion similar to the way the recipient processes α2Ms. For the purpose of producing large amounts of α2M, it is preferable that the type of host cell used in the present invention has been used for expression of heterologous genes, and is reasonably well characterized and developed for large-scale production processes. In a specific embodiment, the host cells are from the same patient to whom α2M polypeptide-antigenic molecule complexes or recombinant cells expressing α2M polypeptide-antigenic molecule complexes are going to be administered. Otherwise said, the cells used to express the α2M polypeptide and used subsequently to administer immunotherapy to a subject are autologous to the subject.

Preferred mammalian host cells include but are not limited to those derived from humans, monkeys and rodents, (see, for example, Kriegler M. in "Gene Transfer and Expression: A Laboratory Manual", New York, Freeman & Co. 1990), such as monkey kidney cell line transformed by SV40 (COS-7, ATCC CRL 1651); human embryonic kidney line (293, 293-EBNA, or 293 cells subcloned for growth in suspension culture, Graham et al., J. Gen. Virol., 36:59, 1977; baby hamster kidney cells (BHK, ATCC CCL 10); chinese hamster ovary-cells-DHFR (CHO, Urlaub and Chasin. Proc. Natl. Acad. Sci. 77; 4216, 1980); mouse sertoli cells (Mather, Biol. Reprod. 23:243-251, 1980); mouse fibroblast cells (NIH-3T3), monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); and mouse mammary tumor cells (MMT 060562, ATCC CCL51). Exemplary cancer cell types used for demonstrating the utility of recombinant cells (producing α2M polypeptide-antigenic molecule complexes) as a cancer vaccine are provided as follows: mouse fibroblast cell line, NIH3T3, mouse Lewis lung carcinoma cell line, LLC, mouse mastocytoma cell line, P815, mouse lymphoma cell line, EL4 and its ovalbumin transfectant, E.G7, mouse melanoma cell line, B16F10, mouse fibrosarcoma cell line, MC57, and human small cell lung carcinoma cell lines, SCLC#2 and SCLC#7.

A number of viral-based expression systems may also be utilized with mammalian cells to produce α2M polypeptides. Vectors using DNA virus backbones have been derived from simian virus 40 (SV40) (Hamer et al., 1979, Cell 17:725), adenovirus (Van Doren et al., 1984, Mol Cell Biol 4:1653), adeno-associated virus (McLaughlin et al., 1988, J Virol 62:1963), and bovine papillomas virus (Zinn et al., 1982, Proc Natl Acad Sci 79:4897). In cases where an adenovirus is used as an expression vector, the donor DNA sequence may be ligated to an adenovirus transcription/translation control region, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts (see e.g., Logan and Shenk, 1984, Proc. Natl. Acad. Sci. (USA) 81:3655-3659).

Bovine papillomavirus (BPV) can infect many higher vertebrates, including man, and its DNA replicates as an episome. A number of shuttle vectors have been developed for recombinant gene expression which exist as stable, multicopy (20-300 copies/cell) extrachromosomal elements in mammalian cells. Typically, these vectors contain a segment of BPV DNA (the entire genome or a 69% transforming fragment), a promoter with a broad host range, a polyadenylation signal, splice signals, a selectable marker, and "poisonless" plasmid sequences that allow the vector to be propagated in *E. coli*. Following construction and amplification in bacteria, the expression gene construct is transfected into cultured mammalian cells, for example, by the techniques of calcium phosphate coprecipitation or electroporation. For those host cells that do not manifest a transformed phenotype, selection of transformants is achieved by use of a dominant selectable marker, such as histidinol and G418 resistance. For example, BPV vectors such as pBCMGSNeo and pBCMGHis may be used to express α2M polypeptide sequences (Karasuyama et al., Eur. J. Immunol. 18:97-104; Ohe et al., Human Gene Therapy, 6:325-33) which may then be transfected into a diverse range of cell types for expression of the α2M polypeptide.

Alternatively, the vaccinia 7.5K promoter may be used (see, e.g., Mackett et al., 1982, Proc. Natl. Acad. Sci. (USA) 79:7415-7419; Mackett et al., 1984, J. Virol. 49:857-864; Panicali et al., 1982, Proc. Natl. Acad. Sci. 79:4927-4931.) In cases where a human host cell is used, vectors based on the Epstein-Barr virus (EBV) origin (OriP) and EBV nuclear antigen 1 (EBNA-1; a trans-acting replication factor) may be used. Such vectors can be used with a broad range of human host cells, e.g., EBO-pCD (Spickofsky et al, 1990, DNA Prot Eng Tech 2:14-18), pDR2 and λDR2 (available from Clontech Laboratories).

α2M polypeptides may also be made with a retrovirus-based expression system. In contrast to transfection, retroviruses can efficiently infect and transfer genes to a wide range of cell types including, for example, primary hematopoietic cells. In retroviruses such as Moloney murine leukemia virus, most of the viral gene sequences can be removed and replaced with nucleic acid sequences encoding α2M, while the missing viral functions can be supplied in trans. The host range for infection by a retroviral vector can also be manipulated by the choice of envelope used for vector packaging.

For example, a retroviral vector can comprise a 5' long terminal repeat (LTR), a 3' LTR, a packaging signal, a bacterial origin of replication, and a selectable marker. The α2M polypeptide DNA is inserted into a position between the 5' LTR and 3' LTR, such that transcription from the 5' LTR promoter transcribes the cloned DNA. The 5' LTR comprises a promoter, including but not limited to an LTR promoter, an R region, a U5 region and a primer binding site, in that order. Nucleotide sequences of these LTR elements are well known in the art. A heterologous promoter as well as multiple drug selection markers may also be included in the expression vector to facilitate selection of infected cells (see McLauchlin et al., 1990, Prog. Nucleic Acid Res. and Molec. Biol. 38:91-135; Morgenstern et al., 1990, Nucleic Acid Res. 18:3587-3596; Choulika et al., 1996, J. Virol 70:1792-1798; Boesen et al., 1994, Biotherapy 6:291-302; Salmons and Gunzberg, 1993, Human Gene Therapy 4:129-141; and Grossman and Wilson, 1993, Curr. Opin. in Genetics and Devel. 3:110-114).

Other useful eukaryotic host-vector system may include yeast and insect systems. In yeast, a number of vectors containing constitutive or inducible promoters may be used with *Saccharomyces cerevisiae* (baker's yeast), *Schizosaccharomyces pombe* (fission yeast), *Pichia pastoris*, and *Hansenula polymorpha* (methylotropic yeasts). For a review see, "Current Protocols in Molecular Biology", Vol. 2, 1988, Ausubel et al. (eds.), Greene Publish. Assoc. & Wiley Interscience, Ch. 13; Grant et al., 1987, Expression and Secretion Vectors for Yeast, 1987, in "Methods in Enzymology", Wu and Grossman (eds.), Acad. Press, N.Y., Vol. 153, pp. 516-544; Glover, 1986, DNA Cloning, Vol. 11, IRL Press, Wash., D.C., Ch. 3; and Bitter, 1987, Heterologous Gene Expression in Yeast, in "Methods in Enzymology", Berger and Kimmel (eds.), Acad. Press, N.Y., Vol. 152, pp. 673-684; and "The Molecular Biology of the Yeast *Saccharomyces*", 1982, Strathem et al. (eds.), Cold Spring Harbor Press, Vols. I and II.

In an insect system a baculovirus, *Autographa californica* nuclear polyhidrosis virus (AcNPV), can be used as a vector to express an α2M polypeptide in *Spodoptera frugiperda* cells. The α2M polypeptide DNA may be cloned into non-essential regions (for example the polyhedrin gene) of the virus and placed under control of an AcNPV promoter (for example the polyhedrin promoter). These recombinant viruses are then used to infect host cells in which the inserted DNA is expressed (see, e.g., Smith et al., 1983, J. Virol. 46:584; Smith, U.S. Pat. No. 4,215,051).

Any of the cloning and expression vectors described herein may be synthesized and assembled from known DNA sequences by techniques well known in the art. The regulatory regions and enhancer elements can be of a variety of origins, both natural and synthetic. Some vectors and host cells may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

5.1.1.5 Synthetic Production

An alternative to producing α2M by recombinant techniques is peptide synthesis. For example, a peptide corresponding to a portion of an α2M comprising the substrate-binding domain, or which binds peptides in vitro, can be synthesized by use of a peptide synthesizer. Conventional peptide synthesis may be used or other synthetic protocols well known in the art.

In addition, analogs and derivatives of α2M polypeptides can be chemically synthesized. Furthermore, if desired, non-classical amino acids or chemical amino acid analogs can be introduced as a substitution or addition into the α2M sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

Peptides having α2M amino acid sequences, or a fragment, analog, mutant or derivative thereof, may be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art and so are not discussed in detail herein (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting α2M polypeptides accomplished using conventional procedures, such as preparative HPLC using gel permeation, partition and/or ion exchange chromatography. The choice of appropriate matrices and buffers are well known in the art and so are not described in detail herein.

5.2 Antigenic Complexes Comprising α2M Polypeptides 5.2.1 Isolation of Intracellular Complexes of α2M Polypeptides with Antigenic Molecules Described herein are methods for purifying α2M polypeptides or α2M polypeptide-antigenic molecule complexes of the invention from recombinant cells, and, with minor modifications known in the art, the α2M polypeptide or α2M-antigenic molecule complexes from the cell culture. Recombinant cells include, for example, cells expressing antigenic molecules and recombinantly expressing an α2M polypeptide. Such cells may be derived from a variety of sources, including, but not limited to, cells infected with an infectious agent and cancer cells.

The invention provides methods for purification of recombinant α2M polypeptide-antigenic molecule complexes by affinity purification, based on the properties of the affinity label present on the α2M polypeptide. One approach is based on specific molecular interactions between a tag and its binding partner. The other approach relies on the immunospecific binding of an antibody to an epitope present on the tag. The principle of affinity chromatography well known in the art is generally applicable to both of these approaches.

To produce α2M polypeptide-antigenic molecule complexes, a nucleotide sequence encoding an α2M polypeptide can be introduced into a cell. When an antigenic molecule is present in the cell, the α2M polypeptide can associate intracellularly with the antigenic molecule, forming a covalent or a noncovalent complex of α2M polypeptide and the antigenic molecule. Cells into which an α2M polypeptide-encoding nucleotide sequence can be introduced, include, but are not limited to, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. The choice of cell type depends on the type of tumor or infectious disease being treated or prevented, and can be determined by one of skill in the art. In a specific embodiment, an expression construct comprising a nucleic acid sequence encoding the α2M polypeptide is introduced into an antigenic cell. As used herein, antigenic cells may include cells that are infected with an infectious agent or pathogen, cells infected with non-infectious or non-pathogenic forms of an infectious agent or pathogen (e.g., by use of a helper infectious agent), cells infected by or engineered to express an attenuated form of an infectious agent or a non-pathogenic or replication-deficient variant of a pathogen, pre-neoplastic cells that are infected with a cancer-causing infectious agent, such as a virus, but which are not yet neoplastic; or antigenic cells that have been exposed to a mutagen or cancer-causing agent, such as, for example DNA-damaging agents, radiation, etc. Other cells that can be used are pre-neoplastic cells which are in transition from a normal to a neoplastic form as characterized by morphology, physiological or biochemical functions. Preferably, the cancer cells and pre-neoplastic cells used in the methods of the invention are of mammalian origin. Mammals contemplated by this aspect of the invention include humans, companion animals (e.g., dogs and cats), livestock animals (e.g., sheep, cattle, goats, pigs and horses), laboratory animals (e.g., mice, rats and rabbits), and captive or free wild animals.

In various embodiments, any cancer cell, preferably a human cancer cell, can be used in the present methods for producing α2M polypeptide-antigenic molecule complexes. The cancer cells provide the antigenic peptides which become associated covalently or noncovalently with the expressed α2M polypeptide. α2M polypeptide-antigenic molecule complexes are then purified from the cells and used to treat such cancers. Cancers which can be treated or prevented with immunogenic compositions prepared by methods of the invention include, but are not limited to, tumors such as sarcomas and carcinomas. Examples of cancers that are amenable to the methods of the invention are listed in Section 5.6. Accordingly, any tissues or cells isolated from a pre-neoplastic lesion, a cancer, including cancer that has metastasized to multiple remote sites, can be used in the present method. For example, cells found in abnormally growing tissue, circulating leukemic cells, metastatic lesions as well as solid tumor tissue can be used.

In another embodiment, cell lines derived from a pre-neoplastic lesion, cancer tissues or cancer cells can also be used, provided that the cells of the cell line have at least one or more antigenic determinants in common with antigens on the target cancer cells. Cancer tissues, cancer cells, cells infected with a cancer-causing agent, other pre-neoplastic cells, and cell lines of human origin are preferred.

Cancer and pre-neoplastic cells can be identified by any method known in the art. For example, cancer cells can be identified by morphology, enzyme assays, proliferation assays, cytogenetic characterization, DNA mapping, DNA sequencing, the presence of cancer-causing virus, or a history of exposure to mutagen or cancer-causing agent, imaging, etc. Cancer cells may also be obtained by surgery, endoscopy, or other biopsy techniques. If some distinctive characteristics of the cancer cells are known, they can also be obtained or purified by any biochemical or immunological methods known in the art, such as but not limited to affinity chromatography, and fluorescence activated cell sorting (e.g., with fluorescently tagged antibody against an antigen expressed by the cancer cells). Cancer tissues, cancer cells or cell lines may be obtained from a single individual or pooled from several individuals. It is not essential that clonal, homogeneous, or purified population of cancer cells be used. It is also not necessary to use cells of the ultimate target in vivo (e.g., cells from the tumor of the intended recipient), so long as at least one or more antigenic determinants on the target cancer cells is present on the cells used for expression of the α2M polypeptide. In addition, cells derived from distant metastases may be used to prepare an immunogenic composition against the primary cancer. A mixture of cells can be used provided that a substantial number of cells in the mixture are cancer cells and share at least one antigenic determinant with the target cancer cell. In a specific embodiment, the cancer cells to be used in expressing an α2M polypeptide are purified.

5.2.2 In Vitro Complexing

In another embodiment, complexes of α2M polypeptides and antigenic molecules are produced in vitro. Immunogenic α2M polypeptide-antigenic molecule complexes can be generated in vitro by any method known in the art for forming α2M polypeptide-antigenic molecule complexes. Procedures for forming such α2M-antigenic molecule complexes and methods for isolating antigenic peptides are described in detail herein.

Methods for formation in vitro of noncovalent immunogenic complexes are well known in the art. For example, such complexes can be generated in vitro by noncovalent complexing of an α2M polypeptide with an antigenic molecule using methods which have been previously described for noncovalent coupling of an HSP with an antigenic molecule (see e.g., Blachere et al., 1997, supra; PCT publication WO 97/10000, dated Mar. 20, 1997). Preferably, the immunogenic molecular complex is not prepared by treatment with a protease, or with an activating agent such as ammonia or methyamine. In another preferred embodiment, the α2M molecule of the immunogenic molecular complex is not cleaved within the "bait" region. In yet another embodiment, the α2M polypeptide is not covalently associated with the antigenic molecule through a thioester linkage.

Methods for covalent coupling are also well known in the art (see, e.g., Osada et al., 1987, supra; Osada et al., 1988, supra; Chu and Pizzo 1993, supra; Chu et al., 1994, supra; Mitsuda et al., 1993, supra). In one embodiment, for example, when an α2M polypeptide is mixed with protease. During proteolytic activation of α2M, non-proteolytic ligands can become covalently bound to the activated thioesters. Non-proteolytic ligands can also be incorporated into the activated α2M molecule by ammonia or methylamine during reversal of the nucleophilic activation, employing heat (Grøn and Pizzo, 1998, Biochemistry, 37: 6009-6014). Such conditions that allow fortuitous trapping of peptides by α2M are employed to prepare the α2M polypeptide-antigenic molecule complexes of the invention.

For example, in various embodiments of the invention, an α2M polypeptide may be mixed with antigenic molecule in the presence of a protease, ammonia or other small amine nucleophiles such as methylamine and ethylamine. Non-limiting examples of proteases which may be used include trypsin, porcine pancreatic elastase (PEP), human neutrophil elastase, cathepsin G, S. aureus V-8 proteinase trypsin, α-chymotrypsin, V8 protease, papain, and proteinase K (see Ausubel et al., (eds.), in "Current Protocols in Molecular Biology", Greene Publishing Associates and Wiley Interscience, New York, 17.4.6-17.4.8).

In another embodiment for preparation of covalent α2M polypeptide-antigenic molecule complexes, α2M polypeptides and antigenic molecules are prepared, and then covalently coupled using, for example, chemical crosslinking. Chemical crosslinking methods are well known in the art. For example, in a preferred embodiment, glutaraldehyde crosslinking may be used. Glutaradehyde crosslinking has been used for formation of covalent complexes of peptides and hsps (see Barrios et al., 1992, Eur. J. Immunol. 22: 1365-1372). In one embodiment, the following protocol is used. Optionally, α2M polypeptides may be pretreated with ATP or low pH prior to complexing, in order to remove any peptides that may be associated with the α2M polypeptide. Preferably, 1 mg of α2M polypeptide is crosslinked to 1 mg of peptide in the presence of 0.002% glutaraldehyde for 2 hours. Glutaraldehyde is removed by dialysis against phosphate buffered saline (PBS) overnight (Lussow et al., 1991, Eur. J. Immunol. 21: 2297-2302).

Other methods for chemical crosslinking may also be used, in addition other methods for covalent attachment of proteins, such as photocrosslinking (see Current Protocols in Molecular Biology, Ausubel et al. (eds.), Greene Publishing Associates and Wiley Interscience, New York).

Antigenic molecules for covalent or noncovalent α2M polypeptide-antigenic molecule complexes may be isolated from various sources, chemically synthesized, or produced recombinantly. Such methods can be readily adapted for medium or large scale production of the immunotherapeutic or prophylactic vaccines of the invention.

Following complexing, the immunogenic α2M-antigenic molecule complexes can optionally be purified. In a preferred embodiment, such complexes are at least 65%, 70%, 75%, 80%, 85%, 90%, 95%, 98%, or 100% nonconvalent complexes of α2M and the antigenic molecule. Such complexes may be assayed in vitro using, for example, the mixed lymphocyte target cell assay (MLTC) described below. Once immunogenic complexes have been isolated they can be optionally characterized further in animal models using the preferred administration protocols and excipients discussed below.

5.2.3. α2M-Antigenic Molecule Fusion Proteins

In another embodiment, recombinant fusion proteins, comprised of α2M sequences linked to antigenic molecule sequences, may be used for immunotherapy. To produce such a recombinant fusion protein, an expression vector is constructed using nucleic acid sequences encoding α2M fused to sequences encoding an antigenic molecule, using recombinant methods known in the art, such as those described in Sections 5.1.1.1 and 5.1.1.2, above (see Suzue et al., 1997, Proc. Natl. Acad. Sci. U.S.A. 94: 13146-51). α2M-antigenic peptide fusions are then expressed and isolated. By specifically designing the antigenic peptide portion of the molecule, such fusion proteins can be used to elicit an immune response and in immunotherapy against target cancer and infectious diseases.

5.2.4 Sources of Antigenic Molecules

Antigenic molecules, or antigenic portions thereof, specific to one or more types of cancer or infected cells, can be chosen from among those known in the art. Alternatively, such antigenic molecules can be selected for their antigenicity or their immunogenicity, as determined by immunoassays or by their ability to generate an immune response.

5.2.4.1 Exogenous Antigenic Molecules

Preferably, where it is desired to treat or prevent cancer, known tumor-specific antigenic molecules or fragments or derivatives thereof are used. For example, such tumor specific or tumor-associated antigenic molecules include but are not limited to KS 1/4 pan-carcinoma antigen (Perez and Walker, 1990, J. Immunol. 142:3662-3667; Bumal, 1988, Hybridoma 7(4):407-415); ovarian carcinoma antigen (CA125) (Yu, et al., 1991, Cancer Res. 51(2):468-475); prostatic acid phosphate (Tailer, et al., 1990, Nucl. Acids Res. 18(16):4928); prostate specific antigen (Henttu and Vihko, 1989, Biochem. Biophys. Res. Comm. 160(2):903-910; Israeli, et al., 1993, Cancer Res. 53:227-230); melanoma-associated antigen p97 (Estin, et al., 1989, J. Natl. Cancer Inst. 81(6):445-446); melanoma antigen gp75 (Vijayasardahl, et al., 1990, J. Exp. Med. 171(4):1375-1380); high molecular weight melanoma antigen (Natali, et al., 1987, Cancer 59:55-63) and prostate specific membrane antigen.

In a specific embodiment, an antigenic molecule or fragment or derivative thereof specific to a certain tumor is selected for complexing to α2M polypeptide and subsequent administration to a patient having that tumor.

In a preferred embodiment, where it is desired to treat or prevent viral diseases, molecules comprising epitopes of known viruses are used. For example, such antigenic epitopes may be prepared from viruses including, but not limited to, hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II).

In another preferred embodiment, where it is desired to treat or prevent bacterial infections, molecules comprising epitopes of known bacteria are used. For example, such antigenic epitopes may be prepared from bacteria including, but not limited to, mycobacteria rickettsia, mycoplasma, neisseria and legionella.

In another preferred embodiment, where it is desired to treat or prevent protozoal infections, molecules comprising epitopes of known protozoa are used. For example, such antigenic epitopes may be prepared from protozoa including, but not limited to, leishmania, kokzidioa, and trypanosoma.

In yet another preferred embodiment, where it is desired to treat or prevent parasitic infections, molecules comprising epitopes of known parasites are used. For example, such antigenic epitopes may be from parasites including, but not limited to, chlamydia and rickettsia.

To determine immunogenicity or antigenicity of a putative antigen by detecting binding to antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in vivo immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, etc. In one aspect, antibody binding is detected by detecting a label on the primary antibody. In another aspect, the primary antibody is detected by detecting binding of a secondary antibody or reagent to the primary antibody. In a further aspect, the secondary antibody is labeled. Many means are known in the art for detecting binding in an immunoassay and are envisioned for use. In one embodiment for detecting immunogenicity, T cell-mediated responses can be assayed by standard methods, e.g., in vitro cytoxicity assays or in vivo delayed-type hypersensitivity assays.

Potentially useful antigenic molecules, or derivatives thereof, can be identified by various criteria, such as the antigen's involvement in neutralization of a pathogen's infectivity (wherein it is desired to treat or prevent infection by such a pathogen) (Norrby, 1985, Summary, in Vaccines 85, Lerner, et al. (eds.), Cold Spring Harbor Laboratory, Cold Spring Harbor, N.Y., pp. 388-389), type or group specificity, recognition by patients' antisera or immune cells, and/or the demonstration of protective effects of antisera or immune cells specific for the antigen. In addition, where it is desired to treat or prevent a disease caused by pathogen, the antigen's encoded epitope should preferably display a small or no degree of antigenic variation in time or amongst different isolates of the same pathogen.

5.2.4.2 Antigenic Molecules from α2M Complexes

Antigenic peptides for complexing in vitro to α2M polypeptides of the invention can also be obtained from endogenous complexes of peptides and α2Ms. Two methods may be used to elute the peptide from an α2M-antigenic molecule complex. One approach involves incubating the α2M-antigenic molecule complex in the presence of ATP. The other approach involves incubating the complexes in a low pH buffer.

Briefly, the complex of interest is centrifuged through a Centricon 10 assembly (Millipore) to remove any low molecular weight material loosely associated with the complex. The large molecular weight fraction may be removed and analyzed by SDS-PAGE while the low molecular weight may be analyzed by HPLC as described below. In the ATP incubation protocol, the α2M-antigenic molecule complex in the large molecular weight fraction is incubated with 10 mM ATP for 30 minutes at room temperature. In the low pH protocol, acetic acid or trifluoroacetic acid (TFA) is added to the α2M-antigenic molecule complex to give a final concentration of 10% (vol/vol) and the mixture incubated at room temperature or in a boiling water bath or any temperature in between, for 10 minutes.

The resulting samples are centrifuged through a Centricon10 assembly as mentioned previously. The high and low molecular weight fractions are recovered. The remaining large molecular weight α2M-antigenic molecule complexes can be reincubated with ATP or low pH to remove any remaining peptides.

The resulting lower molecular weight fractions are pooled, concentrated by evaporation and dissolved in 0.1% TFA. The dissolved material is then fractionated by reverse phase high pressure liquid chromatography (HPLC) using for example a VYDAC C18 reverse phase column equilibrated with 0.1% TFA. The bound material is then eluted at a flow rate of about 0.8 ml/min by developing the column with a linear gradient of 0 to 80% acetonitrile in 0.1% TFA. The elution of the peptides can be monitored by $OD_{210}$ and the fractions containing the peptides collected.

5.2.4.3 Peptide Antigens from MHC Complexes

Peptides bound to MHC molecules in vivo can also be used in vitro to form complexes with α2M polypeptides of the invention. The isolation of potentially immunogenic peptides from MHC molecules is well known in the art and so is not described in detail herein (see, Falk, et al., 1990, Nature 348:248-251; Rotzsche, at al., 1990, Nature 348:252-254; Elliott, et al., 1990, Nature 348:191-197; Falk, et al., 1991, Nature 351:290-296; Demotz, et al., 1989, Nature 343:682-684; Rotzsche, et al., 1990, Science 249:283-287), the disclosures of which are incorporated herein by reference.

Briefly, MHC-antigenic molecule complexes may be isolated by a conventional immunoaffinity procedure. The peptides then may be eluted from the MHC-antigenic molecule complex by incubating the complexes in the presence of about 0.1% TFA in acetonitrile. The eluted peptides may be fractionated and purified by reverse phase HPLC, as before.

5.2.4.4 Synthetic Antigenic Molecules

The amino acid sequences of the peptides eluted from MHC molecules or α2M may be determined either by manual or automated amino acid sequencing techniques well known in the art. Once the amino acid sequence of a potentially protective peptide has been determined, the peptide may be synthesized in using conventional peptide synthesis or other protocols well known in the art.

Peptides having the same amino acid sequence as those isolated above may be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art and so are not discussed in detail herein (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting peptides is accomplished using conventional procedures, such as preparative HPLC using gel permeation, partition and/or ion exchange chromatography. The choice of appropriate matrices and buffers are well known in the art and so are not described in detail herein.

5.2.4.5 Recombinantly Produced Antigenic Molecules

In a particular embodiment of the invention, a nucleotide sequence encoding a protein antigenic molecule or portions thereof can be introduced into a host cell for production of the antigenic molecule. The nucleotide sequence encoding any antigenic protein can be obtained and cloned into an expression vector for expression essentially by the same methods described for the cloning and expression of a nucleotide sequence encoding an α2M polypeptide. The techniques are described in Sections 5.1.1.1 and 5.1.1.2, and are well known in the art. The recombinant antigenic protein or portions thereof can be purified by any methods appropriate for the protein, and then used to form complexes with α2M polypeptides in vitro as described in Section 5.2.2. Such an α2M polypeptide-antigenic molecule complex can be used as a vaccine to stimulate an immune response against the antigenic protein in a subject for the purpose of treatment or prevention of infectious diseases or cancer.

5.3 Therapeutic Applications for α2M Complexes

The present invention encompasses the use of α2M polypeptides in methods for treatment of and prevention of infectious diseases and cancer. In various embodiments described in detail herein, an effective amount of α2M polypeptide in a covalent or noncovalent complex with an antigenic molecule is administered to a patient for therapeutic purposes.

5.3.1 Prevention and Treatment of Infectious Diseases

For treatment and prevention of infectious disease, α2M-antigenic molecule complexes are prepared from a cell that displays the antigenicity of an antigen of an infectious agent or pathogenic agent, and used as vaccines against the infectious disease. As will be appreciated by those skilled in the art, the protocols described herein may be used to isolate α2M polypeptide-antigenic molecule complexes from any cell that displays the antigenicity of an antigen of the infectious agent. For example, cells may be infected by the infectious agent itself, or alternatively, cells may be infected by or engineered to express an attenuated form of the infectious agent or a non-pathogenic or replication-deficient variant of the pathogen. In one embodiment, α2M-antigenic molecule complexes can be prepared from cells infected with non-infectious or non-pathogenic forms of the infectious agent (e.g., by use of a helper infectious agent). In another embodiment, the α2M-antigenic molecule complexes of the invention may be prepared from cells infected with an intracellular pathogen. In another embodiment, α2M polypeptide-complexes can be prepared from cells that have been transformed by an intracellular pathogen. For example, immunogenic α2M polypeptide-antigenic molecule complexes may be isolated from eukaryotic cells transformed with a transforming virus such as SV40.

A preferred method for treatment or prevention of an infectious disease comprises introducing into a cell that displays the antigenicity of an infectious agent an expressible α2M polypeptide gene sequence, preferably as an expression gene construct. The α2M polypeptide gene sequence is manipulated by recombinant methods, such as those described above in Sections 5.1.1.1 and 5.1.1.2 above, so that the α2M polypeptide gene sequence, in the form of an expression construct, located extrachromosomally or integrated in the chromosome, is suitable for expression of the α2M polypeptide in the recombinant cells.

The recombinant cells containing the expression gene constructs are cultured under conditions such that α2M polypeptides encoded by the expression gene construct are expressed. Complexes of α2M polypeptides covalently or noncovalently associated with antigenic molecules of the infectious agent are purified from the cell culture or culture medium by the methods described in Section 5.2.1.

In various embodiments, α2M-antigenic molecule complexes are prepared from a cell genetically manipulated to express an α2M polypeptide, for example, tissues, isolated cells or immortalized eukaryotic cell lines infected with an intracellular pathogen. When immortalized animal cell lines are used as a source of the α2M polypeptide-antigenic molecule complex, it is important to use cell lines that can be infected with the pathogen of interest. In addition, it is preferable to use cells that are derived from the same species as the intended recipient of the vaccine. Techniques for introducing an expressible form of the α2M polypeptide gene sequences into these cell lines are described above in Section 5.1.1.2. If a pathogen is expected to cause lysis of the host cells, it is preferred to introduce the expressible α2M polypeptide gene sequence into the host cell prior to infecting the cells with the pathogen. For example, in order to prepare an α2M polypeptide-antigenic molecule complex for administration to humans that may be effective against HIV-1, the virus may be propagated in human cells which include, but are not limited to, human CD4+ T cells, HepG2 cells, and U937 promonocytic cells, which have already been transfected with an expressible α2M polypeptide sequence. Similarly, influenza viruses may be propagated in, for example, transfected human fibroblast cell lines and MDCK cells, and mycobacteria may be cultured in, for example, transfected human Schwaan cells. The cell supernatant containing α2M-antigenic molecule complex may be collected just prior to lysis of the host cell.

In a preferred aspect of the invention, the purified α2M-antigenic molecule complex vaccines may have particular utility in the treatment of human diseases caused by intracellular pathogens. It is appreciated, however, that the vaccines developed using the principles described herein will be useful in treating diseases of other mammals, for example, farm animals including: cattle; horses; sheep; goats; and pigs, and household pets including: cats; and dogs, that similarly are caused by intracellular pathogens.

In accordance with the methods described herein, vaccines may be prepared that stimulate an immune response, in particular a cytotoxic T cell responses, against cells infected with viruses including, but not limited to, hepatitis type A, hepatitis type B, hepatitis type C, influenza, varicella, adenovirus, HSV-I, HSV-II, rinderpest rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, HIV-I, and HIV-II. Similarly, vaccines may also be prepared that stimulate cytotoxic T cell responses against cells infected with intracellular bacteria, including, but not limited to, *Mycobacteria, Rickettsia, Mycoplasma, Neisseria* and *Legionella*. In addition, vaccines may also be prepared that stimulate cytotoxic T cell responses against cells infected with intracellular protozoa, including, but not limited to, *Leishmani*, Kokzidioa, and *Trypanosoma*. Furthermore, vaccines may be prepared that stimulate cytotoxic T cell responses against cells infected with intracellular parasites including, but not limited to, *Chlamydia* and *Rickettsia*.

The effect of immunotherapy with modified α2M polypeptide-antigenic molecule complexes on progression of infectious diseases can be monitored by any methods known to one skilled in the art.

5.3.2 Prevention and Treatment of Cancer

There are many reasons why immunotherapy as provided by the covalent or noncovalent α2M polypeptide-antigenic molecule complexes or recombinant cells expressing α2M polypeptides prepared by the present invention is desired for use in cancer patients. First, if cancer patients are immunosuppressed, and surgery with anesthesia, and subsequent chemotherapy, may worsen the immunosuppression, then with appropriate immunotherapy in the preoperative period, this immunosuppression may be prevented or reversed. This could lead to fewer infectious complications and to accelerated wound healing. Second, tumor bulk is minimal following surgery and immunotherapy is most likely to be effective in this situation. A third reason is the possibility that tumor cells are shed into the circulation at surgery and effective immunotherapy applied at this time can eliminate these cells.

In a specific embodiment, the preventive and therapeutic utility of the invention is directed at enhancing the immunocompetence of the cancer patient either before surgery, at or after surgery, and at inducing tumor-specific immunity to cancer cells, with the objective being inhibition of cancer, and with the ultimate clinical objective being total cancer regression and eradication.

According to the invention, preferred methods of treatment or prevention of cancer comprise isolating cancer cells from one or more individual, preferably the individual in need of treatment, and introducing into such cells an expressible α2M polypeptide gene sequence, preferably as an expression gene construct. The α2M polypeptide gene sequence is manipulated by methods described above in Sections 5.1.1.1 and 5.1.1.2, such that the α2M polypeptide gene sequence, in the form of an expression construct, or intrachromosomally integrated, are suitable for expression of the α2M polypeptide in the recombinant cells. The recombinant cells containing the expression gene constructs are cultured under conditions such that α2M polypeptides encoded by the expression gene construct are expressed by the recombinant host cells. Complexes of α2M polypeptides covalently or noncovalently associated with antigenic molecules of the cancer cell are purified from the cell culture or culture medium by the methods described in Section 5.2.1. Depending on the route of administration, the α2M polypeptide-antigenic molecule complexes are formulated accordingly as described in Section 5.7, and administered to the individual autologously (e.g., to treat the primary cancer or metastases thereof), or to other individuals who are in need of treatment for cancer of a similar tissue type, or to individuals at enhanced risk of cancer due to familial history or environmental risk factors.

For example, treatment with α2M polypeptide-antigenic molecule complexes prepared as described above may be started any time after surgery. However, if the patient has received chemotherapy, α2M-antigenic molecule complexes are usually administered after an interval of four weeks or more so as to allow the immune system to recover. The therapeutic regimen may include weekly injections of the α2M polypeptide-antigenic molecule complex, dissolved in saline or other physiologically compatible solution. The route and site of injection is varied each time, for example, the first injection is given subcutaneously on the left arm, the second injection on the right arm, the third injection on the left abdominal region, the fourth injection on the right abdominal region, the fifth injection on the left thigh, the sixth injection on the right thigh, etc. The same site is repeated after a gap of one or more injections. In addition, injections are split and each half of the dose is administered at a different site on the same day. Overall, the first four to six injections are given at weekly intervals. Subsequently, two injections are given at two-week intervals, followed by a regimen of injections at monthly intervals.

Alternatively, recombinant tumor cells expressing α2M-antigenic molecule complexes can be used as a vaccine for injection into a patient to stimulate an immune response against the tumor cells or cells bearing tumor antigens. Autologous recombinant tumor cells stably expressing α2M polypeptide-antigenic molecule complexes are preferred. To determine the appropriate dose, the amount of α2M polypeptide-antigenic molecule complex produced by the recombinant cells is quantitated, and the number of recombinant cells used for vaccination is adjusted accordingly to assure a consistent level of expression in vivo. A preferred dose is the number of recombinant cells that can produce about 100 ng α2M polypeptide per 24 hours. For the safety of the patient, the recombinant tumor cells can be irradiated (12000 rad) immediately prior to injection into a patient. Irradiated cells do not proliferate, and can continue to express α2M polypeptide-antigenic molecule complexes for about 7-10 days which is sufficient to induce an immune response.

Cancers that can be treated or prevented by using covalent or noncovalent α2M-antigenic molecule complexes prepared by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

In a specific embodiment, the cancer is metastatic. In another specific embodiment, the patient having a cancer is immunosuppressed by reason of having undergone anti-cancer therapy (e.g., chemotherapy radiation) prior to administration of the α2M-antigenic molecule complexes of the invention. In another specific embodiment, the cancer is a tumor.

The effect of immunotherapy with α2M polypeptide-antigenic molecule complexes on progression of neoplastic diseases can be monitored by any methods known to one skilled in the art, including but not limited to measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; e) changes in levels of putative biomarkers of risk for a particular cancer in individuals at high risk, and f) changes in the morphology of tumors using a sonogram. Other techniques that can also be used include scintigraphy and endoscopy.

The preventive effect of immunotherapy using α2M polypeptide-antigenic molecule complexes may also be estimated by determining levels of a putative biomarker for risk of a specific cancer. For example, in individuals at enhanced risk for prostate cancer, serum prostate-specific antigen (PSA) is measured by the procedure described by Brawer et al., 1992, J. Urol. 147:841-845, and Catalona et al., 1993, JAMA 270:948-958; or in individuals at risk for colorectal cancer, CEA is measured by methods known in the art; and in individuals at enhanced risk for breast cancer, 16-α-hydroxylation of estradiol is measured by the procedure described by Schneider et al., 1982, Proc. Natl. Acad. Sci. USA 79:3047-3051. The references cited above are incorporated by reference herein in their entirety.

5.3.3 Combination with Adoptive Immunotherapy

Adoptive immunotherapy refers to a therapeutic approach for treating infectious diseases or cancer in which immune cells are administered to a host with the aim that the cells mediate specific immunity, either directly or indirectly, to the infected cells or tumor cells and/or antigenic components, and result in treatment of the infectious disease or regression of the tumor, as the case may be (see U.S. patent application Ser. No. 08/527,546, filed Sep. 13, 1995, which is incorporated by reference herein in its entirety). α2M polypeptides may be used to sensitize antigen presenting cells (APCs) using in covalent or noncovalent complexes with antigenic (or immunogenic) molecules, for adoptive immunotherapy.

According to the invention, therapy by administration of α2M polypeptide-antigenic molecule complexes, using any desired route of administration, is combined with adoptive immunotherapy using APC sensitized with α2M polypeptide-antigenic molecule complexes. The α2M polypeptide-antigenic molecule complex-sensitized APC can be administered concurrently with α2M polypeptide-antigenic molecule complexes, or before or after administration of α2M polypeptide-antigenic molecule complexes. Furthermore, the mode of administration can be varied, including but not limited to, e.g., subcutaneously, intravenously, intraperitoneally, intramuscularly, intradermally or mucosally.

5.3.3.1 Sensitization of Antigen Presenting Cells with α2M Complexes

The antigen-presenting cells, including but not limited to macrophages, dendritic cells and B-cells, are preferably obtained by production in vitro from stem and progenitor cells from human peripheral blood or bone marrow as described by Inaba et al., 1992, J. Exp. Med. 176:1693-1702. APC can be obtained by any of various methods known in the art. In a preferred aspect human macrophages are used, obtained from human blood cells.

By way of example, but not limitation, macrophages can be obtained as follows: Mononuclear cells are isolated from peripheral blood of a patient (preferably the patient to be treated), by Ficoll-Hypaque gradient centrifugation and are seeded on tissue culture dishes which are pre-coated with the patient's own serum or with other AB+ human serum. The cells are incubated at 37° C. for 1 hr, then non-adherent cells are removed by pipetting. To the adherent cells left in the dish, is added cold (4° C.) 1 mM EDTA in phosphate-buffered saline and the dishes are left at room temperature for 15 minutes. The cells are harvested, washed with RPMI buffer and suspended in RPMI buffer. Increased numbers of macrophages may be obtained by incubating at 37° C. with macrophage-colony stimulating factor (M-CSF); increased numbers of dendritic cells may be obtained by incubating with granulocyte-macrophage-colony stimulating factor (GM-CSF) as described in detail by Inaba, K., et al., 1992, J. Exp. Med. 176:1693-1702.

APC are sensitized with α2M polypeptides covalently or noncovalently bound to antigenic molecules by incubating the cells in vitro with the complexes. The APC are sensitized with complexes of α2M polypeptide and antigenic molecules preferably by incubating in vitro with the α2M polypeptide-complex at 37° C. for 15 minutes to 24 hours. By way of example but not limitation, $4 \times 10^7$ macrophages can be incubated with 10 microgram α2M-antigenic molecule complexes per ml or 100 microgram α2M-antigenic molecule complexes per ml at 37° C. for 15 mins to 24 hrs in 1 ml plain RPMI medium. The cells are washed three times and resuspended in a physiological medium preferably sterile, at a convenient concentration (e.g., $1 \times 10^7$/ml) for injection in a patient. In a preferred embodiment, the antigen presenting cells are autologous to the patient, that is, the patient into which the sensitized APCs are injected is the patient from which the APC were originally isolated.

Optionally, the ability of sensitized APC to stimulate, for example, the antigen-specific, class I-restricted cytotoxic T-lymphocytes (CTL) can be monitored by their ability to stimulate CTLs to release tumor necrosis factor, and by their ability to act as targets of such CTLs.

5.3.3.2 Reinfusion of Sensitized APC

The α2M polypeptide-antigen-sensitized APC are reinfused into the patient systemically, preferably intravenously, by conventional clinical procedures. These activated cells are reinfused, preferentially by systemic administration into the autologous patient. Patients generally receive from about $10^6$ to about $10^{12}$ sensitized macrophages, depending on the condition of the patient. In some regimens, patients may optionally receive in addition a suitable dosage of a biological response modifier including but not limited to the cytokines IFN-α, IFN-γ, IL-2, IL-4, IL-6, TNF or other cytokine growth factor.

5.3.4 Determination of Immunogenicity of α2M-antigen Molecule Complexes

In an optional procedure, the purified α2M polypeptide-antigenic molecule complexes can be assayed for immunogenicity using the mixed lymphocyte target culture assay (MLTC) well known in the art.

By way of example but not limitation, the following procedure can be used. Briefly, mice are injected subcutaneously with the candidate α2M polypeptide-antigenic molecule complexes. As a positive control another set of mice are immunized with whole cancer cells of the type from which the α2M polypeptides are derived. As a negative control, mice are injected with either α2M-antigenic molecule complexes isolated from normal, non-recombinant cells or whole cells (i.e., antigenically distinct from the type of cell from which the α2M polypeptides are derived). The mice are injected twice, 7-10 days apart. The mice are injected twice, 7-10 days apart. Ten days after the last immunization, the spleens are removed and the lymphocytes released. The released lymphocytes may be restimulated subsequently in vitro by the addition of dead cells that expressed the complex of interest.

For example, $8 \times 10^6$ immune spleen cells may be stimulated with $4 \times 10^4$ mitomycin C treated or γ-irradiated (5-10, 000 rads) pathogen-infected cells (or cells transfected with a gene encoding an antigen of the infectious agent, as the case may be), or tumor cells in 3 ml RPMI medium containing 10% fetal calf serum. In certain cases 33% secondary mixed lymphocyte culture supernatant or interleukin 2 (IL-2) may be included in the culture medium as a source of T cell growth factors (See, Glasebrook et al., 1980, J. Exp. Med. 151:876). To test the primary cytotoxic T cell response after immunization, spleen cells may be cultured without stimulation. In some experiments spleen cells of the immunized mice may also be restimulated with antigenically distinct cells, to determine the specificity of the cytotoxic T cell response.

Six days later the cultures are tested for cytotoxicity in a 4 hour $^{51}$Cr-release assay (See, Palladino et al., 1987, Cancer Res. 47:5074-5079 and Blachere, at al., 1993, J. Immunotherapy 14:352-356). In this assay, the mixed lymphocyte culture is added to a target cell suspension to give different effector:target (E:T) ratios (usually 1:1 to 40:1). The target cells are prelabelled by incubating $1 \times 10^6$ target cells in culture medium containing 200 mCi $^{51}$Cr/ml for one hour at 37° C. The cells are washed three times following labeling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are pelleted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

In order to block the MHC class I cascade a concentrated hybridoma supernatant derived from K-44 hybridoma cells (an anti-MHC class I hybridoma) is added to the test samples to a final concentration of 12.5% (Heike et al., 1994, J. Immunotherapy 15:165-174).

An alternative to the chromium-release assay is the ELISPOT assay which measures cytokine release by cytotoxic T cells in vitro after stimulation with specific antigen. Cytokine release is detected by antibodies which are specific for a particular cytokine, such as interleukin-2, tumor necrosis factor α or interferon-γ (for example, see Scheibenbogen et al., 1997, Int. J. Cancer, 71:932-936). The assay is carried out in a microtiter plate which has been pre-coated with an antibody specific for a cytokine of interest which captures the cytokine secreted by T cells. After incubation of T cells for 24-48 hours in the coated wells, the cytotoxic T cells are removed and replaced with a second labeled antibody that recognizes a different epitope on the cytokine. After extensive washing to remove unbound antibody, an enzyme substrate which produces a colored reaction product is added to the plate. The number of cytokine-producing cells is counted under a microscope. This method has the advantages of short assay time, and sensitivity without the need of a large number of cytotoxic T cells.

5.3.5 Monitoring of Effects During Immunotherapy

The effect of immunotherapy with α2M polypeptide-antigenic molecule complexes can be monitored by any methods known to one skilled in the art, including but not limited to measuring: a) delayed hypersensitivity as an assessment of cellular immunity; b) activity of cytolytic T-lymphocytes in vitro; c) levels of infective agent-agent or tumor-specific antigens, e.g., carcinoembryonic (CEA) antigens. In the case of the use of α2M-antigenic molecule complexes for prevention or treatment of cancer, the effect can additionally be monitored by: d) changes in the morphology of tumors using techniques such as a computed tomographic (CT) scan; and e) changes in levels of putative biomarkers of risk for a particular cancer in individuals at high risk, and f) changes in the morphology of tumors using a sonogram.

5.3.5.1 Delayed Hypersensitivity Skin Test

Delayed hypersensitivity skin tests are of great value in the overall immunocompetence and cellular immunity to an antigen. Inability to react to a battery of common skin antigens is termed anergy (Sato et al., 1995, Clin. Immunol. Pathol. 74:35-43).

Proper technique of skin testing requires that the antigens be stored sterile at 4° C., protected from light and reconstituted shorted before use. A 25- or 27-gauge needle ensures intradermal, rather than subcutaneous, administration of antigen. Twenty-four and 48 hours after intradermal administration of the antigen, the largest dimensions of both erythema and induration are measured with a ruler. Hypoactivity to any given antigen or group of antigens is confirmed by testing with higher concentrations of antigen or, in ambiguous circumstances, by a repeat test with an intermediate test.

5.3.5.2 In Vitro Activation of Cytotoxic T Cells

The activity of cytotoxic T-lymphocytes can be assessed in vitro using the following method. Eight$\times 10^6$ peripheral blood-derived T lymphocytes isolated by the Ficoll-Hypaque centrifugation gradient technique, are restimulated with $4 \times 10^4$ mitomycinC-treated tumor cells in 3 ml RPMI medium containing 10% fetal calf serum. In some experiments, 33% secondary mixed lymphocyte culture supernatant or IL-2, is included in the culture medium as a source of T cell growth factors.

In order to measure the primary response of cytolytic T-lymphocytes after immunization, T cells are cultured without the stimulator tumor cells. In other experiments, T cells are restimulated with antigenically distinct cells. After six days, the cultures are tested for cytotoxicity in a 4 hour $^{51}$Cr-release assay. The spontaneous $^{51}$Cr-release of the targets should reach a level less than 20%. For the anti-MHC class I blocking activity, a tenfold concentrated supernatant of W6/32 hybridoma is added to the test at a final concentration of 12.5% (Heike M., et al., *J Immunotherapy* 15:165-174).

5.3.5.3 Levels of Tumor Specific Antigens

Although it may not be possible to detect unique tumor antigens on all tumors, many tumors display antigens that distinguish them from normal cells. The monoclonal antibody reagents have permitted the isolation and biochemical characterization of the antigens and have been invaluable diagnostically for distinction of transformed from nontransformed cells and for definition of the cell lineage of transformed cells. The best-characterized human tumor-associated antigens are the oncofetal antigens. These antigens are expressed during embryogenesis, but are absent or very difficult to detect in normal adult tissue. The prototype antigen is carcinoembryonic antigen (CEA), a glycoprotein found on fetal gut and human colon cancer cells, but not on normal adult colon cells. Since CEA is shed from colon carcinoma cells and found in the serum, it was originally thought that the presence of this antigen in the serum could be used to screen patients for colon cancer. However, patients with other tumors, such as pancreatic and breast cancer, also have elevated serum levels of CEA. Therefore, monitoring the fall and rise of CEA levels in cancer patients undergoing therapy has proven useful for predicting tumor progression and responses to treatment.

Several other oncofetal antigens have been useful for diagnosing and monitoring human tumors, e.g., alpha-fetoprotein, an alpha-globulin normally secreted by fetal liver and yolk sac cells, is found in the serum of patients with liver and germinal cell tumors and can be used as a marker of disease status.

5.3.5.4 Computed Tomographic (CT) Scan

CT remains the choice of techniques for the accurate staging of cancers. CT has proved more sensitive and specific than any other imaging techniques for the detection of metastases. A sonogram remains an alternative choice of technique for the accurate staging of cancers.

5.3.5.5 Measurement of Putative Biomarkers

The levels of a putative biomarker for risk of a specific cancer are measured to monitor the effect of α2M covalently or noncovalently bound to antigenic molecule complexes. For example, in individuals at enhanced risk for prostate cancer, serum prostate-specific antigen (PSA) is measured by the procedure described by Brawer et. al., 1992, J. Urol. 147:841-845, and Catalona et al., 1993, JAMA 270:948-958; and in individuals at enhanced risk for breast cancer, 16-α-hydroxylation of estradiol is measured by the procedure described by Schneider et al., 1982, Proc. Natl. Acad. Sci. ISA 79:3047-3051.

5.4 Target Autoimmune Diseases

Autoimmune diseases that can be treated by the methods of the present invention include, but are not limited to, insulin dependent diabetes mellitus (i.e., IDDM, or autoimmune diabetes), multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, and dense deposit disease. The diseases set forth above, as referred to herein, include those exhibited by animal models for such diseases, such as, for example non-obese diabetic (NOD) mice for IDDM and experimental autoimmune encephalomyelitis (EAE) mice for multiple sclerosis.

The methods of the present invention can be used to treat such autoimmune diseases by reducing or eliminating the immune response to the patient's own (self) tissue, or, alternatively, by reducing or eliminating a pre-existing autoimmune response directed at tissues or organs transplanted to replace self tissues or organs damaged by the autoimmune response.

5.5 Target Infectious Diseases

The infectious diseases that can be treated or prevented using the methods and compositions of the present invention include those caused by intracellular pathogens such as viruses, bacteria, protozoans, and intracellular parasites. Viruses include, but are not limited to viral diseases such as those caused by hepatitis type B virus, parvoviruses, such as adeno-associated virus and cytomegalovirus, papovaviruses such as papilloma virus, polyoma viruses, and SV40, adenoviruses, herpes viruses such as herpes simplex type I (HSV-I), herpes simplex type II (HSV-II), and Epstein-Barr virus, poxviruses, such as variola (smallpox) and vaccinia virus, RNA viruses, including but not limited to human immunodeficiency virus type I (HIV-I), human immunodeficiency virus type II (HIV-II), human T-cell lymphotropic virus type I (HTLV-I), and human T-cell lymphotropic virus type II (HTLV-II); influenza virus, measles virus, rabies virus, Sendai virus, picomaviruses such as poliomyelitis virus, coxsackieviruses, rhinoviruses, reoviruses, togaviruses such as rubella virus (German measles) and Semliki forest virus, arboviruses, and hepatitis type A virus.

In another embodiment, bacterial infections can be treated or prevented such as, but not limited to disorders caused by pathogenic bacteria including, but not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter* (Vibrio) *fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhiimurium, Salmonella typhii, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp., and *Helicobacter pylori.*

In another preferred embodiment, the methods can be used to treat or prevent infections caused by pathogenic protozoans such as, but not limited to, *Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum,* and *Plasmodium malaria.*

5.6 Target Proliferative Cell Disorders

With respect to specific proliferative and oncogenic disease associated with α2M-α2M activity, the diseases that can be treated or prevented by the methods of the present invention include, but are not limited to: human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

Diseases and disorders involving a deficiency in cell proliferation or in which cell proliferation is desired for treatment or prevention, and that can be treated or prevented by inhibiting the α2M function, include but are not limited to degenerative disorders, growth deficiencies, hypoproliferative disorders, physical trauma, lesions, and wounds; for example, to promote wound healing, or to promote regeneration in degenerated, lesioned or injured tissues, etc.

5.7 Dosage Regimens and Formulation

Covalent or noncovalent complexes of α2M polypeptides and antigenic molecules of the invention may be formulated into pharmaceutical preparations for administration to mammals for treatment or prevention of infectious diseases or cancer at therapeutically effective doses for immunotherapy.

Selection of the preferred effective dose will be determined by a skilled artisan based upon considering several factors which will be known to one of ordinary skill in the art. Such factors include the particular form of α2M, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, according to standard clinical techniques.

Covalent or noncovalent complexes of α2M polypeptides and antigenic molecules of the invention may be formulated into pharmaceutical preparations for administration to mammals for treatment or prevention of infectious diseases or cancer. Drug solubility and the site of absorption are factors which should be considered when choosing the route of administration of a therapeutic agent.

α2M polypeptide-antigenic molecule complexes of the invention may optionally be administered with one or more adjuvants in order to enhance the immunological response. For example, depending on the host species, adjuvants which may be used include, but are not limited to: mineral salts or mineral gels such as aluminum hydroxide, aluminum phosphate, and calcium phosphate; surface active substances such as lysolecithin, pluronic polyols, polyanions, peptides, oil emulsions, keyhole limpet hemocyanins, and dinitrophenol; immunostimulatory molecules, such as cytokines, saponins, muramyl dipeptides and tripeptide derivatives, CpG dinucleotides, CpG oligonucleotides, monophosphoryl Lipid A, and polyphosphazenes; particulate and microparticulate adjuvant, such as emulsions, liposomes, virosomes, cochleates; or an immune stimulating complex mucosal adjuvants, Freund's (complete and incomplete, and potentially useful human adjuvants such as BCG (bacille Calmette-Guerin) and *corynebacterium parvum.*).

α2M polypeptide-antigenic molecule complexes of the invention may be administered using any desired route of administration, including but not limited to, e.g., subcutaneously, intravenously or intramuscularly, although intradermally or mucosally is preferred. Advantages of intradermal or mucosal administration include use of lower doses and rapid absorption, respectively. Mucosal routes of administration include, but are not limited to, oral, rectal and nasal administration. Preparations for mucosal administrations are suitable in various formulations as described below. The route of administration can be varied during a course of treatment.

The doses recited above are preferably given once weekly for a period of about 4-6 weeks, and the mode or site of administration is preferably varied with each administration. In a preferred example, subcutaneous administrations are given, with each site of administration varied sequentially.

Thus, by way of example and not limitation, the first injection may be given subcutaneously on the left arm, the second on the right arm, the third on the left belly, the fourth on the right belly, the fifth on the left thigh, the sixth on the right thigh, etc. The same site may be repeated after a gap of one or more injections. Also, split injections may be given. Thus, for example, half the dose may be given in one site and the other half on an other site on the same day.

Alternatively, the mode of administration is sequentially varied, e.g., weekly injections are given in sequence subcutaneously, intramuscularly, intravenously or intraperitoneally.

After 4-6 weeks, further injections are preferably given at two-week intervals over a period of time of one month. Later injections may be given monthly. The pace of later injections may be modified, depending upon the patient's clinical progress and responsiveness to the immunotherapy.

Compositions comprising covalent or noncovalent complexes formulated in a compatible pharmaceutical carrier may be prepared, packaged, and labeled for treatment of the indicated infectious disease or tumor. In preferred aspects, an amount of α2M polypeptide-antigenic molecule complex is administered to a human that is in the range of about 2 to 150 µg, preferably 2 to 50 µg, most preferably about 25 µg, given once weekly for about 4-6 weeks, intradermally with the site of administration varied sequentially.

If the complex is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, or polyethylene glycol. Thus, the covalent or noncovalent complexes and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the complexes. Such compositions may take the form of tablets or lozenges formulated in conventional manner.

For administration by inhalation, the complexes may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the complexes and a suitable powder base such as lactose or starch.

The complexes may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The complexes may also be formulated in rectal compositions such as suppositories or retention enemas, e.g., containing conventional suppository bases such as cocoa butter or other glycerides.

In addition to the formulations described previously, the complexes may also be formulated as a depot preparation. Such long acting formulations may be administered by implantation (for example, subcutaneously or intramuscularly) or by intramuscular injection. Thus, for example, the complexes may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The complexes may, if desired, be presented in a pack or dispenser device which may contain one or more unit dosage forms containing the covalent or noncovalent complexes. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the covalent or noncovalent α2M polypeptide-antigenic molecule complexes in pharmaceutically acceptable form. The α2M polypeptide-antigenic molecule complexes in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of α2M polypeptide-antigenic molecule complexes by a clinician or by the patient.

6. EXAMPLE

α2M Antagonizes HSP-Mediated Antigen Presentation Via the α2M Receptor

6.1 Introduction

The Example presented herein describes the successful identification of an interaction between gp96 and the α2M receptor present in macrophages and dendritic cells in vivo, and the blocking of this interaction by α2M. The experiments presented herein form the basis for the compositions and therapeutic methods of the present invention which relate to the use of α2M polypeptide-antigenic molecule complexes as immunotherapeutic agents for treatment of immune disorders, proliferative disorders, and infectious diseases.

The Applicant of the present invention noted that certain observations were inconsistent with a "direct transfer" model of HSP-chaperoned peptide antigen presentation. First, the immunogenicity of HSP preparations is dependent on the presence of functional phagocytic cells but not B cells or other nonprofessional antigen-presenting cells (Udono and Srivastava, 1993, supra; Suto and Srivastava, 1995, supra), whereas free peptides can sensitize all cell types. Second, extremely small quantities of HSP-peptide complexes were effective in eliciting specific immunity, i.e., gp96-chaperoned peptides are several hundred times as effective as free peptides in sensitizing macrophages for CTL recognition, suggesting the possibility of a specific uptake mechanism. Third, gp96-chaperoned peptides elicited an MHC I response that was not limited by the size of peptide. Finally, the processing of gp96-peptide complexes in macrophage was found to be sensitive to Brefeldin A (BFA), which blocks transport through the Golgi apparatus, suggesting that processing occurred through an intercellular mechanism. These observations led to the hypothesis that HSP-chaperoned peptides may be processed internally and re-presented by MHC class I molecules on the cell surfaces of macrophages (Suto and Srivastava, 1995, supra). There is also the hypothesis that the mannose receptor is used in the uptake of gp96 but no mechanism has been proposed for the non-glycosylated HSPs, such as HSP70 (Ciupitu et al., 1998, J. Exp. Med., 187: 685-691). Others suggested that a novel intracellular trafficking pathway may be involved for the transport of peptides from the extracellular medium into the lumen of ER) Day et al., 1997, Proc. Natl. Acad. Sci. 94:8065-8069; Nicchitta, 1998, Curr. Opin. in Immunol. 10:103-109). Further suggestions include the involvement of phagocytes which (a) possess an ill-defined pathway to shunt protein from the phagosome into thecytosol where it would enter the normal class I pathway; (b) digest ingested material in lysosomes and regurgitate peptides for loading on the surface to class I molecules (Bevan, 1995, J. Exp. Med. 192:639-41). The discovery of a receptor for heat shock protein as disclosed herein helps to resolve the paradox of how extracellular antigenic peptides complexed to HSPs can be presented by MHC class I molecules on antigen presenting cells.

6.2 Materials and Methods

Affinity chromatography. Proteins (1 mg) in 2 ml volume were incubated with 2 ml of equilibrated AminoLink beads in PBS with a reductant (NaCNBH$_3$) for 1 hour. Uncoupled protein was removed by extensive washing of the column and unreactive groups quenched. Immobilization yields were typically >92% of the starting amount of protein. Columns were stored at 4° C. until used. Such columns were made with gp96 (purified as described in Srivastava et al., 1986, Proc. Natl. Acad. Sci., U.S.A. 83:3407-3411) and albumin. For membrane purification, cells were lysed by dounce homogenization in hypotonic buffer containing PMSF. Unlyzed cells and nuclei were removed by centrifugation at 100 g for 5 mm. The postnuclear supernatant was centrifuged at 100,000 g for 90 mins. The pellet contains total membranes and was fractionated by aqueous two-phase partition with a dextran/polyethylene glycol biphase. Briefly membranes were resuspended in PEG (33% wt/wt in 0.22 M sodium phosphate buffer, pH 6.5) and underlaid gently with dextran (20% wt/wt in 0.22M sodium phosphate buffer, pH 6.5). The two phases were mixed gently and centrifuged at 2000 g for 15 mins. The white material at the interphase was enriched for plasma membranes, whose proteins were extracted by 2 hr incubation in 20 mM Tris buffer (pH8, containing 0.08% octylglucoside) at 4° C.

Photo cross-linking of gp96 to putative receptor. The cross-linker (SASD, (Pierce) was labeled with I$^{125}$ using iodobeads (Pierce). Radiolabeled SASD was covalently attached to gp96 by incubation at room temperature for 1 hr. Free SASD and I$^{125}$ were removed by size exclusion column (KwikSep columns, Pierce). For cross-linking studies, I$^{125}$-SASD-gp96 (50 µg gp96) was incubated with purified CD11b$^+$ cells. Unbound protein was removed by washing. All procedures to this point were carried out in very dim light. Proteins were cross-linked with UV light. Cells were lysed with lysis buffer (0.5% NP40, 10 mM Tris, 1 mMEDTA, 150 mM NaCl) and treated with 100 mM 2-mercaptoethanol to cleave the cross-linker. Cell lysates were analyzed by SDS-PAGE and autoradiography.

Re-presentation assays. Re-presentation assays were carried out as described (Suto and Srivastava, 1995, Science 269:1585-1588). Antigen presenting cells (RAW264.7 macrophage cell line) were plated at a 1:1 ratio with AH I-specific T cells in complete RPMI. Approximately 10,000 cells of each type were used. Gp96 (10 µg/ml) chaperoning the AH1-20 mer peptide (RVTYHSPSYVYHQFERRAK, SEQ ID NO: 7) was added to the cells and the entire culture was incubated for 20 hrs. Stimulation of T cells was measured by quantifying the amount of IFN-γ released into the supernatants by ELISA (Endogen).

Protein Microsequencing. Proteins identified by affinity chromatography were analyzed on SDS-PAGE and stained with coomasie blue or transferred onto PVDF membrane and stained with coomasie blue, all of it under keratin-free conditions. Protein bands were excised with a razor from the gel or membrane. Tryptic peptides from an 80 kDa faint coomassie band were extracted by 50% acetonitrile, 5% formic acid, dried, and loaded onto a 75 m 10 cm, reverse-phase C18, microcapillary column (3 µl vol) and tryptic peptides were separated by on-line microcapillary liquid chromatography-tendem mass spectrometry followed by database searching using the SEQUEST program as previously described. (Gatlin et al.,2000, Anal. Chem. 72:757-63; Link et al., 1999, Nat. Biotechnol. 17:676-82). The analysis was carried out in a data-dependent auto-MS/MS fashion using a Finnigan LCQ iontrap Mass Spectrometer.

6.3 Results

Identification of an 80 kDa protein as a potential gp96 receptor. Homogenous preparations of gp96 were coupled to FITC and the gp96-FITC was used to stain RAW264.7 cells, shown to be functionally capable of re-presenting gp96-chaperoned peptides. Gp96-FITC but not control albumin-FITC preparations stained the cell surface of RAW264.7 cells (FIG. 1A). Plasma membrane preparations of cell surface-biotinylated RAW264.7 cells were solubilized in 0.08% octyl-glucoside and the soluble extract was applied to a gp96-Sepharose column. The bound proteins were eluted with 3M sodium chloride. SDS-PAGE analysis of the eluate showed 2 major bands of ~75-80 kDa size (FIG. 1B, top left). Blotting of this gel with avidin-peroxidase showed that both bands were biotinylated, indicating their surface localization (FIG. 1B, bottom left). Affinity purification of membrane extracts of RAW264.7 cells over control serum albumin affinity columns did not result in isolation of any proteins, nor did probing of immunoblots of such gels with avidin peroxidase detect any albumin-binding surface proteins (FIG. 1B, top and bottom center lanes). As an additional control, chromatography of membrane extracts of P815 cells which do not bind gp96-FITC and which do not re-present gp96-chaperoned peptides, on gp96 affinity columns did not result in elution of any gp96-binding proteins (FIG. 1B, top and bottom right lanes).

In parallel experiments, gp96 molecules were coupled to the radio-iodinated linker sulfosuccinimidyl (4-azidosalicylamido) hexanoate (SASD) which contains a photo cross-linkable group. Gp96-SASD-$I^{125}$ was pulsed onto peritoneal macrophages, which have been shown previously to re-present gp96-chaperoned peptides (Suto and Srivastava, 1995, Science 269:1585-1588). Excess gp96-SASD was removed by multiple rounds of washing of the cells and photoactivation was carried out by exposure of cells to UV light for 10 mm. Cell lysates were reduced in order to transfer the $I^{125}$ group to the putative gp96 ligand and were analyzed by SDS-PAGE followed by autoradiography. The gp96 molecule was observed to cross-link to an ~80 kDa band specifically present in re-presentation-competent macrophage but not in the re-presentation-incompetent P815 cells (FIG. 1C). This band appears to correspond in size to the larger of the two bands seen in eluates of gp96 affinity columns (FIG. 1D). No band corresponding to the lower band in that preparation is seen in the photo cross-linked preparation. The observation of a specific binding of gp96 to an 80 kDa protein in two different re-presentation-competent cell types, but not in a representation-incompetent cell line, and by two independent assays supported the candidacy of the 80 kDa molecule for the gp96 receptor.

Antiserum against the 80 kDa protein inhibits re-presentation of a gp96-chaperoned antigenic peptide. The eluates containing the 75-80 kDa proteins were used to immunize a New Zealand white rabbit, and pre-immune and immune sera were used to probe blots of plasma membrane extracts of the re-presentation-competent RAW264.7 and primary peritoneal macrophages and the re-presentation-incompetent P815 cells. The immune but not the pre-immune serum detected the 80 kDa band (and a faint lower 75 kDa band) in plasma membrane extracts of primary macrophage and the RAW264.7 membranes but not of P815 cells (FIG. 2A). The pre-immune and immune sera were tested in a functional assay for their ability to block re-presentation of gp96-chaperoned peptides. The $L^d$-restricted epitope AH1 derived from the gp70 antigen of murine colon carcinoma CT26 (Huang et al., 1996, Proc. Natl. Acad. Sci. U.S.A. 93:9730-9735) was used as the model system. Complexes of gp96 with an AH1 precursor (used to inhibit direct presentation) were pulsed onto RAW264.7 cells which were used to stimulate a $L^d$/AH1-specific CD8+ T cell clone. Release of interferon-γ by the clones was measured as a marker of their activation. RAW264.7 cells were able to re-present gp96-chaperoned AH1 precursor effectively in this assay. It was observed that at the highest concentration, the immune sera inhibited re-presentation completely (FIG. 2B). Although the pre-immune serum was ineffective in inhibiting re-presentation as compared to the immune sera, it did inhibit re-presentation significantly at higher concentrations. The significance of this observation became clear later when we determined the identity of the gp96 receptor. Repeated immunizations with the affinity-purified gp96-binding proteins did not result in corresponding increase in antibody titers.

Identification of the 80 kDa protein as an amino terminal fragment of the heavy chain of the α2M receptor. The 80 kDa protein eluted from the gp96 affinity column was resolved on SDS-PAGE and visualized by staining with Coomassie Brilliant Blue. The protein band was subjected to in-gel trypsin digestion and mass spectrometry-based protein microsequencing as described in the methods in Section 6.2. Four independent tryptic peptides corresponding to N-terminal region of the α2-macroglobulin (α2M) receptor, designated by immunologists as CD91, were identified (FIG. 3C).

α2M inhibits re-presentation of a gp96-chaperoned antigenic peptide by RA W264.7. α2M receptor is one of the known natural ligands for the α2M receptor. Its ability to inhibit re-presentation of gp96-chaperoned antigenic peptide AH1 was tested in the assay described in FIG. 2. α2M but not control proteins selectin (CD62) or serum albumin was observed to inhibit re-presentation completely and titratably (FIG. 4). This observation was also consistent with the result in FIG. 2 that while the pre-immune serum did not detect an 80 kDa band in plasma membranes of RAW264.7 cells, it did inhibit re-presentation to some degree at high concentrations. Thus, by structural as well as functional criteria, the α2M receptor was determined to fulfill the criteria essential for a receptor for gp96.

6.4 Discussion

The α2M receptor, which is also designated CD91, was initially identified as a protein related to the low density lipoprotein (LDL) receptor Related Protein (LRP) (Strickland et al., 1990, J. Biol. Chem.265:17401-17404; Kristensen et al., 1990, FEBS Lett. 276:151-155). The protein consists of an 420 kDa α subunit, an 85 kDa β subunit and a 39 kDa tightly associated molecule (RAP). The α and β subunits are encoded by a single transcript of ~15 Kb in size (Van Leuven et al., 1993, Biochim. Biophys. Acta. 1173:71-74. The receptor has been shown to be present in cells of the monocytic lineage and in hepatocytes, fibroblasts and keratinocytes. CD91 has been shown previously to bind the activated form of the plasma glycoprotein α2M, which binds to and inhibits a wide variety of endoproteinases. α2M receptor also binds to other ligands such as transforming growth factor β (O Connor-McCourt et al., 1987, J. Biol. Chem. 262:14090-14099), platelet-derived growth factor (Huang et al., 1984, Proc. Natl. Acad. Sci. U.S.A. 81:342-346), and fibroblast growth factor (Dennis et al., 1989, J. Biol. Chem. 264:7210-7216). α2M is thus believed to regulate, and specifically diminish, the activities of its various ligands. Complexed with these various ligands, α2M binds α2M receptor on the cell surface and is internalized through receptor-mediated endocytosis. Uptake of α2M-complexed ligands has been assumed thus far to be the primary function of the α2M receptor, although a role for it in lipid metabolism is also assumed. α2M receptor ligands other than α2M, such as tissue-specific plasminogen activator-inhibitor complex (Orth et al., 1992, Proc. Natl. Acad. Sci. U.S.A. 89:7422-7426) and urokinase-PAI1 complex (Nykjaer et al., 1992, J. Biol. Chem. 267:14543-14546), have been identified. These ligands attest to a role for α2M receptor in clearing a range of extracellular, plasma products.

The studies reported here show that the heat shock protein gp96 is an additional ligand for the α2M receptor. The human gp96-coding gene has been mapped previously by us at chromosome 12 (q24.2→q24.3) (Maki et al., 1993, Somatic Cell Mol. Gen. 19:73-81). It is of interest in this regard that the α2M receptor gene has been mapped to the same chromosome and at a not too distant location (q13→q14) (Hilliker et al. Genomics 13:472-474). Gp96 binds α2M receptor directly and not through other ligands such as α2M. Homogenous preparations of gp96, in solution, or cross-linked to a solid matrix, bind to the α2M receptor. Indeed, the major ligand for the α2M receptor, α2M, actually inhibits interaction of gp96 with α2M receptor, instead of promoting it, providing evidence that gp96 is a direct ligand for the α2M receptor. The 80 kDa protein shown to bind gp96 is clearly an amino terminal degradation product of the a subunit of the α2M receptor. Degradation products of the α2M receptor in this size range have also been observed in previous studies (Jensen et al., 1989, Biochem. Arch. 5:171-176), and may indicate the existence of a discrete ectodomain in the α2M receptor which may be particularly sensitive to proteolytic cleavage.

As shown here, the gp96-α2M receptor interaction provides a new type of function for α2M receptor, a function of a sensor, not only of the extracellular environment with its previously known plasma-based ligands, but also a sensor of the intracellular milieu as well. HSPs such as gp96 are obligate intracellular molecules and are released into the extracellular milieu only under conditions of necrotic (but not apoptotic) cell death. Thus, the α2M receptor may act as a sensor for necrotic cell death (see FIG. 5), just as the scavenger receptor CD36 and the recently identified phosphatidyl serine-binding protein act as sensors of apoptotic cell death and receptors for apoptotic cells (Savill et al., 1992, J. Clin. Invest.90:1513-1522; Fadok et al., 2000, Nature 405:85-90). Interaction of the macrophages with the apoptotic cells leads to a down-regulation of the inflammatory cytokines such as TNF (Fadok et al., 2000, supra), while gp96-APC interaction leads to re-presentation of gp96-chaperoned peptides by MHC I molecules of the APC, followed by stimulation of antigen-specific T cells (Suto and Srivastava, 1995, supra) and, in addition, secretion of pro-inflammatory cytokines such as TNF, GM-CSF and IL-12. Interestingly, α2M, an independent ligand for the α2M receptor, inhibits representation of gp96-chaperoned peptides by macrophages. This observation suggests that re-presentation of gp96-chaperoned peptides can not occur physiologically in blood, but only within tissues as a result of localized necrotic cell death. This is consistent with the complete absence of gp96 or other HSPs in blood under all conditions tested. Together, these observations point towards a possible mechanism whereby the release of HSPs in the blood as a result of severe tissue injury and lysis will not lead to a systemic and lethal pro-inflammatory cytokine cascade.

It is possible, therefore, that the α2M receptor renders it possible for the APCs to sample (i) the extracellular milieu of the blood through α2M and other plasma ligands and (ii) the intracellular milieu of the tissues through HSPs, particularly of the gp96 family. The former permits APCs to implement their primordial phagocytic function, while the latter allows them to execute its innate and adaptive immunological functions. Viewed in another perspective, recognition of apoptotic cells by APCs through CD36 or phophatidyl serine, leads to anti-inflammatory signals, while interaction of the APC with necrotic cells through α2M receptor leads to pro-inflammatory innate and adaptive immune responses (see Srivastava et al., 1998, Immunity 8: 657-665).

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein, including patent applications, patents, and other publications, are incorporated by reference herein in their entireties for all purposes.

What is claimed is:

1. A pharmaceutical composition comprising an amount of a purified molecular complex effective for treatment of an infectious disease and a pharmaceutically acceptable carrier, said molecular complex comprising an alpha (2) macroglobulin polypeptide, which comprises the alpha (2) macroglobulin receptor binding domain, said polypeptide noncovalently associated with an antigenic molecule which displays the antigenicity of an antigen of an infectious agent of the infectious disease, with the proviso that the infectious agent is other than hepatitis type B virus.

2. A purified molecular complex comprising an alpha (2) macroglobulin polypeptide, comprising the alpha (2) macroglobulin receptor binding domain, said polypeptide noncovalently associated with an antigenic molecule that displays the antigenicity of an antigen of an infectious agent of the infectious disease, with the proviso that the infectious agent is other than hepatitis type B virus.

3. The purified molecular complex of claim 1 or 2, wherein the antigenic molecule is an antigen of an infectious agent of the infectious disease.

4. The pharmaceutical composition of claim 1 comprising an amount of a purified molecular complex effective for treatment of an infectious disease, wherein the infectious disease is caused by a pathogen of adeno-associated virus, cytomegalovirus, papilloma virus, polyoma viruses, SV40, herpes simplex type I (HSV-I), herpes simplex type II (HSV-II), Epstein-Ban virus, variola (smallpox), vaccinia virus, human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, poliomyelitis virus, coxsackieviruses, rhinoviruses, reoviruses, rubella virus (German measles), Semliki forest virus, arboviruses, hepatitis type A virus, *Streptococcus pyogenes, Streptococcus pneumoniae, Neisseria gonorrhoea, Neisseri meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter* (Vibrio) *fetus, Campylobacterjejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhiimurium, Salmonella typhii, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii,*

*Francisella tularensis, Brucella abortus, Brucella suis, Brucella melitensis, Mycoplasma* spp., *Rickettsia prowazeki, Rickettsia tsutsugumushi, Chlamydia* spp., *Helicobacter pylori, Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, or Plasmodium malaria.*

5. A purified population of molecular complexes which are at least 65% noncovalent complexes, each noncovalent complex comprising (i) an alpha (2) macroglobulin polypeptide, which comprises the alpha (2) macroglobulin receptor binding domain, and (ii) an antigenic molecule that displays the antigenicity of an antigen of an infectious agent of the infectious disease, with the proviso that the infectious agent is other than hepatitis type B virus.

6. The pharmaceutical composition of claim 1, further comprising one or more adjuvants.

7. The pharmaceutical composition of claim 6, wherein the adjuvant is aluminum hydroxide, aluminum phosphate, calcium phosphate, lysolecithin, pluronic polyols, polyanions, peptides, oil emulsions, keyhole limpet hemocyanins, and dinitrophenol, cytokines, saponins, muramyl dipeptides, tripeptide derivatives, CpG dinucleotides, CpG oligonucleotides, monophosphoryl Lipid A, polyphosphazenes, emulsions, liposomes, virosomes, cochleates, Freund's complete adjuvant, Freund's incomplete adjuvant, bacille Calmette-Guerin, or corynebacterium parvum.

8. The pharmaceutical composition of claim 1, wherein said molecular complex consists essentially of (i) the alpha (2) macroglobulin polypeptide, and (ii) the antigenic molecule.

9. The purified molecular complex of claim 2, wherein said molecular complex consists essentially of (i) the alpha (2) macroglobulin polypeptide, and (ii) the antigenic molecule.

10. The purified population of molecular complexes of claim 5, wherein said noncovalent complexes consist essentially of (i) the alpha (2) macroglobulin polypeptide, and (ii) the antigenic molecule.

* * * * *

SEQUENCE LISTING

```
<160> NUMBER OF SEQ ID NOS: 5

<210> SEQ ID NO 1
<211> LENGTH: 14849
<212> TYPE: DNA
<213> ORGANISM: Mus musculus

<400> SEQUENCE: 1
cgctgctccc cgccagtgca ctgaggaggc ggaaacgggg gagcccctag tgctccatca        60
ggcccctacc aaggcacccc catcgggtcc acgccccca cccccaccc cgcctcctcc         120 caattgtgca tttttgcagc cggagtcggc tccgagatgg ggctgtgagc ttcgccctgg       180 gaggggaga ggagcgagga gtaaagcagg ggtgaagggt tcgaatttgg gggcaggggg        240
cgcacccgcg tcagcaggcc cttcccaggg ggctcggaac tgtaccattt cacctatgcc       300
cctggttcgc tttgcttaag gaaggataag atagaagagt cggggagagg aagataaagg       360 gggaccccc aattgggggg ggcgaggaca agaagtaaca ggaccagagg gtgggggctg        420
ctgtttgcat cggcccacac catgctgacc ccgccgttgc tgctgctcgt gccgctgctt       480
tcagctctgg tctccggggc cactatggat gcccctaaaa cttgcagccc taagcagttt       540
gcctgcagag accaaatcac ctgtatctca aagggctggc ggtgtgacgg tgaaagagat       600
```

-continued

```
tgccccgacg gctctgatga agcccctgag atctgtccac agagtaaagc ccagagatgc   660
ccgccaaatg agcacagttg tctggggact gagctatgtg tccccatgtc tcgtctctgc   720
aacgggatcc aggactgcat ggatggctca gacgagggtg ctcactgccg agagctccga   780
gccaactgtt ctcgaatggg ttgtcaacac cattgtgtac ctacacccag tgggcccacg   840
tgctactgta acagcagctt ccagctcgag gcagatggca agacgtgcaa agattttgac   900
gagtgttccg tgtatggcac ctgcagccag ctttgcacca acacagatgg ctccttcaca   960
tgtggctgtg ttgaaggcta cctgctgcaa ccggacaacc gctcctgcaa ggccaagaat  1020
gagccagtag atcggccgcc agtgctactg attgccaact ctcagaacat cctagctacg  1080
tacctgagtg gggcccaagt gtctaccatc acacccacca gcacccgaca aaccacggcc  1140
atggacttca gttatgccaa tgagaccgta tgctgggtgc acgttgggga cagtgctgcc  1200
cagacacagc tcaagtgtgc ccggatgcct ggcctgaagg ctttgtggat gagcatacc   1260
atcaacatct ccctcagcct gcaccacgtg agcagatggc aatcgactg gctgacggga  1320
aacttctact tgtcgacga cattgacgac aggatctttg tctgtaaccg aaacggggac  1380
acctgtgtca ctctgctgga cctggaactc tacaacccca aaggcatcgc cttggacccc  1440
gccatgggga aggtgttctt cactgactac gggcagatcc caaaggtgga gcgctgtgac  1500
atggatggac agaaccgcac caagctggtg gatagcaaga tcgtgtttcc acacggcatc  1560
accctggacc tggtcagccg cctcgtctac tgggcggacg cctacctaga ctacatcgag  1620
gtggtagact acgaagggaa gggtcggcag accatcatcc aaggcatcct gatcgagcac  1680
ctgtacggcc tgaccgtgtt tgagaactat ctctacgcca ccaactcgga caatgccaac  1740
acgcagcaga gacgagcgt gatccgagtg aaccggttca cagtactga gtaccaggtc   1800
gtcaccgtg tggacaaggg tggtgccctg catatctacc accagcgacg ccagccccga   1860
gtgcggagtc acgcctgtga gaatgaccag tacgggaagc caggtggctg ctccgacatc  1920
tgcctcctgg ccaacagtca aaggcaagg acctgcaggt gcaggtctgg cttcagcctg   1980
ggaagtgatg ggaagtcttg taagaaacct gaacatgagc tgttcctcgt gtatggcaag  2040
ggccgaccag gcatcattag aggcatggac atggggggcca aggtcccaga tgagcacatg  2100
atccccatcg agaaccttat gaatccacgc gctctggact ccacgccga ccggcttc    2160
atctactttg ctgacaccac cagctacctc attggccgcc agaaaattga tggcacggag  2220
agagagacta tcctgaagga tggcatccac aatgtggagg gcgtagccgt ggactggatg  2280
ggagacaatc tttactggac tgatgatggc cccaagaaga ccattagtgt ggccaggctg  2340
gagaaagccg ctcagacccg gaagactcta attgagggca agatgacaca ccccagggcc  2400
attgtagtgg atccactcaa tgggtggatg tactggacag actgggagga ggaccccaag  2460
gacagtcggc gagggcggct cgagagggct tggatggacg gctcacaccg agatatcttt  2520
gtcacctcca agacagtgct ttggcccaat gggctaagcc tggatatccc agccggacgc  2580
ctctactggg tggatgcctt ctatgaccga attgagacca tactgctcaa tggcacagac  2640
cggaagattg tatatgaggg tcctgaactg aatcatgcct tcggcctgtg tcaccatggc  2700
aactacctct ttttggaccg gtaccggagc ggcagcgtct accgcttgga acggggcgtg  2760
gcaggcgcac cgcccactgt gacccttctg cgcagcgaga accgcctat ctttgagatc   2820
cgaatgtacg acgcgcacga gcagcaagtg gtaccaaca aatgccgggt aaataacgga   2880
ggctgcagca gcctgtgcct cgccacccc gggagccgcc agtgtgcctg tgccgaggac   2940
caggtgttgg acacagatgg tgtcacctgc ttggcgaacc catcctacgt gccccacccc  3000
```

```
cagtgccagc cgggccagtt tgcctgtgcc aacaaccgct gcatccagga gcgctggaag    3060
tgtgacggag acaacgactg tctggacaac agcgatgagg ccccagcact gtgccatcaa    3120
cacacctgtc cctcggaccg attcaagtgt gagaacaacc ggtgtatccc caaccgctgg    3180
ctctgtgatg gggataatga ttgtggcaac agcgaggacg aatccaatgc cacgtgctca    3240
gcccgcacct gtccacccaa ccagttctcc tgtgccagtg gccgatgcat tcctatctca    3300
tggacctgtg atctggatga tgactgtggg gaccggtccg atgagtcagc ctcatgcgcc    3360
taccccacct gcttcccct gactcaattt acctgcaaca atggcagatg tattaacatc    3420
aactggcggt gtgacaacga caatgactgt ggggacaaca gcgacgaagc cggctgcagt    3480
cactcctgct ccagtaccca gttcaagtgc aacagtggca gatgcatccc cgagcactgg    3540
acgtgtgatg gggacaatga ttgtggggac tacagcgacg agacacacgc caactgtacc    3600
aaccaggcta caagacctcc tggtggctgc cactcggatg agttccagtg cccgctagat    3660
ggcctgtgca tcccctgag gtggcgctgc gacgggggaca ccgactgcat ggattccagc    3720
gatgagaaga gctgtgaggg cgtgacccat gtttgtgacc cgaatgtcaa gtttggctgc    3780
aaggactccg cccggtgcat cagcaaggcg tgggtgtgtg atggcgacag cgactgtgaa    3840
gataactccg acgaggagaa ctgtgaggcc ctggcctgca ggccaccctc ccatccctgc    3900
gccaacaaca cctctgtctg cctgcctcct gacaagctgt gcgacggcaa ggatgactgt    3960
ggagacggct cggatgaggg cgagctctgt gaccagtgtt ctctgaataa tggtggctgt    4020
agtcacaact gctcagtggc ccctggtgaa ggcatcgtgt gctcttgccc tctgggcatg    4080
gagctgggct ctgacaacca cacctgccag atccagagct actgtgccaa gcacctcaaa    4140
tgcagccaga gtgtgaccca gaacaagttc agtgtgaagt gctcctgcta cgagggctgg    4200
gtcttggagc ctgacgggga aacgtgccgc agtctggatc ccttcaaact gttcatcatc    4260
ttctccaacc gccacgagat caggcgcatt gaccttcaca gggggactaa cagcgtccta    4320
gtgcctggcc tgcgcaacac tattgccctg gacttccacc tcagccagag tgccctctac    4380
tggaccgacg cggtagagga caagatctac cgtgggaaac tcctggacaa cggagccctg    4440
accagctttg aggtggtgat tcagtatggc ttggccacac cagagggcct ggctgtagat    4500
tggattgcag gcaacatcta ctgggtggag agcaacctgg accagatcga agtggccaag    4560
ctggacggaa ccctccgaac cactctgctg gcgggtgaca ttgagcaccc gagggccatc    4620
gctctgaccc tcgggatgg gattctgttt tggacagact gggatgccag cctgccacga    4680
atcgaggctg catccatgag tggagctggc cgccgaacca tccaccggga gacaggctct    4740
gggggctgcg ccaatgggct caccgtggat tacctggaga gcgcatcct ctggattgat    4800 gctaggtcag atgccatcta ttcagcccgg tatgacggct ccggccacat ggaggtgctt    4860
cggggacacg agttcctgtc acacccattt gccgtgacac tgtacggtgg ggaggtgtac    4920
tggaccgact ggcgaacaaa tacactggct aaggccaaca gtggactggc cacaacgtc    4980 accgtggtac agaggaccaa cacccagccc ttcgacctgc aggtgtatca cccttcccgg    5040
cagcccatgg ctccaaaccc atgtgaggcc aatggcggcc ggggccctg ttcccatctg    5100 tgcctcatca actacaaccg gaccgtctcc tgggcctgtc cccacctcat gaagctgcac    5160
aaggacaaca ccacctgcta tgagtttaag aagttcctgc tgtacgcacg tcagatggag    5220 atccgggggcg tggacctgga tgccccgtac tacaattata tcatctcctt cacggtgcct    5280
gatatcgaca atgtcacggt gctggactat gatgcccgag agcagcgagt ttactggtct    5340
```

```
gatgtgcgga ctcaagccat caaaagggca tttatcaacg gcactggcgt ggagaccgtt    5400
gtctctgcag acttgcccaa cgcccacggg ctggctgtgg actgggtctc ccgaaatctg    5460
ttttggacaa gttacgacac caacaagaag cagattaacg tggcccggct ggacggctcc    5520
ttcaagaatg cggtggtgca gggcctggag cagccccacg gcctggtcgt ccacccgctt    5580
cgtggcaagc tctactggac tgatggggac aacatcagca tggccaacat ggatgggagc    5640
aaccacactc tgctcttcag tggccagaag ggccctgtgg ggttggccat tgacttccct    5700
gagagcaaac tctactggat cagctctggg aaccacacaa tcaaccgttg caatctggat    5760
gggagcgagc tggaggtcat cgacaccatg cggagccagc tgggcaaggc cactgccctg    5820
gccatcatgg ggacaagct gtggtgggca gatcaggtgt cagagaagat gggcacgtgc    5880
aacaaagccg atggctctgg gtccgtggtg ctgcggaaca gtaccacgtt ggttatgcac    5940
atgaaggtgt atgacgagag catccagcta gagcatgagg gcaccaaccc ctgcagtgtc    6000
aacaacggag actgttccca gctctgcctg ccaacatcag agacgactcg ctcctgtatg    6060
tgtacagccg gttacagcct ccggagcgga cagcaggcct gtgagggtgt gggctctttt    6120
ctcctgtact ctgtacatga gggaattcgg gggattccac tagatcccaa tgacaagtcg    6180
gatgccctgg tcccagtgtc cggaacttca ctggctgtcg gaatcgactt ccatgccgaa    6240
aatgacacta tttattgggt ggatatgggc ctaagcacca tcagcagggc caagcgtgac    6300
cagacatggc gagaggatgt ggtgaccaac ggtattggcc gtgtggaggg catcgccgtg    6360
gactggatcg caggcaacat atactggacg gaccagggct tcgatgtcat cgaggttgcc    6420
cggctcaatg gctcttttcg ttatgtggtc atttcccagg gtctggacaa gcctcgggcc    6480
atcactgtcc acccagagaa ggggtacttg ttctggaccg agtggggtca ttacccacgt    6540
attgagcggt ctcgccttga tggcacagag agagtggtgt tggttaatgt cagcatcagc    6600
tggcccaatg gcatctcagt agactatcag ggcggcaagc tctactggtg tgatgctcgg    6660
atggacaaga tcgagcgcat cgacctggaa acgggcgaga accgggaggt ggtcctgtcc    6720
agcaataaca tggatatgtt ctccgtgtcc gtgtttgagg acttcatcta ctggagtgac    6780
agaactcacg ccaatggctc catcaagcgc ggctgcaaag acaatgctac agactccgtg    6840
cctctgagga caggcattgg tgttcagctt aaagacatca aggtcttcaa cagggacagg    6900
cagaaggta ccaatgtgtg cgcggtagcc aacggcgggt gccagcagct ctgcttgtat    6960
cggggtggcg gacagcgagc ctgtgcctgt gcccacggga tgctggcaga agacggggcc    7020
tcatgccgag agtacgctgg ctacctgctc tactcagagc ggaccatcct caagagcatc    7080
cacctgtcgg atgagcgtaa cctcaacgca ccggtgcagc cctttgaaga ccccgagcac    7140
atgaaaaatg tcatcgccct ggcctttgac taccgagcag gcacctcccc ggggacccct    7200
aaccgcatct tcttcagtga catccacttt gggaacatcc agcagatcaa tgacgatggc    7260
tcgggcagga ccaccatcgt ggaaaatgtg ggctctgtgg aaggcctggc ctatcaccgt    7320
ggctgggaca cactgtactg gacaagctac accacatcca ccatcacccg ccacaccgtg    7380
gaccagactc gcccagggc cttgagagg gagacagtca tcaccatgtc cggagacgac    7440
cacccgagag cctttgtgct ggatgagtgc cagaacctga tgttctggac caattggaac    7500
gagctccatc caagcatcat gcgggcagcc ctatccggag ccaacgtcct gacccctcatt    7560
gagaaggaca tccgcacgcc caatgggttg gccatcgacc accgggcgga gaagctgtac    7620
ttctcggatg ccaccttgga caagatcgag cgctgcgagt acgacggctc ccaccgctat    7680
gtgatcctaa agtcggagcc cgtccacccc tttgggttgg cggtgtacgg agagcacatt    7740
```

```
ttctggactg actgggtgcg gcgggctgtg cagcgagcca acaagtatgt gggcagcgac    7800
atgaagctgc ttcgggtgga cattccccag caacccatgg gcatcatcgc cgtggccaat    7860
gacaccaaca gctgtgaact ctcccctgc cgtatcaaca atggaggctg ccaggatctg     7920
tgtctgctca cccaccaagg ccacgtcaac tgttcctgtc gaggggccg gatcctccag     7980
gaggacttca cctgccgggc tgtgaactcc tcttgtcggg cacaagatga gtttgagtgt    8040
gccaatgggg aatgtatcag cttcagcctc acctgtgatg gcgtctccca ctgcaaggac    8100
aagtccgatg agaagccctc ctactgcaac tcacgccgct gcaagaagac tttccgccag    8160
tgtaacaatg ccgctgtgt atccaacatg ctgtggtgca atggggtgga ttactgtggg     8220
gatggctctg atgagatacc ttgcaacaag actgcctgtg tgtgggtga gttccgctgc     8280
cgggatgggt cctgcatcgg gaactccagt cgctgcaacc agtttgtgga ttgtgaggat    8340
gcctcggatg agatgaattg cagtgccaca gactgcagca gctatttccg cctgggcgtg    8400
aaaggtgtcc tcttccagcc gtgcgagcgg acatccctgt gctacgcacc tagctgggtg    8460
tgtgatggcg ccaacgactg tggagactac agcgatgaac gtgactgtcc aggtgtgaag    8520
cgccctaggt gcccgctcaa ttactttgcc tgccccagcg ggcgctgtat ccccatgagc    8580
tggacgtgtg acaaggagga tgactgtgag aacggcgagg atgagaccca ctgcaacaag    8640
ttctgctcag aggcacagtt cgagtgccag aaccaccggt gtatctccaa gcagtggctg    8700
tgtgacggta gcgatgattg cggggatggc tccgatgagg cagctcactg tgaaggcaag    8760
acatgtggcc cctcctcctt ctcctgtccc ggcacccacg tgtgtgtccc tgagcgctgg    8820
ctctgtgatg cgacaagga ctgtaccgat ggcgcggatg agagtgtcac tgctggctgc     8880
ctgtacaaca gcacctgtga tgaccgtgag ttcatgtgcc agaaccgctt gtgtattccc    8940
aagcatttcg tgtgcgacca tgaccgtgac tgtgctgatg ctctgatga atccctgag     9000
tgtgagtacc caacctgcgg gcccaatgaa ttccgctgtg ccaatgggcg ttgtctgagc    9060
tcccgtcagt gggaatgtga tgggagaat gactgtcacg accacagcga tgaggctccc    9120
aagaacccac actgcaccag cccagagcac aaatgcaatg cctcatcaca gttcctgtgc    9180
agcagcgggc gctgcgtggc tgaggcgttg ctctgcaacg gccaggacga ctgtggggac    9240
ggttcagacg aacgcgggtg ccatgtcaac gagtgtctca gccgcaagct cagtggctgc    9300
agtcaggact gcgaggacct caagataggc tttaagtgcc gctgtcgccc gggcttccgg    9360
ctaaaggacg atggcaggac ctgtgccgac ctggatgagt gcagcaccac cttccctgc     9420
agccagctct gcatcaacac ccacggaagt tacaagtgtc tgtgtgtgga gggctatgca    9480
ccccgtggcg gtgacccca cagctgcaaa gctgtgaccg atgaggagcc atttctcatc    9540
tttgccaacc ggtactacct gcggaagctc aacctggacg gctccaacta cacactgctt    9600
aagcagggcc tgaacaatgc ggtcgccttg gcatttgact accgagagca gatgatctac    9660
tggacgggcg tgaccaccca gggcagcatg attcgcagga tgcacctcaa cggcagcaac    9720
gtgcaggttc tgcaccggac gggccttagt aacccagatg gctcgctgt ggactgggtg      9780
ggtggcaacc tgtactggtg tgacaagggc agagatacca ttgaggtgtc caagcttaac    9840
ggggcctatc ggacagtgct ggtcagctct ggcctccggg agcccagagc tctggtagtg    9900
gatgtacaga atgggtacct gtactggaca gactggggtg accactcact gatcggccgg    9960
attggcatgg atggatctgg ccgcagcatc atcgtggaca ctaagatcac atggcccaat    10020
ggcctgaccg tggactacgt cacggaacgc atctactggg ctgacgcccg tgaggactac    10080
```

```
atcgagttcg ccagcctgga tggctccaac cgtcacgttg tgctgagcca agacatccca   10140
cacatctttg cgctgaccct atttgaagac tacgtctact ggacagactg ggaaacgaag   10200
tccatcaacc gggcccacaa gaccacgggt gccaacaaaa cactcctcat cagcaccctg   10260
caccggccca tggacttaca tgtattccac gccctgcgcc agccagatgt gcccaatcac   10320
ccctgcaaag tcaacaatgg tggctgcagc aacctgtgcc tgctgtcccc tgggggtggt   10380
cacaagtgcg cctgccccac caacttctat ctgggtggcg atggccgtac ctgtgtgtcc   10440
aactgcacag caagccagtt tgtgtgcaaa aatgacaagt gcatcccctt ctggtggaag   10500
tgtgacacgg aggacgactg tggggatcac tcagacgagc ctccagactg tcccgagttc   10560
aagtgccgcc caggccagtt ccagtgctcc accggcatct gcaccaaccc tgccttcatc   10620
tgtgatgggc acaatgactg ccaagacaat agtgacgagc caattgcga cattcacgtc   10680
tgcttgccca gccaattcaa gtgcaccaac accaaccgct gcattcctgg catcttccgt   10740
tgcaatgggc aggacaactg cggggacggc gaggatgagc gggattgccc tgaggtgacc   10800
tgcgccccca accagttcca gtgctccatc accaagcgct gcatccctcg cgtctgggtc   10860
tgtgacaggg ataatcactg tgtggacggc agtgatgagc ctgccaactg tacccaaatg   10920
acctgtggag tggatgagtt ccgctgcaag gattctggcc gctgcatccc cgcgcgctgg   10980
aagtgtgacg gagaagatga ctgtgggat ggttcagatg agcccaagga agagtgtgat   11040
gagcgcacct gtgagccata ccagttccgc tgcaaaaaca ccgctgtgt cccaggccgt   11100
tggcaatgtg actacgacaa cgactgcgga gataactcgg acgaggagag ctgcacacct   11160
cggccctgct ctgagagtga gttttttctgt gccaatggcc gctgcatcgc tgggcgctgg   11220
aagtgtgatg ggaccatga ctgtgccgac ggctcagacg agaaagactg cacccccgc   11280
tgtgatatgg accagttcca gtgcaagagt ggccactgca tcccctgcg ctggccgtgt   11340
gacgcggatg ctgactgtat ggacggcagt gacgaggaag cctgtggcac tggggtgagg   11400
acctgcccat tggatgagtt tcaatgtaac aacaccttgt gcaagccgct ggcctggaag   11460
tgtgatggag aggacgactg tggggacaac tcagatgaga ccccgagga atgcgcccgg   11520
ttcatctgcc ctcccaaccg gcctttccgc tgcaagaatg accgagtctg cctgtggatt   11580
gggcgccagt gtgatggcgt ggacaactgt ggagatggga ctgacgagga ggactgtgag   11640
cccccacgg cccagaaccc ccactgcaaa gacaagaagg agttcctgtg ccgaaaccag   11700
cgctgtctat catcctccct gcgctgtaac atgttcgatg actgcggcga tggctccgat   11760
gaagaagatt gcagcatcga ccccaagctg accagctgtg ccaccaatgc cagcatgtgt   11820
ggggacgaag ctcgttgtgt gcgcactgag aaagctgcct actgtgcctg ccgctcgggc   11880
ttccatactg tgccgggcca gcccggatgc caggacatca acgagtgcct gcgctttggt   11940
acctgctctc agctctggaa caaacccaag ggaggccacc tctgcagctg tgcccgcaac   12000
ttcatgaaga cacacaacac ctgcaaagct gaaggctccg agtaccaggt gctatacatc   12060
gcggatgaca acgagatccg cagcttgttc ccgggccacc cccactcagc ctacgagcag   12120
acattccagg gcgatgagag tgtccgcata gatgccatgg atgtccatgt caaggccggc   12180
cgtgtctact ggactaactg gcacacgggc acaatctcct acaggagcct gccccctgcc   12240
gcccctccta cccacttcaa ccgccaccgg aggcagatcg accggggtgt cacccacctc   12300
aatatttcag ggctgaagat gccgaggggt atcgctatcg actgggtggc cgggaatgtg   12360
tactggaccg attccggccg agacgtgatt gaggtggcgc aaatgaaggg cgagaaccgc   12420
aagacgctca tctcgggcat gattgatgag ccccatgcca tcgtggtgga ccctctgagg   12480
```

-continued

```
ggcaccatgt actggtcaga ctgggggaac cacccccaaga ttgaaacagc agcgatggat    12540
ggcacccttc gggagactct cgtgcaagac aacattcagt ggcctacagg gctggctgtg    12600
gactatcaca atgaacggct ctactgggca gatgccaagc tttcggtcat cggcagcatc    12660
cggctcaacg gcactgaccc cattgtggct gctgacagca acgaggcct aagtcacccc     12720
ttcagcatcg atgtgtttga agactacatc tacggagtca cttacatcaa taatcgtgtc    12780
ttcaagatcc acaagtttgg acacagcccc ttgtacaacc taactggggg cctgagccat    12840
gcctctgatg tagtccttta ccatcaacac aagcagcctg aagtgaccaa cccctgtgac    12900
cgcaagaaat gcgaatggct gtgtctgctg agccccagcg ggcctgtctg cacctgtccc    12960
aatggaaaga ggctggataa tggcacctgt gtgcctgtgc cctctccaac accccctcca    13020
gatgccccta ggcctggaac ctgcactctg cagtgcttca atggtggtag ttgtttcctc    13080
aacgctcgga ggcagcccaa gtgccgttgc cagccccgtt acacaggcga taagtgtgag    13140
ctggatcagt gctgggaata ctgtcacaac ggaggcacct gtgcggcttc ccatctggc     13200
atgcccacgt gccgctgtcc cactggcttc acgggcccca aatgcaccgc acaggtgtgt    13260
gcaggctact gctctaacaa cagcacctgc accgtcaacc agggcaacca gccccagtgc    13320
cgatgtctac ctggcttcct gggcgaccgt tgccagtacc ggcagtgctc tggcttctgt    13380
gagaactttg gcacctgtca gatggctgct gatggctccc gacaatgtcg ctgcaccgtc    13440
tactttgagg gaccaaggtg tgaggtgaac aagtgtagtc gctgtctcca aggcgcctgt    13500
gtggtcaata agcagaccgg agatgtcaca tgcaactgca ctgatggccg ggtagccccc    13560
agttgtctca cctgcatcga tcactgtagc aatggtggct cctgcaccat gaacagcaag    13620
atgatgcctg agtgccagtg cccgcccat atgacaggac cccggtgcca ggagcaggtt    13680
gttagtcagc aacagcctgg gcatatggcc tccatcctga tccctctgct gctgcttctc    13740
ctgctgcttc tggtggctgg cgtggtgttc tggtataagc ggcgagtccg aggggctaag    13800
ggcttccagc accagcggat gaccaatggg gccatgaatg tggaaattgg aaaccctacc    13860
tacaagatgt atgaaggtgg agagcccgat gatgtcgggg gcctactgga tgctgatttt    13920
gcccttgacc ctgacaagcc taccaacttc accaacccag tgtatgccac gctctacatg    13980
gggggccacg gcagccgcca ttccctggcc agcacggacg agaagcgaga actgctgggc    14040
cggggacctg aagacgagat aggagatccc ttggcatagg gcctgcccc gacggatgtc     14100
cccagaaagc cccctgccac atgagtcttt caatgaaccc cctccccagc cggcccttct    14160
ccggccctgc cgggtgtaca atgtaaaaa tgaaggaatt acttttttata tgtgagcgag    14220
caagcgagca agcacagtat tatctctttg catttccttc ctgcctgctc ctcagtatcc    14280
cccccatgct gccttgaggg ggcggggagg gctttgtggc tcaaaggtat gaaggagtcc    14340
acatgttccc taccgagcat acccctggaa gcctggcggc acggcctccc caccacgcct    14400
gtgcaagaca ctcaacgggg ctccgtgtcc cagctttcct ttccttggct ctctggggtt    14460
agttcagggg aggtggagtc ctctgctgac cctgtctgga agatttggct ctagctgagg    14520
aaggagtctt ttagttgagg gaagtcaccc caaacccag ctcccacttt caggggcacc     14580
tctcagatgg ccatgctcag tatcccttcc agacaggccc tcccctctct agcgcccct     14640
ctgtggctcc tagggctgaa cacattcttt ggtaactgtc ccccaagcct cccatccccc    14700
tgagggccag gaaagtcgg ggcacaccaa ggaagggcaa gcgggcagcc ccatttggg      14760
gacgtgaacg tttaataat ttttgctgaa ttcctttaca actaaataac acagatattg     14820
```
ttataaataa aattgtaaaa aaaaaaaaa    14849

<210> SEQ ID NO 2
<211> LENGTH: 4545
<212> TYPE: PRT
<213> ORGANISM: Mus musculus

<400> SEQUENCE: 2

Met Leu Thr Pro Pro Leu Leu Leu Val Pro Leu Leu Ser Ala Leu
1               5                   10                  15

Val Ser Gly Ala Thr Met Asp Ala Pro Lys Thr Cys Ser Pro Lys Gln
            20                  25                  30

Phe Ala Cys Arg Asp Gln Ile Thr Cys Ile Ser Lys Gly Trp Arg Cys
        35                  40                  45

Asp Gly Glu Arg Asp Cys Pro Asp Gly Ser Asp Glu Ala Pro Glu Ile
    50                  55                  60

Cys Pro Gln Ser Lys Ala Gln Arg Cys Pro Pro Asn Glu His Ser Cys
65                  70                  75                  80

Leu Gly Thr Glu Leu Cys Val Pro Met Ser Arg Leu Cys Asn Gly Ile
                85                  90                  95

Gln Asp Cys Met Asp Gly Ser Asp Glu Gly Ala His Cys Arg Glu Leu
            100                 105                 110

Arg Ala Asn Cys Ser Arg Met Gly Cys Gln His Cys Val Pro Thr
        115                 120                 125

Pro Ser Gly Pro Thr Cys Tyr Cys Asn Ser Ser Phe Gln Leu Glu Ala
    130                 135                 140

Asp Gly Lys Thr Cys Lys Asp Phe Asp Glu Cys Ser Val Tyr Gly Thr
145                 150                 155                 160

Cys Ser Gln Leu Cys Thr Asn Thr Asp Gly Ser Phe Thr Cys Gly Cys
                165                 170                 175

Val Glu Gly Tyr Leu Leu Gln Pro Asp Asn Arg Ser Cys Lys Ala Lys
            180                 185                 190

Asn Glu Pro Val Asp Arg Pro Pro Val Leu Leu Ile Ala Asn Ser Gln
        195                 200                 205

Asn Ile Leu Ala Thr Tyr Leu Ser Gly Ala Gln Val Ser Thr Ile Thr
    210                 215                 220

Pro Thr Ser Thr Arg Gln Thr Thr Ala Met Asp Phe Ser Tyr Ala Asn
225                 230                 235                 240

Glu Thr Val Cys Trp Val His Val Gly Asp Ser Ala Ala Gln Thr Gln
                245                 250                 255

Leu Lys Cys Ala Arg Met Pro Gly Leu Lys Gly Phe Val Asp Glu His
            260                 265                 270

Thr Ile Asn Ile Ser Leu Ser Leu His His Val Glu Gln Met Ala Ile
        275                 280                 285

Asp Trp Leu Thr Gly Asn Phe Tyr Phe Val Asp Asp Ile Asp Asp Arg
    290                 295                 300

Ile Phe Val Cys Asn Arg Asn Gly Asp Thr Cys Val Thr Leu Leu Asp
305                 310                 315                 320

Leu Glu Leu Tyr Asn Pro Lys Gly Ile Ala Leu Asp Pro Ala Met Gly
                325                 330                 335

Lys Val Phe Phe Thr Asp Tyr Gly Gln Ile Pro Lys Val Glu Arg Cys
            340                 345                 350

Asp Met Asp Gly Gln Asn Arg Thr Lys Leu Val Asp Ser Lys Ile Val
        355                 360                 365

-continued

```
Phe Pro His Gly Ile Thr Leu Asp Leu Val Ser Arg Leu Val Tyr Trp
    370                 375                 380

Ala Asp Ala Tyr Leu Asp Tyr Ile Glu Val Val Asp Tyr Glu Gly Lys
385                 390                 395                 400

Gly Arg Gln Thr Ile Ile Gln Gly Ile Leu Ile Glu His Leu Tyr Gly
                    405                 410                 415

Leu Thr Val Phe Glu Asn Tyr Leu Tyr Ala Thr Asn Ser Asp Asn Ala
            420                 425                 430

Asn Thr Gln Gln Lys Thr Ser Val Ile Arg Val Asn Arg Phe Asn Ser
                435                 440                 445

Thr Glu Tyr Gln Val Val Thr Arg Val Asp Lys Gly Gly Ala Leu His
        450                 455                 460

Ile Tyr His Gln Arg Arg Gln Pro Arg Val Arg Ser His Ala Cys Glu
465                 470                 475                 480

Asn Asp Gln Tyr Gly Lys Pro Gly Gly Cys Ser Asp Ile Cys Leu Leu
                    485                 490                 495

Ala Asn Ser His Lys Ala Arg Thr Cys Arg Cys Arg Ser Gly Phe Ser
            500                 505                 510

Leu Gly Ser Asp Gly Lys Ser Cys Lys Lys Pro Glu His Glu Leu Phe
                515                 520                 525

Leu Val Tyr Gly Lys Gly Arg Pro Gly Ile Ile Arg Gly Met Asp Met
        530                 535                 540

Gly Ala Lys Val Pro Asp Glu His Met Ile Pro Ile Glu Asn Leu Met
545                 550                 555                 560

Asn Pro Arg Ala Leu Asp Phe His Ala Glu Thr Gly Phe Ile Tyr Phe
                    565                 570                 575

Ala Asp Thr Thr Ser Tyr Leu Ile Gly Arg Gln Lys Ile Asp Gly Thr
            580                 585                 590

Glu Arg Glu Thr Ile Leu Lys Asp Gly Ile His Asn Val Glu Gly Val
                595                 600                 605

Ala Val Asp Trp Met Gly Asp Asn Leu Tyr Trp Thr Asp Asp Gly Pro
        610                 615                 620

Lys Lys Thr Ile Ser Val Ala Arg Leu Glu Lys Ala Ala Gln Thr Arg
625                 630                 635                 640

Lys Thr Leu Ile Glu Gly Lys Met Thr His Pro Arg Ala Ile Val Val
                    645                 650                 655

Asp Pro Leu Asn Gly Trp Met Tyr Trp Thr Asp Trp Glu Glu Asp Pro
            660                 665                 670

Lys Asp Ser Arg Arg Gly Arg Leu Glu Arg Ala Trp Met Asp Gly Ser
                675                 680                 685

His Arg Asp Ile Phe Val Thr Ser Lys Thr Val Leu Trp Pro Asn Gly
        690                 695                 700

Leu Ser Leu Asp Ile Pro Ala Gly Arg Leu Tyr Trp Val Asp Ala Phe
705                 710                 715                 720

Tyr Asp Arg Ile Glu Thr Ile Leu Leu Asn Gly Thr Asp Arg Lys Ile
                    725                 730                 735

Val Tyr Glu Gly Pro Glu Leu Asn His Ala Phe Gly Leu Cys His His
            740                 745                 750

Gly Asn Tyr Leu Phe Trp Thr Glu Tyr Arg Ser Gly Ser Val Tyr Arg
                755                 760                 765

Leu Glu Arg Gly Val Ala Gly Ala Pro Pro Thr Val Thr Leu Leu Arg
        770                 775                 780

Ser Glu Arg Pro Pro Ile Phe Glu Ile Arg Met Tyr Asp Ala His Glu
```

-continued

```
            785                 790                 795                 800
Gln Gln Val Gly Thr Asn Lys Cys Arg Val Asn Asn Gly Gly Cys Ser
                805                 810                 815
Ser Leu Cys Leu Ala Thr Pro Gly Ser Arg Gln Cys Ala Cys Ala Glu
                820                 825                 830
Asp Gln Val Leu Asp Thr Asp Gly Val Thr Cys Leu Ala Asn Pro Ser
                835                 840                 845
Tyr Val Pro Pro Gln Cys Gln Pro Gly Gln Phe Ala Cys Ala Asn
            850                 855                 860
Asn Arg Cys Ile Gln Glu Arg Trp Lys Cys Asp Gly Asp Asn Asp Cys
865                 870                 875                 880
Leu Asp Asn Ser Asp Glu Ala Pro Ala Leu Cys His Gln His Thr Cys
                885                 890                 895
Pro Ser Asp Arg Phe Lys Cys Glu Asn Asn Arg Cys Ile Pro Asn Arg
                900                 905                 910
Trp Leu Cys Asp Gly Asp Asn Asp Cys Gly Asn Ser Glu Asp Glu Ser
                915                 920                 925
Asn Ala Thr Cys Ser Ala Arg Thr Cys Pro Pro Asn Gln Phe Ser Cys
                930                 935                 940
Ala Ser Gly Arg Cys Ile Pro Ile Ser Trp Thr Cys Asp Leu Asp Asp
945                 950                 955                 960
Asp Cys Gly Asp Arg Ser Asp Glu Ser Ala Ser Cys Ala Tyr Pro Thr
                965                 970                 975
Cys Phe Pro Leu Thr Gln Phe Thr Cys Asn Asn Gly Arg Cys Ile Asn
                980                 985                 990
Ile Asn Trp Arg Cys Asp Asn Asp Asn Asp Cys Gly Asp Asn Ser Asp
                995                 1000                1005
Glu Ala Gly Cys Ser His Ser Cys Ser Ser Thr Gln Phe Lys Cys Asn
            1010                1015                1020
Ser Gly Arg Cys Ile Pro Glu His Trp Thr Cys Asp Gly Asp Asn Asp
1025                1030                1035                1040
Cys Gly Asp Tyr Ser Asp Glu Thr His Ala Asn Cys Thr Asn Gln Ala
                1045                1050                1055
Thr Arg Pro Pro Gly Gly Cys His Ser Asp Glu Phe Gln Cys Pro Leu
                1060                1065                1070
Asp Gly Leu Cys Ile Pro Leu Arg Trp Arg Cys Asp Gly Asp Thr Asp
                1075                1080                1085
Cys Met Asp Ser Ser Asp Glu Lys Ser Cys Glu Gly Val Thr His Val
                1090                1095                1100
Cys Asp Pro Asn Val Lys Phe Gly Cys Lys Asp Ser Ala Arg Cys Ile
1105                1110                1115                1120
Ser Lys Ala Trp Val Cys Asp Gly Asp Ser Asp Cys Glu Asp Asn Ser
                1125                1130                1135
Asp Glu Glu Asn Cys Glu Ala Leu Ala Cys Arg Pro Pro Ser His Pro
                1140                1145                1150
Cys Ala Asn Asn Thr Ser Val Cys Leu Pro Pro Asp Lys Leu Cys Asp
                1155                1160                1165
Gly Lys Asp Asp Cys Gly Asp Gly Ser Asp Glu Gly Glu Leu Cys Asp
                1170                1175                1180
Gln Cys Ser Leu Asn Asn Gly Gly Cys Ser His Asn Cys Ser Val Ala
                1185                1190                1195                1200
Pro Gly Glu Gly Ile Val Cys Ser Cys Pro Leu Gly Met Glu Leu Gly
                1205                1210                1215
```

```
Ser Asp Asn His Thr Cys Gln Ile Gln Ser Tyr Cys Ala Lys His Leu
        1220                1225                1230
Lys Cys Ser Gln Lys Cys Asp Gln Asn Lys Phe Ser Val Lys Cys Ser
        1235                1240                1245
Cys Tyr Glu Gly Trp Val Leu Glu Pro Asp Gly Glu Thr Cys Arg Ser
        1250                1255                1260
Leu Asp Pro Phe Lys Leu Phe Ile Ile Phe Ser Asn Arg His Glu Ile
1265                1270                1275                1280
Arg Arg Ile Asp Leu His Lys Gly Asp Tyr Ser Val Leu Val Pro Gly
                1285                1290                1295
Leu Arg Asn Thr Ile Ala Leu Asp Phe His Leu Ser Gln Ser Ala Leu
                1300                1305                1310
Tyr Trp Thr Asp Ala Val Glu Asp Lys Ile Tyr Arg Gly Lys Leu Leu
                1315                1320                1325
Asp Asn Gly Ala Leu Thr Ser Phe Glu Val Val Ile Gln Tyr Gly Leu
                1330                1335                1340
Ala Thr Pro Glu Gly Leu Ala Val Asp Trp Ile Ala Gly Asn Ile Tyr
1345                1350                1355                1360
Trp Val Glu Ser Asn Leu Asp Gln Ile Glu Val Ala Lys Leu Asp Gly
                1365                1370                1375
Thr Leu Arg Thr Thr Leu Leu Ala Gly Asp Ile Glu His Pro Arg Ala
                1380                1385                1390
Ile Ala Leu Asp Pro Arg Asp Gly Ile Leu Phe Trp Thr Asp Trp Asp
                1395                1400                1405
Ala Ser Leu Pro Arg Ile Glu Ala Ala Ser Met Ser Gly Ala Gly Arg
                1410                1415                1420
Arg Thr Ile His Arg Glu Thr Gly Ser Gly Gly Cys Ala Asn Gly Leu
1425                1430                1435                1440
Thr Val Asp Tyr Leu Glu Lys Arg Ile Leu Trp Ile Asp Ala Arg Ser
                1445                1450                1455
Asp Ala Ile Tyr Ser Ala Arg Tyr Asp Gly Ser Gly His Met Glu Val
                1460                1465                1470
Leu Arg Gly His Glu Phe Leu Ser His Pro Phe Ala Val Thr Leu Tyr
                1475                1480                1485
Gly Gly Glu Val Tyr Trp Thr Asp Trp Arg Thr Asn Thr Leu Ala Lys
                1490                1495                1500
Ala Asn Lys Trp Thr Gly His Asn Val Thr Val Val Gln Arg Thr Asn
1505                1510                1515                1520
Thr Gln Pro Phe Asp Leu Gln Val Tyr His Pro Ser Arg Gln Pro Met
                1525                1530                1535
Ala Pro Asn Pro Cys Glu Ala Asn Gly Gly Arg Gly Pro Cys Ser His
                1540                1545                1550
Leu Cys Leu Ile Asn Tyr Asn Arg Thr Val Ser Trp Ala Cys Pro His
                1555                1560                1565
Leu Met Lys Leu His Lys Asp Asn Thr Thr Cys Tyr Glu Phe Lys Lys
                1570                1575                1580
Phe Leu Leu Tyr Ala Arg Gln Met Glu Ile Arg Gly Val Asp Leu Asp
1585                1590                1595                1600
Ala Pro Tyr Tyr Asn Tyr Ile Ile Ser Phe Thr Val Pro Asp Ile Asp
                1605                1610                1615
Asn Val Thr Val Leu Asp Tyr Asp Ala Arg Glu Gln Arg Val Tyr Trp
                1620                1625                1630
```

-continued

```
Ser Asp Val Arg Thr Gln Ala Ile Lys Arg Ala Phe Ile Asn Gly Thr
        1635                1640                1645

Gly Val Glu Thr Val Val Ser Ala Asp Leu Pro Asn Ala His Gly Leu
    1650                1655                1660

Ala Val Asp Trp Val Ser Arg Asn Leu Phe Trp Thr Ser Tyr Asp Thr
1665                1670                1675                1680

Asn Lys Lys Gln Ile Asn Val Ala Arg Leu Asp Gly Ser Phe Lys Asn
            1685                1690                1695

Ala Val Val Gln Gly Leu Glu Gln Pro His Gly Leu Val His Pro
        1700                1705                1710

Leu Arg Gly Lys Leu Tyr Trp Thr Asp Gly Asp Asn Ile Ser Met Ala
        1715                1720                1725

Asn Met Asp Gly Ser Asn His Thr Leu Leu Phe Ser Gly Gln Lys Gly
        1730                1735                1740

Pro Val Gly Leu Ala Ile Asp Phe Pro Glu Ser Lys Leu Tyr Trp Ile
1745                1750                1755                1760

Ser Ser Gly Asn His Thr Ile Asn Arg Cys Asn Leu Asp Gly Ser Glu
            1765                1770                1775

Leu Glu Val Ile Asp Thr Met Arg Ser Gln Leu Gly Lys Ala Thr Ala
        1780                1785                1790

Leu Ala Ile Met Gly Asp Lys Leu Trp Trp Ala Asp Gln Val Ser Glu
        1795                1800                1805

Lys Met Gly Thr Cys Asn Lys Ala Asp Gly Ser Gly Ser Val Val Leu
        1810                1815                1820

Arg Asn Ser Thr Thr Leu Val Met His Met Lys Val Tyr Asp Glu Ser
1825                1830                1835                1840

Ile Gln Leu Glu His Glu Gly Thr Asn Pro Cys Ser Val Asn Asn Gly
            1845                1850                1855

Asp Cys Ser Gln Leu Cys Leu Pro Thr Ser Glu Thr Thr Arg Ser Cys
        1860                1865                1870

Met Cys Thr Ala Gly Tyr Ser Leu Arg Ser Gly Gln Gln Ala Cys Glu
        1875                1880                1885

Gly Val Gly Ser Phe Leu Leu Tyr Ser Val His Glu Gly Ile Arg Gly
        1890                1895                1900

Ile Pro Leu Asp Pro Asn Asp Lys Ser Asp Ala Leu Val Pro Val Ser
1905                1910                1915                1920

Gly Thr Ser Leu Ala Val Gly Ile Asp Phe His Ala Glu Asn Asp Thr
            1925                1930                1935

Ile Tyr Trp Val Asp Met Gly Leu Ser Thr Ile Ser Arg Ala Lys Arg
            1940                1945                1950

Asp Gln Thr Trp Arg Glu Asp Val Val Thr Asn Gly Ile Gly Arg Val
            1955                1960                1965

Glu Gly Ile Ala Val Asp Trp Ile Ala Gly Asn Ile Tyr Trp Thr Asp
        1970                1975                1980

Gln Gly Phe Asp Val Ile Glu Val Ala Arg Leu Asn Gly Ser Phe Arg
1985                1990                1995                2000

Tyr Val Val Ile Ser Gln Gly Leu Asp Lys Pro Arg Ala Ile Thr Val
                2005                2010                2015

His Pro Glu Lys Gly Tyr Leu Phe Trp Thr Glu Trp Gly His Tyr Pro
            2020                2025                2030

Arg Ile Glu Arg Ser Arg Leu Asp Gly Thr Glu Arg Val Val Leu Val
            2035                2040                2045

Asn Val Ser Ile Ser Trp Pro Asn Gly Ile Ser Val Asp Tyr Gln Gly
```

-continued

```
            2050                2055                2060
Gly Lys Leu Tyr Trp Cys Asp Ala Arg Met Asp Lys Ile Glu Arg Ile
2065                2070                2075                2080

Asp Leu Glu Thr Gly Glu Asn Arg Glu Val Val Leu Ser Ser Asn Asn
                2085                2090                2095

Met Asp Met Phe Ser Val Ser Val Phe Glu Asp Phe Ile Tyr Trp Ser
                2100                2105                2110

Asp Arg Thr His Ala Asn Gly Ser Ile Lys Arg Gly Cys Lys Asp Asn
                2115                2120                2125

Ala Thr Asp Ser Val Pro Leu Arg Thr Gly Ile Gly Val Gln Leu Lys
                2130                2135                2140

Asp Ile Lys Val Phe Asn Arg Asp Arg Gln Lys Gly Thr Asn Val Cys
2145                2150                2155                2160

Ala Val Ala Asn Gly Gly Cys Gln Gln Leu Cys Leu Tyr Arg Gly Gly
                2165                2170                2175

Gly Gln Arg Ala Cys Ala Cys Ala His Gly Met Leu Ala Glu Asp Gly
                2180                2185                2190

Ala Ser Cys Arg Glu Tyr Ala Gly Tyr Leu Leu Tyr Ser Glu Arg Thr
                2195                2200                2205

Ile Leu Lys Ser Ile His Leu Ser Asp Glu Arg Asn Leu Asn Ala Pro
                2210                2215                2220

Val Gln Pro Phe Glu Asp Pro Glu His Met Lys Asn Val Ile Ala Leu
2225                2230                2235                2240

Ala Phe Asp Tyr Arg Ala Gly Thr Ser Pro Gly Thr Pro Asn Arg Ile
                2245                2250                2255

Phe Phe Ser Asp Ile His Phe Gly Asn Ile Gln Gln Ile Asn Asp Asp
                2260                2265                2270

Gly Ser Gly Arg Thr Thr Ile Val Glu Asn Val Gly Ser Val Glu Gly
                2275                2280                2285

Leu Ala Tyr His Arg Gly Trp Asp Thr Leu Tyr Trp Thr Ser Tyr Thr
                2290                2295                2300

Thr Ser Thr Ile Thr Arg His Thr Val Asp Gln Thr Arg Pro Gly Ala
2305                2310                2315                2320

Phe Glu Arg Glu Thr Val Ile Thr Met Ser Gly Asp Asp His Pro Arg
                2325                2330                2335

Ala Phe Val Leu Asp Glu Cys Gln Asn Leu Met Phe Trp Thr Asn Trp
                2340                2345                2350

Asn Glu Leu His Pro Ser Ile Met Arg Ala Ala Leu Ser Gly Ala Asn
                2355                2360                2365

Val Leu Thr Leu Ile Glu Lys Asp Ile Arg Thr Pro Asn Gly Leu Ala
                2370                2375                2380

Ile Asp His Arg Ala Glu Lys Leu Tyr Phe Ser Asp Ala Thr Leu Asp
2385                2390                2395                2400

Lys Ile Glu Arg Cys Glu Tyr Asp Gly Ser His Arg Tyr Val Ile Leu
                2405                2410                2415

Lys Ser Glu Pro Val His Pro Phe Gly Leu Ala Val Tyr Gly Glu His
                2420                2425                2430

Ile Phe Trp Thr Asp Trp Val Arg Arg Ala Val Gln Arg Ala Asn Lys
                2435                2440                2445

Tyr Val Gly Ser Asp Met Lys Leu Leu Arg Val Asp Ile Pro Gln Gln
                2450                2455                2460

Pro Met Gly Ile Ile Ala Val Ala Asn Asp Thr Asn Ser Cys Glu Leu
2465                2470                2475                2480
```

```
Ser Pro Cys Arg Ile Asn Asn Gly Gly Cys Gln Asp Leu Cys Leu Leu
                2485                2490                2495

Thr His Gln Gly His Val Asn Cys Ser Cys Arg Gly Gly Arg Ile Leu
                2500                2505                2510

Gln Glu Asp Phe Thr Cys Arg Ala Val Asn Ser Ser Cys Arg Ala Gln
                2515                2520                2525

Asp Glu Phe Glu Cys Ala Asn Gly Glu Cys Ile Ser Phe Ser Leu Thr
                2530                2535                2540

Cys Asp Gly Val Ser His Cys Lys Asp Lys Ser Asp Glu Lys Pro Ser
2545                2550                2555                2560

Tyr Cys Asn Ser Arg Arg Cys Lys Lys Thr Phe Arg Gln Cys Asn Asn
                2565                2570                2575

Gly Arg Cys Val Ser Asn Met Leu Trp Cys Asn Gly Val Asp Tyr Cys
                2580                2585                2590

Gly Asp Gly Ser Asp Glu Ile Pro Cys Asn Lys Thr Ala Cys Gly Val
                2595                2600                2605

Gly Glu Phe Arg Cys Arg Asp Gly Ser Cys Ile Gly Asn Ser Ser Arg
                2610                2615                2620

Cys Asn Gln Phe Val Asp Cys Glu Asp Ala Ser Asp Glu Met Asn Cys
2625                2630                2635                2640

Ser Ala Thr Asp Cys Ser Ser Tyr Phe Arg Leu Gly Val Lys Gly Val
                2645                2650                2655

Leu Phe Gln Pro Cys Glu Arg Thr Ser Leu Cys Tyr Ala Pro Ser Trp
                2660                2665                2670

Val Cys Asp Gly Ala Asn Asp Cys Gly Asp Tyr Ser Asp Glu Arg Asp
                2675                2680                2685

Cys Pro Gly Val Lys Arg Pro Arg Cys Pro Leu Asn Tyr Phe Ala Cys
                2690                2695                2700

Pro Ser Gly Arg Cys Ile Pro Met Ser Trp Thr Cys Asp Lys Glu Asp
2705                2710                2715                2720

Asp Cys Glu Asn Gly Glu Asp Glu Thr His Cys Asn Lys Phe Cys Ser
                2725                2730                2735

Glu Ala Gln Phe Glu Cys Gln Asn His Arg Cys Ile Ser Lys Gln Trp
                2740                2745                2750

Leu Cys Asp Gly Ser Asp Cys Gly Asp Gly Ser Asp Glu Ala Ala
                2755                2760                2765

His Cys Glu Gly Lys Thr Cys Gly Pro Ser Ser Phe Ser Cys Pro Gly
                2770                2775                2780

Thr His Val Cys Val Pro Glu Arg Trp Leu Cys Asp Gly Asp Lys Asp
2785                2790                2795                2800

Cys Thr Asp Gly Ala Asp Glu Ser Val Thr Ala Gly Cys Leu Tyr Asn
                2805                2810                2815

Ser Thr Cys Asp Asp Arg Glu Phe Met Cys Gln Asn Arg Leu Cys Ile
                2820                2825                2830

Pro Lys His Phe Val Cys Asp His Asp Arg Asp Cys Ala Asp Gly Ser
                2835                2840                2845

Asp Glu Ser Pro Glu Cys Glu Tyr Pro Thr Cys Gly Pro Asn Glu Phe
                2850                2855                2860

Arg Cys Ala Asn Gly Arg Cys Leu Ser Ser Arg Gln Trp Glu Cys Asp
2865                2870                2875                2880

Gly Glu Asn Asp Cys His Asp His Ser Asp Glu Ala Pro Lys Asn Pro
                2885                2890                2895
```

-continued

```
His Cys Thr Ser Pro Glu His Lys Cys Asn Ala Ser Ser Gln Phe Leu
            2900                2905                2910

Cys Ser Ser Gly Arg Cys Val Ala Glu Ala Leu Leu Cys Asn Gly Gln
        2915                2920                2925

Asp Asp Cys Gly Asp Gly Ser Asp Glu Arg Gly Cys His Val Asn Glu
    2930                2935                2940

Cys Leu Ser Arg Lys Leu Ser Gly Cys Ser Gln Asp Cys Glu Asp Leu
2945                2950                2955                2960

Lys Ile Gly Phe Lys Cys Arg Cys Arg Pro Gly Phe Arg Leu Lys Asp
            2965                2970                2975

Asp Gly Arg Thr Cys Ala Asp Leu Asp Glu Cys Ser Thr Thr Phe Pro
        2980                2985                2990

Cys Ser Gln Leu Cys Ile Asn Thr His Gly Ser Tyr Lys Cys Leu Cys
    2995                3000                3005

Val Glu Gly Tyr Ala Pro Arg Gly Gly Asp Pro His Ser Cys Lys Ala
3010                3015                3020

Val Thr Asp Glu Glu Pro Phe Leu Ile Phe Ala Asn Arg Tyr Tyr Leu
3025                3030                3035                3040

Arg Lys Leu Asn Leu Asp Gly Ser Asn Tyr Thr Leu Leu Lys Gln Gly
            3045                3050                3055

Leu Asn Asn Ala Val Ala Leu Ala Phe Asp Tyr Arg Glu Gln Met Ile
        3060                3065                3070

Tyr Trp Thr Gly Val Thr Thr Gln Gly Ser Met Ile Arg Arg Met His
    3075                3080                3085

Leu Asn Gly Ser Asn Val Gln Val Leu His Arg Thr Gly Leu Ser Asn
    3090                3095                3100

Pro Asp Gly Leu Ala Val Asp Trp Val Gly Gly Asn Leu Tyr Trp Cys
3105                3110                3115                3120

Asp Lys Gly Arg Asp Thr Ile Glu Val Ser Lys Leu Asn Gly Ala Tyr
            3125                3130                3135

Arg Thr Val Leu Val Ser Ser Gly Leu Arg Glu Pro Arg Ala Leu Val
        3140                3145                3150

Val Asp Val Gln Asn Gly Tyr Leu Tyr Trp Thr Asp Trp Gly Asp His
    3155                3160                3165

Ser Leu Ile Gly Arg Ile Gly Met Asp Gly Ser Gly Arg Ser Ile Ile
    3170                3175                3180

Val Asp Thr Lys Ile Thr Trp Pro Asn Gly Leu Thr Val Asp Tyr Val
3185                3190                3195                3200

Thr Glu Arg Ile Tyr Trp Ala Asp Ala Arg Glu Asp Tyr Ile Glu Phe
            3205                3210                3215

Ala Ser Leu Asp Gly Ser Asn Arg His Val Val Leu Ser Gln Asp Ile
        3220                3225                3230

Pro His Ile Phe Ala Leu Thr Leu Phe Glu Asp Tyr Val Tyr Trp Thr
    3235                3240                3245

Asp Trp Glu Thr Lys Ser Ile Asn Arg Ala His Lys Thr Thr Gly Ala
3250                3255                3260

Asn Lys Thr Leu Leu Ile Ser Thr Leu His Arg Pro Met Asp Leu His
3265                3270                3275                3280

Val Phe His Ala Leu Arg Gln Pro Asp Val Pro Asn His Pro Cys Lys
            3285                3290                3295

Val Asn Asn Gly Gly Cys Ser Asn Leu Cys Leu Leu Ser Pro Gly Gly
        3300                3305                3310

Gly His Lys Cys Ala Cys Pro Thr Asn Phe Tyr Leu Gly Gly Asp Gly
```

```
                   3315                3320                3325
Arg Thr Cys Val Ser Asn Cys Thr Ala Ser Gln Phe Val Cys Lys Asn
    3330                3335                3340
Asp Lys Cys Ile Pro Phe Trp Lys Cys Asp Thr Glu Asp Cys
3345                3350                3355                3360
Gly Asp His Ser Asp Glu Pro Pro Asp Cys Pro Glu Phe Lys Cys Arg
                3365                3370                3375
Pro Gly Gln Phe Gln Cys Ser Thr Gly Ile Cys Thr Asn Pro Ala Phe
        3380                3385                3390
Ile Cys Asp Gly Asp Asn Asp Cys Gln Asp Asn Ser Asp Glu Ala Asn
        3395                3400                3405
Cys Asp Ile His Val Cys Leu Pro Ser Gln Phe Lys Cys Thr Asn Thr
    3410                3415                3420
Asn Arg Cys Ile Pro Gly Ile Phe Arg Cys Asn Gly Gln Asp Asn Cys
3425                3430                3435                3440
Gly Asp Gly Glu Asp Glu Arg Asp Cys Pro Glu Val Thr Cys Ala Pro
                3445                3450                3455
Asn Gln Phe Gln Cys Ser Ile Thr Lys Arg Cys Ile Pro Arg Val Trp
        3460                3465                3470
Val Cys Asp Arg Asp Asn His Cys Val Asp Gly Ser Asp Glu Pro Ala
    3475                3480                3485
Asn Cys Thr Gln Met Thr Cys Gly Val Asp Glu Phe Arg Cys Lys Asp
    3490                3495                3500
Ser Gly Arg Cys Ile Pro Ala Arg Trp Lys Cys Asp Gly Glu Asp Asp
3505                3510                3515                3520
Cys Gly Asp Gly Ser Asp Glu Pro Lys Glu Glu Cys Asp Glu Arg Thr
                3525                3530                3535
Cys Glu Pro Tyr Gln Phe Arg Cys Lys Asn Asn Arg Cys Val Pro Gly
        3540                3545                3550
Arg Trp Gln Cys Asp Tyr Asp Asn Asp Cys Gly Asp Asn Ser Asp Glu
        3555                3560                3565
Glu Ser Cys Thr Pro Arg Pro Cys Ser Glu Ser Glu Phe Phe Cys Ala
    3570                3575                3580
Asn Gly Arg Cys Ile Ala Gly Arg Trp Lys Cys Asp Gly Asp His Asp
3585                3590                3595                3600
Cys Ala Asp Gly Ser Asp Glu Lys Asp Cys Thr Pro Arg Cys Asp Met
                3605                3610                3615
Asp Gln Phe Gln Cys Lys Ser Gly His Cys Ile Pro Leu Arg Trp Pro
        3620                3625                3630
Cys Asp Ala Asp Ala Asp Cys Met Asp Gly Ser Asp Glu Glu Ala Cys
        3635                3640                3645
Gly Thr Gly Val Arg Thr Cys Pro Leu Asp Glu Phe Gln Cys Asn Asn
        3650                3655                3660
Thr Leu Cys Lys Pro Leu Ala Trp Lys Cys Asp Gly Glu Asp Asp Cys
3665                3670                3675                3680
Gly Asp Asn Ser Asp Glu Asn Pro Glu Glu Cys Ala Arg Phe Ile Cys
                3685                3690                3695
Pro Pro Asn Arg Pro Phe Arg Cys Lys Asn Asp Arg Val Cys Leu Trp
        3700                3705                3710
Ile Gly Arg Gln Cys Asp Gly Val Asp Asn Cys Gly Asp Gly Thr Asp
        3715                3720                3725
Glu Glu Asp Cys Glu Pro Pro Thr Ala Gln Asn Pro His Cys Lys Asp
    3730                3735                3740
```

-continued

```
Lys Lys Glu Phe Leu Cys Arg Asn Gln Arg Cys Leu Ser Ser Ser Leu
3745                3750                3755                3760

Arg Cys Asn Met Phe Asp Asp Cys Gly Asp Gly Ser Asp Glu Glu Asp
                3765                3770                3775

Cys Ser Ile Asp Pro Lys Leu Thr Ser Cys Ala Thr Asn Ala Ser Met
                3780                3785                3790

Cys Gly Asp Glu Ala Arg Cys Val Arg Thr Glu Lys Ala Ala Tyr Cys
                3795                3800                3805

Ala Cys Arg Ser Gly Phe His Thr Val Pro Gly Gln Pro Gly Cys Gln
                3810                3815                3820

Asp Ile Asn Glu Cys Leu Arg Phe Gly Thr Cys Ser Gln Leu Trp Asn
3825                3830                3835                3840

Lys Pro Lys Gly Gly His Leu Cys Ser Cys Ala Arg Asn Phe Met Lys
                3845                3850                3855

Thr His Asn Thr Cys Lys Ala Glu Gly Ser Glu Tyr Gln Val Leu Tyr
                3860                3865                3870

Ile Ala Asp Asp Asn Glu Ile Arg Ser Leu Phe Pro Gly His Pro His
                3875                3880                3885

Ser Ala Tyr Glu Gln Thr Phe Gln Gly Asp Glu Ser Val Arg Ile Asp
                3890                3895                3900

Ala Met Asp Val His Val Lys Ala Gly Arg Val Tyr Trp Thr Asn Trp
3905                3910                3915                3920

His Thr Gly Thr Ile Ser Tyr Arg Ser Leu Pro Pro Ala Ala Pro Pro
                3925                3930                3935

Thr Thr Ser Asn Arg His Arg Arg Gln Ile Asp Arg Gly Val Thr His
                3940                3945                3950

Leu Asn Ile Ser Gly Leu Lys Met Pro Arg Gly Ile Ala Ile Asp Trp
                3955                3960                3965

Val Ala Gly Asn Val Tyr Trp Thr Asp Ser Gly Arg Asp Val Ile Glu
                3970                3975                3980

Val Ala Gln Met Lys Gly Glu Asn Arg Lys Thr Leu Ile Ser Gly Met
3985                3990                3995                4000

Ile Asp Glu Pro His Ala Ile Val Val Asp Pro Leu Arg Gly Thr Met
                4005                4010                4015

Tyr Trp Ser Asp Trp Gly Asn His Pro Lys Ile Glu Thr Ala Ala Met
                4020                4025                4030

Asp Gly Thr Leu Arg Glu Thr Leu Val Gln Asp Asn Ile Gln Trp Pro
                4035                4040                4045

Thr Gly Leu Ala Val Asp Tyr His Asn Glu Arg Leu Tyr Trp Ala Asp
                4050                4055                4060

Ala Lys Leu Ser Val Ile Gly Ser Ile Arg Leu Asn Gly Thr Asp Pro
4065                4070                4075                4080

Ile Val Ala Ala Asp Ser Lys Arg Gly Leu Ser His Pro Phe Ser Ile
                4085                4090                4095

Asp Val Phe Glu Asp Tyr Ile Tyr Gly Val Thr Tyr Ile Asn Asn Arg
                4100                4105                4110

Val Phe Lys Ile His Lys Phe Gly His Ser Pro Leu Tyr Asn Leu Thr
                4115                4120                4125

Gly Gly Leu Ser His Ala Ser Asp Val Val Leu Tyr His Gln His Lys
                4130                4135                4140

Gln Pro Glu Val Thr Asn Pro Cys Asp Arg Lys Lys Cys Glu Trp Leu
4145                4150                4155                4160
```

```
Cys Leu Leu Ser Pro Ser Gly Pro Val Cys Thr Cys Pro Asn Gly Lys
                4165                4170                4175

Arg Leu Asp Asn Gly Thr Cys Val Pro Val Pro Ser Pro Thr Pro Pro
            4180                4185                4190

Pro Asp Ala Pro Arg Pro Gly Thr Cys Thr Leu Gln Cys Phe Asn Gly
        4195                4200                4205

Gly Ser Cys Phe Leu Asn Ala Arg Arg Gln Pro Lys Cys Arg Cys Gln
    4210                4215                4220

Pro Arg Tyr Thr Gly Asp Lys Cys Glu Leu Asp Gln Cys Trp Glu Tyr
4225                4230                4235                4240

Cys His Asn Gly Gly Thr Cys Ala Ala Ser Pro Ser Gly Met Pro Thr
                4245                4250                4255

Cys Arg Cys Pro Thr Gly Phe Thr Gly Pro Lys Cys Thr Ala Gln Val
            4260                4265                4270

Cys Ala Gly Tyr Cys Ser Asn Asn Ser Thr Cys Thr Val Asn Gln Gly
        4275                4280                4285

Asn Gln Pro Gln Cys Arg Cys Leu Pro Gly Phe Leu Gly Asp Arg Cys
    4290                4295                4300

Gln Tyr Arg Gln Cys Ser Gly Phe Cys Glu Asn Phe Gly Thr Cys Gln
4305                4310                4315                4320

Met Ala Ala Asp Gly Ser Arg Gln Cys Arg Cys Thr Val Tyr Phe Glu
                4325                4330                4335

Gly Pro Arg Cys Glu Val Asn Lys Cys Ser Arg Cys Leu Gln Gly Ala
            4340                4345                4350

Cys Val Val Asn Lys Gln Thr Gly Asp Val Thr Cys Asn Cys Thr Asp
        4355                4360                4365

Gly Arg Val Ala Pro Ser Cys Leu Thr Cys Ile Asp His Cys Ser Asn
    4370                4375                4380

Gly Gly Ser Cys Thr Met Asn Ser Lys Met Met Pro Glu Cys Gln Cys
4385                4390                4395                4400

Pro Pro His Met Thr Gly Pro Arg Cys Gln Glu Gln Val Val Ser Gln
                4405                4410                4415

Gln Gln Pro Gly His Met Ala Ser Ile Leu Ile Pro Leu Leu Leu Leu
            4420                4425                4430

Leu Leu Leu Leu Leu Val Ala Gly Val Val Phe Trp Tyr Lys Arg Arg
        4435                4440                4445

Val Arg Gly Ala Lys Gly Phe Gln His Gln Arg Met Thr Asn Gly Ala
    4450                4455                4460

Met Asn Val Glu Ile Gly Asn Pro Thr Tyr Lys Met Tyr Glu Gly Gly
4465                4470                4475                4480

Glu Pro Asp Asp Val Gly Gly Leu Leu Asp Ala Asp Phe Ala Leu Asp
                4485                4490                4495

Pro Asp Lys Pro Thr Asn Phe Thr Asn Pro Val Tyr Ala Thr Leu Tyr
            4500                4505                4510

Met Gly Gly His Gly Ser Arg His Ser Leu Ala Ser Thr Asp Glu Lys
        4515                4520                4525

Arg Glu Leu Leu Gly Arg Gly Pro Glu Asp Glu Ile Gly Asp Pro Leu
    4530                4535                4540

Ala
4545

<210> SEQ ID NO 3
<211> LENGTH: 4577
<212> TYPE: DNA
```

<213> ORGANISM: Homo sapiens

<400> SEQUENCE: 3

| | | | | | |
|---|---|---|---|---|---|
| gctacaatcc | atctggtctc | ctccagctcc | ttctttctgc | aacatgggga | agaacaaact | 60 |
| ccttcatcca | agtctggttc | ttctcctctt | ggtcctcctg | cccacagacg | cctcagtctc | 120 |
| tggaaaaccg | cagtatatgg | ttctggtccc | ctccctgctc | cacactgaga | ccactgagaa | 180 |
| gggctgtgtc | cttctgagct | acctgaatga | gacagtgact | gtaagtgctt | ccttggagtc | 240 |
| tgtcagggga | aacaggagcc | tcttcactga | cctggaggcg | gagaatgacg | tactccactg | 300 |
| tgtcgccttc | gctgtcccaa | agtcttcatc | caatgaggag | gtaatgttcc | tcactgtcca | 360 |
| agtgaaagga | ccaacccaag | aatttaagaa | gcggaccaca | gtgatggtta | agaacgagga | 420 |
| cagtctggtc | tttgtccaga | cagacaaatc | aatctacaaa | ccagggcaga | cagtgaaatt | 480 |
| tcgtgttgtc | tccatggatg | aaaactttca | cccctgaat | gagttgattc | cactagtata | 540 |
| cattcaggat | cccaaaggaa | atcgcatcgc | acaatggcag | agtttccagt | tagagggtgg | 600 |
| cctcaagcaa | ttttcttttc | ccctctcatc | agagcccttc | cagggctcct | acaaggtggt | 660 |
| ggtacagaag | aaatcaggtg | gaaggacaga | gcaccctttc | accgtggagg | aatttgttct | 720 |
| tcccaagttt | gaagtacaag | taacagtgcc | aaagataatc | accatcttgg | aagaagagat | 780 |
| gaatgtatca | gtgtgtggcc | tatacacata | tgggaagcct | gtccctggac | atgtgactgt | 840 |
| gagcatttgc | agaaagtata | gtgacgcttc | cgactgccac | ggtgaagatt | cacaggcttt | 900 |
| ctgtgagaaa | ttcagtggac | agctaaacag | ccatggctgc | ttctatcagc | aagtaaaaac | 960 |
| caaggtcttc | cagctgaaga | ggaaggagta | tgaaatgaaa | cttcacactg | aggcccagat | 1020 |
| ccaagaagaa | ggaacagtgg | tggaattgac | tggaaggcag | tccagtgaaa | tcacaagaac | 1080 |
| cataaccaaa | ctctcatttg | tgaaagtgga | ctcacacttt | cgacagggaa | ttcccttctt | 1140 |
| tgggcaggtg | cgcctagtag | atgggaaagg | cgtccctata | ccaaataaag | tcatattcat | 1200 |
| cagaggaaat | gaagcaaact | attactccaa | tgctaccacg | gatgagcatg | gccttgtaca | 1260 |
| gttctctatc | aacaccacca | acgttatggg | tacctctctt | actgttaggg | tcaattacaa | 1320 |
| ggatcgtagt | ccctgttacg | gctaccagtg | ggtgtcagaa | gaacacgaag | aggcacatca | 1380 |
| cactgcttat | cttgtgttct | ccccaagcaa | gagctttgtc | caccttgagc | ccatgtctca | 1440 |
| tgaactaccc | tgtggccata | tcagacagt | ccaggcacat | tatattctga | atggaggcac | 1500 |
| cctgctgggg | ctgaagaagc | tctccttta | ttatctgata | atggcaaagg | gaggcattgt | 1560 |
| ccgaactggg | actcatggac | tgcttgtgaa | gcaggaagac | atgaagggcc | atttttccat | 1620 |
| ctcaatccct | gtgaagtcag | acattgctcc | tgtcgctcgg | ttgctcatct | atgctgtttt | 1680 |
| acctaccggg | gacgtgattg | gggattctgc | aaaatatgat | gttgaaaatt | gtctggccaa | 1740 |
| caaggtggat | ttgagcttca | gcccatcaca | aagtctccca | gcctcacacg | cccacctgcg | 1800 |
| agtcacagcg | gctcctcagt | ccgtctgcgc | cctccgtgct | gtggaccaaa | gcgtgctgct | 1860 |
| catgaagcct | gatgctgagc | tctcggcgtc | ctcggtttac | aacctgctac | agaaaaggaa | 1920 |
| cctcactggc | ttccctgggc | ctttgaatga | ccaggacgat | gaagactgca | tcaatcgtca | 1980 |
| taatgtctat | attaatggaa | tcacatatac | tccagtatca | agtacaaatg | aaaaggatat | 2040 |
| gtacagcttc | ctagaggaca | tgggcttaaa | ggcattcacc | aactcaaaga | ttcgtaaacc | 2100 |
| caaaatgtgt | ccacagcttc | aacagtatga | aatgcatgga | cctgaaggtc | tacgtgtagg | 2160 |
| ttttttatgag | tcagatgtaa | tgggaagagg | ccatgcacgc | ctggtgcatg | ttgaagagcc | 2220 |
| tcacacggag | accgtacgaa | agtacttccc | tgagacatgg | atctgggatt | tggtggtggt | 2280 |

```
aaactcagca ggggtggctg aggtaggagt aacagtccct gacaccatca ccgagtggaa    2340
ggcaggggcc ttctgcctgt ctgaagatgc tggacttggt atctcttcca ctgcctctct    2400
ccgagccttc cagcccttct tgtggagct acaatgcct tactctgtga ttcgtggaga     2460
ggccttcaca ctcaaggcca cggtcctaaa ctaccttccc aaatgcatcc gggtcagtgt    2520
gcagctggaa gcctctcccg ccttccttgc tgtcccagtg gagaaggaac aagcgcctca    2580
ctgcatctgt gcaaacgggc ggcaaactgt gtcctgggca gtaaccccaa agtcattagg    2640
aaatgtgaat ttcactgtga gcgcagaggc actagagtct caagagctgt gtgggactga    2700
ggtgccttca gttcctgaac acggaaggaa agacacagtc atcaagcctc tgttggttga    2760
acctgaagga ctagagaagg aaacaacatt caactcccta ctttgtccat caggtggtga    2820
ggtttctgaa gaattatccc tgaaactgcc accaaatgtg gtagaagaat ctgcccgagc    2880
ttctgtctca gttttgggag acatattagg ctctgccatg caaaacacac aaaatcttct    2940
ccagatgccc tatggctgtg gagagcagaa tatggtcctc tttgctccta acatctatgt    3000
actggattat ctaaatgaaa cacagcagct tactccagag gtcaagtcca aggccattgg    3060
ctatctcaac actggttacc agagacagtt gaactacaaa cactatgatg gctcctacag    3120 caccttggg gagcgatatg caggaaccaa gggcaacacc tggctcacag cctttgttct    3180
gaagactttt gcccaagctc gagcctacat cttcatcgat gaagcacaca ttacccaagc    3240
cctcatatgg ctctcccaga ggcagaagga caatggctgt ttcaggagct ctgggtcact    3300
gctcaacaat gccataaagg gaggagtaga agatgaagtg accctctccg cctatatcac    3360
catcgccctt ctggagattc ctctcacagt cactcaccct gttgtccgca atgccctgtt    3420
ttgcctggag tcagcctgga agacagcaca agaaggggac catggcagcc atgtatatac    3480
caaagcactg ctggcctatg cttttgccct ggcaggtaac caggacaaga ggaaggaagt    3540
actcaagtca cttaatgagg aagctgtgaa gaaagacaac tctgtccatt gggagcgccc    3600
tcagaaaccc aaggcaccag tggggcattt ttacgaaccc caggctccct ctgctgaggt    3660
ggagatgaca tcctatgtgc tcctcgctta tctcacggcc cagccagccc caacctcgga    3720
ggacctgacc tctgcaacca acatcgtgaa gtggatcacg aagcagcaga tgcccaggg    3780 cggtttctcc tccacccagg acacagtggt ggctctccat gctctgtcca atatggagc    3840 cgccacattt accaggactg ggaaggctgc acaggtgact atccagtctt cagggacatt    3900
ttccagcaaa ttccaagtgg acaacaacaa tcgcctgtta ctgcagcagg tctcattgcc    3960
agagctgcct ggggaataca gcatgaaagt gacaggagaa ggatgtgtct acctccagac    4020
ctccttgaaa tacaatattc tcccagaaaa ggaagagttc ccctttgctt taggagtgca    4080
gactctgcct caaacttgtg atgaacccaa agcccacacc agcttccaaa tctccctaag    4140
tgtcagttac acagggagcc gctctgcctc caacatggcg atcgttgatg tgaagatggt    4200
ctctggcttc attcccctga agccaacagt gaaaatgctt gaaagatcta accatgtgag    4260
ccggacagaa gtcagcagca accatgtctt gatttacctt gataaggtgt caaatcagac    4320
actgagcttg ttcttcacgg ttctgcaaga tgtcccagta agagatctca accagccat    4380 agtgaaagtc tatgattact acgagacgga tgagtttgca atcgctgagt acaatgctcc    4440
ttgcagcaaa gatcttggaa atgcttgaag accacaaggc tgaaaagtgc tttgctggag    4500
tcctgttctc tgagctccac agaagacacg tgtttttgta tctttaaaga cttgatgaat    4560
aaacactttt tctggtc                                                   4577
```

<210> SEQ ID NO 4
<211> LENGTH: 4422
<212> TYPE: DNA
<213> ORGANISM: Homo sapiens

<400> SEQUENCE: 4

| | | | | | |
|---|---|---|---|---|---|
| atgggaaga | acaaactcct | tcatccaagt | ctggttcttc | tcctcttggt | cctcctgccc | 60 |
| acagacgcct | cagtctctgg | aaaaccgcag | tatatggttc | tggtcccctc | cctgctccac | 120 |
| actgagacca | ctgagaaggg | ctgtgtcctt | ctgagctacc | tgaatgagac | agtgactgta | 180 |
| agtgcttcct | tggagtctgt | caggggaaac | aggagcctct | tcactgacct | ggaggcggag | 240 |
| aatgacgtac | tccactgtgt | cgccttcgct | gtcccaaagt | cttcatccaa | tgaggaggta | 300 |
| atgttcctca | ctgtccaagt | gaaaggacca | acccaagaat | taagaagcg | gaccacagtg | 360 |
| atggttaaga | acgaggacag | tctggtcttt | gtccagacag | acaaatcaat | ctacaaacca | 420 |
| gggcagacag | tgaaatttcg | tgttgtctcc | atggatgaaa | actttcaccc | cctgaatgag | 480 |
| ttgattccac | tagtatacat | tcaggatccc | aaaggaaatc | gcatcgcaca | atggcagagt | 540 |
| ttccagttag | agggtggcct | caagcaattt | tcttttcccc | tctcatcaga | gcccttccag | 600 |
| ggctcctaca | aggtggtggt | acagaagaaa | tcaggtggaa | ggacagagca | ccctttcacc | 660 |
| gtggaggaat | tgttcttcc | caagtttgaa | gtacaagtaa | cagtgccaaa | gataatcacc | 720 |
| atcttggaag | aagagatgaa | tgtatcagtg | tgtggcctat | acacatatgg | gaagcctgtc | 780 |
| cctggacatg | tgactgtgag | catttgcaga | aagtatagtg | acgcttccga | ctgccacggt | 840 |
| gaagattcac | aggctttctg | tgagaaattc | agtggacagc | taaacagcca | tggctgcttc | 900 |
| tatcagcaag | taaaaaccaa | ggtcttccag | ctgaagagga | aggagtatga | aatgaaactt | 960 |
| cacactgagg | cccagatcca | agaagaagga | acagtggtgg | aattgactgg | aaggcagtcc | 1020 |
| agtgaaatca | aagaaccat | aaccaaactc | tcatttgtga | agtggactc | acactttcga | 1080 |
| cagggaattc | ccttctttgg | gcaggtgcgc | ctagtagatg | ggaaaggcgt | ccctatacca | 1140 |
| aataaagtca | tattcatcag | aggaaatgaa | gcaaactatt | actccaatgc | taccacggat | 1200 |
| gagcatggcc | ttgtacagtt | ctctatcaac | accaccaacg | ttatgggtac | ctctcttact | 1260 |
| gttagggtca | attacaagga | tcgtagtccc | tgttacggct | accagtgggt | gtcagaagaa | 1320 |
| cacgaagagg | cacatcacac | tgcttatctt | gtgttctccc | caagcaagag | ctttgtccac | 1380 |
| cttgagccca | tgtctcatga | actaccctgt | ggccatactc | agacagtcca | ggcacattat | 1440 |
| attctgaatg | gaggcaccct | gctggggctg | aagaagctct | cctttttatta | tctgataatg | 1500 |
| gcaaagggag | gcattgtccg | aactgggact | catggactgc | ttgtgaagca | ggaagacatg | 1560 |
| aagggccatt | tttccatctc | aatccctgtg | aagtcagaca | ttgctcctgt | cgctcggttg | 1620 |
| ctcatctatg | ctgttttacc | taccggggac | gtgattgggg | attctgcaaa | atatgatgtt | 1680 |
| gaaaattgtc | tggccaacaa | ggtggatttg | agcttcagcc | catcacaaag | tctcccagcc | 1740 |
| tcacacgccc | acctgcgagt | cacagcggct | cctcagtccg | tctgcgccct | ccgtgctgtg | 1800 |
| gaccaaagcg | tgctgctcat | gaagcctgat | gctgagctct | cggcgtcctc | ggtttacaac | 1860 |
| ctgctaccag | aaaaggacct | cactggcttc | cctgggcctt | gaatgacca | ggacgatgaa | 1920 |
| gactgcatca | atcgtcataa | tgtctatatt | aatggaatca | catatactcc | agtatcaagt | 1980 |
| acaaatgaaa | aggatatgta | cagcttccta | gaggacatgg | gcttaaaggc | attcaccaac | 2040 |
| tcaaagatc | gtaaacccaa | aatgtgtcca | cagcttcaac | agtatgaaat | gcatggacct | 2100 |
| gaaggtctac | gtgtaggttt | ttatgagtca | gatgtaatgg | gaagaggcca | tgcacgcctg | 2160 |

-continued

| | |
|---|---|
| gtgcatgttg aagagcctca cacggagacc gtacgaaagt acttccctga gacatggatc | 2220 |
| tgggatttgg tggtggtaaa ctcagcaggg gtggctgagg taggagtaac agtccctgac | 2280 |
| accatcaccg agtggaaggc aggggccttc tgcctgtctg aagatgctgg acttggtatc | 2340 |
| tcttccactg cctctctccg agccttccag cccttctttg tggagcttac aatgccttac | 2400 |
| tctgtgattc gtggagaggc cttcacactc aaggccacgg tcctaaacta ccttcccaaa | 2460 |
| tgcatccggg tcagtgtgca gctggaagcc tctcccgcct tccttgctgt cccagtggag | 2520 |
| aaggaacaag cgcctcactg catctgtgca aacgggcggc aaactgtgtc ctgggcagta | 2580 |
| accccaaagt cattaggaaa tgtgaatttc actgtgagcg cagaggcact agagtctcaa | 2640 |
| gagctgtgtg ggactgaggt gccttcagtt cctgaacacg gaaggaaaga cacagtcatc | 2700 |
| aagcctctgt tggttgaacc tgaaggacta gagaaggaaa caacattcaa ctccctactt | 2760 |
| tgtccatcag gtggtgaggt ttctgaagaa ttatccctga aactgccacc aaatgtggta | 2820 |
| gaagaatctg cccgagcttc tgtctcagtt ttgggagaca tattaggctc tgccatgcaa | 2880 |
| aacacacaaa atcttctcca gatgcccttat ggctgtggag agcagaatat ggtcctcttt | 2940 |
| gctcctaaca tctatgtact ggattatcta aatgaaacac agcagcttac tccagaggtc | 3000 |
| aagtccaagg ccattggcta tctcaacact ggttaccaga gacagttgaa ctacaaacac | 3060 |
| tatgatggct cctacagcac cttttgggag cgatatggca ggaaccaggg caacacctgg | 3120 |
| ctcacagcct ttgttctgaa gacttttgcc caagctcgag cctacatctt catcgatgaa | 3180 |
| gcacacatta cccaagccct catatggctc tcccagaggc agaaggacaa tggctgtttc | 3240 |
| aggagctctg ggtcactgct caacaatgcc ataaagggag gagtagaaga tgaagtgacc | 3300 |
| ctctccgcct atatcaccat cgcccttctg gagattcctc tcacagtcac tcaccctgtt | 3360 |
| gtccgcaatg ccctgttttg cctggagtca gcctggaaga cagcacaaga aggggaccat | 3420 |
| ggcagccatg tatataccaa agcactgctg gcctatgctt ttgccctggc aggtaaccag | 3480 |
| gacaagagga aggaagtact caagtcactt aatgaggaag ctgtgaagaa agacaactct | 3540 |
| gtccattggg agcgccctca gaaacccaag gcaccagtgg ggcatttta cgaaccccag | 3600 |
| gctccctctg ctgaggtgga gatgacatcc tatgtgctcc tcgcttatct cacggcccag | 3660 |
| ccagccccaa cctcggagga cctgacctct gcaaccaaca tcgtgaagtg gatcacgaag | 3720 |
| cagcagaatg cccagggcgg tttctcctcc acccaggaca cagtggtggc tctccatgct | 3780 |
| ctgtccaaat atggagccgc cacatttacc aggactggga aggctgcaca ggtgactatc | 3840 |
| cagtcttcag ggacattttc cagcaaattc caagtggaca acaacaatcg cctgttactg | 3900 |
| cagcaggtct cattgccaga gctgcctggg gaatacagca tgaaagtgac aggagaagga | 3960 |
| tgtgtctacc tccagaccctc cttgaaatac aatattctcc cagaaaagga agagttcccc | 4020 |
| tttgctttag gagtgcagac tctgcctcaa acttgtgatg aacccaaagc ccacaccagc | 4080 |
| ttccaaatct ccctaagtgt cagttacaca gggagccgct ctgcctccaa catggcgatc | 4140 |
| gttgatgtga agatggtctc tggcttcatt cccctgaagc caacagtgaa aatgcttgaa | 4200 |
| agatctaacc atgtgagccg acagaagtc agcagcaacc atgtcttgat ttaccttgat | 4260 |
| aaggtgtcaa atcagacact gagccttgttc ttcacggttc tgcaagatgt cccagtaaga | 4320 |
| gatctcaaac cagccatagt gaaagtctat gattactacg agacggatga gtttgcaatc | 4380 |
| gctgagtaca atgctccttg cagcaaagat cttggaaatg ct | 4422 |

<210> SEQ ID NO 5

<211> LENGTH: 1474
<212> TYPE: PRT
<213> ORGANISM: Homo sapiens

<400> SEQUENCE: 5

Met Gly Lys Asn Lys Leu Leu His Pro Ser Leu Val Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
    210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
    290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Glu Gly Thr Val Val Glu Leu Thr
                325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
        355                 360                 365

Val Arg Leu Val Asp Gly Lys Gly Val Pro Ile Pro Asn Lys Val Ile
    370                 375                 380

Phe Ile Arg Gly Asn Glu Ala Asn Tyr Tyr Ser Asn Ala Thr Thr Asp

-continued

```
            385                 390                 395                 400
Glu His Gly Leu Val Gln Phe Ser Ile Asn Thr Thr Asn Val Met Gly
                    405                 410                 415

Thr Ser Leu Thr Val Arg Val Asn Tyr Lys Asp Arg Ser Pro Cys Tyr
                420                 425                 430

Gly Tyr Gln Trp Val Ser Glu His Glu Glu Ala His His Thr Ala
            435                 440                 445

Tyr Leu Val Phe Ser Pro Ser Lys Ser Phe Val His Leu Glu Pro Met
        450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
            500                 505                 510

Leu Leu Val Lys Gln Glu Asp Met Lys Gly His Phe Ser Ile Ser Ile
        515                 520                 525

Pro Val Lys Ser Asp Ile Ala Pro Val Ala Arg Leu Leu Ile Tyr Ala
    530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
            580                 585                 590

Ser Val Cys Ala Leu Arg Ala Val Asp Gln Ser Val Leu Leu Met Lys
        595                 600                 605

Pro Asp Ala Glu Leu Ser Ala Ser Ser Val Tyr Asn Leu Leu Pro Glu
    610                 615                 620

Lys Asp Leu Thr Gly Phe Pro Gly Pro Leu Asn Asp Gln Asp Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
            660                 665                 670

Met Gly Leu Lys Ala Phe Thr Asn Ser Lys Ile Arg Lys Pro Lys Met
        675                 680                 685

Cys Pro Gln Leu Gln Gln Tyr Glu Met His Gly Pro Glu Gly Leu Arg
    690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Val Asn Ser Ala Gly Val Ala
            740                 745                 750

Glu Val Gly Val Thr Val Pro Asp Thr Ile Thr Glu Trp Lys Ala Gly
        755                 760                 765

Ala Phe Cys Leu Ser Glu Asp Ala Gly Leu Gly Ile Ser Ser Thr Ala
    770                 775                 780

Ser Leu Arg Ala Phe Gln Pro Phe Val Glu Leu Thr Met Pro Tyr
785                 790                 795                 800

Ser Val Ile Arg Gly Glu Ala Phe Thr Leu Lys Ala Thr Val Leu Asn
                805                 810                 815
```

-continued

```
Tyr Leu Pro Lys Cys Ile Arg Val Ser Val Gln Leu Glu Ala Ser Pro
            820                 825                 830
Ala Phe Leu Ala Val Pro Val Glu Lys Glu Gln Ala Pro His Cys Ile
        835                 840                 845
Cys Ala Asn Gly Arg Gln Thr Val Ser Trp Ala Val Thr Pro Lys Ser
    850                 855                 860
Leu Gly Asn Val Asn Phe Thr Val Ser Ala Glu Ala Leu Glu Ser Gln
865                 870                 875                 880
Glu Leu Cys Gly Thr Glu Val Pro Ser Val Pro Glu His Gly Arg Lys
                885                 890                 895
Asp Thr Val Ile Lys Pro Leu Leu Val Glu Pro Glu Gly Leu Glu Lys
            900                 905                 910
Glu Thr Thr Phe Asn Ser Leu Leu Cys Pro Ser Gly Gly Glu Val Ser
        915                 920                 925
Glu Glu Leu Ser Leu Lys Leu Pro Pro Asn Val Val Glu Glu Ser Ala
    930                 935                 940
Arg Ala Ser Val Ser Val Leu Gly Asp Ile Leu Gly Ser Ala Met Gln
945                 950                 955                 960
Asn Thr Gln Asn Leu Leu Gln Met Pro Tyr Gly Cys Gly Glu Gln Asn
                965                 970                 975
Met Val Leu Phe Ala Pro Asn Ile Tyr Val Leu Asp Tyr Leu Asn Glu
            980                 985                 990
Thr Gln Gln Leu Thr Pro Glu Val Lys Ser Lys Ala Ile Gly Tyr Leu
        995                 1000                1005
Asn Thr Gly Tyr Gln Arg Gln Leu Asn Tyr Lys His Tyr Asp Gly Ser
    1010                1015                1020
Tyr Ser Thr Phe Gly Glu Arg Tyr Gly Arg Asn Gln Gly Asn Thr Trp
1025                1030                1035                1040
Leu Thr Ala Phe Val Leu Lys Thr Phe Ala Gln Ala Arg Ala Tyr Ile
                1045                1050                1055
Phe Ile Asp Glu Ala His Ile Thr Gln Ala Leu Ile Trp Leu Ser Gln
            1060                1065                1070
Arg Gln Lys Asp Asn Gly Cys Phe Arg Ser Ser Gly Ser Leu Leu Asn
        1075                1080                1085
Asn Ala Ile Lys Gly Gly Val Glu Asp Glu Val Thr Leu Ser Ala Tyr
    1090                1095                1100
Ile Thr Ile Ala Leu Leu Glu Ile Pro Leu Thr Val Thr His Pro Val
1105                1110                1115                1120
Val Arg Asn Ala Leu Phe Cys Leu Glu Ser Ala Trp Lys Thr Ala Gln
                1125                1130                1135
Glu Gly Asp His Gly Ser His Val Tyr Thr Lys Ala Leu Leu Ala Tyr
            1140                1145                1150
Ala Phe Ala Leu Ala Gly Asn Gln Asp Lys Arg Lys Glu Val Leu Lys
        1155                1160                1165
Ser Leu Asn Glu Glu Ala Val Lys Lys Asp Asn Ser Val His Trp Glu
    1170                1175                1180
Arg Pro Gln Lys Pro Lys Ala Pro Val Gly His Phe Tyr Glu Pro Gln
1185                1190                1195                1200
Ala Pro Ser Ala Glu Val Glu Met Thr Ser Tyr Val Leu Leu Ala Tyr
                1205                1210                1215
Leu Thr Ala Gln Pro Ala Pro Thr Ser Glu Asp Leu Thr Ser Ala Thr
            1220                1225                1230
```

-continued

```
Asn Ile Val Lys Trp Ile Thr Lys Gln Gln Asn Ala Gln Gly Gly Phe
        1235                1240                1245

Ser Ser Thr Gln Asp Thr Val Val Ala Leu His Ala Leu Ser Lys Tyr
    1250                1255                1260

Gly Ala Ala Thr Phe Thr Arg Thr Gly Lys Ala Ala Gln Val Thr Ile
1265                1270                1275                1280

Gln Ser Ser Gly Thr Phe Ser Ser Lys Phe Gln Val Asp Asn Asn Asn
                1285                1290                1295

Arg Leu Leu Leu Gln Gln Val Ser Leu Pro Glu Leu Pro Gly Glu Tyr
                1300                1305                1310

Ser Met Lys Val Thr Gly Glu Gly Cys Val Tyr Leu Gln Thr Ser Leu
        1315                1320                1325

Lys Tyr Asn Ile Leu Pro Glu Lys Glu Glu Phe Pro Phe Ala Leu Gly
        1330                1335                1340

Val Gln Thr Leu Pro Gln Thr Cys Asp Glu Pro Lys Ala His Thr Ser
1345                1350                1355                1360

Phe Gln Ile Ser Leu Ser Val Ser Tyr Thr Gly Ser Arg Ser Ala Ser
                1365                1370                1375

Asn Met Ala Ile Val Asp Val Lys Met Val Ser Gly Phe Ile Pro Leu
            1380                1385                1390

Lys Pro Thr Val Lys Met Leu Glu Arg Ser Asn His Val Ser Arg Thr
        1395                1400                1405

Glu Val Ser Ser Asn His Val Leu Ile Tyr Leu Asp Lys Val Ser Asn
        1410                1415                1420

Gln Thr Leu Ser Leu Phe Phe Thr Val Leu Gln Asp Val Pro Val Arg
1425                1430                1435                1440

Asp Leu Lys Pro Ala Ile Val Lys Val Tyr Asp Tyr Tyr Glu Thr Asp
                1445                1450                1455

Glu Phe Ala Ile Ala Glu Tyr Asn Ala Pro Cys Ser Lys Asp Leu Gly
            1460                1465                1470

Asn Ala
```